US009290748B2

(12) United States Patent
Danos et al.

(10) Patent No.: US 9,290,748 B2
(45) Date of Patent: Mar. 22, 2016

(54) USE OF ENDONUCLEASES FOR INSERTING TRANSGENES INTO SAFE HARBOR LOCI

(75) Inventors: Olivier Danos, Fontainebleau (FR); Aymeric Duclert, Saint Maur des Fosses (FR)

(73) Assignee: Cellectis, Paris (FR)

( * ) Notice: Subject to any disclaimer, the term of this patent is extended or adjusted under 35 U.S.C. 154(b) by 47 days.

(21) Appl. No.: 13/036,343

(22) Filed: Feb. 28, 2011

(65) Prior Publication Data

US 2011/0239319 A1    Sep. 29, 2011

Related U.S. Application Data

(60) Provisional application No. 61/308,509, filed on Feb. 26, 2010.

(30) Foreign Application Priority Data

Feb. 26, 2010  (EP) .................................. 10305202

(51) Int. Cl.
| | | |
|---|---|---|
| C12N 15/85 | (2006.01) | |
| C12N 9/16 | (2006.01) | |
| C12Q 1/68 | (2006.01) | |
| A61K 48/00 | (2006.01) | |
| C12N 9/22 | (2006.01) | |
| C12N 15/90 | (2006.01) | |

(52) U.S. Cl.
CPC .. *C12N 9/16* (2013.01); *C12N 9/22* (2013.01); *C12N 15/90* (2013.01)

(58) Field of Classification Search
CPC ............................ A61K 48/00; C12N 15/8213
See application file for complete search history.

(56) References Cited

U.S. PATENT DOCUMENTS

| | | | | |
|---|---|---|---|---|
| 7,531,647 | B2 * | 5/2009 | Yee et al. ...................... | 536/23.4 |
| 2007/0117128 | A1 | 5/2007 | Smith et al. | |
| 2009/0220476 | A1 * | 9/2009 | Paques ......................... | 424/94.1 |
| 2009/0222937 | A1 * | 9/2009 | Arnould et al. ................ | 800/13 |
| 2009/0271881 | A1 * | 10/2009 | Arnould et al. ................ | 800/13 |
| 2010/0146651 | A1 * | 6/2010 | Smith et al. ..................... | 800/13 |
| 2010/0229252 | A1 * | 9/2010 | Perez-Michaut ............... | 800/13 |
| 2010/0325745 | A1 * | 12/2010 | Gouble .......................... | 800/13 |
| 2011/0091441 | A1 * | 4/2011 | Gouble et al. ............. | 424/94.61 |
| 2011/0113509 | A1 | 5/2011 | Jantz et al. | |
| 2011/0123509 | A1 | 5/2011 | Jantz et al. | |
| 2011/0225664 | A1 * | 9/2011 | Smith ............................ | 800/13 |

FOREIGN PATENT DOCUMENTS

| | | |
|---|---|---|
| WO | WO-03/078619 | 9/2003 |
| WO | WO-2006/097784 | 9/2006 |
| WO | WO 2008/152523 | * 12/2008 |
| WO | WO-2009/095793 | 8/2009 |
| WO | WO-2010/015899 | 2/2010 |

OTHER PUBLICATIONS

G Friedrich and P Soriano. Promoter traps in embryonic stem cells: a genetic screen to identify and mutate developmental genes in mice. Genes Dev. 1991 5: 1513-1523.*
Friedrich and Soriano, Promoter traps in embryonic stem cells: a genetic screen to identify and mutate developmental genes in mice. Genes Dev. 1991 5: 1513-1523.*
Dorothe Hameyer et al., Toxicity of ligand-dependent Cre recombinases and generation of a conditional Cre deleter mouse allowing mosaic recombination in peripheral tissues. Physiol Genomics 31: 32-41, 2007.*
Chalberg et al., Integration Specificity of Phage PhiC31 Integrase in the Human Genome. JMB, 2006, 357:28-48.*
International Search Reporting and Written Opinion regarding PCT/EP2011/052916.
Deichmann et al, "Vector integration is nonrandom and clustered and influences the fate of lymphopoiesis in SCID-X1 gene therapy.", Aug. 2007, pp. 2225-2232, vol. 117, No. 8, The Journal of Clinical Investigation.
Paques et al, "Meganucleases and DNA double-strand break-induced recombination: perspectives for gene therapy", Feb. 1, 2007, pp. 49-66, vol. 7, No. 1, Current Gene Therapy, Bentham Science Publishers Ltd., NL.
Grizot et al, "Efficient targeting of a SCID gene by an engineered single-chain homing endonuclease.", Sep. 2009, pp. 5405-5419, vol. 37, No. 16, Nucleic Acids Research.
Arnould et al, "Engineered I-CreI Derivatives Cleaving Sequences from the Human XPC Gene can Induce Highly Efficient Gene Correction in Mammalian Cells", Jul. 9, 2007, pp. 49-65, vol. 371, No. 1, Journal of Molecular Biology.
Seligman et al, "Mutations altering the cleavage specifically of a homing endonuclease", Sep. 1, 2002, pp. 3870-3879, vol. 30, No. 17, Nucleic Acids Research, Oxford University Press, Surrey, GB.
Smith et al, "A combinatorial approach to create artificial homing endonucleases cleaving chosen sequences", Nov. 27, 2006, pp. E149-1, vol. 34, No. 22, Nucleic Acids Research, Oxford University Press, Surrey, GB.
Pessach et al, "Gene therapy for primary immunodeficiencies: Looking ahead, toward gene correction.", Jun. 2011, pp. 1344-1350, vol. 127, No. 6, The Journal of Allergy and Clinical Immunology.
Arnould et al, "The I-CreI meganuclease and its engineered derivatives: applications from cell modification to gene therapy. (Latest version)", Jan. 2011, pp. 1-5, vol. 24, No. 1-2, Protein Engineering, Design and Selection: PEDS.
USPTO, Office Action in U.S. Appl. No. 13/702,066, filed Dec. 5, 2014.

* cited by examiner

*Primary Examiner* — Scott Long
*Assistant Examiner* — Arthur S Leonard
(74) *Attorney, Agent, or Firm* — Law Office of Salvatore Arrigo and Scott Lee, LLP

(57) ABSTRACT

The present invention concerns the endonucleases capable of cleaving a target sequence located in a "safe harbor loci", i.e. a loci allowing safe expression of a transgene. The present invention further concerns the use of such endonucleases for inserting transgenes into a cell, tissue or individual.

8 Claims, 16 Drawing Sheets

| | | |
|---|---|---|
| C1221 | (T)-C-AAA-AC-GTC-GTAC-GAC-GT-TTT-G-(A) | SEQ ID NO: 4 |
| 10AAT_P | (T)-C-AAT-AC-GTC-GTAC-GAC-GT-ATT-G-(A) | SEQ ID NO: 5 |
| 5AAG_P | (T)-C-AAA-AC-AAG-GTAC-CTT-GT-TTT-G-(A) | SEQ ID NO: 6 |
| 10AGG_P | (T)-C-AGG-AC-GTC-GTAC-GAC-GT-CCT-G-(A) | SEQ ID NO: 7 |
| 5TTT_P | (T)-C-AAA-AC-TTT-GTAC-AAA-GT-TTT-G-(A) | SEQ ID NO: 8 |
| SH3.1 | (C)-C-AAT-AC-AAG-GTAC-AAA-GT-CCT-G-(A) | SEQ ID NO: 2 |
| SH3.3 | (C)-C-AAT-AC-AAG-GTAC-CTT-GT-ATT-G-(G) | SEQ ID NO: 9 |
| SH3.4 | (T)-C-AGG-AC-TTT-GTAC-AAA-GT-CCT-G-(A) | SEQ ID NO: 10 |

FIG.1

| | | |
|---|---|---|
| C1221 | (T)-C-AAAA-AC-GTC-GTAC-GAC-GT-TTT-G-(A) | SEQ ID NO: 4 |
| 10AAAA_P = C1221 | (T)-C-AAAA-AC-GTC-GTAC-GAC-GT-TTT-G-(A) | SEQ ID NO: 4 |
| 5ACT_P | (T)-C-AAAA-AC-ACT-GTAC-AGT-GT-TTT-G-(A) | SEQ ID NO: 16 |
| 5GGT_P | (T)-C-AAAA-AC-GGT-GTAC-ACC-GT-TTT-G-(A) | SEQ ID NO: 17 |
| SH4.1 | (T)-T-AAAA-AC-ACT-GTAC-ACC-AT-TTT-G-(A) | SEQ ID NO: 3 |
| SH4.3 | (T)-T-AAAA-AC-ACT-GTAC-AGT-GT-TTT-A-(A) | SEQ ID NO: 18 |
| SH4.4 | (T)-C-AAAA-AT-GGT-GTAC-ACC-AT-TTT-G-(A) | SEQ ID NO: 19 |

FIG.4

| | | |
|---|---|---|
| C1221 | (T)-C-AAA-AC-GTC-GTAC-GAC-GT-TTT-G-(A) | SEQ ID NO: 4 |
| 10AAT_P | (T)-C-AAT-AC-GTC-GTAC-GAC-GT-ATT-G-(A) | SEQ ID NO: 60 |
| 5CCC_P | (T)-C-AAA-AC-CCC-GTAC-GGG-GT-TTT-G-(A) | SEQ ID NO: 61 |
| 5TAG_P | (T)-C-AAA-AC-TAG-GTAC-CTA-GT-TTT-G-(A) | SEQ ID NO: 62 |
| SH6 | (T)-T-AAT-AC-CCC-GTAC-CTA-AT-ATT-G-(C) | SEQ ID NO: 59 |
| SH6.3 | (T)-T-AAT-AC-CCC-GTAC-GGG-GT-ATT-A-(A) | SEQ ID NO: 63 |
| SH6.4 | (G)-C-AAT-AT-TAG-GTAC-CTA-AT-ATT-G-(C) | SEQ ID NO: 64 |

FIG.9

```
SEQ ID NO: 1      1  M-NTKYNKEFLLYLAGFVDGDGSIIAQIKPNQSYKFKHQLSLTFQVTQKT   49
                     | |||||||||||||||||||||||||||||||||||||||||||||||
SEQ ID NO: 42     1  MANTKYNKEFLLYLAGFVDGDGSIIAQIKPNQSYKFKHQLSLTFQVTQKT  50

SEQ ID NO: 1     50  QRRWFLDKLVDEIGVGYVRDRGSVSDYILSEIKPLHNFLTQLQPFLKLKQ   99
                     |||||||||||||||||||||||||||||||||||||||||||||||||
SEQ ID NO: 42    51  QRRWFLDKLVDEIGVGYVRDRGSVSDYILSEIKPLHNFLTQLQPFLKLKQ  100

SEQ ID NO: 1    100  KQANLVLKIIEQLPSAKESPDKFLEVCTWVDQIAALNDSKTRKTTSETVR  149
                     |||||||||||||||||||||||||||||||||||||||||||||||||
SEQ ID NO: 42   101  KQANLVLKIIEQLPSAKESPDKFLEVCTWVDQIAALNDSKTRKTTSETVR  150

SEQ ID NO: 1    150  AVLDSLSEKKKSSP---      163
                     ||||||||||||||
SEQ ID NO: 42   151  AVLDSLSEKKKSSPAAD     167
```

FIG.11

```
                                                        44A               54L
                                                         ↓                 ↓
SEQ ID NO: 57    1  M-NTKYNKEFLLYLAGFVDGDGSIIAQIKPNQSYKFKHQLSLTFAVTQKTQRRWLLDKLV   59
SEQ ID NO: 58    1  MANTKYNKEFLLYLAGFVDGDGSIIAQIKPNQSYKFKHQLSLTFAVTQKTQFRWLLDKLV   60
SEQ ID NO:  1    1  M-NTKYNKEFLLYLAGFVDGDGSIIAQIKPNQSYKFKHQLSLTEQVTQKTQRRWFLDKLV   59
                    * *************************************:.***** **** ******

64A     70Q   75N
                         ↓       ↓     ↓
SEQ ID NO: 57   60  DEIGAGYVRDQGSVSNYILSEIKPLHNFLTQLQPFLKLKQKQANLVLKIIEQLPSAKESP  119
SEQ ID NO: 58   61  DEIGAGYVRDQGSVSNYILSEIKPLHNFLTQLQPFLKLKQKQANLVLKIIEQLPSAKESP  120
SEQ ID NO:  1   60  DEIGVGYVRDRGSVSDYILSEIKPLHNFLTQLQPFLKLKQKQANLVLKIIEQLPSAKESP  119
                    ****.*****:****:********************************************

158R 162A
                                ↓   ↓
SEQ ID NO: 57  120  DKFLEVCTWVDQIAAALNDSKTRKTTSETVRAVLDSLSERKKSAP---              163
SEQ ID NO: 58  121  DKFLEVCTWVDQIAAALNDSKTRKTTSETVRAVLDSLSERKKSAPAAD              167
SEQ ID NO:  1  120  DKFLEVCTWVDQIAAALNDSKTRKTTSETVRAVLDSLSERKKSSP---              163
                    *******************************************:.
```

FIG.12

SEQUENCE LISTING

```
<160> NUMBER OF SEQ ID NOS: 326

<210> SEQ ID NO 1
<211> LENGTH: 163
<212> TYPE: PRT
<213> ORGANISM: Chlamydomonas reinhardtii
<220> FEATURE:
<221> NAME/KEY: MISC_FEATURE
<222> LOCATION: (75)..(75)
<223> OTHER INFORMATION: allelic variation: Asp or Asn

<400> SEQUENCE: 1

Met Asn Thr Lys Tyr Asn Lys Glu Phe Leu Leu Tyr Leu Ala Gly Phe
1               5                   10                  15

Val Asp Gly Asp Gly Ser Ile Ile Ala Gln Ile Lys Pro Asn Gln Ser
            20                  25                  30

Tyr Lys Phe Lys His Gln Leu Ser Leu Thr Phe Gln Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Arg Gly Ser Val Ser Asp Tyr Ile Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Ser Glu Lys Lys Lys
145                 150                 155                 160

Ser Ser Pro

<210> SEQ ID NO 2
<211> LENGTH: 24
<212> TYPE: DNA
<213> ORGANISM: Artificial
<220> FEATURE:
<223> OTHER INFORMATION: SH3 target sequence

<400> SEQUENCE: 2
ccaatacaag gtacaaagtc ctga                                          24

<210> SEQ ID NO 3
<211> LENGTH: 24
<212> TYPE: DNA
<213> ORGANISM: Artificial
<220> FEATURE:
<223> OTHER INFORMATION: SH4 target sequence

<400> SEQUENCE: 3
```
ttaaaacact gtacaccatt ttga                                        24

<210> SEQ ID NO 4
<211> LENGTH: 24
<212> TYPE: DNA
<213> ORGANISM: Artificial
<220> FEATURE:
<223> OTHER INFORMATION: wild-type target sequence

<400> SEQUENCE: 4
tcaaaacgtc gtacgacgtt ttga                                        24

<210> SEQ ID NO 5
<211> LENGTH: 24
<212> TYPE: DNA
<213> ORGANISM: Artificial
<220> FEATURE:
<223> OTHER INFORMATION: target sequence

<400> SEQUENCE: 5
tcaatacgtc gtacgacgta ttga                                        24

<210> SEQ ID NO 6
<211> LENGTH: 24
<212> TYPE: DNA
<213> ORGANISM: Artificial
<220> FEATURE:
<223> OTHER INFORMATION: target sequence

<400> SEQUENCE: 6
tcaaaacaag gtaccttgtt ttga                                        24

<210> SEQ ID NO 7
<211> LENGTH: 24
<212> TYPE: DNA
<213> ORGANISM: Artificial
<220> FEATURE:
<223> OTHER INFORMATION: target sequence

<400> SEQUENCE: 7
tcaggacgtc gtacgacgtc ctga                                        24

<210> SEQ ID NO 8
<211> LENGTH: 24
<212> TYPE: DNA
<213> ORGANISM: Artificial
<220> FEATURE:
<223> OTHER INFORMATION: target sequence

<400> SEQUENCE: 8
tcaaaacttt gtacaaagtt ttga                                        24

<210> SEQ ID NO 9
<211> LENGTH: 24
<212> TYPE: DNA
<213> ORGANISM: Artificial
<220> FEATURE:
<223> OTHER INFORMATION: target sequence

<400> SEQUENCE: 9
ccaatacaag gtaccttgta ttgg                                        24

<210> SEQ ID NO 10
<211> LENGTH: 24
<212> TYPE: DNA
<213> ORGANISM: Artificial

```
<220> FEATURE:
<223> OTHER INFORMATION: target sequence

<400> SEQUENCE: 10
tcaggacttt gtacaaagtc ctga                                              24

<210> SEQ ID NO 11
<211> LENGTH: 51
<212> TYPE: DNA
<213> ORGANISM: Artificial
<220> FEATURE:
<223> OTHER INFORMATION: oligonucleotide

<400> SEQUENCE: 11
tggcatacaa gtttccaata caaggtacaa agtcctgaca atcgtctgtc a                51

<210> SEQ ID NO 12
<211> LENGTH: 51
<212> TYPE: DNA
<213> ORGANISM: Artificial
<220> FEATURE:
<223> OTHER INFORMATION: oligonucleotide

<400> SEQUENCE: 12
tggcatacaa gtttccaata caaggtacaa agtcctgaca atcgtctgtc a                51

<210> SEQ ID NO 13
<211> LENGTH: 43
<212> TYPE: DNA
<213> ORGANISM: Artificial
<220> FEATURE:
<223> OTHER INFORMATION: primer

<400> SEQUENCE: 13
aaaaagcagg ctggcgcgcc tacacagcgg ccttgccacc atg                         43

<210> SEQ ID NO 14
<211> LENGTH: 36
<212> TYPE: DNA
<213> ORGANISM: Artificial
<220> FEATURE:
<223> OTHER INFORMATION: primer

<400> SEQUENCE: 14
agaaagctgg gtgctagcgc tcgagttatc agtcgg                                 36

<210> SEQ ID NO 15
<211> LENGTH: 32
<212> TYPE: PRT
<213> ORGANISM: Artificial
<220> FEATURE:
<223> OTHER INFORMATION: peptidic linker

<400> SEQUENCE: 15

Ala Ala Gly Gly Ser Asp Lys Tyr Asn Gln Ala Leu Ser Lys Tyr Asn
 1               5                  10                  15

Gln Ala Leu Ser Lys Tyr Asn Gln Ala Leu Ser Gly Gly Gly Gly Ser
                20                  25                  30

<210> SEQ ID NO 16
<211> LENGTH: 24
<212> TYPE: DNA
<213> ORGANISM: Artificial
<220> FEATURE:
<223> OTHER INFORMATION: target sequence
```

<400> SEQUENCE: 16
tcaaaacact gtacagtgtt ttga                                          24

<210> SEQ ID NO 17
<211> LENGTH: 24
<212> TYPE: DNA
<213> ORGANISM: Artificial
<220> FEATURE:
<223> OTHER INFORMATION: target sequence

<400> SEQUENCE: 17
tcaaaacggt gtacaccgtt ttga                                          24

<210> SEQ ID NO 18
<211> LENGTH: 24
<212> TYPE: DNA
<213> ORGANISM: Artificial
<220> FEATURE:
<223> OTHER INFORMATION: target sequence

<400> SEQUENCE: 18
ttaaaacact gtacagtgtt ttaa                                          24

<210> SEQ ID NO 19
<211> LENGTH: 24
<212> TYPE: DNA
<213> ORGANISM: Artificial
<220> FEATURE:
<223> OTHER INFORMATION: target sequence

<400> SEQUENCE: 19
tcaaaatggt gtacaccatt ttga                                          24

<210> SEQ ID NO 20
<211> LENGTH: 51
<212> TYPE: DNA
<213> ORGANISM: Artificial
<220> FEATURE:
<223> OTHER INFORMATION: oligonucleotide

<400> SEQUENCE: 20
tggcatacaa gttttaaaa cactgtacac cattttgaca atcgtctgtc a              51

<210> SEQ ID NO 21
<211> LENGTH: 51
<212> TYPE: DNA
<213> ORGANISM: Artificial
<220> FEATURE:
<223> OTHER INFORMATION: oligonucleotide

<400> SEQUENCE: 21
tggcatacaa gttttaaaa cactgtacac cattttgaca atcgtctgtc a              51

<210> SEQ ID NO 22
<211> LENGTH: 43
<212> TYPE: DNA
<213> ORGANISM: Artificial
<220> FEATURE:
<223> OTHER INFORMATION: primer

<400> SEQUENCE: 22
aaaaagcagg ctggcgcgcc tacacagcgg ccttgccacc atg                     43

<210> SEQ ID NO 23
<211> LENGTH: 36

```
<212> TYPE: DNA
<213> ORGANISM: Artificial
<220> FEATURE:
<223> OTHER INFORMATION: primer

<400> SEQUENCE: 23
agaaagctgg gtgctagcgc tcgagttatc agtcgg                    36

<210> SEQ ID NO 24
<211> LENGTH: 32
<212> TYPE: PRT
<213> ORGANISM: Artificial
<220> FEATURE:
<223> OTHER INFORMATION: peptidic linker

<400> SEQUENCE: 24
```

Ala Ala Gly Gly Ser Asp Lys Tyr Asn Gln Ala Leu Ser Lys Tyr Asn
1               5                   10                  15

Gln Ala Leu Ser Lys Tyr Asn Gln Ala Leu Ser Gly Gly Gly Gly Ser
            20                  25                  30

```
<210> SEQ ID NO 25
<211> LENGTH: 354
<212> TYPE: PRT
<213> ORGANISM: artificial sequence
<220> FEATURE:
<223> OTHER INFORMATION: SCOH-SH3-b56-A

<400> SEQUENCE: 25
```

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Tyr Lys Phe Lys His Gln Leu Ser Leu Thr Phe Ala Val Thr Gln
            35                  40                  45

Lys Thr Gln Arg Arg Trp Leu Leu Asp Lys Leu Val Asp Glu Ile Gly
    50                  55                  60

Val Gly Tyr Val Arg Asp Gln Gly Ser Val Ser Tyr Tyr Ile Leu Ser
65                  70                  75                  80

Glu Ile Lys Pro Leu His Asn Phe Leu Thr Gln Leu Arg Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Arg Lys
145                 150                 155                 160

Lys Ser Ala Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Ile Ala Gln Ile Lys Pro Gly Gln Ser Tyr
    210                 215                 220

Lys Phe Lys His Arg Leu Ser Leu Thr Phe Gln Val Thr Gln Lys Thr
225                 230                 235                 240

```
Arg Arg Arg Trp Phe Leu Asp Lys Leu Val Asp Arg Ile Gly Val Gly
                245                 250                 255

Tyr Val Arg Asp Asp Gly Ser Val Ser Asn Tyr Ile Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 26
<211> LENGTH: 354
<212> TYPE: PRT
<213> ORGANISM: artificial sequence
<220> FEATURE:
<223> OTHER INFORMATION: SCOH-SH3-b56-B

<400> SEQUENCE: 26

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
                20                  25                  30

Ser Tyr Lys Phe Lys His Gln Leu Ser Leu Thr Phe Ala Val Thr Gln
            35                  40                  45

Lys Thr Gln Arg Arg Trp Leu Leu Asp Lys Leu Val Asp Glu Ile Gly
    50                  55                  60

Val Gly Tyr Val Arg Asp Gln Gly Ser Val Ser Tyr Tyr Ile Leu Ser
65                  70                  75                  80

Glu Ile Lys Pro Leu His Asn Phe Leu Thr Gln Leu Arg Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
    115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Arg Lys
145                 150                 155                 160

Lys Ser Ala Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Ser Asn Lys Lys Phe Leu Leu Tyr Leu Ala Gly Phe Val
    195                 200                 205

Asp Ser Asp Gly Ser Ile Ile Ala Gln Ile Lys Pro Gly Gln Ser Tyr
    210                 215                 220

Lys Phe Lys His Arg Leu Ser Leu Thr Phe Gln Val Thr Gln Lys Thr
225                 230                 235                 240
```

Arg Arg Arg Trp Phe Leu Asp Lys Leu Val Asp Arg Ile Gly Val Gly
                245                 250                 255

Tyr Val Arg Asp Asp Gly Ser Val Ser Asn Tyr Ile Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 27
<211> LENGTH: 354
<212> TYPE: PRT
<213> ORGANISM: artificial sequence
<220> FEATURE:
<223> OTHER INFORMATION: SCOH-SH3-b56-C

<400> SEQUENCE: 27

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Tyr Lys Phe Lys His Gln Leu Ser Leu Thr Phe Ala Val Thr Gln
        35                  40                  45

Lys Thr Gln Arg Arg Trp Leu Leu Asp Lys Leu Val Asp Glu Ile Gly
    50                  55                  60

Val Gly Tyr Val Arg Asp Gln Gly Ser Val Ser Tyr Tyr Ile Leu Ser
65                  70                  75                  80

Glu Ile Lys Pro Leu His Asn Phe Leu Thr Gln Leu Arg Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Arg Lys
145                 150                 155                 160

Lys Ser Ala Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Ile Ala Gln Ile Lys Pro Gly Gln Ser Tyr
    210                 215                 220

Lys Phe Lys His Arg Leu Ser Leu Thr Phe Gln Val Thr Gln Lys Thr
225                 230                 235                 240

Arg Arg Arg Trp Phe Leu Asp Lys Leu Val Asp Arg Ile Gly Val Gly

```
                 245                 250                 255
Tyr Val Arg Asp Asp Gly Ser Val Ser Asn Tyr Ile Leu Ser Glu Ile
                260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
        290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Arg Thr Thr Ser
                325                 330                 335

Glu Thr Val Arg Ala Val Leu Asp Ser Leu Ser Glu Lys Lys Lys Ser
                340                 345                 350

Ser Pro

<210> SEQ ID NO 28
<211> LENGTH: 354
<212> TYPE: PRT
<213> ORGANISM: artificial sequence
<220> FEATURE:
<223> OTHER INFORMATION: SCOH-SH3-b56-D

<400> SEQUENCE: 28

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
                20                  25                  30

Ser Tyr Lys Phe Lys His Gln Leu Ser Leu Thr Phe Ala Val Thr Gln
            35                  40                  45

Lys Thr Gln Arg Arg Trp Leu Leu Asp Lys Leu Val Asp Glu Ile Gly
        50                  55                  60

Val Gly Tyr Val Arg Asp Gln Gly Ser Val Ser Tyr Tyr Ile Leu Ser
65                  70                  75                  80

Glu Ile Lys Pro Leu His Asn Phe Leu Thr Gln Leu Arg Pro Phe Leu
                85                  90                  95

Glu Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
        130                 135                 140

Thr Ser Glu Thr Val Arg Ala Val Leu Asp Ser Leu Ser Glu Arg Lys
145                 150                 155                 160

Lys Ser Ala Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Ile Ala Gln Ile Lys Pro Gly Gln Ser Tyr
    210                 215                 220

Lys Phe Lys His Arg Leu Ser Leu Thr Phe Gln Val Thr Gln Lys Thr
225                 230                 235                 240

Arg Arg Arg Trp Phe Leu Asp Lys Leu Val Asp Arg Ile Gly Val Gly
                245                 250                 255
```

```
Tyr Val Arg Asp Asp Gly Ser Val Ser Asn Tyr Ile Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Thr Thr Ser
                325                 330                 335

Glu Thr Val Arg Ala Val Leu Asp Ser Leu Ser Glu Lys Lys Ser
            340                 345                 350

Ser Pro

<210> SEQ ID NO 29
<211> LENGTH: 354
<212> TYPE: PRT
<213> ORGANISM: artificial sequence
<220> FEATURE:
<223> OTHER INFORMATION: SCOH-SH3-b1-A

<400> SEQUENCE: 29

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
                20                  25                  30

Ser Tyr Lys Phe Lys His Gln Leu Ser Leu Thr Phe Ala Val Thr Gln
            35                  40                  45

Lys Thr Gln Arg Arg Trp Leu Leu Asp Lys Leu Val Asp Glu Ile Gly
        50                  55                  60

Val Gly Tyr Val Arg Asp Gln Gly Ser Val Ser Tyr Tyr Ile Leu Ser
65                  70                  75                  80

Glu Ile Lys Pro Leu His Asn Phe Leu Thr Gln Leu Arg Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
130                 135                 140

Thr Ser Glu Thr Val Arg Ala Val Leu Asp Ser Leu Ser Glu Arg Lys
145                 150                 155                 160

Lys Ser Ala Pro Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Ile Ala Gln Ile Lys Pro Gly Gln Ser Tyr
        210                 215                 220

Lys Phe Lys His Arg Leu Ser Leu Thr Phe Gln Val Thr Gln Lys Thr
225                 230                 235                 240

Gln Arg Arg Trp Phe Leu Asp Lys Leu Val Asp Arg Ile Gly Val Gly
                245                 250                 255
```

```
Tyr Val Arg Asp Asp Gly Ser Val Ser Asn Tyr Ile Leu Ser Glu Ile
            260                 265                 270

Lys Pro Leu His Asp Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 30
<211> LENGTH: 354
<212> TYPE: PRT
<213> ORGANISM: artificial sequence
<220> FEATURE:
<223> OTHER INFORMATION: SCOH-SH3-b1-B

<400> SEQUENCE: 30

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Tyr Lys Phe Lys His Gln Leu Ser Leu Thr Phe Ala Val Thr Gln
        35                  40                  45

Lys Thr Gln Arg Arg Trp Leu Leu Asp Lys Leu Val Asp Glu Ile Gly
    50                  55                  60

Val Gly Tyr Val Arg Asp Gln Gly Ser Val Ser Tyr Tyr Ile Leu Ser
65                  70                  75                  80

Glu Ile Lys Pro Leu His Asn Phe Leu Thr Gln Leu Arg Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Arg Lys
145                 150                 155                 160

Lys Ser Ala Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Ser Asn Lys Lys Phe Leu Leu Tyr Leu Ala Gly Phe Val
        195                 200                 205

Asp Ser Asp Gly Ser Ile Ile Ala Gln Ile Lys Pro Gly Gln Ser Tyr
    210                 215                 220

Lys Phe Lys His Arg Leu Ser Leu Thr Phe Gln Val Thr Gln Lys Thr
225                 230                 235                 240

Gln Arg Arg Trp Phe Leu Asp Lys Leu Val Asp Arg Ile Gly Val Gly
                245                 250                 255

Tyr Val Arg Asp Asp Gly Ser Val Ser Asn Tyr Ile Leu Ser Glu Ile
```

```
                260                 265                 270
Lys Pro Leu His Asp Phe Leu Thr Gln Leu Gln Pro Phe Leu Lys Leu
            275                 280                 285
Lys Gln Lys Gln Ala Asn Leu Val Leu Lys Ile Ile Glu Gln Leu Pro
        290                 295                 300
Ser Ala Lys Glu Ser Pro Asp Lys Phe Leu Glu Val Cys Thr Trp Val
305                 310                 315                 320
Asp Gln Ile Ala Ala Leu Asn Asp Ser Lys Thr Arg Lys Thr Thr Ser
                325                 330                 335
Glu Thr Val Arg Ala Val Leu Asp Ser Leu Ser Glu Lys Lys Lys Ser
            340                 345                 350
Ser Pro

<210> SEQ ID NO 31
<211> LENGTH: 354
<212> TYPE: PRT
<213> ORGANISM: artificial sequence
<220> FEATURE:
<223> OTHER INFORMATION: SCOH-SH3-b1-C

<400> SEQUENCE: 31

Met Ala Asn Thr Lys Tyr Asn Glu Glu Phe Leu Leu Tyr Leu Ala Gly
1               5                   10                  15
Phe Val Asp Gly Asp Gly Ser Ile Ile Ala Gln Ile Lys Pro Asn Gln
            20                  25                  30
Ser Tyr Lys Phe Lys His Gln Leu Ser Leu Thr Phe Ala Val Thr Gln
        35                  40                  45
Lys Thr Gln Arg Arg Trp Leu Leu Asp Lys Leu Val Asp Glu Ile Gly
50                  55                  60
Val Gly Tyr Val Arg Asp Gln Gly Ser Val Ser Tyr Tyr Ile Leu Ser
65                  70                  75                  80
Glu Ile Lys Pro Leu His Asn Phe Leu Thr Gln Leu Arg Pro Phe Leu
                85                  90                  95
Glu Leu Lys Gln Lys Gln Ala Asn Leu Val Leu Lys Ile Ile Glu Gln
            100                 105                 110
Leu Pro Ser Ala Lys Glu Ser Pro Asp Lys Phe Leu Glu Val Cys Thr
        115                 120                 125
Trp Val Asp Gln Val Ala Ala Leu Asn Asp Ser Lys Thr Arg Lys Thr
130                 135                 140
Thr Ser Glu Thr Val Arg Ala Val Leu Asp Ser Leu Ser Glu Arg Lys
145                 150                 155                 160
Lys Ser Ala Pro Ala Ala Gly Gly Ser Asp Lys Tyr Asn Gln Ala Leu
                165                 170                 175
Ser Lys Tyr Asn Gln Ala Leu Ser Lys Tyr Asn Gln Ala Leu Ser Gly
            180                 185                 190
Gly Gly Ser Asn Lys Lys Phe Leu Leu Tyr Leu Ala Gly Phe Val
        195                 200                 205
Asp Ser Asp Gly Ser Ile Ile Ala Gln Ile Lys Pro Gly Gln Ser Tyr
210                 215                 220
Lys Phe Lys His Arg Leu Ser Leu Thr Phe Gln Val Thr Gln Lys Thr
225                 230                 235                 240
Gln Arg Arg Trp Phe Leu Asp Lys Leu Val Asp Arg Ile Gly Val Gly
                245                 250                 255
Tyr Val Arg Asp Asp Gly Ser Val Ser Asn Tyr Ile Leu Ser Glu Ile
            260                 265                 270
```

```
Lys Pro Leu His Asp Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
                340                 345                 350

Ser Pro
```

<210> SEQ ID NO 32
<211> LENGTH: 354
<212> TYPE: PRT
<213> ORGANISM: artificial sequence
<220> FEATURE:
<223> OTHER INFORMATION: SCOH-SH3-b1-D

<400> SEQUENCE: 32

```
Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
                20                  25                  30

Ser Tyr Lys Phe Lys His Gln Leu Ser Leu Thr Phe Ala Val Thr Gln
            35                  40                  45

Lys Thr Gln Arg Arg Trp Leu Leu Asp Lys Leu Val Asp Glu Ile Gly
50                  55                  60

Val Gly Tyr Val Arg Asp Gln Gly Ser Val Ser Tyr Tyr Ile Leu Ser
65                  70                  75                  80

Glu Ile Lys Pro Leu His Asn Phe Leu Thr Gln Leu Arg Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
130                 135                 140

Thr Ser Glu Thr Val Arg Ala Val Leu Asp Ser Leu Ser Glu Arg Lys
145                 150                 155                 160

Lys Ser Ala Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Ile Ala Gln Ile Lys Pro Gly Gln Ser Tyr
210                 215                 220

Lys Phe Lys His Arg Leu Ser Leu Thr Phe Gln Val Thr Gln Lys Thr
225                 230                 235                 240

Gln Arg Arg Trp Phe Leu Asp Lys Leu Val Asp Arg Ile Gly Val Gly
                245                 250                 255

Tyr Val Arg Asp Asp Gly Ser Val Ser Asn Tyr Ile Leu Ser Glu Ile
            260                 265                 270
```

```
Lys Pro Leu His Asp Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
        290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 33
<211> LENGTH: 354
<212> TYPE: PRT
<213> ORGANISM: artificial sequence
<220> FEATURE:
<223> OTHER INFORMATION: SCOH-SH4-b56-A

<400> SEQUENCE: 33

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Tyr Lys Phe Lys His Gln Leu Ser Leu Thr Phe Arg Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Tyr Tyr Asn Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Val Ala Gln Ile Lys Pro Asn Gln Ser Tyr
    210                 215                 220

Lys Phe Lys His Gln Leu Ser Leu Thr Phe Tyr Val Thr Gln Lys Thr
225                 230                 235                 240

Gln Arg Arg Trp Phe Leu Asp Lys Leu Val Asp Arg Ile Gly Val Gly
                245                 250                 255

Tyr Val Arg Asp Ser Gly Ser Val Ser Asp Tyr Val Leu Ser Glu Ile
            260                 265                 270

Lys Pro Leu His Asn Phe Leu Thr Gln Leu Gln Pro Phe Leu Lys Leu
```

```
            275                 280                 285
Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 34
<211> LENGTH: 354
<212> TYPE: PRT
<213> ORGANISM: artificial sequence
<220> FEATURE:
<223> OTHER INFORMATION: SCOH-SH4-b56-B

<400> SEQUENCE: 34

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
                20                  25                  30

Ser Tyr Lys Phe Lys His Gln Leu Ser Leu Thr Phe Arg Val Thr Gln
            35                  40                  45

Lys Thr Gln Arg Arg Trp Phe Leu Asp Lys Leu Val Asp Glu Ile Gly
50                  55                  60

Val Gly Tyr Val Tyr Asp Ser Gly Ser Val Ser Tyr Tyr Asn Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Ser Asn Lys Lys Phe Leu Leu Tyr Leu Ala Gly Phe Val
        195                 200                 205

Asp Ser Asp Gly Ser Ile Val Ala Gln Ile Lys Pro Asn Gln Ser Tyr
210                 215                 220

Lys Phe Lys His Gln Leu Ser Leu Thr Phe Tyr Val Thr Gln Lys Thr
225                 230                 235                 240

Gln Arg Arg Trp Phe Leu Asp Lys Leu Val Asp Arg Ile Gly Val Gly
                245                 250                 255

Tyr Val Arg Asp Ser Gly Ser Val Ser Asp Tyr Val Leu Ser Glu Ile
            260                 265                 270

Lys Pro Leu His Asn Phe Leu Thr Gln Leu Gln Pro Phe Leu Lys Leu
        275                 280                 285
```

```
Lys Gln Lys Gln Ala Asn Leu Val Leu Lys Ile Ile Glu Gln Leu Pro
            290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
            325                 330                 335

Glu Thr Val Arg Ala Val Leu Asp Ser Leu Ser Glu Lys Lys Lys Ser
            340                 345                 350

Ser Pro

<210> SEQ ID NO 35
<211> LENGTH: 354
<212> TYPE: PRT
<213> ORGANISM: artificial sequence
<220> FEATURE:
<223> OTHER INFORMATION: SCOH-SH4-b56-C

<400> SEQUENCE: 35

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Tyr Lys Phe Lys His Gln Leu Ser Leu Thr Phe Arg Val Thr Gln
        35                  40                  45

Lys Thr Gln Arg Arg Trp Phe Leu Asp Lys Leu Val Asp Glu Ile Gly
50                  55                  60

Val Gly Tyr Val Tyr Asp Ser Gly Ser Val Ser Tyr Tyr Asn Leu Ser
65                  70                  75                  80

Glu Ile Lys Pro Leu His Asn Phe Leu Thr Gln Leu Gln Pro Phe Leu
            85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
            165                 170                 175

Ser Lys Tyr Asn Gln Ala Leu Ser Lys Tyr Asn Gln Ala Leu Ser Gly
        180                 185                 190

Gly Gly Gly Ser Asn Lys Lys Phe Leu Leu Tyr Leu Ala Gly Phe Val
    195                 200                 205

Asp Ser Asp Gly Ser Ile Val Ala Gln Ile Lys Pro Asn Gln Ser Tyr
210                 215                 220

Lys Phe Lys His Gln Leu Ser Leu Thr Phe Tyr Val Thr Gln Lys Thr
225                 230                 235                 240

Gln Arg Arg Trp Phe Leu Asp Lys Leu Val Asp Arg Ile Gly Val Gly
            245                 250                 255

Tyr Val Arg Asp Ser Gly Ser Val Ser Asp Tyr Val Leu Ser Glu Ile
            260                 265                 270

Lys Pro Leu His Asn Phe Leu Thr Gln Leu Gln Pro Phe Leu Lys Leu
        275                 280                 285
```

```
Lys Gln Lys Gln Ala Asn Leu Val Leu Lys Ile Ile Glu Gln Leu Pro
            290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 36
<211> LENGTH: 354
<212> TYPE: PRT
<213> ORGANISM: artificial sequence
<220> FEATURE:
<223> OTHER INFORMATION: SCOH-SH4-b56-D

<400> SEQUENCE: 36

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Tyr Lys Phe Lys His Gln Leu Ser Leu Thr Phe Arg Val Thr Gln
        35                  40                  45

Lys Thr Gln Arg Arg Trp Phe Leu Asp Lys Leu Val Asp Glu Ile Gly
50                  55                  60

Val Gly Tyr Val Tyr Asp Ser Gly Ser Val Ser Tyr Tyr Asn Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Ser Asn Lys Lys Phe Leu Leu Tyr Leu Ala Gly Phe Val
        195                 200                 205

Asp Ser Asp Gly Ser Ile Val Ala Gln Ile Lys Pro Asn Gln Ser Tyr
210                 215                 220

Lys Phe Lys His Gln Leu Ser Leu Thr Phe Tyr Val Thr Gln Lys Thr
225                 230                 235                 240

Gln Arg Arg Trp Phe Leu Asp Lys Leu Val Asp Arg Ile Gly Val Gly
                245                 250                 255

Tyr Val Arg Asp Ser Gly Ser Val Ser Asp Tyr Val Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
```

```
                    290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 37
<211> LENGTH: 354
<212> TYPE: PRT
<213> ORGANISM: artificial sequence
<220> FEATURE:
<223> OTHER INFORMATION: SCOH-SH4-b1-A

<400> SEQUENCE: 37

Met Ala Asn Thr Lys Tyr Asn Glu Glu Phe Leu Leu Tyr Leu Ala Gly
1               5                   10                  15

Phe Val Asp Gly Asp Gly Ser Ile Val Ala Gln Ile Lys Pro Asn Gln
                20                  25                  30

Ser Tyr Lys Phe Lys His Gln Leu Ser Leu Thr Phe Arg Val Thr Gln
            35                  40                  45

Lys Thr Gln Arg Arg Trp Phe Leu Asp Lys Leu Val Asp Glu Ile Gly
50                  55                  60

Val Gly Tyr Val Tyr Asp Ser Gly Ser Val Ser Tyr Tyr Asn Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Val Ala Gln Ile Lys Pro Asn Gln Ser Tyr
210                 215                 220

Lys Phe Lys His Gln Leu Ser Leu Thr Phe Tyr Val Thr Gln Lys Thr
225                 230                 235                 240

Gln Arg Arg Trp Phe Leu Asp Lys Leu Val Asp Arg Ile Gly Val Gly
                245                 250                 255

Tyr Val Arg Asp Ser Gly Ser Val Ser Asp Tyr Val Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
290                 295                 300
```

```
Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
            325                 330                 335

Glu Thr Val Arg Ala Val Leu Asp Ser Leu Ser Glu Lys Lys Lys Ser
            340                 345                 350

Ser Pro

<210> SEQ ID NO 38
<211> LENGTH: 354
<212> TYPE: PRT
<213> ORGANISM: artificial sequence
<220> FEATURE:
<223> OTHER INFORMATION: SCOH-SH4-b1-B

<400> SEQUENCE: 38

Met Ala Asn Thr Lys Tyr Asn Glu Glu Phe Leu Leu Tyr Leu Ala Gly
1               5                   10                  15

Phe Val Asp Gly Asp Gly Ser Ile Val Ala Gln Ile Lys Pro Asn Gln
                20                  25                  30

Ser Tyr Lys Phe Lys His Gln Leu Ser Leu Thr Phe Arg Val Thr Gln
            35                  40                  45

Lys Thr Gln Arg Arg Trp Phe Leu Asp Lys Leu Val Asp Glu Ile Gly
50                  55                  60

Val Gly Tyr Val Tyr Asp Ser Gly Ser Val Ser Tyr Tyr Asn Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Val Ala Gln Ile Lys Pro Asn Gln Ser Tyr
210                 215                 220

Lys Phe Lys His Gln Leu Ser Leu Thr Phe Tyr Val Thr Gln Lys Thr
225                 230                 235                 240

Gln Arg Arg Trp Phe Leu Asp Lys Leu Val Asp Arg Ile Gly Val Gly
                245                 250                 255

Tyr Val Arg Asp Ser Gly Ser Val Ser Asp Tyr Val Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
290                 295                 300
```

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
            325                 330                 335

Glu Thr Val Arg Ala Val Leu Asp Ser Leu Ser Glu Lys Lys Lys Ser
        340                 345                 350

Ser Pro

<210> SEQ ID NO 39
<211> LENGTH: 354
<212> TYPE: PRT
<213> ORGANISM: artificial sequence
<220> FEATURE:
<223> OTHER INFORMATION: SCOH-SH4-b1-C

<400> SEQUENCE: 39

Met Ala Asn Thr Lys Tyr Asn Glu Glu Phe Leu Leu Tyr Leu Ala Gly
1               5                   10                  15

Phe Val Asp Gly Asp Gly Ser Ile Val Ala Gln Ile Lys Pro Asn Gln
            20                  25                  30

Ser Tyr Lys Phe Lys His Gln Leu Ser Leu Thr Phe Arg Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Tyr Tyr Asn Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Val Ala Gln Ile Lys Pro Asn Gln Ser Tyr
    210                 215                 220

Lys Phe Lys His Gln Leu Ser Leu Thr Phe Tyr Val Thr Gln Lys Thr
225                 230                 235                 240

Gln Arg Arg Trp Phe Leu Asp Lys Leu Val Asp Arg Ile Gly Val Gly
                245                 250                 255

Tyr Val Arg Asp Ser Gly Ser Val Ser Asp Tyr Val Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val

```
              305                 310                 315                 320
Asp Gln Val Ala Ala Leu Asn Asp Ser Lys Thr Arg Lys Thr Thr Ser
                    325                 330                 335
Glu Thr Val Arg Ala Val Leu Asp Ser Leu Ser Glu Lys Lys Lys Ser
                340                 345                 350
Ser Pro

<210> SEQ ID NO 40
<211> LENGTH: 354
<212> TYPE: PRT
<213> ORGANISM: artificial sequence
<220> FEATURE:
<223> OTHER INFORMATION: SCOH-SH4-b1-D

<400> SEQUENCE: 40

Met Ala Asn Thr Lys Tyr Asn Glu Glu Phe Leu Leu Tyr Leu Ala Gly
1               5                   10                  15

Phe Val Asp Gly Asp Gly Ser Ile Val Ala Gln Ile Lys Pro Asn Gln
            20                  25                  30

Ser Tyr Lys Phe Lys His Gln Leu Ser Leu Thr Phe Arg Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Tyr Tyr Asn Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Val Ala Gln Ile Lys Pro Asn Gln Ser Tyr
    210                 215                 220

Lys Phe Lys His Gln Leu Ser Leu Thr Phe Tyr Val Thr Gln Lys Thr
225                 230                 235                 240

Gln Arg Arg Trp Phe Leu Asp Lys Leu Val Asp Arg Ile Gly Val Gly
                245                 250                 255

Tyr Val Arg Asp Ser Gly Ser Val Ser Asp Tyr Val Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320
```

```
Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
                340                 345                 350

Ser Pro

<210> SEQ ID NO 41
<211> LENGTH: 354
<212> TYPE: PRT
<213> ORGANISM: artificial sequence
<220> FEATURE:
<223> OTHER INFORMATION: SCOH-RAG

<400> SEQUENCE: 41

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Asn Pro Asn Gln
                20                  25                  30

Ser Ser Lys Phe Lys His Arg Leu Arg Leu Thr Phe Tyr Val Thr Gln
                35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Gln Tyr Val Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
                115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Gly Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
                180                 185                 190

Gly Gly Gly Ser Asn Lys Glu Phe Leu Leu Tyr Leu Ala Gly Phe Val
                195                 200                 205

Asp Ser Asp Gly Ser Ile Ile Ala Gln Ile Lys Pro Arg Gln Ser Asn
    210                 215                 220

Lys Phe Lys His Gln Leu Ser Leu Thr Phe Ala Val Thr Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Ser Gly Ser Val Ser Asp Tyr Arg Leu Ser Glu Ile
                260                 265                 270

Lys Pro Leu His Asn Phe Leu Thr Gln Leu Gln Pro Phe Leu Lys Leu
                275                 280                 285

Lys Gln Lys Gln Ala Asn Leu Val Leu Lys Ile Ile Glu Gln Leu Pro
                290                 295                 300

Ser Ala Lys Glu Ser Pro Asp Lys Phe Leu Glu Val Cys Thr Trp Val
305                 310                 315                 320
```

```
Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 42
<211> LENGTH: 167
<212> TYPE: PRT
<213> ORGANISM: Artificial
<220> FEATURE:
<223> OTHER INFORMATION: I-CreI monomer
<220> FEATURE:
<221> NAME/KEY: MISC_FEATURE
<222> LOCATION: (76)..(76)
<223> OTHER INFORMATION: allelic variantion: Asp or Asn

<400> SEQUENCE: 42

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Tyr Lys Phe Lys His Gln Leu Ser Leu Thr Phe Gln Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Arg Gly Ser Val Ser Asp Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 43
<211> LENGTH: 32
<212> TYPE: PRT
<213> ORGANISM: Artificial
<220> FEATURE:
<223> OTHER INFORMATION: RM2 peptidic linker

<400> SEQUENCE: 43

Ala Ala Gly Gly Ser Asp Lys Tyr Asn Gln Ala Leu Ser Lys Tyr Asn
1               5                   10                  15

Gln Ala Leu Ser Lys Tyr Asn Gln Ala Leu Ser Gly Gly Gly Gly Ser
            20                  25                  30

<210> SEQ ID NO 44
<211> LENGTH: 22
<212> TYPE: DNA
<213> ORGANISM: Artificial
<220> FEATURE:
<223> OTHER INFORMATION: primer
```

<400> SEQUENCE: 44
tgggggtctt actctgtttc cc                                                 22

<210> SEQ ID NO 45
<211> LENGTH: 20
<212> TYPE: DNA
<213> ORGANISM: Artificial
<220> FEATURE:
<223> OTHER INFORMATION: primer

<400> SEQUENCE: 45
aggagagtcc ttctttggcc                                                    20

<210> SEQ ID NO 46
<211> LENGTH: 22
<212> TYPE: DNA
<213> ORGANISM: Artificial
<220> FEATURE:
<223> OTHER INFORMATION: primer

<400> SEQUENCE: 46
gagtgatagc ataatgaaaa cc                                                 22

<210> SEQ ID NO 47
<211> LENGTH: 22
<212> TYPE: DNA
<213> ORGANISM: Artificial
<220> FEATURE:
<223> OTHER INFORMATION: primer

<400> SEQUENCE: 47
ctcaccataa gtcaactgtc tc                                                 22

<210> SEQ ID NO 48
<211> LENGTH: 30
<212> TYPE: DNA
<213> ORGANISM: Artificial
<220> FEATURE:
<223> OTHER INFORMATION: primer

<400> SEQUENCE: 48
ccatctcatc cctgcgtgtc tccgactcag                                         30

<210> SEQ ID NO 49
<211> LENGTH: 30
<212> TYPE: DNA
<213> ORGANISM: Artificial
<220> FEATURE:
<223> OTHER INFORMATION: primer

<400> SEQUENCE: 49
cctatcccct gtgtgccttg gcagtctcag                                         30

<210> SEQ ID NO 50
<211> LENGTH: 20
<212> TYPE: DNA
<213> ORGANISM: Artificial
<220> FEATURE:
<223> OTHER INFORMATION: primer

<400> SEQUENCE: 50
ctgtgtgcta tgatcttgcc                                                    20

<210> SEQ ID NO 51
<211> LENGTH: 20

```
<212> TYPE: DNA
<213> ORGANISM: Artificial
<220> FEATURE:
<223> OTHER INFORMATION: primer

<400> SEQUENCE: 51
cctgtctctt gatcagatcc                                              20

<210> SEQ ID NO 52
<211> LENGTH: 20
<212> TYPE: DNA
<213> ORGANISM: Artificial
<220> FEATURE:
<223> OTHER INFORMATION: primer

<400> SEQUENCE: 52
gtggcctctc agtctgttta                                              20

<210> SEQ ID NO 53
<211> LENGTH: 20
<212> TYPE: DNA
<213> ORGANISM: Artificial
<220> FEATURE:
<223> OTHER INFORMATION: primer

<400> SEQUENCE: 53
agtcatagcc gaatagcctc                                              20

<210> SEQ ID NO 54
<211> LENGTH: 24
<212> TYPE: DNA
<213> ORGANISM: Homo sapiens

<400> SEQUENCE: 54
ccaatacaag gtacaaagtc ctga                                         24

<210> SEQ ID NO 55
<211> LENGTH: 24
<212> TYPE: DNA
<213> ORGANISM: Homo sapiens

<400> SEQUENCE: 55
ttaaaacact gtacaccatt ttga                                         24

<210> SEQ ID NO 56
<211> LENGTH: 24
<212> TYPE: DNA
<213> ORGANISM: Homo sapiens

<400> SEQUENCE: 56
ttaatacccc gtacctaata ttgc                                         24

<210> SEQ ID NO 57
<211> LENGTH: 163
<212> TYPE: PRT
<213> ORGANISM: Artificial
<220> FEATURE:
<223> OTHER INFORMATION: I-CreI monomer comprising 44A 54L 64A 70Q 75N
      158R 162A mutations

<400> SEQUENCE: 57

Met Asn Thr Lys Tyr Asn Lys Glu Phe Leu Leu Tyr Leu Ala Gly Phe
1               5                   10                  15

Val Asp Gly Asp Gly Ser Ile Ile Ala Gln Ile Lys Pro Asn Gln Ser
            20                  25                  30
```

Tyr Lys Phe Lys His Gln Leu Ser Leu Thr Phe Ala Val Thr Gln Lys
            35                  40                  45

Thr Gln Arg Arg Trp Leu Leu Asp Lys Leu Val Asp Glu Ile Gly Ala
    50                  55                  60

Gly Tyr Val Arg Asp Gln Gly Ser Val Ser Asn Tyr Ile Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Ser Glu Arg Lys Lys
145                 150                 155                 160

Ser Ala Pro

<210> SEQ ID NO 58
<211> LENGTH: 167
<212> TYPE: PRT
<213> ORGANISM: Artificial
<220> FEATURE:
<223> OTHER INFORMATION: I-CreI monomer comprising 44A 54L 64A 70Q 75N
      158R 162A mutations

<400> SEQUENCE: 58

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Tyr Lys Phe Lys His Gln Leu Ser Leu Thr Phe Ala Val Thr Gln
        35                  40                  45

Lys Thr Gln Arg Arg Trp Leu Leu Asp Lys Leu Val Asp Glu Ile Gly
    50                  55                  60

Ala Gly Tyr Val Arg Asp Gln Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
        130                 135                 140

Thr Ser Glu Thr Val Arg Ala Val Leu Asp Ser Leu Ser Glu Arg Lys
145                 150                 155                 160

Lys Ser Ala Pro Ala Ala Asp
                165

<210> SEQ ID NO 59
<211> LENGTH: 24
<212> TYPE: DNA
<213> ORGANISM: Artificial
<220> FEATURE:
<223> OTHER INFORMATION: SH6 target sequence

<400> SEQUENCE: 59
ttaatacccc gtacctaata ttgc        24

<210> SEQ ID NO 60
<211> LENGTH: 24
<212> TYPE: DNA
<213> ORGANISM: Artificial
<220> FEATURE:
<223> OTHER INFORMATION: target sequence

<400> SEQUENCE: 60
tcaatacgtc gtacgacgta ttga        24

<210> SEQ ID NO 61
<211> LENGTH: 24
<212> TYPE: DNA
<213> ORGANISM: Artificial
<220> FEATURE:
<223> OTHER INFORMATION: target sequence

<400> SEQUENCE: 61
tcaaaacccc gtacggggtt ttga        24

<210> SEQ ID NO 62
<211> LENGTH: 24
<212> TYPE: DNA
<213> ORGANISM: Artificial
<220> FEATURE:
<223> OTHER INFORMATION: target sequence

<400> SEQUENCE: 62
tcaaaactag gtacctagtt ttga        24

<210> SEQ ID NO 63
<211> LENGTH: 24
<212> TYPE: DNA
<213> ORGANISM: Artificial
<220> FEATURE:
<223> OTHER INFORMATION: target sequence

<400> SEQUENCE: 63
ttaatacccc gtacgggta ttaa         24

<210> SEQ ID NO 64
<211> LENGTH: 24
<212> TYPE: DNA
<213> ORGANISM: Artificial
<220> FEATURE:
<223> OTHER INFORMATION: target sequence

<400> SEQUENCE: 64
gcaatattag gtacctaata ttgc        24

<210> SEQ ID NO 65
<211> LENGTH: 51
<212> TYPE: DNA
<213> ORGANISM: Artificial
<220> FEATURE:
<223> OTHER INFORMATION: oligonucleotide

<400> SEQUENCE: 65
tggcatacaa gtttttaata ccccgtacct aatattgcca atcgtctgtc a        51

<210> SEQ ID NO 66
<211> LENGTH: 43

```
<212> TYPE: DNA
<213> ORGANISM: Artificial
<220> FEATURE:
<223> OTHER INFORMATION: oligonucleotide

<400> SEQUENCE: 66
aaaaagcagg ctggcgcgcc tacacagcgg ccttgccacc atg                    43

<210> SEQ ID NO 67
<211> LENGTH: 36
<212> TYPE: DNA
<213> ORGANISM: Artificial
<220> FEATURE:
<223> OTHER INFORMATION: oligonucleotide

<400> SEQUENCE: 67
agaaagctgg gtgctagcgc tcgagttatc agtcgg                            36

<210> SEQ ID NO 68
<211> LENGTH: 33
<212> TYPE: DNA
<213> ORGANISM: Artificial
<220> FEATURE:
<223> OTHER INFORMATION: oligonucleotide

<400> SEQUENCE: 68
acccagcgcc gttggctgct ggacaaacta gtg                               33

<210> SEQ ID NO 69
<211> LENGTH: 33
<212> TYPE: DNA
<213> ORGANISM: Artificial
<220> FEATURE:
<223> OTHER INFORMATION: oligonucleotide

<400> SEQUENCE: 69
cactagtttg tccagcagcc aacggcgctg ggt                               33

<210> SEQ ID NO 70
<211> LENGTH: 33
<212> TYPE: DNA
<213> ORGANISM: Artificial
<220> FEATURE:
<223> OTHER INFORMATION: oligonucleotide

<400> SEQUENCE: 70
aaacaggcaa ccctggctct gaaaattatc gaa                               33

<210> SEQ ID NO 71
<211> LENGTH: 33
<212> TYPE: DNA
<213> ORGANISM: Artificial
<220> FEATURE:
<223> OTHER INFORMATION: oligonucleotide

<400> SEQUENCE: 71
ttcgataatt ttcagagcca gggttgcctg ttt                               33

<210> SEQ ID NO 72
<211> LENGTH: 32
<212> TYPE: DNA
<213> ORGANISM: Artificial
<220> FEATURE:
<223> OTHER INFORMATION: oligonucleotide

<400> SEQUENCE: 72
```

```
cacaaagaag gtggttgttg gacaaattgg tt                                32
```

<210> SEQ ID NO 73
<211> LENGTH: 32
<212> TYPE: DNA
<213> ORGANISM: Artificial
<220> FEATURE:
<223> OTHER INFORMATION: oligonucleotide

<400> SEQUENCE: 73

```
aaccaatttg tccaacaacc accttctttg tg                                32
```

<210> SEQ ID NO 74
<211> LENGTH: 32
<212> TYPE: DNA
<213> ORGANISM: Artificial
<220> FEATURE:
<223> OTHER INFORMATION: oligonucleotide

<400> SEQUENCE: 74

```
tgtctaaaat taagcctctt cataactttc tc                                32
```

<210> SEQ ID NO 75
<211> LENGTH: 32
<212> TYPE: DNA
<213> ORGANISM: Artificial
<220> FEATURE:
<223> OTHER INFORMATION: oligonucleotide

<400> SEQUENCE: 75

```
gagaaagtta tgaagaggct taattttaga ca                                32
```

<210> SEQ ID NO 76
<211> LENGTH: 354
<212> TYPE: PRT
<213> ORGANISM: artificial sequence
<220> FEATURE:
<223> OTHER INFORMATION: SCOH-SH6-b1-B

<400> SEQUENCE: 76

```
Met Ala Asn Thr Lys Tyr Asn Arg Glu Phe Leu Leu Tyr Leu Ala Gly
1               5                   10                  15

Phe Val Asp Gly Asp Gly Ser Ile Ile Ala Gln Ile Gln Pro Asn Gln
            20                  25                  30

Ser Tyr Lys Phe Lys His Gln Leu Arg Leu Thr Phe Ala Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Leu Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Thr Leu Val Leu Lys Ile Ile Glu Gln
            100                 105                 110

Leu Pro Ser Ala Lys Glu Ser Pro Asp Glu Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Arg Ser Ser Pro Ala Ala Gly Gly Ser Asp Lys Tyr Asn Gln Ala Leu
```

```
              165                 170                 175
Ser Lys Tyr Asn Gln Ala Leu Ser Lys Tyr Asn Gln Ala Leu Ser Gly
            180                 185                 190
Gly Gly Gly Ser Asn Lys Lys Phe Leu Leu Tyr Leu Ala Gly Phe Val
            195                 200                 205
Asp Ser Asp Gly Ser Ile Ile Ala Gln Ile Lys Pro Asn Gln Ser Tyr
210                 215                 220
Lys Phe Lys His Gln Leu Ser Leu Thr Phe Lys Val Thr Gln Lys Thr
225                 230                 235                 240
Gln Arg Arg Trp Phe Leu Asp Lys Leu Val Asp Arg Ile Gly Val Gly
            245                 250                 255
Tyr Val Arg Asp Ser Gly Ser Val Ser Asn Tyr Ile Leu Ser Glu Ile
            260                 265                 270
Lys Pro Leu His Asn Phe Leu Thr Gln Leu Gln Pro Phe Leu Lys Leu
            275                 280                 285
Lys Gln Lys Gln Ala Asn Leu Val Leu Lys Ile Ile Glu Gln Leu Pro
            290                 295                 300
Ser Ala Lys Glu Ser Pro Asp Lys Phe Leu Glu Val Cys Thr Trp Val
305                 310                 315                 320
Asp Gln Ile Ala Ala Leu Asn Asp Ser Lys Thr Arg Lys Thr Thr Ser
            325                 330                 335
Glu Thr Val Arg Ala Val Leu Asp Ser Leu Ser Glu Lys Lys Lys Ser
            340                 345                 350
Ser Pro

<210> SEQ ID NO 77
<211> LENGTH: 354
<212> TYPE: PRT
<213> ORGANISM: artificial sequence
<220> FEATURE:
<223> OTHER INFORMATION: SCOH-SH6-b1-C

<400> SEQUENCE: 77

Met Ala Asn Thr Lys Tyr Asn Arg Glu Phe Leu Leu Tyr Leu Ala Gly
1               5                   10                  15
Phe Val Asp Gly Asp Gly Ser Ile Ile Ala Gln Ile Gln Pro Asn Gln
            20                  25                  30
Ser Tyr Lys Phe Lys His Gln Leu Arg Leu Thr Phe Ala Val Thr Gln
            35                  40                  45
Lys Thr Gln Arg Arg Trp Phe Leu Asp Lys Leu Val Asp Glu Ile Gly
        50                  55                  60
Val Gly Tyr Val Arg Asp Leu Gly Ser Val Ser Asn Tyr Ile Leu Ser
65                  70                  75                  80
Glu Ile Lys Pro Leu His Asn Phe Leu Thr Gln Leu Gln Pro Phe Leu
                85                  90                  95
Glu Leu Lys Gln Lys Gln Ala Thr Leu Val Leu Lys Ile Ile Glu Gln
            100                 105                 110
Leu Pro Ser Ala Lys Glu Ser Pro Asp Glu Phe Leu Glu Val Cys Thr
            115                 120                 125
Trp Val Asp Gln Val Ala Ala Leu Asn Asp Ser Lys Thr Arg Lys Thr
        130                 135                 140
Thr Ser Glu Thr Val Arg Ala Val Leu Asp Ser Leu Ser Glu Lys Lys
145                 150                 155                 160
Arg Ser Ser Pro Ala Ala Gly Gly Ser Asp Lys Tyr Asn Gln Ala Leu
                165                 170                 175
```

```
Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Ile Ala Gln Ile Lys Pro Asn Gln Ser Tyr
    210                 215                 220

Lys Phe Lys His Gln Leu Ser Leu Thr Phe Lys Val Thr Gln Lys Thr
225                 230                 235                 240

Gln Arg Arg Trp Phe Leu Asp Lys Leu Val Asp Arg Ile Gly Val Gly
                245                 250                 255

Tyr Val Arg Asp Ser Gly Ser Val Ser Asn Tyr Ile Leu Ser Glu Ile
            260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
        290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 78
<211> LENGTH: 354
<212> TYPE: PRT
<213> ORGANISM: artificial sequence
<220> FEATURE:
<223> OTHER INFORMATION: SCOH-SH6-b1-C

<400> SEQUENCE: 78

Met Ala Asn Thr Lys Tyr Asn Arg Glu Phe Leu Leu Tyr Leu Ala Gly
1               5                   10                  15

Phe Val Asp Gly Asp Gly Ser Ile Ile Ala Gln Ile Gln Pro Asn Gln
            20                  25                  30

Ser Tyr Lys Phe Lys His Gln Leu Arg Leu Thr Phe Ala Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Leu Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Thr Leu Val Leu Lys Ile Ile Glu Gln
            100                 105                 110

Leu Pro Ser Ala Lys Glu Ser Pro Asp Glu Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Arg Ser Ser Pro Ala Ala Gly Gly Ser Asp Lys Tyr Asn Gln Ala Leu
                165                 170                 175
```

```
Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Ile Ala Gln Ile Lys Pro Asn Gln Ser Tyr
    210                 215                 220

Lys Phe Lys His Gln Leu Ser Leu Thr Phe Lys Val Thr Gln Lys Thr
225                 230                 235                 240

Gln Arg Arg Trp Phe Leu Asp Lys Leu Val Asp Arg Ile Gly Val Gly
                245                 250                 255

Tyr Val Arg Asp Ser Gly Ser Val Ser Asn Tyr Ile Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 79
<211> LENGTH: 354
<212> TYPE: PRT
<213> ORGANISM: artificial sequence
<220> FEATURE:
<223> OTHER INFORMATION: QCSH61-A01

<400> SEQUENCE: 79

Met Ala Asn Thr Lys Tyr Asn Arg Glu Phe Leu Leu Tyr Leu Ala Gly
1               5                   10                  15

Phe Val Asp Gly Asp Gly Ser Ile Ile Ala Gln Ile Gln Pro Asn Gln
                20                  25                  30

Ser Tyr Lys Phe Lys His Gln Leu Arg Leu Thr Phe Ala Val Thr Gln
            35                  40                  45

Lys Thr Gln Arg Arg Trp Phe Leu Asp Lys Leu Val Asp Glu Ile Gly
50                  55                  60

Val Gly Tyr Val Arg Asp Leu Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Thr Leu Ala Leu Lys Ile Ile Glu Gln
            100                 105                 110

Leu Pro Ser Ala Lys Glu Ser Pro Asp Glu Phe Leu Glu Val Cys Thr
        115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Arg Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
```

```
            180                 185                 190
Gly Gly Gly Ser Asn Lys Lys Phe Leu Leu Tyr Leu Ala Gly Phe Val
            195                 200                 205

Asp Ser Asp Gly Ser Ile Ile Ala Gln Ile Lys Pro Asn Gln Ser Tyr
            210                 215                 220

Lys Phe Lys His Gln Leu Ser Leu Thr Phe Lys Val Thr Gln Lys Thr
225                 230                 235                 240

Gln Arg Arg Trp Phe Leu Asp Lys Leu Val Asp Arg Ile Gly Val Gly
            245                 250                 255

Tyr Val Arg Asp Ser Gly Ser Val Ser Asn Tyr Ile Leu Ser Glu Ile
            260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
            290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
            325                 330                 335

Glu Thr Val Arg Ala Val Leu Asp Ser Leu Ser Glu Lys Lys Lys Ser
            340                 345                 350

Ser Pro

<210> SEQ ID NO 80
<211> LENGTH: 354
<212> TYPE: PRT
<213> ORGANISM: artificial sequence
<220> FEATURE:
<223> OTHER INFORMATION: QCSH61-E01

<400> SEQUENCE: 80

Met Ala Asn Thr Lys Tyr Asn Arg Glu Phe Leu Leu Tyr Leu Ala Gly
1               5                   10                  15

Phe Val Asp Gly Asp Gly Ser Ile Ile Ala Gln Ile Gln Pro Asn Gln
            20                  25                  30

Ser Tyr Lys Phe Lys His Gln Leu Arg Leu Thr Phe Ala Val Thr Gln
        35                  40                  45

Lys Thr Gln Arg Arg Trp Phe Leu Asp Lys Leu Val Asp Glu Ile Gly
50                  55                  60

Val Gly Tyr Val Arg Asp Leu Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Thr Leu Val Leu Lys Ile Ile Glu Gln
            100                 105                 110

Leu Pro Ser Ala Lys Glu Ser Pro Asp Glu Phe Leu Glu Val Cys Thr
            115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Arg Ser Ser Pro Ala Ala Gly Gly Ser Asp Lys Tyr Asn Gln Ala Leu
            165                 170                 175

Ser Lys Tyr Asn Gln Ala Leu Ser Lys Tyr Asn Gln Ala Leu Ser Gly
            180                 185                 190
```

```
Gly Gly Gly Ser Asn Lys Lys Phe Leu Leu Tyr Leu Ala Gly Phe Val
            195                 200                 205

Asp Ser Asp Gly Ser Ile Ile Ala Gln Ile Lys Pro Asn Gln Ser Tyr
210                 215                 220

Lys Phe Lys His Gln Leu Ser Leu Thr Phe Lys Val Thr Gln Lys Thr
225                 230                 235                 240

Gln Arg Arg Trp Leu Leu Asp Lys Leu Val Asp Arg Ile Gly Val Gly
            245                 250                 255

Tyr Val Arg Asp Ser Gly Ser Val Ser Asn Tyr Ile Leu Ser Glu Ile
                260                 265                 270

Lys Pro Leu His Asn Phe Leu Thr Gln Leu Gln Pro Phe Leu Lys Leu
                275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 81
<211> LENGTH: 354
<212> TYPE: PRT
<213> ORGANISM: artificial sequence
<220> FEATURE:
<223> OTHER INFORMATION: QCSH61-H01a

<400> SEQUENCE: 81

Met Ala Asn Thr Lys Tyr Asn Arg Glu Phe Leu Leu Tyr Leu Ala Gly
1               5                   10                  15

Phe Val Asp Gly Asp Gly Ser Ile Ile Ala Gln Ile Gln Pro Asn Gln
            20                  25                  30

Ser Tyr Lys Phe Lys His Gln Leu Arg Leu Thr Phe Ala Val Thr Gln
        35                  40                  45

Lys Thr Gln Arg Arg Trp Phe Leu Asp Lys Leu Val Asp Glu Ile Gly
50                  55                  60

Val Gly Tyr Val Arg Asp Leu Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Thr Leu Ala Leu Lys Ile Ile Glu Gln
            100                 105                 110

Leu Pro Ser Ala Lys Glu Ser Pro Asp Glu Phe Leu Glu Val Cys Thr
        115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Arg Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190
```

-continued

```
Gly Gly Gly Ser Asn Lys Lys Phe Leu Leu Tyr Leu Ala Gly Phe Val
            195                 200                 205
Asp Ser Asp Gly Ser Ile Ile Ala Gln Ile Lys Pro Asn Gln Ser Tyr
        210                 215                 220
Lys Phe Lys His Gln Leu Ser Leu Thr Phe Lys Val Thr Gln Lys Thr
225                 230                 235                 240
Gln Arg Arg Trp Leu Leu Asp Lys Leu Val Asp Arg Ile Gly Val Gly
                245                 250                 255
Tyr Val Arg Asp Ser Gly Ser Val Ser Asn Tyr Ile Leu Ser Lys Ile
            260                 265                 270
Lys Pro Leu His Asn Phe Leu Thr Gln Leu Gln Pro Phe Leu Lys Leu
        275                 280                 285
Lys Gln Lys Gln Ala Asn Leu Val Leu Lys Ile Ile Glu Gln Leu Pro
    290                 295                 300
Ser Ala Lys Glu Ser Pro Asp Lys Phe Leu Glu Val Cys Thr Trp Val
305                 310                 315                 320
Asp Gln Val Ala Ala Leu Asn Asp Ser Lys Thr Arg Lys Thr Thr Ser
                325                 330                 335
Glu Thr Val Arg Ala Val Leu Asp Ser Leu Ser Glu Lys Lys Lys Ser
            340                 345                 350
Ser Pro

<210> SEQ ID NO 82
<211> LENGTH: 354
<212> TYPE: PRT
<213> ORGANISM: artificial sequence
<220> FEATURE:
<223> OTHER INFORMATION: QCSH62-A02

<400> SEQUENCE: 82

Met Ala Asn Thr Lys Tyr Asn Arg Glu Phe Leu Leu Tyr Leu Ala Gly
1               5                   10                  15
Phe Val Asp Gly Asp Gly Ser Ile Ile Ala Gln Ile Gln Pro Asn Gln
            20                  25                  30
Ser Tyr Lys Phe Lys His Gln Leu Arg Leu Thr Phe Ala Val Thr Gln
        35                  40                  45
Lys Thr Gln Arg Arg Trp Leu Leu Asp Lys Leu Val Asp Glu Ile Gly
    50                  55                  60
Val Gly Tyr Val Arg Asp Leu Gly Ser Val Ser Asn Tyr Ile Leu Ser
65                  70                  75                  80
Glu Ile Lys Pro Leu His Asn Phe Leu Thr Gln Leu Gln Pro Phe Leu
                85                  90                  95
Glu Leu Lys Gln Lys Gln Ala Thr Leu Val Leu Lys Ile Ile Glu Gln
            100                 105                 110
Leu Pro Ser Ala Lys Glu Ser Pro Asp Glu Phe Leu Glu Val Cys Thr
        115                 120                 125
Trp Val Asp Gln Val Ala Ala Leu Asn Asp Ser Lys Thr Arg Lys Thr
    130                 135                 140
Thr Ser Glu Thr Val Arg Ala Val Leu Asp Ser Leu Ser Glu Lys Lys
145                 150                 155                 160
Arg Ser Ser Pro Ala Ala Gly Gly Ser Asp Lys Tyr Asn Gln Ala Leu
                165                 170                 175
Ser Lys Tyr Asn Gln Ala Leu Ser Lys Tyr Asn Gln Ala Leu Ser Gly
            180                 185                 190
Gly Gly Gly Ser Asn Lys Lys Phe Leu Leu Tyr Leu Ala Gly Phe Val
```

```
            195                 200                 205
Asp Ser Asp Gly Ser Ile Ile Ala Gln Ile Lys Pro Asn Gln Ser Tyr
    210                 215                 220

Lys Phe Lys His Gln Leu Ser Leu Thr Phe Val Thr Gln Lys Thr
225                 230                 235                 240

Gln Arg Arg Trp Phe Leu Asp Lys Leu Val Asp Arg Ile Gly Val Gly
                    245                 250                 255

Tyr Val Arg Asp Ser Gly Ser Val Ser Asn Tyr Ile Leu Ser Glu Ile
                260                 265                 270

Lys Pro Leu His Asn Phe Leu Thr Gln Leu Gln Pro Phe Leu Lys Leu
                    275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                    325                 330                 335

Glu Thr Val Arg Ala Val Leu Asp Ser Leu Ser Glu Lys Lys Lys Ser
                340                 345                 350

Ser Pro

<210> SEQ ID NO 83
<211> LENGTH: 354
<212> TYPE: PRT
<213> ORGANISM: artificial sequence
<220> FEATURE:
<223> OTHER INFORMATION: QCSH61-H01b

<400> SEQUENCE: 83

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Gln Pro Asn Gln
                20                  25                  30

Ser Tyr Lys Phe Lys His Gln Leu Arg Leu Thr Phe Ala Val Thr Gln
            35                  40                  45

Lys Thr Gln Arg Arg Trp Phe Leu Asp Lys Leu Val Asp Glu Ile Gly
        50                  55                  60

Val Gly Tyr Val Arg Asp Leu Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Thr Leu Ala Leu Lys Ile Ile Glu Gln
            100                 105                 110

Leu Pro Ser Ala Lys Glu Ser Pro Asp Glu Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Arg Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205
```

```
Asp Ser Asp Gly Ser Ile Ile Ala Gln Ile Lys Pro Asn Gln Ser Tyr
    210                 215                 220

Lys Phe Lys His Gln Leu Ser Leu Thr Phe Lys Val Thr Gln Lys Thr
225                 230                 235                 240

Gln Arg Arg Trp Leu Leu Asp Lys Leu Val Asp Arg Ile Gly Val Gly
                245                 250                 255

Tyr Val Arg Asp Ser Gly Ser Val Ser Asn Tyr Ile Leu Ser Lys Ile
                260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
                340                 345                 350

Ser Pro
```

<210> SEQ ID NO 84
<211> LENGTH: 354
<212> TYPE: PRT
<213> ORGANISM: artificial sequence
<220> FEATURE:
<223> OTHER INFORMATION: QCSH61-H01c

<400> SEQUENCE: 84

```
Met Ala Asn Thr Lys Tyr Asn Arg Glu Phe Leu Leu Tyr Leu Ala Gly
1               5                   10                  15

Phe Val Asp Gly Asp Gly Ser Ile Ile Ala Gln Ile Gln Pro Asn Gln
                20                  25                  30

Ser Tyr Lys Phe Lys His Gln Leu Arg Leu Thr Phe Ala Val Thr Gln
                35                  40                  45

Lys Thr Gln Arg Arg Trp Phe Leu Asp Lys Leu Val Asp Glu Ile Gly
50                  55                  60

Val Gly Tyr Val Arg Asp Leu Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Thr Leu Ala Leu Lys Ile Ile Glu Gln
                100                 105                 110

Leu Pro Ser Ala Lys Glu Ser Pro Asp Glu Phe Leu Glu Val Cys Thr
            115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Arg Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
            195                 200                 205
```

```
Asp Ser Asp Gly Ser Ile Ile Ala Gln Ile Lys Pro Asn Gln Ser Tyr
    210                 215                 220

Lys Phe Lys His Gln Leu Ser Leu Thr Phe Lys Val Thr Gln Lys Thr
225                 230                 235                 240

Gln Arg Arg Trp Leu Leu Asp Lys Leu Val Asp Arg Ile Gly Val Gly
                245                 250                 255

Tyr Val Arg Asp Arg Gly Ser Val Ser Asp Tyr Ile Leu Ser Lys Ile
                260                 265                 270

Lys Pro Leu His Asn Phe Leu Thr Gln Leu Gln Pro Phe Leu Lys Leu
                275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
                340                 345                 350

Ser Pro

<210> SEQ ID NO 85
<211> LENGTH: 354
<212> TYPE: PRT
<213> ORGANISM: artificial sequence
<220> FEATURE:
<223> OTHER INFORMATION: QCSH61-H01d

<400> SEQUENCE: 85

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Gln Pro Asn Gln
                20                  25                  30

Ser Tyr Lys Phe Lys His Gln Leu Arg Leu Thr Phe Ala Val Thr Gln
            35                  40                  45

Lys Thr Gln Arg Arg Trp Phe Leu Asp Lys Leu Val Asp Glu Ile Gly
50                  55                  60

Val Gly Tyr Val Arg Asp Leu Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Thr Leu Ala Leu Lys Ile Ile Glu Gln
                100                 105                 110

Leu Pro Ser Ala Lys Glu Ser Pro Asp Glu Phe Leu Glu Val Cys Thr
                115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Arg Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
                180                 185                 190

Gly Gly Ser Asn Lys Lys Phe Leu Leu Tyr Leu Ala Gly Phe Val
                195                 200                 205

Asp Ser Asp Gly Ser Ile Ile Ala Gln Ile Lys Pro Asn Gln Ser Tyr
```

```
                210                 215                 220
Lys Phe Lys His Gln Leu Ser Leu Thr Phe Lys Val Thr Gln Lys Thr
225                 230                 235                 240

Gln Arg Arg Trp Leu Leu Asp Lys Leu Val Asp Arg Ile Gly Val Gly
                245                 250                 255

Tyr Val Arg Asp Arg Gly Ser Val Ser Asp Tyr Ile Leu Ser Lys Ile
                260                 265                 270

Lys Pro Leu His Asn Phe Leu Thr Gln Leu Gln Pro Phe Leu Lys Leu
                275                 280                 285

Lys Gln Lys Gln Ala Asn Leu Val Leu Lys Ile Ile Glu Gln Leu Pro
                290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
                340                 345                 350

Ser Pro

<210> SEQ ID NO 86
<211> LENGTH: 354
<212> TYPE: PRT
<213> ORGANISM: artificial sequence
<220> FEATURE:
<223> OTHER INFORMATION: SH7a

<400> SEQUENCE: 86

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Arg Pro Asn Gln
                20                  25                  30

Ser Arg Lys Phe Lys His Tyr Leu Gln Leu Thr Phe Gln Val Thr Gln
            35                  40                  45

Lys Thr Gln Arg Arg Trp Phe Leu Asp Lys Leu Val Asp Glu Ile Gly
50                  55                  60

Val Gly Tyr Val Arg Asp Ser Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Ile Ala Gln Ile Lys Pro Thr Gln Ser Thr
    210                 215                 220
```

Lys Phe Lys His Gln Leu Ser Leu Thr Phe Gln Val Thr Gln Lys Thr
225                 230                 235                 240

Gln Arg Arg Trp Phe Leu Asp Lys Leu Val Asp Arg Ile Gly Val Gly
            245                 250                 255

Tyr Val Arg Asp Arg Gly Ser Val Ser Asp Tyr Ile Leu Ser Glu Ile
        260                 265                 270

Lys Pro Leu His Asn Phe Leu Thr Gln Leu Gln Pro Phe Leu Lys Leu
    275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 87
<211> LENGTH: 354
<212> TYPE: PRT
<213> ORGANISM: artificial sequence
<220> FEATURE:
<223> OTHER INFORMATION: SH7b

<400> SEQUENCE: 87

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Arg Lys Phe Lys His Gln Leu Gln Leu Thr Phe Gln Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Ser Asn Lys Lys Phe Leu Leu Tyr Leu Ala Gly Phe Val
        195                 200                 205

Asp Ser Asp Gly Ser Ile Ile Ala Gln Ile Lys Pro His Gln Ser Lys
    210                 215                 220

```
Lys Phe Lys His Gln Leu Ser Leu Thr Phe Gln Val Thr Gln Lys Thr
225                 230                 235                 240

Gln Arg Arg Trp Phe Leu Asp Lys Leu Val Asp Arg Ile Gly Val Gly
            245                 250                 255

Tyr Val Arg Asp Arg Gly Ser Val Ser Asp Tyr Ile Leu Ser Glu Ile
        260                 265                 270

Lys Pro Leu His Asn Phe Leu Thr Gln Leu Gln Pro Phe Leu Lys Leu
    275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
            325                 330                 335

Glu Thr Val Arg Ala Val Leu Asp Ser Leu Ser Glu Lys Lys Lys Ser
        340                 345                 350

Ser Pro

<210> SEQ ID NO 88
<211> LENGTH: 354
<212> TYPE: PRT
<213> ORGANISM: artificial sequence
<220> FEATURE:
<223> OTHER INFORMATION: SH8

<400> SEQUENCE: 88

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Gln Pro Asn Gln
            20                  25                  30

Ser Tyr Lys Phe Lys His Arg Leu Lys Leu Thr Phe Asn Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Arg Tyr Gln Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Ser Asn Lys Lys Phe Leu Leu Tyr Leu Ala Gly Phe Val
        195                 200                 205

Asp Ser Asp Gly Ser Ile Ile Ala Gln Ile Lys Pro Asn Gln Ser Tyr
210                 215                 220

Lys Phe Lys His Gln Leu Ser Leu Thr Phe Asn Val Thr Gln Lys Thr
```

```
                225                 230                 235                 240

Gln Arg Arg Trp Phe Leu Asp Lys Leu Val Asp Arg Ile Gly Val Gly
            245                 250                 255

Tyr Val His Asp Ser Gly Ser Val Ser Tyr Tyr Asn Leu Ser Lys Ile
            260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
            290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
            325                 330                 335

Glu Thr Val Arg Ala Val Leu Asp Ser Leu Ser Glu Lys Lys Lys Ser
            340                 345                 350

Ser Pro

<210> SEQ ID NO 89
<211> LENGTH: 354
<212> TYPE: PRT
<213> ORGANISM: artificial sequence
<220> FEATURE:
<223> OTHER INFORMATION: SH12

<400> SEQUENCE: 89

Met Ala Asn Thr Lys Tyr Asn Glu Glu Phe Leu Leu Tyr Leu Ala Gly
1               5                   10                  15

Phe Val Asp Gly Asp Gly Ser Ile Val Ala Gln Ile Lys Pro Asn Gln
            20                  25                  30

Ser Tyr Lys Phe Lys His Gln Leu Ser Leu Thr Phe Ala Val Thr Gln
            35                  40                  45

Lys Thr Gln Arg Arg Trp Phe Leu Asp Lys Leu Val Asp Glu Ile Gly
        50                  55                  60

Val Gly Tyr Val Arg Asp Ser Gly Ser Val Ser Tyr Tyr Ile Leu Ser
65                  70                  75                  80

Glu Ile Lys Pro Leu His Asn Phe Leu Thr Gln Leu Gln Pro Phe Leu
            85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Val Asp Gln Val Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
            165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
            195                 200                 205

Asp Ser Asp Gly Ser Ile Ile Ala Gln Ile Lys Pro Asn Gln Ser Tyr
            210                 215                 220

Lys Phe Lys His Gln Leu Ser Leu Thr Phe Ile Val Thr Gln Lys Thr
225                 230                 235                 240
```

```
Gln Arg Arg Trp Phe Leu Asp Lys Leu Val Asp Arg Ile Gly Val Gly
                245                 250                 255

Tyr Val Ser Asp Arg Gly Ser Val Ser Asp Tyr Lys Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 90
<211> LENGTH: 354
<212> TYPE: PRT
<213> ORGANISM: artificial sequence
<220> FEATURE:
<223> OTHER INFORMATION: SH13

<400> SEQUENCE: 90

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Arg Pro Asn Gln
                20                  25                  30

Ser Ser Lys Phe Lys His Tyr Leu Gln Leu Thr Phe Lys Val Thr Gln
            35                  40                  45

Lys Thr Gln Arg Arg Trp Phe Leu Asp Lys Leu Val Asp Glu Ile Gly
        50                  55                  60

Val Gly Tyr Val Gly Asp Thr Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Ile Ala Gln Ile Lys Pro Asn Gln Ser Tyr
    210                 215                 220

Lys Phe Lys His Gln Leu Ser Leu Thr Phe Cys Val Thr Gln Lys Thr
225                 230                 235                 240
```

```
Gln Arg Arg Trp Phe Leu Asp Lys Leu Val Asp Arg Ile Gly Val Gly
            245                 250                 255

Tyr Val Ser Asp Arg Gly Ser Val Ser Asp Tyr Arg Leu Ser Glu Ile
        260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
        290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 91
<211> LENGTH: 354
<212> TYPE: PRT
<213> ORGANISM: artificial sequence
<220> FEATURE:
<223> OTHER INFORMATION: SH19

<400> SEQUENCE: 91

Met Ala Asn Thr Lys Tyr Asn Glu Glu Phe Leu Leu Tyr Leu Ala Gly
1               5                   10                  15

Phe Val Asp Gly Asp Gly Ser Ile Val Ala Gln Ile Lys Pro Asn Gln
            20                  25                  30

Ser Tyr Lys Phe Lys His Gln Leu Ser Leu Thr Phe Leu Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Asn Gly Ser Val Ser Asn Tyr Ile Leu Ser
65                  70                  75                  80

Lys Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Ser Asn Lys Lys Phe Leu Leu Tyr Leu Ala Gly Phe Val
        195                 200                 205

Asp Ser Asp Gly Ser Ile Ile Ala Gln Ile Lys Pro Asn Gln Thr His
    210                 215                 220

Lys Phe Lys His Gln Leu Ser Leu Thr Phe Gln Val Thr Gln Lys Thr
225                 230                 235                 240

Gln Arg Arg Trp Phe Leu Asp Lys Leu Val Asp Arg Ile Gly Val Gly
```

```
                        245                 250                 255
Tyr Val Arg Asp Arg Gly Ser Val Ser Asp Tyr Ile Leu Ser Glu Ile
                260                 265                 270
Lys Pro Leu His Asn Phe Leu Thr Gln Leu Gln Pro Phe Leu Lys Leu
            275                 280                 285
Lys Gln Lys Gln Ala Asn Leu Val Leu Lys Ile Ile Glu Gln Leu Pro
        290                 295                 300
Ser Ala Lys Glu Ser Pro Asp Lys Phe Leu Glu Val Cys Thr Trp Val
305                 310                 315                 320
Asp Gln Val Ala Ala Leu Asn Asp Ser Lys Thr Arg Lys Thr Thr Ser
                325                 330                 335
Glu Thr Val Arg Ala Val Leu Asp Ser Leu Ser Glu Lys Lys Lys Ser
            340                 345                 350
Ser Pro

<210> SEQ ID NO 92
<211> LENGTH: 354
<212> TYPE: PRT
<213> ORGANISM: artificial sequence
<220> FEATURE:
<223> OTHER INFORMATION: SH20

<400> SEQUENCE: 92

Met Ala Asn Thr Lys Tyr Asn Glu Glu Phe Leu Leu Tyr Leu Ala Gly
1               5                   10                  15
Phe Val Asp Gly Asp Gly Ser Ile Ile Ala Gln Ile Lys Pro Asn Gln
            20                  25                  30
Ser Cys Lys Phe Lys His Tyr Leu Ser Leu Thr Phe Asn Val Thr Gln
        35                  40                  45
Lys Thr Gln Arg Arg Trp Phe Leu Asp Lys Leu Val Asp Glu Ile Gly
    50                  55                  60
Val Gly Tyr Val Tyr Asp Ser Gly Ser Val Ser Tyr Tyr Asn Leu Ser
65                  70                  75                  80
Glu Ile Lys Pro Leu His Asn Phe Leu Thr Gln Leu Gln Pro Phe Leu
                85                  90                  95
Glu Leu Lys Gln Lys Gln Ala Asn Leu Val Leu Lys Ile Ile Glu Gln
            100                 105                 110
Leu Pro Ser Ala Lys Glu Ser Pro Asp Lys Phe Leu Glu Val Cys Thr
        115                 120                 125
Trp Val Asp Gln Val Ala Ala Leu Asn Asp Ser Lys Thr Arg Lys Thr
    130                 135                 140
Thr Ser Glu Thr Val Arg Ala Val Leu Asp Ser Leu Ser Glu Lys Lys
145                 150                 155                 160
Lys Ser Ser Pro Ala Ala Gly Gly Ser Asp Lys Tyr Asn Gln Ala Leu
                165                 170                 175
Ser Lys Tyr Asn Gln Ala Leu Ser Lys Tyr Asn Gln Ala Leu Ser Gly
            180                 185                 190
Gly Gly Gly Ser Asn Lys Lys Phe Leu Leu Tyr Leu Ala Gly Phe Val
        195                 200                 205
Asp Ser Asp Gly Ser Ile Ile Ala Gln Ile Lys Pro Asn Gln Ser Cys
    210                 215                 220
Lys Phe Lys His Ser Leu Ser Leu Thr Phe Arg Val Thr Gln Lys Thr
225                 230                 235                 240
Gln Arg Arg Trp Phe Leu Asp Lys Leu Val Asp Arg Ile Gly Val Gly
                245                 250                 255
```

```
Tyr Val Tyr Asp Ser Gly Ser Val Ser Asn Tyr Asn Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Ser
            340                 345                 350

Ser Pro

<210> SEQ ID NO 93
<211> LENGTH: 354
<212> TYPE: PRT
<213> ORGANISM: artificial sequence
<220> FEATURE:
<223> OTHER INFORMATION: SH21a

<400> SEQUENCE: 93

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Thr Cys Lys Phe Lys His Gln Leu Ser Leu Thr Phe Arg Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Asn Tyr Asn Leu Ser
65                  70                  75                  80

Glu Ile Lys Pro Leu His Asn Phe Leu Thr Gln Leu Gln Pro Phe Leu
            85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
            165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Ile Ala Gln Ile Lys Pro Asn Arg Ser His
    210                 215                 220

Lys Phe Lys His Gln Leu Gln Leu Thr Phe Lys Val Thr Gln Lys Thr
225                 230                 235                 240

Gln Arg Arg Trp Phe Leu Asp Lys Leu Val Asp Arg Ile Gly Val Gly
            245                 250                 255
```

```
Tyr Val Tyr Asp Ser Gly Ser Val Ser Glu Tyr Val Leu Ser Glu Ile
                260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
        290                 295                 300

Ser Ala Lys Gly Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Asn Leu Ser Glu Lys Lys Lys Ser
            340                 345                 350

Ser Pro

<210> SEQ ID NO 94
<211> LENGTH: 354
<212> TYPE: PRT
<213> ORGANISM: artificial sequence
<220> FEATURE:
<223> OTHER INFORMATION: SH21b

<400> SEQUENCE: 94

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Thr Cys Lys Phe Lys His Gln Leu Ser Leu Thr Phe Arg Val Thr Gln
        35                  40                  45

Lys Thr Gln Arg Arg Trp Leu Leu Asp Lys Leu Val Asp Glu Ile Gly
    50                  55                  60

Val Gly Tyr Val Tyr Asp Ser Gly Ser Val Ser Asn Tyr Asn Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Ser Asn Lys Lys Phe Leu Leu Tyr Leu Ala Gly Phe Val
        195                 200                 205

Asp Ser Asp Gly Ser Ile Ile Ala Gln Ile Lys Pro Asn Arg Ser His
    210                 215                 220

Lys Phe Lys His Gln Leu Gln Leu Thr Phe Lys Val Thr Gln Lys Thr
225                 230                 235                 240

Gln Arg Arg Trp Phe Leu Asp Lys Leu Val Asp Arg Ile Gly Val Gly
                245                 250                 255

Tyr Val Tyr Asp Ser Gly Ser Val Ser Glu Tyr Val Leu Ser Glu Ile
```

```
                260                 265                 270
Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
        290                 295                 300

Ser Ala Lys Gly Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Asn Leu Ser Glu Lys Lys Lys Ser
            340                 345                 350

Ser Pro

<210> SEQ ID NO 95
<211> LENGTH: 354
<212> TYPE: PRT
<213> ORGANISM: artificial sequence
<220> FEATURE:
<223> OTHER INFORMATION: SH21c

<400> SEQUENCE: 95

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Thr Cys Lys Phe Lys His Gln Leu Ser Leu Thr Phe Arg Val Thr Gln
        35                  40                  45

Lys Thr Gln Arg Arg Trp Leu Leu Asp Lys Leu Val Asp Glu Ile Gly
    50                  55                  60

Val Gly Tyr Val Tyr Asp Ser Gly Ser Val Ser Asn Tyr Asn Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Ser Asn Lys Lys Phe Leu Leu Tyr Leu Ala Gly Phe Val
        195                 200                 205

Asp Ser Asp Gly Ser Ile Ile Ala Gln Ile Lys Pro Asn Gln Ser His
    210                 215                 220

Lys Phe Lys His Gln Leu Gln Leu Thr Phe Lys Val Thr Gln Lys Thr
225                 230                 235                 240

Gln Arg Arg Trp Phe Leu Asp Lys Leu Val Asp Arg Ile Gly Val Gly
                245                 250                 255

Tyr Val Tyr Asp Ser Gly Ser Val Ser Glu Tyr Val Leu Ser Glu Ile
            260                 265                 270
```

```
Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
        290                 295                 300

Ser Ala Lys Gly Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Asn Leu Ser Glu Lys Lys Lys Ser
            340                 345                 350

Ser Pro

<210> SEQ ID NO 96
<211> LENGTH: 354
<212> TYPE: PRT
<213> ORGANISM: artificial sequence
<220> FEATURE:
<223> OTHER INFORMATION: SH33

<400> SEQUENCE: 96

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Cys Gln
            20                  25                  30

Ser Cys Lys Phe Lys His Asn Leu Ser Leu Thr Phe Ala Val Thr Gln
        35                  40                  45

Lys Thr Gln Arg Arg Trp Phe Leu Asp Lys Leu Val Asp Glu Ile Gly
    50                  55                  60

Val Gly Cys Val Tyr Asp Arg Gly Ser Val Ser Asp Tyr Lys Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Ala Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Val Ala Gln Ile Lys Pro Asn Gln Ser Tyr
    210                 215                 220

Lys Phe Lys His Gln Leu Ser Leu Thr Phe Arg Val Thr Gln Lys Thr
225                 230                 235                 240

Gln Arg Arg Trp Phe Leu Asp Lys Leu Val Asp Arg Ile Gly Val Gly
                245                 250                 255

Tyr Val Tyr Asp Ser Gly Ser Val Ser Tyr Tyr Asn Leu Ser Glu Ile
            260                 265                 270
```

```
            Lys Pro Leu His Asn Phe Leu Thr Gln Leu Gln Pro Phe Leu Lys Leu
                275                 280                 285

Lys Gln Lys Gln Ala Asn Leu Val Leu Lys Ile Ile Glu Gln Leu Pro
            290                 295                 300

Ser Ala Lys Glu Ser Pro Asp Lys Phe Leu Glu Val Cys Thr Trp Val
            305                 310                 315                 320

Asp Gln Val Ala Ala Leu Asn Asp Ser Lys Thr Arg Lys Thr Thr Ser
                            325                 330                 335

Glu Thr Val Arg Ala Val Leu Asp Ser Leu Ser Glu Lys Lys Lys Ser
                        340                 345                 350

Ser Pro

<210> SEQ ID NO 97
            <211> LENGTH: 24
            <212> TYPE: DNA
            <213> ORGANISM: Artificial
            <220> FEATURE:
            <223> OTHER INFORMATION: SH12

<400> SEQUENCE: 97
ataaaacaag tcacgttatt ttgg                                          24

<210> SEQ ID NO 98
            <211> LENGTH: 24
            <212> TYPE: DNA
            <213> ORGANISM: Artificial
            <220> FEATURE:
            <223> OTHER INFORMATION: SH13

<400> SEQUENCE: 98
attacactct ttaagtgatt ttaa                                          24

<210> SEQ ID NO 99
            <211> LENGTH: 24
            <212> TYPE: DNA
            <213> ORGANISM: Artificial
            <220> FEATURE:
            <223> OTHER INFORMATION: SH19

<400> SEQUENCE: 99
gcaaaacatt gtaagacatg ccaa                                          24

<210> SEQ ID NO 100
            <211> LENGTH: 24
            <212> TYPE: DNA
            <213> ORGANISM: Artificial
            <220> FEATURE:
            <223> OTHER INFORMATION: SH20

<400> SEQUENCE: 100
gctggctgct tcacattgga gaga                                          24

<210> SEQ ID NO 101
            <211> LENGTH: 24
            <212> TYPE: DNA
            <213> ORGANISM: Artificial
            <220> FEATURE:
            <223> OTHER INFORMATION: SH21

<400> SEQUENCE: 101
tagaaatctg ttaaaagaga tgat                                          24

<210> SEQ ID NO 102
```

```
<211> LENGTH: 24
<212> TYPE: DNA
<213> ORGANISM: Artificial
<220> FEATURE:
<223> OTHER INFORMATION: SH33

<400> SEQUENCE: 102
ttttcatcac ttaaagtgtt ttaa                                            24

<210> SEQ ID NO 103
<211> LENGTH: 24
<212> TYPE: DNA
<213> ORGANISM: Artificial
<220> FEATURE:
<223> OTHER INFORMATION: SH7

<400> SEQUENCE: 103
acaacacttt gtgagacgtc taag                                            24

<210> SEQ ID NO 104
<211> LENGTH: 24
<212> TYPE: DNA
<213> ORGANISM: Artificial
<220> FEATURE:
<223> OTHER INFORMATION: SH8

<400> SEQUENCE: 104
acaatctgag gtaagtaata ctga                                            24

<210> SEQ ID NO 105
<211> LENGTH: 24
<212> TYPE: DNA
<213> ORGANISM: Artificial
<220> FEATURE:
<223> OTHER INFORMATION: SH18

<400> SEQUENCE: 105
cttaccccac gtaccacaga ctgt                                            24

<210> SEQ ID NO 106
<211> LENGTH: 24
<212> TYPE: DNA
<213> ORGANISM: Artificial
<220> FEATURE:
<223> OTHER INFORMATION: SH31

<400> SEQUENCE: 106
ttgtaatgtc ttacaaggtt ttaa                                            24

<210> SEQ ID NO 107
<211> LENGTH: 24
<212> TYPE: DNA
<213> ORGANISM: Artificial
<220> FEATURE:
<223> OTHER INFORMATION: SH38

<400> SEQUENCE: 107
ctgggatgtc tcacgacagc atgg                                            24

<210> SEQ ID NO 108
<211> LENGTH: 24
<212> TYPE: DNA
<213> ORGANISM: Artificial
<220> FEATURE:
<223> OTHER INFORMATION: SH39

<400> SEQUENCE: 108
```

```
tccttctgtc ttaagagatt tatc                                        24

<210> SEQ ID NO 109
<211> LENGTH: 24
<212> TYPE: DNA
<213> ORGANISM: Artificial
<220> FEATURE:
<223> OTHER INFORMATION: SH41

<400> SEQUENCE: 109
cctctcttag gtgagacggt acat                                        24

<210> SEQ ID NO 110
<211> LENGTH: 24
<212> TYPE: DNA
<213> ORGANISM: Artificial
<220> FEATURE:
<223> OTHER INFORMATION: SH42

<400> SEQUENCE: 110
tatatcccat gtgagacatg cagt                                        24

<210> SEQ ID NO 111
<211> LENGTH: 24
<212> TYPE: DNA
<213> ORGANISM: Artificial
<220> FEATURE:
<223> OTHER INFORMATION: SH43

<400> SEQUENCE: 111
taaatacgtc ttacattatt ttgc                                        24

<210> SEQ ID NO 112
<211> LENGTH: 24
<212> TYPE: DNA
<213> ORGANISM: Artificial
<220> FEATURE:
<223> OTHER INFORMATION: SH44

<400> SEQUENCE: 112
aagaaatgtc tcacagaatt ttac                                        24

<210> SEQ ID NO 113
<211> LENGTH: 24
<212> TYPE: DNA
<213> ORGANISM: Artificial
<220> FEATURE:
<223> OTHER INFORMATION: SH45

<400> SEQUENCE: 113
cagatatgtc ttaaaatgtc actg                                        24

<210> SEQ ID NO 114
<211> LENGTH: 24
<212> TYPE: DNA
<213> ORGANISM: Artificial
<220> FEATURE:
<223> OTHER INFORMATION: SH46

<400> SEQUENCE: 114
accagatgtc gtgagacggg ggag                                        24

<210> SEQ ID NO 115
<211> LENGTH: 24
<212> TYPE: DNA
```

```
<213> ORGANISM: Artificial
<220> FEATURE:
<223> OTHER INFORMATION: SH47

<400> SEQUENCE: 115
gcaggcttat tcaccagggt ttac                                              24

<210> SEQ ID NO 116
<211> LENGTH: 24
<212> TYPE: DNA
<213> ORGANISM: Artificial
<220> FEATURE:
<223> OTHER INFORMATION: SH48

<400> SEQUENCE: 116
ttgaaattag ttacaggagg ttat                                              24

<210> SEQ ID NO 117
<211> LENGTH: 24
<212> TYPE: DNA
<213> ORGANISM: Artificial
<220> FEATURE:
<223> OTHER INFORMATION: SH49

<400> SEQUENCE: 117
ataatacaat ttacctaatc ctat                                              24

<210> SEQ ID NO 118
<211> LENGTH: 24
<212> TYPE: DNA
<213> ORGANISM: Artificial
<220> FEATURE:
<223> OTHER INFORMATION: SH50

<400> SEQUENCE: 118
cccggcccct ttaatccatc ttaa                                              24

<210> SEQ ID NO 119
<211> LENGTH: 24
<212> TYPE: DNA
<213> ORGANISM: Artificial
<220> FEATURE:
<223> OTHER INFORMATION: SH51

<400> SEQUENCE: 119
ttgagctcac tcacatggtc tcag                                              24

<210> SEQ ID NO 120
<211> LENGTH: 24
<212> TYPE: DNA
<213> ORGANISM: Artificial
<220> FEATURE:
<223> OTHER INFORMATION: SH52

<400> SEQUENCE: 120
ctccactgtc ttacctaatc cagc                                              24

<210> SEQ ID NO 121
<211> LENGTH: 24
<212> TYPE: DNA
<213> ORGANISM: Artificial
<220> FEATURE:
<223> OTHER INFORMATION: SH70

<400> SEQUENCE: 121
catgtatgat ttacatcggt ttga                                              24
```

-continued

<210> SEQ ID NO 122
<211> LENGTH: 24
<212> TYPE: DNA
<213> ORGANISM: Artificial
<220> FEATURE:
<223> OTHER INFORMATION: SH71

<400> SEQUENCE: 122
gttgtattat ttacctcaga tgaa                                              24

<210> SEQ ID NO 123
<211> LENGTH: 24
<212> TYPE: DNA
<213> ORGANISM: Artificial
<220> FEATURE:
<223> OTHER INFORMATION: SH72

<400> SEQUENCE: 123
tttggatgct gtaaagaatt tcct                                              24

<210> SEQ ID NO 124
<211> LENGTH: 24
<212> TYPE: DNA
<213> ORGANISM: Artificial
<220> FEATURE:
<223> OTHER INFORMATION: SH73

<400> SEQUENCE: 124
ataaaacgac ttacaaggtc tgaa                                              24

<210> SEQ ID NO 125
<211> LENGTH: 24
<212> TYPE: DNA
<213> ORGANISM: Artificial
<220> FEATURE:
<223> OTHER INFORMATION: SH74

<400> SEQUENCE: 125
ttcagatctc gtacagggga tgac                                              24

<210> SEQ ID NO 126
<211> LENGTH: 24
<212> TYPE: DNA
<213> ORGANISM: Artificial
<220> FEATURE:
<223> OTHER INFORMATION: SH75

<400> SEQUENCE: 126
ctgccatagg gtaactgagt caat                                              24

<210> SEQ ID NO 127
<211> LENGTH: 354
<212> TYPE: PRT
<213> ORGANISM: artificial sequence
<220> FEATURE:
<223> OTHER INFORMATION: SCOH-SH18-b11-C-pCLS5518

<400> SEQUENCE: 127

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Arg Pro Asn Gln
            20                  25                  30

Ser Ser Lys Phe Lys His Tyr Leu Gln Leu Thr Phe Asn Val Thr Gln
        35                  40                  45

```
Lys Thr Gln Arg Arg Trp Phe Leu Asp Lys Leu Val Asp Glu Ile Gly
 50                  55                  60

Val Gly Tyr Val Tyr Asp Ser Gly Ser Val Ser Arg Tyr Tyr Leu Ser
 65                  70                  75                  80

Glu Ile Lys Pro Leu His Asn Phe Leu Thr Gln Leu Gln Pro Phe Leu
                 85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
            195                 200                 205

Asp Ser Asp Gly Ser Ile Ile Ala Gln Ile Gln Pro Asn Gln Ser Tyr
210                 215                 220

Lys Phe Lys His Arg Leu Lys Leu Thr Phe Gln Val Thr Gln Lys Thr
225                 230                 235                 240

Gln Arg Arg Trp Phe Leu Asp Lys Leu Val Asp Arg Ile Gly Val Gly
                245                 250                 255

Tyr Val Arg Asp Ser Gly Ser Val Ser Asp Tyr Ile Leu Ser Glu Ile
            260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 128
<211> LENGTH: 354
<212> TYPE: PRT
<213> ORGANISM: artificial sequence
<220> FEATURE:
<223> OTHER INFORMATION: SCOH-SH18-b11-C.2-pCLS5519

<400> SEQUENCE: 128

Met Ala Asn Thr Lys Tyr Asn Glu Glu Phe Leu Leu Tyr Leu Ala Gly
 1               5                  10                  15

Phe Val Asp Gly Asp Gly Ser Ile Ile Ala Gln Ile Arg Pro Asn Gln
                 20                  25                  30

Ser Ser Lys Phe Lys His Tyr Leu Gln Leu Thr Phe Asn Val Thr Gln
             35                  40                  45
```

```
Lys Thr Gln Arg Arg Trp Phe Leu Asp Lys Leu Val Asp Glu Ile Gly
 50                  55                  60

Val Gly Tyr Val Tyr Asp Arg Gly Ser Val Ser Asp Tyr Tyr Leu Ser
 65                  70                  75                  80

Glu Ile Lys Pro Leu His Asn Phe Leu Thr Gln Leu Gln Pro Phe Leu
                 85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Ile Ala Gln Ile Gln Pro Asn Gln Ser Tyr
210                 215                 220

Lys Phe Lys His Arg Leu Lys Leu Thr Phe Gln Val Thr Gln Lys Thr
225                 230                 235                 240

Gln Arg Arg Trp Phe Leu Asp Lys Leu Val Asp Arg Ile Gly Val Gly
                245                 250                 255

Tyr Val Arg Asp Ser Gly Ser Val Ser Asp Tyr Ile Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 129
<211> LENGTH: 354
<212> TYPE: PRT
<213> ORGANISM: artificial sequence
<220> FEATURE:
<223> OTHER INFORMATION: SCOH-SH18-b12-C-pCLS5520

<400> SEQUENCE: 129

Met Ala Asn Thr Lys Tyr Asn Glu Glu Phe Leu Leu Tyr Leu Ala Gly
 1               5                  10                  15

Phe Val Asp Gly Asp Gly Ser Ile Ile Ala Gln Ile Arg Pro Asn Gln
                 20                  25                  30

Ser Ser Lys Phe Lys His Tyr Leu Gln Leu Thr Phe Asn Val Thr Gln
            35                  40                  45

Lys Thr Gln Arg Arg Trp Phe Leu Asp Lys Leu Val Asp Glu Ile Gly
```

```
                    50                  55                  60
Val Gly Tyr Val Tyr Asp Ser Gly Ser Val Ser Arg Tyr Tyr Leu Ser
 65                      70                  75                  80

Glu Ile Lys Pro Leu His Asn Phe Leu Thr Gln Leu Gln Pro Phe Leu
                     85                  90                  95

Glu Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
                115                 120                 125

Trp Val Asp Gln Val Ala Ala Leu Asn Asp Ser Lys Thr Arg Lys Thr
            130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
                180                 185                 190

Gly Gly Gly Ser Asn Lys Lys Phe Leu Leu Tyr Leu Ala Gly Phe Val
            195                 200                 205

Asp Ser Asp Gly Ser Ile Ile Ala Gln Ile Gln Pro Asn Gln Ser Tyr
            210                 215                 220

Lys Phe Lys His Arg Leu Lys Leu Thr Phe Gln Val Thr Gln Lys Thr
225                 230                 235                 240

Gln Arg Arg Trp Ile Leu Asp Lys Leu Ala Asp Arg Ile Gly Val Gly
                245                 250                 255

Tyr Val Arg Asp Ser Gly Ser Val Ser Asn Tyr Ile Leu Ser Glu Ile
                260                 265                 270

Lys Pro Leu His Asn Phe Leu Thr Gln Leu Gln Pro Phe Leu Lys Leu
                275                 280                 285

Lys Gln Lys Gln Ala Asn Leu Val Leu Lys Ile Ile Glu Gln Leu Pro
            290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
                340                 345                 350

Ser Pro

<210> SEQ ID NO 130
<211> LENGTH: 354
<212> TYPE: PRT
<213> ORGANISM: artificial sequence
<220> FEATURE:
<223> OTHER INFORMATION: SCOH-SH18-b12-C.2-pCLS5521

<400> SEQUENCE: 130

Met Ala Asn Thr Lys Tyr Asn Glu Glu Phe Leu Leu Tyr Leu Ala Gly
  1               5                  10                  15

Phe Val Asp Gly Asp Gly Ser Ile Ile Ala Gln Ile Arg Pro Asn Gln
                 20                  25                  30

Ser Ser Lys Phe Lys His Tyr Leu Gln Leu Thr Phe Asn Val Thr Gln
                 35                  40                  45

Lys Thr Gln Arg Arg Trp Phe Leu Asp Lys Leu Val Asp Glu Ile Gly
             50                  55                  60
```

-continued

Val Gly Tyr Val Tyr Asp Arg Gly Ser Val Ser Asp Tyr Tyr Leu Ser
 65                  70                  75                  80

Glu Ile Lys Pro Leu His Asn Phe Leu Thr Gln Leu Gln Pro Phe Leu
                 85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Ile Ala Gln Ile Gln Pro Asn Gln Ser Tyr
    210                 215                 220

Lys Phe Lys His Arg Leu Lys Leu Thr Phe Gln Val Thr Gln Lys Thr
225                 230                 235                 240

Gln Arg Arg Trp Ile Leu Asp Lys Leu Ala Asp Arg Ile Gly Val Gly
                245                 250                 255

Tyr Val Arg Asp Ser Gly Ser Val Ser Asn Tyr Ile Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 131
<211> LENGTH: 354
<212> TYPE: PRT
<213> ORGANISM: artificial sequence
<220> FEATURE:
<223> OTHER INFORMATION: SC-SH31-pCLS3904

<400> SEQUENCE: 131

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Arg Lys Phe Lys His Ala Leu Gln Leu Thr Phe Gln Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Asn Tyr Ile Leu Ser
65                  70                  75                  80

Glu Ile Lys Pro Leu His Asn Phe Leu Thr Gln Leu Gln Pro Phe Leu
            85                  90                  95

Glu Leu Lys Gln Lys Gln Ala Asn Leu Val Leu Lys Ile Ile Glu Gln
        100                 105                 110

Leu Pro Ser Ala Lys Glu Ser Pro Asp Lys Phe Leu Glu Val Cys Thr
    115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Ile Ala Gln Ile Lys Pro Asn Gln Ser Tyr
    210                 215                 220

Lys Phe Lys His Gln Leu Ser Leu Thr Phe Gln Val Thr Gln Lys Thr
225                 230                 235                 240

Gln Arg Arg Trp Phe Leu Asp Lys Leu Val Asp Arg Ile Gly Val Gly
                245                 250                 255

Tyr Val Arg Asp Asn Gly Ser Val Ser Asp Tyr Ile Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 132
<211> LENGTH: 354
<212> TYPE: PRT
<213> ORGANISM: artificial sequence
<220> FEATURE:
<223> OTHER INFORMATION: SC-SH31.2-pCLS4076

<400> SEQUENCE: 132

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Arg Lys Phe Lys His Ala Leu Gln Leu Thr Phe Gln Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Arg Gly Ser Val Ser Asp Tyr Ile Leu Ser

```
            65                  70                  75                  80
    Glu Ile Lys Pro Leu His Asn Phe Leu Thr Gln Leu Gln Pro Phe Leu
                        85                  90                  95

Glu Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
                115                 120                 125

Trp Val Asp Gln Val Ala Ala Leu Asn Asp Ser Lys Thr Arg Lys Thr
                130                 135                 140

Thr Ser Glu Thr Val Arg Ala Val Leu Asp Ser Leu Ser Glu Lys Lys
    145                 150                 155                 160

Lys Ser Ser Pro Ala Ala Gly Gly Ser Asp Lys Tyr Asn Gln Ala Leu
                        165                 170                 175

Ser Lys Tyr Asn Gln Ala Leu Ser Lys Tyr Asn Gln Ala Leu Ser Gly
                        180                 185                 190

Gly Gly Gly Ser Asn Lys Lys Phe Leu Leu Tyr Leu Ala Gly Phe Val
                        195                 200                 205

Asp Ser Asp Gly Ser Ile Ile Ala Gln Ile Lys Pro Asn Gln Ser Tyr
                210                 215                 220

Lys Phe Lys His Gln Leu Ser Leu Thr Phe Lys Val Thr Gln Lys Thr
    225                 230                 235                 240

Gln Arg Arg Trp Phe Leu Asp Lys Leu Val Asp Arg Ile Gly Val Gly
                        245                 250                 255

Tyr Val Arg Asp Asn Gly Ser Val Ser Asp Tyr Ile Leu Ser Glu Ile
                        260                 265                 270

Lys Pro Leu His Asn Phe Leu Thr Gln Leu Gln Pro Phe Leu Lys Leu
                275                 280                 285

Lys Gln Lys Gln Ala Asn Leu Val Leu Lys Ile Ile Glu Gln Leu Pro
                290                 295                 300

Ser Ala Lys Glu Ser Pro Asp Lys Phe Leu Glu Val Cys Thr Trp Val
    305                 310                 315                 320

Asp Gln Val Ala Ala Leu Asn Asp Ser Lys Thr Arg Lys Thr Thr Ser
                        325                 330                 335

Glu Thr Val Arg Ala Val Leu Asp Ser Leu Ser Glu Lys Lys Lys Ser
                        340                 345                 350

Ser Pro

<210> SEQ ID NO 133
<211> LENGTH: 354
<212> TYPE: PRT
<213> ORGANISM: artificial sequence
<220> FEATURE:
<223> OTHER INFORMATION: SCOH-SH39-b11-C-pCLS6038

<400> SEQUENCE: 133

Met Ala Asn Thr Lys Tyr Asn Glu Glu Phe Leu Leu Tyr Leu Ala Gly
    1               5                   10                  15

Phe Val Asp Gly Asp Gly Ser Ile Ile Ala Gln Ile Lys Pro Asp Gln
                        20                  25                  30

Thr Cys Lys Phe Lys His Arg Leu Ser Leu Thr Phe Gln Val Thr Gln
                        35                  40                  45

Lys Thr Gln Arg Arg Trp Phe Leu Asp Lys Leu Val Asp Glu Ile Gly
                50                  55                  60

Val Gly Tyr Val Arg Asp Arg Gly Ser Val Ser Asp Tyr Ile Leu Ser
    65                  70                  75                  80
```

```
Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Ala
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Ile Ala Gln Ile Lys Pro Asn Gln Ser Cys
    210                 215                 220

Lys Phe Lys His Gln Leu Gln Ser Thr Phe Lys Val Thr Gln Lys Thr
225                 230                 235                 240

Gln Arg Arg Trp Phe Leu Asp Lys Leu Val Asp Arg Ile Gly Val Gly
                245                 250                 255

Tyr Val Ala Asp Arg Gly Ser Val Ser Asp Tyr Ile Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Ala
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 134
<211> LENGTH: 354
<212> TYPE: PRT
<213> ORGANISM: artificial sequence
<220> FEATURE:
<223> OTHER INFORMATION: SCOH-SH39-b12-C-pCLS6039

<400> SEQUENCE: 134

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Thr Gln
            20                  25                  30

Asp Tyr Lys Phe Lys His Gln Leu Ser Leu Thr Phe Gln Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Arg Gly Ser Val Ser Asp Tyr Ile Leu Ser
65                  70                  75                  80
```

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
            195                 200                 205

Asp Ser Asp Gly Ser Ile Ile Ala Gln Ile Lys Pro Asn Gln Ser Cys
210                 215                 220

Lys Phe Lys His Gln Leu Gln Ser Thr Phe Lys Val Thr Gln Lys Thr
225                 230                 235                 240

Gln Arg Arg Trp Phe Leu Asp Lys Leu Val Asp Arg Ile Gly Val Gly
                245                 250                 255

Tyr Val Ala Asp Arg Gly Ser Val Ser Asp Tyr Ile Leu Ser Glu Ile
            260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Ala
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 135
<211> LENGTH: 354
<212> TYPE: PRT
<213> ORGANISM: artificial sequence
<220> FEATURE:
<223> OTHER INFORMATION: SCOH-SH41-b11-C-pCLS5187

<400> SEQUENCE: 135

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Pro Lys Phe Lys His Gln Leu Gln Leu Thr Phe Gln Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Arg Gly Ser Val Ser Asp Tyr Ile Leu Ser
65                  70                  75                  80

Glu Ile Lys Pro Leu His Asn Phe Leu Thr Gln Leu Gln Pro Phe Leu 85                  90                  95
Glu Leu Lys Gln Lys Gln Ala Asn Leu Val Leu Lys Ile Ile Glu Gln
                100                 105                 110
Leu Pro Ser Ala Lys Glu Ser Pro Asp Lys Phe Leu Glu Val Cys Thr
            115                 120                 125
Trp Val Asp Gln Val Ala Ala Leu Asn Asp Ser Lys Thr Arg Lys Thr
        130                 135                 140
Thr Ser Glu Thr Val Arg Ala Val Leu Asp Ser Leu Ser Glu Lys Lys
145                 150                 155                 160
Lys Ser Ser Pro Ala Ala Gly Gly Ser Asp Lys Tyr Asn Gln Ala Leu
                165                 170                 175
Ser Lys Tyr Asn Gln Ala Leu Ser Lys Tyr Asn Gln Ala Leu Ser Gly
                180                 185                 190
Gly Gly Gly Ser Asn Lys Lys Phe Leu Leu Tyr Leu Ala Gly Phe Val
            195                 200                 205
Asp Ser Asp Gly Ser Ile Ile Ala Gln Ile Lys Pro Asn Gln Ser Cys
        210                 215                 220
Lys Phe Lys His Tyr Leu Ser Leu Thr Phe Ala Val Thr Gln Lys Thr
225                 230                 235                 240
Gln Arg Arg Trp Phe Leu Asp Lys Leu Val Asp Arg Ile Gly Val Gly
                245                 250                 255
His Val Tyr Asp Gln Gly Tyr Val Ser Asn Tyr Ile Leu Ser Glu Ile
                260                 265                 270
Lys Pro Leu His Asn Phe Leu Thr Gln Leu Gln Pro Phe Leu Lys Leu
            275                 280                 285
Lys Gln Lys Gln Ala Asn Leu Ala Leu Lys Ile Ile Glu Gln Leu Pro
        290                 295                 300
Ser Ala Lys Glu Ser Pro Asp Lys Phe Leu Glu Val Cys Thr Trp Val
305                 310                 315                 320
Asp Gln Val Ala Ala Leu Asn Asp Ser Lys Thr Arg Lys Thr Thr Ser
                325                 330                 335
Glu Thr Val Arg Ala Val Leu Asp Ser Leu Ser Glu Lys Lys Lys Ser
            340                 345                 350
Ser Pro

<210> SEQ ID NO 136
<211> LENGTH: 354
<212> TYPE: PRT
<213> ORGANISM: artificial sequence
<220> FEATURE:
<223> OTHER INFORMATION: SCOH-SH41-b12-C-pCLS5188

<400> SEQUENCE: 136

Met Ala Asn Thr Lys Tyr Asn Glu Glu Phe Leu Leu Tyr Leu Ala Gly
1               5                   10                  15
Phe Val Asp Gly Asp Gly Ser Ile Ile Ala Gln Ile Lys Pro Asn Gln
            20                  25                  30
Ser Gly Lys Phe Lys His Gln Leu Gln Leu Thr Phe Gln Val Thr Gln
        35                  40                  45
Lys Thr Gln Arg Arg Trp Phe Leu Asp Lys Leu Val Asp Glu Ile Gly
    50                  55                  60
Val Gly Tyr Val Arg Asp Arg Gly Ser Val Ser Asp Tyr Ile Leu Ser
65                  70                  75                  80
Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Ile Ala Gln Ile Lys Pro Asn Gln Ser Cys
    210                 215                 220

Lys Phe Lys His Tyr Leu Ser Leu Thr Phe Ala Val Thr Gln Lys Thr
225                 230                 235                 240

Gln Arg Arg Trp Phe Leu Asp Lys Leu Val Asp Arg Ile Gly Val Gly
                245                 250                 255

His Val Tyr Asp Gln Gly Tyr Val Ser Asn Tyr Ile Leu Thr Glu Ile
            260                 265                 270

Lys Pro Leu Arg Asn Phe Leu Thr Gln Leu Gln Pro Phe Leu Lys Leu
        275                 280                 285

Lys Gln Lys Gln Ala Asp Leu Val Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 137
<211> LENGTH: 354
<212> TYPE: PRT
<213> ORGANISM: artificial sequence
<220> FEATURE:
<223> OTHER INFORMATION: SCOH-SH42-b11-C-pCLS5549

<400> SEQUENCE: 137

Met Ala Asn Thr Lys Tyr Asn Glu Glu Phe Leu Leu Tyr Leu Ala Gly
1               5                   10                  15

Phe Val Asp Ser Asp Gly Ser Ile Ile Ala Gln Ile Lys Pro Asn Gln
            20                  25                  30

Thr Cys Lys Phe Lys His Gln Leu Ser Leu Thr Phe Asn Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Tyr Tyr Asn Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Asn
    130                 135                 140

Thr Ser Glu Thr Val Arg Ala Val Leu Asp Ser Leu Ser Glu Lys Lys
145                 150                 155                 160

Lys Ser Ser Pro Ser Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Gly Asp Gly Ser Ile Ile Ala Gln Ile Lys Pro Asn Gln Ser Tyr
    210                 215                 220

Lys Phe Lys His Tyr Leu Ser Leu Thr Phe Gln Val Thr Gln Lys Thr
225                 230                 235                 240

Gln Arg Arg Trp Phe Leu Asp Lys Leu Val Asp Arg Ile Gly Val Gly
                245                 250                 255

Tyr Val Arg Asp Arg Gly Ser Val Ser Asp Tyr Ile Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 138
<211> LENGTH: 354
<212> TYPE: PRT
<213> ORGANISM: artificial sequence
<220> FEATURE:
<223> OTHER INFORMATION: SCOH-SH42-b12-C-pCLS5550

<400> SEQUENCE: 138

Met Ala Asn Thr Lys Tyr Asn Glu Glu Phe Leu Leu Tyr Leu Ala Gly
1               5                   10                  15

Phe Val Asp Ser Asp Gly Ser Ile Ile Ala Gln Ile Lys Pro Asn Gln
            20                  25                  30

Thr Cys Lys Phe Lys His Gln Leu Ser Leu Thr Phe Asn Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Tyr Tyr Asn Leu Ser
65                  70                  75                  80

Glu Ile Lys Pro Leu His Asn Phe Leu Thr Gln Leu Gln Pro Phe Leu
            85                  90                  95

Glu Leu Lys Gln Lys Gln Ala Asn Leu Val Leu Lys Ile Ile Glu Gln

```
            100                 105                 110
Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Asn
    130                 135                 140

Thr Ser Glu Thr Val Arg Ala Val Leu Asp Ser Leu Ser Glu Lys Lys
145                 150                 155                 160

Lys Ser Ser Pro Ser Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Tyr Leu Ala Gly Phe Val
        195                 200                 205

Asp Gly Asp Gly Ser Ile Ile Ala Gln Ile Lys Pro Asn Gln Ser Cys
    210                 215                 220

Lys Phe Lys His Ser Leu Ser Leu Thr Phe Gln Val Thr Gln Lys Thr
225                 230                 235                 240

Gln Arg Arg Trp Phe Leu Asp Lys Leu Val Asp Arg Ile Gly Val Gly
                245                 250                 255

Tyr Val Arg Asp Arg Gly Ser Val Ser Asp Tyr Ile Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 139
<211> LENGTH: 354
<212> TYPE: PRT
<213> ORGANISM: artificial sequence
<220> FEATURE:
<223> OTHER INFORMATION: SCOH-SH43-b11-C-pCLS5594

<400> SEQUENCE: 139

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Ser Gln
                20                  25                  30

Ser His Lys Phe Lys His Gln Leu Ser Leu Thr Phe Gln Val Thr Gln
            35                  40                  45

Lys Thr Gln Arg Arg Trp Phe Leu Asp Lys Leu Val Asp Glu Ile Gly
        50                  55                  60

Val Gly Tyr Val Arg Asp Arg Gly Ser Val Ser Asp Tyr Ile Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110
```

Leu Pro Ser Ala Lys Glu Ser Pro Asp Lys Phe Leu Glu Val Cys Thr
            115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
            195                 200                 205

Asp Ser Asp Gly Ser Ile Ile Ala Gln Ile Lys Pro Asn Gln Ser Tyr
    210                 215                 220

Lys Phe Lys His Gln Leu Ser Leu Thr Phe Asn Val Thr Gln Lys Thr
225                 230                 235                 240

Gln Arg Arg Trp Phe Leu Asp Lys Leu Val Asp Arg Ile Gly Val Gly
                245                 250                 255

Tyr Val His Asp Ser Gly Ser Val Ser Tyr Tyr Asn Leu Ser Lys Ile
            260                 265                 270

Lys Pro Leu His Asn Leu Leu Thr Gln Leu Gln Pro Phe Leu Lys Leu
            275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 140
<211> LENGTH: 354
<212> TYPE: PRT
<213> ORGANISM: artificial sequence
<220> FEATURE:
<223> OTHER INFORMATION: SCOH-SH43-b12-C-pCLS5595

<400> SEQUENCE: 140

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Ser Gln
                20                  25                  30

Ser His Lys Phe Lys His Gln Leu Ser Leu Thr Phe Gln Val Thr Gln
            35                  40                  45

Lys Thr Gln Arg Arg Trp Phe Leu Asp Lys Leu Val Asp Glu Ile Gly
    50                  55                  60

Val Gly Tyr Val Arg Asp Arg Gly Ser Val Ser Asp Tyr Ile Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Val Asp Gln Val Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Val Ala Gln Ile Lys Pro Asn Gln Ser Tyr
210                 215                 220

Lys Phe Lys His Gln Leu Ser Leu Thr Phe Asn Val Thr Gln Lys Thr
225                 230                 235                 240

Gln Arg Arg Trp Phe Leu Asp Lys Leu Val Asp Arg Ile Gly Val Gly
                245                 250                 255

Tyr Val Tyr Asp Ser Gly Ser Val Ser Tyr Tyr Arg Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
            325                 330                 335

Glu Thr Val Arg Ala Val Leu Asp Ser Leu Ser Glu Lys Lys Lys Ser
        340                 345                 350

Ser Pro

<210> SEQ ID NO 141
<211> LENGTH: 354
<212> TYPE: PRT
<213> ORGANISM: artificial sequence
<220> FEATURE:
<223> OTHER INFORMATION: SCOH-SH44-b11-C-pCLS5868

<400> SEQUENCE: 141

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Ser His Lys Phe Lys His Gln Leu Ser Leu Thr Phe Gln Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Arg Gly Ser Val Ser Asp Tyr Ile Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr

```
            115                 120                 125
Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
                180                 185                 190

Gly Gly Gly Ser Asn Lys Lys Phe Leu Leu Tyr Leu Ala Gly Phe Val
                195                 200                 205

Asp Ser Asp Gly Ser Ile Ile Ala Gln Ile Lys Pro Asn Gln Ser Tyr
    210                 215                 220

Lys Phe Lys His Gln Leu Ser Leu Thr Phe Lys Val Thr Gln Lys Thr
225                 230                 235                 240

Gln Arg Arg Trp Phe Leu Asp Lys Leu Val Asp Arg Ile Gly Val Gly
                245                 250                 255

Tyr Val Tyr Asp Ser Gly Ser Val Ser Asn Tyr Ile Leu Ser Lys Ile
                260                 265                 270

Lys Pro Leu His Asn Phe Leu Thr Gln Leu Gln Pro Phe Leu Lys Leu
                275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
                340                 345                 350

Ser Pro

<210> SEQ ID NO 142
<211> LENGTH: 354
<212> TYPE: PRT
<213> ORGANISM: artificial sequence
<220> FEATURE:
<223> OTHER INFORMATION: SCOH-SH44-b12-C-pCLS5869

<400> SEQUENCE: 142

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
                20                  25                  30

Ser Trp Lys Phe Lys His Gln Leu Gln Leu Thr Phe Gln Val Thr Gln
                35                  40                  45

Lys Thr Gln Arg Arg Trp Phe Leu Asp Lys Leu Val Asp Glu Ile Gly
    50                  55                  60

Val Gly Tyr Val Arg Asp Arg Gly Ser Val Ser Asp Tyr Ile Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
                115                 120                 125
```

Trp Val Asp Gln Val Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Ile Ala Gln Ile Lys Pro Asn Gln Ser Tyr
210                 215                 220

Lys Phe Lys His Gln Leu Ser Leu Thr Phe Lys Val Thr Gln Lys Thr
225                 230                 235                 240

Gln Arg Arg Trp Phe Leu Asp Lys Leu Val Asp Arg Ile Gly Val Gly
                245                 250                 255

Tyr Val His Asp Gly Gly Ser Val Ser Asn Tyr Ile Leu Ser Glu Ile
            260                 265                 270

Lys Pro Leu His Asn Ile Leu Thr Gln Leu Gln Pro Phe Leu Lys Leu
        275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Leu Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 143
<211> LENGTH: 354
<212> TYPE: PRT
<213> ORGANISM: artificial sequence
<220> FEATURE:
<223> OTHER INFORMATION: SCOH-SH52-b11-C-pCLS5870

<400> SEQUENCE: 143

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
                20                  25                  30

Ser Cys Lys Phe Lys His Ala Leu Ser Leu Thr Phe Ala Val Thr Gln
            35                  40                  45

Lys Thr Gln Arg Arg Trp Phe Leu Asp Lys Leu Val Asp Glu Ile Gly
        50                  55                  60

Val Gly Tyr Val Ser Asp Ser Gly Ser Val Ser Tyr Tyr Lys Leu Ser
65                  70                  75                  80

Lys Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Tyr Leu Ala Gly Phe Val
            195                 200                 205

Asp Ser Asp Gly Ser Ile Ile Ala Gln Ile Lys Pro Asn Gln Ser Ser
210                 215                 220

Lys Phe Lys His Tyr Leu Ser Leu Thr Phe Gln Val Thr Gln Lys Thr
225                 230                 235                 240

Gln Arg Arg Trp Phe Leu Asp Lys Leu Val Asp Arg Ile Gly Val Gly
                245                 250                 255

Tyr Val Arg Asp Arg Gly Ser Val Ser Asp Tyr Ile Leu Ser Glu Ile
                260                 265                 270

Lys Pro Leu His Asn Phe Leu Thr Gln Leu Gln Pro Phe Leu Lys Leu
                275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
                340                 345                 350

Ser Pro

<210> SEQ ID NO 144
<211> LENGTH: 354
<212> TYPE: PRT
<213> ORGANISM: artificial sequence
<220> FEATURE:
<223> OTHER INFORMATION: SCOH-SH52-b12-C-pCLS5871

<400> SEQUENCE: 144

Met Ala Ala Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
                20                  25                  30

Ser Cys Lys Phe Lys His Ala Leu Ser Leu Thr Phe Ala Val Thr Gln
                35                  40                  45

Lys Thr Gln Arg Arg Trp Phe Leu Asp Lys Leu Val Asp Glu Ile Gly
50                  55                  60

Val Gly Tyr Val Ser Asp Ser Gly Ser Val Ser Tyr Tyr Lys Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
                115                 120                 125

Trp Val Asp Gln Val Ala Ala Leu Asn Asp Ser Lys Thr Arg Lys Thr

```
                130                 135                 140
Thr Ser Glu Thr Val Arg Ala Val Leu Asp Ser Leu Ser Glu Lys Lys
145                 150                 155                 160

Lys Ser Ser Pro Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
            195                 200                 205

Asp Ser Asp Gly Ser Ile Ile Ala Gln Ile Lys Pro Arg Gln Ser Tyr
210                 215                 220

Lys Phe Lys His Glu Leu Ser Leu Thr Phe Gln Val Thr Gln Lys Thr
225                 230                 235                 240

Gln Arg Arg Trp Phe Leu Asp Lys Leu Val Asp Arg Ile Gly Val Gly
                245                 250                 255

Tyr Val Arg Asp Arg Gly Ser Val Ser Asp Tyr Ile Leu Ser Glu Ile
                260                 265                 270

Lys Pro Leu His Asn Phe Leu Thr Gln Leu Gln Pro Phe Leu Lys Leu
                275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
                340                 345                 350

Ser Pro

<210> SEQ ID NO 145
<211> LENGTH: 354
<212> TYPE: PRT
<213> ORGANISM: artificial sequence
<220> FEATURE:
<223> OTHER INFORMATION: SCOH-SH70-pCLS5957

<400> SEQUENCE: 145

Met Ala Asn Thr Lys Tyr Ser Glu Glu Phe Leu Leu Tyr Leu Ala Gly
1               5                   10                  15

Phe Val Asp Gly Asp Gly Ser Ile Ile Ala Gln Ile Lys Pro His Gln
                20                  25                  30

Thr Cys Lys Phe Lys His Arg Leu Ser Leu Thr Phe Ala Val Thr Gln
            35                  40                  45

Lys Thr Gln Arg Arg Trp Phe Leu Asp Lys Leu Val Asp Glu Ile Gly
50                  55                  60

Val Gly Tyr Val Arg Asp Ser Gly Ser Val Ser Tyr Tyr Thr Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
            115                 120                 125

Trp Val Asp Gln Val Ala Ala Leu Asn Asp Ser Lys Thr Arg Lys Thr
130                 135                 140
```

```
Thr Ser Glu Thr Val Arg Ala Val Leu Asp Ser Leu Ser Glu Lys Lys
145                 150                 155                 160

Lys Ser Ser Pro Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
            195                 200                 205

Asp Ser Asp Gly Ser Ile Ile Ala Gln Ile Lys Pro Asn Gln Ser Tyr
210                 215                 220

Lys Phe Lys His Gln Leu Ser Leu Thr Phe Tyr Val Thr Gln Lys Thr
225                 230                 235                 240

Gln Arg Arg Trp Phe Leu Asp Lys Leu Val Asp Arg Ile Gly Val Gly
                245                 250                 255

Tyr Val Arg Asp Ser Gly Ser Val Ser Asn Tyr Ile Leu Ser Glu Ile
            260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
            290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Ser
            340                 345                 350

Ser Pro

<210> SEQ ID NO 146
<211> LENGTH: 354
<212> TYPE: PRT
<213> ORGANISM: artificial sequence
<220> FEATURE:
<223> OTHER INFORMATION: SCOH-SH71-pCLS5958

<400> SEQUENCE: 146

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asp Gln
                20                  25                  30

Ser Cys Lys Phe Lys His Tyr Leu Ser Leu Thr Phe Ala Val Thr Gln
            35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Tyr Tyr Val Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Val Asp Gln Val Ala Ala Leu Asn Asp Ser Lys Thr Arg Lys Thr
        130                 135                 140
```

```
Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Ile Ala Gln Ile Lys Pro Asn Gln Ser Ser
        210                 215                 220

Lys Phe Lys His Arg Leu Ser Leu Thr Phe Asn Val Thr Gln Lys Thr
225                 230                 235                 240

Gln Arg Arg Trp Phe Leu Asp Lys Leu Val Asp Arg Ile Gly Val Gly
                245                 250                 255

Tyr Val Tyr Asp Ser Gly Ser Val Ser Tyr Tyr Arg Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Ser Leu Ser Glu Lys Lys Lys Lys Ser
            340                 345                 350

Ser Pro

<210> SEQ ID NO 147
<211> LENGTH: 354
<212> TYPE: PRT
<213> ORGANISM: artificial sequence
<220> FEATURE:
<223> OTHER INFORMATION: SCOH-SH72-pCLS5959

<400> SEQUENCE: 147

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Ser Pro Asn Gln
            20                  25                  30

Ser Ser Lys Phe Lys His Arg Leu Arg Leu Thr Phe Gln Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Gly Ser Leu Ser Glu Lys Lys
```

```
                 145                 150                 155                 160
Lys Ser Ser Pro Ala Gly Gly Ser Asp Lys Tyr Asn Gln Ala Leu
                165                 170                 175
Ser Lys Tyr Asn Gln Ala Leu Ser Lys Tyr Asn Gln Ala Leu Ser Gly
                180                 185                 190
Gly Gly Gly Ser Asn Lys Lys Phe Leu Tyr Leu Ala Gly Phe Val
                195                 200                 205
Asp Ser Asp Gly Ser Ile Ile Ala Gln Ile Lys Pro Arg Gln Ser Tyr
                210                 215                 220
Lys Phe Lys His Gln Leu Ala Leu Thr Phe Lys Val Thr Gln Lys Thr
225                 230                 235                 240
Gln Arg Arg Trp Leu Leu Asp Lys Leu Val Asp Arg Ile Gly Val Gly
                245                 250                 255
Tyr Val Tyr Asp Ser Gly Ser Val Ser Asn Tyr Tyr Leu Ser Glu Ile
                260                 265                 270
Lys Pro Leu His Asn Phe Leu Thr Gln Leu Gln Pro Phe Leu Lys Leu
                275                 280                 285
Lys Gln Lys Gln Ala Asn Leu Val Leu Lys Ile Ile Glu Gln Leu Pro
                290                 295                 300
Ser Ala Lys Glu Ser Pro Asp Lys Phe Leu Glu Val Cys Thr Trp Val
305                 310                 315                 320
Asp Gln Val Ala Ala Leu Asn Asp Ser Lys Thr Arg Lys Thr Thr Ser
                325                 330                 335
Glu Thr Val Arg Ala Val Leu Asp Ser Leu Ser Glu Lys Lys Lys Ser
                340                 345                 350
Ser Pro

<210> SEQ ID NO 148
<211> LENGTH: 354
<212> TYPE: PRT
<213> ORGANISM: artificial sequence
<220> FEATURE:
<223> OTHER INFORMATION: SCOH-SH73-pCLS5960

<400> SEQUENCE: 148

Met Ala Asn Thr Lys Tyr Asn Glu Glu Phe Leu Tyr Leu Ala Gly
1               5                   10                  15
Phe Val Asp Gly Asp Gly Ser Ile Ile Ala Gln Ile Lys Pro Cys Gln
                20                  25                  30
Ser Cys Lys Phe Lys His Gln Leu Ser Leu Thr Phe Lys Val Thr Gln
                35                  40                  45
Lys Thr Gln Arg Arg Trp Leu Leu Asp Lys Leu Val Asp Glu Ile Gly
        50                  55                  60
Val Gly Tyr Val Ala Asp Ser Gly Ser Val Ser Asp Tyr Lys Leu Ser
65                  70                  75                  80
Glu Val Lys Pro Leu His Asn Phe Leu Thr Gln Leu Gln Pro Phe Leu
                85                  90                  95
Glu Leu Lys Gln Lys Gln Ala Asn Leu Val Leu Lys Ile Ile Glu Gln
                100                 105                 110
Leu Pro Ser Ala Lys Glu Ser Pro Asp Lys Phe Leu Glu Val Cys Thr
                115                 120                 125
Trp Val Asp Gln Val Ala Ala Leu Asn Asp Ser Lys Thr Arg Lys Thr
        130                 135                 140
Thr Ser Glu Thr Val Arg Ala Val Leu Asp Ser Leu Ser Glu Lys Lys
145                 150                 155                 160
```

```
Lys Ser Ser Pro Ala Gly Gly Asp Lys Tyr Asn Gln Ala Leu
                165                 170                 175

Ser Lys Tyr Asn Gln Ala Leu Ser Lys Tyr Asn Gln Ala Leu Ser Gly
        180                 185                 190

Gly Gly Gly Ser Asn Lys Lys Phe Leu Leu Tyr Leu Ala Gly Phe Val
            195                 200                 205

Asp Ser Asp Gly Ser Ile Ile Ala Gln Ile Lys Pro Asn Gln Ser Tyr
    210                 215                 220

Lys Phe Lys His Gln Leu Ser Leu Thr Phe Val Thr Gln Lys Thr
225                 230                 235                 240

Gln Arg Arg Trp Phe Leu Asp Lys Leu Val Asp Arg Ile Gly Val Gly
                245                 250                 255

Tyr Val Arg Asp Arg Gly Ser Val Ser Asp Tyr His Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Ser
            340                 345                 350

Ser Pro

<210> SEQ ID NO 149
<211> LENGTH: 354
<212> TYPE: PRT
<213> ORGANISM: artificial sequence
<220> FEATURE:
<223> OTHER INFORMATION: SCOH-SH74-pCLS5961

<400> SEQUENCE: 149

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
                20                  25                  30

Thr His Lys Phe Lys His Gln Leu Ser Leu Thr Phe Arg Val Thr Gln
            35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Thr Val Ser Asn Tyr Asn Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
    115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160
```

-continued

```
Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Ile Ala Gln Ile Lys Pro Asp Gln Ser Arg
    210                 215                 220

Lys Phe Lys His Thr Leu Ser Leu Thr Phe Gln Val Thr Gln Lys Thr
225                 230                 235                 240

Gln Arg Arg Trp Phe Leu Asp Lys Leu Val Asp Arg Ile Gly Val Gly
                245                 250                 255

Tyr Val Ala Asp Arg Gly Ser Val Ser Asp Tyr Arg Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Pro Pro

<210> SEQ ID NO 150
<211> LENGTH: 354
<212> TYPE: PRT
<213> ORGANISM: artificial sequence
<220> FEATURE:
<223> OTHER INFORMATION: SCOH-SH75-pCLS5962

<400> SEQUENCE: 150

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Ser Arg Lys Phe Lys His Glu Leu Ser Leu Thr Phe Asp Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Tyr Tyr Gln Leu Ser
65                  70                  75                  80

Glu Ile Lys Pro Leu His Asn Leu Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
```

```
            165                 170                 175
Ser Lys Tyr Asn Gln Ala Leu Ser Lys Tyr Asn Gln Ala Leu Ser Gly
        180                 185                 190

Gly Gly Gly Ser Asn Lys Lys Phe Leu Leu Tyr Leu Ala Gly Phe Val
        195                 200                 205

Asp Ser Asp Gly Ser Ile Ile Ala Gln Ile Lys Pro Asn Gln Ser Val
210                 215                 220

Lys Phe Lys His His Leu Ser Leu Thr Phe Asn Val Thr Gln Lys Thr
225                 230                 235                 240

Gln Arg Arg Trp Phe Leu Asp Lys Leu Val Asp Arg Ile Gly Val Gly
                245                 250                 255

Tyr Val Tyr Asp Ser Gly Ser Val Ser Tyr Tyr Asn Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro
```

<210> SEQ ID NO 151
<211> LENGTH: 24
<212> TYPE: DNA
<213> ORGANISM: Artificial
<220> FEATURE:
<223> OTHER INFORMATION: SH101

<400> SEQUENCE: 151
cctacaccct gtaagatggc tagt                                        24

<210> SEQ ID NO 152
<211> LENGTH: 24
<212> TYPE: DNA
<213> ORGANISM: Artificial
<220> FEATURE:
<223> OTHER INFORMATION: SH106

<400> SEQUENCE: 152
ctaaaatcat gtaagttgta ttat                                        24

<210> SEQ ID NO 153
<211> LENGTH: 24
<212> TYPE: DNA
<213> ORGANISM: Artificial
<220> FEATURE:
<223> OTHER INFORMATION: SH107

<400> SEQUENCE: 153
taaacatttt gtacagaatc tcag                                        24

<210> SEQ ID NO 154
<211> LENGTH: 24
<212> TYPE: DNA
<213> ORGANISM: Artificial
<220> FEATURE:

<223> OTHER INFORMATION: SH102

<400> SEQUENCE: 154
atgagataat gtacaaggtt ttgt                                    24

<210> SEQ ID NO 155
<211> LENGTH: 24
<212> TYPE: DNA
<213> ORGANISM: Artificial
<220> FEATURE:
<223> OTHER INFORMATION: SH105

<400> SEQUENCE: 155
cagggactat ttacaaaaga ttga                                    24

<210> SEQ ID NO 156
<211> LENGTH: 24
<212> TYPE: DNA
<213> ORGANISM: Artificial
<220> FEATURE:
<223> OTHER INFORMATION: SH103

<400> SEQUENCE: 156
ccaaacctag gtaagagata tgaa                                    24

<210> SEQ ID NO 157
<211> LENGTH: 24
<212> TYPE: DNA
<213> ORGANISM: Artificial
<220> FEATURE:
<223> OTHER INFORMATION: SH104

<400> SEQUENCE: 157
tatagatcaa gtaacaagtg taat                                    24

<210> SEQ ID NO 158
<211> LENGTH: 24
<212> TYPE: DNA
<213> ORGANISM: Artificial
<220> FEATURE:
<223> OTHER INFORMATION: SH113

<400> SEQUENCE: 158
ttttactgtc ttacctagtt ttgc                                    24

<210> SEQ ID NO 159
<211> LENGTH: 24
<212> TYPE: DNA
<213> ORGANISM: Artificial
<220> FEATURE:
<223> OTHER INFORMATION: SH109

<400> SEQUENCE: 159
tcaatctcac ttacaaagtt gtga                                    24

<210> SEQ ID NO 160
<211> LENGTH: 24
<212> TYPE: DNA
<213> ORGANISM: Artificial
<220> FEATURE:
<223> OTHER INFORMATION: SH112

<400> SEQUENCE: 160
ctaggatgta gtacagggtg ctat                                    24

```
<210> SEQ ID NO 161
<211> LENGTH: 24
<212> TYPE: DNA
<213> ORGANISM: Artificial
<220> FEATURE:
<223> OTHER INFORMATION: SH108

<400> SEQUENCE: 161
aatatctcat gtaacacata ttgc                                          24

<210> SEQ ID NO 162
<211> LENGTH: 24
<212> TYPE: DNA
<213> ORGANISM: Artificial
<220> FEATURE:
<223> OTHER INFORMATION: SH110

<400> SEQUENCE: 162
ttactcccat ttacaagagc agag                                          24

<210> SEQ ID NO 163
<211> LENGTH: 24
<212> TYPE: DNA
<213> ORGANISM: Artificial
<220> FEATURE:
<223> OTHER INFORMATION: SH114

<400> SEQUENCE: 163
accagacctt gtaagttata caga                                          24

<210> SEQ ID NO 164
<211> LENGTH: 24
<212> TYPE: DNA
<213> ORGANISM: Artificial
<220> FEATURE:
<223> OTHER INFORMATION: SH116

<400> SEQUENCE: 164
ataaaataag ttacagagtt acaa                                          24

<210> SEQ ID NO 165
<211> LENGTH: 24
<212> TYPE: DNA
<213> ORGANISM: Artificial
<220> FEATURE:
<223> OTHER INFORMATION: SH111

<400> SEQUENCE: 165
acttcctgtt ttacaaggtg taat                                          24

<210> SEQ ID NO 166
<211> LENGTH: 24
<212> TYPE: DNA
<213> ORGANISM: Artificial
<220> FEATURE:
<223> OTHER INFORMATION: SH115

<400> SEQUENCE: 166
cctggatatg ttacaacaga aagc                                          24

<210> SEQ ID NO 167
<211> LENGTH: 24
<212> TYPE: DNA
<213> ORGANISM: Artificial
<220> FEATURE:
<223> OTHER INFORMATION: SH121
```

<400> SEQUENCE: 167
tttctctcag gtaaaacagt ccac					24

<210> SEQ ID NO 168
<211> LENGTH: 24
<212> TYPE: DNA
<213> ORGANISM: Artificial
<220> FEATURE:
<223> OTHER INFORMATION: SH120

<400> SEQUENCE: 168
gtaagctatt gtaagaaatg caag					24

<210> SEQ ID NO 169
<211> LENGTH: 24
<212> TYPE: DNA
<213> ORGANISM: Artificial
<220> FEATURE:
<223> OTHER INFORMATION: SH122

<400> SEQUENCE: 169
atgagatgat gtacaaagtc ctag					24

<210> SEQ ID NO 170
<211> LENGTH: 24
<212> TYPE: DNA
<213> ORGANISM: Artificial
<220> FEATURE:
<223> OTHER INFORMATION: SH117

<400> SEQUENCE: 170
actgtatttt gtaaagtgtc cctc					24

<210> SEQ ID NO 171
<211> LENGTH: 24
<212> TYPE: DNA
<213> ORGANISM: Artificial
<220> FEATURE:
<223> OTHER INFORMATION: SH118

<400> SEQUENCE: 171
tcttcatgtt gtaccttgtc ccct					24

<210> SEQ ID NO 172
<211> LENGTH: 24
<212> TYPE: DNA
<213> ORGANISM: Artificial
<220> FEATURE:
<223> OTHER INFORMATION: SH119

<400> SEQUENCE: 172
atcatctgag gtaaagagtt ctga					24

<210> SEQ ID NO 173
<211> LENGTH: 24
<212> TYPE: DNA
<213> ORGANISM: Artificial
<220> FEATURE:
<223> OTHER INFORMATION: SH123

<400> SEQUENCE: 173
gctctctctg gtacctgata gtga					24

<210> SEQ ID NO 174
<211> LENGTH: 24

```
<212> TYPE: DNA
<213> ORGANISM: Artificial
<220> FEATURE:
<223> OTHER INFORMATION: SH126

<400> SEQUENCE: 174
acaaactctt ttacgggatt cagg                                          24

<210> SEQ ID NO 175
<211> LENGTH: 24
<212> TYPE: DNA
<213> ORGANISM: Artificial
<220> FEATURE:
<223> OTHER INFORMATION: SH128

<400> SEQUENCE: 175
ttcacatgct ttcgaaagt tagc                                           24

<210> SEQ ID NO 176
<211> LENGTH: 24
<212> TYPE: DNA
<213> ORGANISM: Artificial
<220> FEATURE:
<223> OTHER INFORMATION: SH129

<400> SEQUENCE: 176
cctacatttc gtaagacatc tatt                                          24

<210> SEQ ID NO 177
<211> LENGTH: 24
<212> TYPE: DNA
<213> ORGANISM: Artificial
<220> FEATURE:
<223> OTHER INFORMATION: SH124

<400> SEQUENCE: 177
gcaaactgtg gtacctaggc ccgt                                          24

<210> SEQ ID NO 178
<211> LENGTH: 24
<212> TYPE: DNA
<213> ORGANISM: Artificial
<220> FEATURE:
<223> OTHER INFORMATION: SH131

<400> SEQUENCE: 178
tcgagccact gtacctagtt ttgt                                          24

<210> SEQ ID NO 179
<211> LENGTH: 24
<212> TYPE: DNA
<213> ORGANISM: Artificial
<220> FEATURE:
<223> OTHER INFORMATION: SH125

<400> SEQUENCE: 179
acaggatcca gtaaaggagc cggc                                          24

<210> SEQ ID NO 180
<211> LENGTH: 24
<212> TYPE: DNA
<213> ORGANISM: Artificial
<220> FEATURE:
<223> OTHER INFORMATION: SH127

<400> SEQUENCE: 180
```

```
gctgtactat ttacggtatt caat                                          24
```

<210> SEQ ID NO 181
<211> LENGTH: 24
<212> TYPE: DNA
<213> ORGANISM: Artificial
<220> FEATURE:
<223> OTHER INFORMATION: SH75

<400> SEQUENCE: 181

```
ataaacttcg gtaagacatc tcaa                                          24
```

<210> SEQ ID NO 182
<211> LENGTH: 349
<212> TYPE: PRT
<213> ORGANISM: artificial sequence
<220> FEATURE:
<223> OTHER INFORMATION: SCOH-SH101-pCLS7518

<400> SEQUENCE: 182

```
Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Arg Pro Asn Gln
            20                  25                  30

Ser Ser Lys Phe Lys His Tyr Leu Gln Leu Thr Phe Arg Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Asn Tyr Asn Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Asp Ser Ser Val Ser Asn Ser Glu His
                165                 170                 175

Ile Ala Pro Leu Ser Leu Pro Ser Ser Pro Ser Val Gly Ser Asn
            180                 185                 190

Lys Lys Phe Leu Leu Tyr Leu Ala Gly Phe Val Asp Ser Asp Gly Ser
        195                 200                 205

Ile Ile Ala Gln Ile Lys Pro Asn Gln Thr Cys Lys Phe Lys His Gln
    210                 215                 220

Leu Ser Leu Thr Phe Ile Val Thr Gln Lys Thr Gln Arg Arg Trp Phe
225                 230                 235                 240

Leu Asp Lys Leu Val Asp Arg Ile Gly Val Gly Tyr Val Ser Asp Arg
                245                 250                 255

Gly Ser Val Ser Asp Tyr Lys Leu Ser Glu Ile Lys Pro Leu His Asn
            260                 265                 270

Phe Leu Thr Gln Leu Gln Pro Phe Leu Lys Leu Lys Gln Lys Gln Ala
        275                 280                 285

Asn Leu Val Leu Lys Ile Ile Glu Gln Leu Pro Ser Ala Lys Glu Ser
```

```
            290                 295                 300
Pro Asp Lys Phe Leu Glu Val Cys Thr Trp Val Asp Gln Val Ala Ala
305                 310                 315                 320

Leu Asn Asp Ser Lys Thr Arg Lys Thr Thr Ser Glu Thr Val Arg Ala
                325                 330                 335

Val Leu Asp Ser Leu Ser Glu Lys Lys Ser Ser Pro
            340                 345
```

<210> SEQ ID NO 183
<211> LENGTH: 349
<212> TYPE: PRT
<213> ORGANISM: artificial sequence
<220> FEATURE:
<223> OTHER INFORMATION: SCOH-SH106-pCLS7523

<400> SEQUENCE: 183

```
Met Ala Asn Thr Lys Tyr Asn Glu Glu Phe Leu Leu Tyr Leu Ala Gly
1               5                   10                  15

Phe Val Asp Gly Asp Gly Ser Ile Val Ala Gln Ile Lys Pro Asn Gln
            20                  25                  30

Ser Tyr Lys Phe Lys His Gln Leu Ser Leu Thr Phe Val Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Arg Gly Ser Val Ser Asp Tyr Lys Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Asp Ser Ser Val Ser Asn Ser Glu His
                165                 170                 175

Ile Ala Pro Leu Ser Leu Pro Ser Pro Ser Val Gly Ser Asn
            180                 185                 190

Lys Lys Phe Leu Leu Tyr Leu Ala Gly Phe Val Asp Ser Asp Gly Ser
        195                 200                 205

Ile Ile Ala Gln Ile Lys Pro Asn Gln Ser Tyr Lys Phe Lys His Gln
    210                 215                 220

Leu Ser Leu Thr Phe Ala Val Thr Gln Lys Thr Gln Arg Arg Trp Phe
225                 230                 235                 240

Leu Asp Lys Leu Val Asp Arg Ile Gly Val Gly Tyr Val Tyr Asp Ser
                245                 250                 255

Gly Ser Val Ser Tyr Tyr Lys Leu Ser Glu Ile Lys Pro Leu His Asn
            260                 265                 270

Phe Leu Thr Gln Leu Gln Pro Phe Leu Lys Leu Lys Gln Lys Gln Ala
        275                 280                 285

Asn Leu Val Leu Lys Ile Ile Glu Gln Leu Pro Ser Ala Lys Glu Ser
    290                 295                 300

Pro Asp Lys Phe Leu Glu Val Cys Thr Trp Val Asp Gln Val Ala Ala
```

305              310              315              320

Leu Asn Asp Ser Lys Thr Arg Lys Thr Thr Ser Glu Thr Val Arg Ala
                325              330              335

Val Leu Asp Ser Leu Ser Glu Lys Lys Lys Ser Ser Pro
                340              345

<210> SEQ ID NO 184
<211> LENGTH: 349
<212> TYPE: PRT
<213> ORGANISM: artificial sequence
<220> FEATURE:
<223> OTHER INFORMATION: SCOH-SH107-pCLS7524

<400> SEQUENCE: 184

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
                20                  25                  30

Ser His Lys Phe Lys His Gln Leu Ser Leu Thr Phe Lys Val Thr Gln
            35                  40                  45

Lys Thr Gln Arg Arg Trp Phe Leu Asp Lys Leu Val Asp Glu Ile Gly
50                  55                  60

Val Gly Tyr Val Tyr Asp Ser Gly Ser Val Ser Asn Tyr Tyr Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Asp Ser Ser Val Ser Asn Ser Glu His
                165                 170                 175

Ile Ala Pro Leu Ser Leu Pro Ser Ser Pro Ser Val Gly Ser Asn
            180                 185                 190

Lys Lys Phe Leu Leu Tyr Leu Ala Gly Phe Val Asp Ser Asp Gly Ser
        195                 200                 205

Ile Ile Ala Gln Ile Lys Pro Arg Gln Cys Arg Lys Phe Lys His Gln
210                 215                 220

Leu Glu Leu Thr Phe Gln Val Thr Gln Lys Thr Gln Arg Arg Trp Leu
225                 230                 235                 240

Leu Asp Lys Leu Val Asp Arg Ile Gly Val Gly Tyr Val His Asp Ser
                245                 250                 255

Gly Ser Val Ser Asn Tyr Arg Leu Ser Glu Ile Lys Pro Leu His Asn
            260                 265                 270

Phe Leu Thr Gln Leu Gln Pro Phe Leu Lys Leu Lys Gln Lys Gln Ala
        275                 280                 285

Asn Leu Val Leu Lys Ile Ile Glu Gln Leu Pro Ser Ala Lys Glu Ser
290                 295                 300

Pro Asp Lys Phe Leu Glu Val Cys Thr Trp Val Asp Gln Val Ala Ala
305                 310                 315                 320

Leu Asn Asp Ser Lys Thr Arg Lys Thr Thr Ser Glu Thr Val Arg Ala

Val Leu Asp Ser Leu Ser Glu Lys Lys Lys Ser Ser Pro
        340                 345

<210> SEQ ID NO 185
<211> LENGTH: 349
<212> TYPE: PRT
<213> ORGANISM: artificial sequence
<220> FEATURE:
<223> OTHER INFORMATION: SCOH-SH102-pCLS7519

<400> SEQUENCE: 185

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Thr His Lys Phe Lys His Gln Leu Ser Leu Thr Phe Ala Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Asp Ser Ser Val Ser Asn Ser Glu His
                165                 170                 175

Ile Ala Pro Leu Ser Leu Pro Ser Ser Pro Ser Val Gly Ser Asn
        180                 185                 190

Lys Lys Phe Leu Leu Tyr Leu Ala Gly Phe Val Asp Ser Asp Gly Ser
    195                 200                 205

Ile Ile Ala Gln Ile Lys Pro Asn Gln Ser Tyr Lys Phe Lys His Gln
210                 215                 220

Leu Ser Leu Thr Phe Lys Val Thr Gln Lys Thr Gln Arg Arg Trp Phe
225                 230                 235                 240

Leu Asp Lys Leu Val Asp Arg Ile Gly Val Gly Tyr Val Arg Asp Asn
                245                 250                 255

Gly Ser Val Ser Asp Tyr Ile Leu Ser Glu Ile Lys Pro Leu His Asn
            260                 265                 270

Phe Leu Thr Gln Leu Gln Pro Phe Leu Lys Leu Lys Gln Lys Gln Ala
        275                 280                 285

Asn Leu Val Leu Lys Ile Ile Glu Gln Leu Pro Ser Ala Lys Glu Ser
    290                 295                 300

Pro Asp Lys Phe Leu Glu Val Cys Thr Trp Val Asp Gln Val Ala Ala
305                 310                 315                 320

Leu Asn Asp Ser Lys Thr Arg Lys Thr Thr Ser Glu Thr Val Arg Ala
                325                 330                 335

Val Leu Asp Ser Leu Ser Glu Lys Lys Lys Ser Ser Pro

<210> SEQ ID NO 186
<211> LENGTH: 349
<212> TYPE: PRT
<213> ORGANISM: artificial sequence
<220> FEATURE:
<223> OTHER INFORMATION: SCOH-SH105-pCLS7522

<400> SEQUENCE: 186

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Ser Tyr Lys Phe Lys His Gln Leu Ser Leu Thr Phe Asn Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Tyr Tyr Lys Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Asp Ser Ser Val Ser Asn Ser Glu His
                165                 170                 175

Ile Ala Pro Leu Ser Leu Pro Ser Ser Pro Ser Val Gly Ser Asn
            180                 185                 190

Lys Lys Phe Leu Leu Tyr Leu Ala Gly Phe Val Asp Ser Asp Gly Ser
        195                 200                 205

Ile Ile Ala Gln Ile Lys Pro Asn Gln Ser Tyr Lys Phe Lys His Gln
    210                 215                 220

Leu Ser Leu Thr Phe Gln Val Thr Gln Lys Thr Gln Arg Arg Trp Phe
225                 230                 235                 240

Leu Asp Lys Leu Val Asp Arg Ile Gly Val Gly Tyr Val Arg Asp Ser
                245                 250                 255

Gly Ser Val Ser Asn Tyr Ile Leu Ser Glu Ile Lys Pro Leu His Asn
            260                 265                 270

Phe Leu Thr Gln Leu Gln Pro Phe Leu Lys Leu Lys Gln Lys Gln Ala
        275                 280                 285

Asn Leu Val Leu Lys Ile Ile Glu Gln Leu Pro Ser Ala Lys Glu Ser
    290                 295                 300

Pro Asp Lys Phe Leu Glu Val Cys Thr Trp Val Asp Gln Val Ala Ala
305                 310                 315                 320

Leu Asn Asp Ser Lys Thr Arg Lys Thr Thr Ser Glu Thr Val Arg Ala
                325                 330                 335

Val Leu Asp Ser Leu Ser Glu Lys Lys Lys Ser Ser Pro
            340                 345

```
<210> SEQ ID NO 187
<211> LENGTH: 349
<212> TYPE: PRT
<213> ORGANISM: artificial sequence
<220> FEATURE:
<223> OTHER INFORMATION: SCOH-SH103-pCLS7520

<400> SEQUENCE: 187

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Tyr Lys Phe Lys His Gln Leu Ser Leu Thr Phe Ala Val Thr Gln
        35                  40                  45

Lys Thr Gln Arg Arg Trp Phe Leu Asp Lys Leu Val Asp Glu Ile Gly
50                  55                  60

Val Gly Tyr Val Arg Asp Ser Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Asp Ser Ser Val Ser Asn Ser Glu His
                165                 170                 175

Ile Ala Pro Leu Ser Leu Pro Ser Ser Pro Ser Val Gly Ser Asn
            180                 185                 190

Lys Lys Phe Leu Leu Tyr Leu Ala Gly Phe Val Asp Ser Asp Gly Ser
        195                 200                 205

Ile Ile Ala Gln Ile Lys Pro Cys Gln Ser Cys Lys Phe Lys His Gln
210                 215                 220

Leu Ser Leu Thr Phe Arg Val Thr Gln Lys Thr Gln Arg Arg Trp Phe
225                 230                 235                 240

Leu Asp Lys Leu Val Asp Arg Ile Gly Val Gly Tyr Val Arg Asp Arg
                245                 250                 255

Gly Ser Val Ser Asp Tyr His Leu Ser Glu Ile Lys Pro Leu His Asn
            260                 265                 270

Phe Leu Thr Gln Leu Gln Pro Phe Leu Lys Leu Lys Gln Lys Gln Ala
        275                 280                 285

Asn Leu Val Leu Lys Ile Ile Glu Gln Leu Pro Ser Ala Lys Glu Ser
290                 295                 300

Pro Asp Lys Phe Leu Glu Val Cys Thr Trp Val Asp Gln Val Ala Ala
305                 310                 315                 320

Leu Asn Asp Ser Lys Thr Arg Lys Thr Thr Ser Glu Thr Val Arg Ala
                325                 330                 335

Val Leu Asp Ser Leu Ser Glu Lys Lys Ser Ser Pro
            340                 345

<210> SEQ ID NO 188
<211> LENGTH: 349
<212> TYPE: PRT
```

<213> ORGANISM: artificial sequence
<220> FEATURE:
<223> OTHER INFORMATION: SCOH-SH104-pCLS7521

<400> SEQUENCE: 188

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Arg Pro Asn Gln
            20                  25                  30

Ser Ala Lys Phe Lys His Tyr Leu Gln Leu Thr Phe Arg Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Asp Tyr Ile Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Asp Ser Ser Val Ser Asn Ser Glu His
                165                 170                 175

Ile Ala Pro Leu Ser Leu Pro Ser Ser Pro Ser Val Gly Ser Asn
            180                 185                 190

Lys Lys Phe Leu Leu Tyr Leu Ala Gly Phe Val Asp Ser Asp Gly Ser
        195                 200                 205

Ile Ile Ala Gln Ile Lys Pro Asn Gln His Cys Lys Phe Lys His Gln
    210                 215                 220

Leu Ala Leu Thr Phe Thr Val Gly Gln Lys Thr Gln Arg Arg Trp Leu
225                 230                 235                 240

Leu Asp Lys Leu Val Asp Arg Ile Gly Val Gly Tyr Val Thr Asp Ser
                245                 250                 255

Gly Ser Met Ser Ala Tyr Arg Leu Ser Glu Ile Lys Pro Leu His Asn
            260                 265                 270

Phe Leu Thr Gln Leu Gln Pro Phe Leu Lys Leu Lys Gln Lys Gln Ala
        275                 280                 285

Asn Leu Val Leu Lys Ile Ile Glu Gln Leu Pro Ser Ala Lys Glu Ser
    290                 295                 300

Pro Asp Lys Phe Leu Glu Val Cys Thr Trp Val Asp Gln Val Ala Ala
305                 310                 315                 320

Leu Asn Asp Ser Lys Thr Arg Lys Thr Thr Ser Glu Thr Val Arg Ala
                325                 330                 335

Val Leu Asp Gly Leu Ser Glu Lys Lys Lys Ser Ser Pro
            340                 345

<210> SEQ ID NO 189
<211> LENGTH: 349
<212> TYPE: PRT
<213> ORGANISM: artificial sequence
<220> FEATURE:
<223> OTHER INFORMATION: SCOH-SH113-pCLS7530

<400> SEQUENCE: 189

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Tyr Lys Phe Lys His Gln Leu Ser Leu Thr Phe Ala Val Thr Gln
        35                  40                  45

Lys Thr Gln Arg Arg Trp Phe Leu Asp Lys Leu Val Asp Glu Ile Gly
50                  55                  60

Val Gly Tyr Val Arg Asp Ser Gly Ser Val Ser Tyr Tyr Ile Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Asp Ser Ser Val Ser Asn Ser Glu His
                165                 170                 175

Ile Ala Pro Leu Ser Leu Pro Ser Ser Pro Ser Val Gly Ser Asn
            180                 185                 190

Lys Lys Phe Leu Leu Tyr Leu Ala Gly Phe Val Asp Ser Asp Gly Ser
        195                 200                 205

Ile Ile Ala Gln Ile Lys Pro Asn Gln Ser Thr Lys Phe Lys His Gln
210                 215                 220

Leu Gln Leu Thr Phe Gln Val Thr Gln Lys Thr Gln Arg Arg Trp Phe
225                 230                 235                 240

Leu Asp Lys Leu Val Asp Arg Ile Gly Val Gly Tyr Val Arg Asp Arg
                245                 250                 255

Gly Ser Val Ser Asp Tyr Ile Leu Ser Glu Ile Lys Pro Leu His Asn
            260                 265                 270

Phe Leu Thr Gln Leu Gln Pro Phe Leu Lys Leu Lys Gln Lys Gln Ala
        275                 280                 285

Asn Leu Val Leu Lys Ile Ile Glu Gln Leu Pro Ser Ala Lys Glu Ser
290                 295                 300

Pro Asp Lys Phe Leu Glu Val Cys Thr Trp Val Asp Gln Val Ala Ala
305                 310                 315                 320

Leu Asn Asp Ser Lys Thr Arg Lys Thr Thr Ser Glu Thr Val Arg Ala
                325                 330                 335

Val Leu Asp Ser Leu Ser Glu Lys Lys Ser Ser Pro
            340                 345

<210> SEQ ID NO 190
<211> LENGTH: 349
<212> TYPE: PRT
<213> ORGANISM: artificial sequence
<220> FEATURE:
<223> OTHER INFORMATION: SCOH-SH109-pCLS7526

<400> SEQUENCE: 190

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Ser Tyr Lys Phe Lys His Glu Leu Ser Leu Thr Phe Lys Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Asp Tyr Thr Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Asp Ser Ser Val Ser Asn Ser Glu His
                165                 170                 175

Ile Ala Pro Leu Ser Leu Pro Ser Ser Pro Ser Val Gly Ser Asn
            180                 185                 190

Lys Lys Phe Leu Leu Tyr Leu Ala Gly Phe Val Asp Ser Asp Gly Ser
        195                 200                 205

Ile Ile Ala Gln Ile Lys Pro Asn Gln Ser Tyr Lys Phe Lys His Gln
    210                 215                 220

Leu Ser Leu Thr Phe Lys Val Thr Gln Lys Thr Gln Arg Arg Trp Phe
225                 230                 235                 240

Leu Asp Lys Leu Val Asp Arg Ile Gly Val Gly Tyr Val Ala Asp Arg
                245                 250                 255

Gly Ser Val Ser Asp Tyr Ile Leu Ser Glu Ile Lys Pro Leu His Asn
            260                 265                 270

Phe Leu Thr Gln Leu Gln Pro Phe Leu Lys Leu Lys Gln Lys Gln Ala
        275                 280                 285

Asn Leu Val Leu Lys Ile Ile Glu Gln Leu Pro Ser Ala Lys Glu Ser
    290                 295                 300

Pro Asp Lys Phe Leu Glu Val Cys Thr Trp Val Asp Gln Val Ala Ala
305                 310                 315                 320

Leu Asn Asp Ser Lys Thr Arg Lys Thr Thr Ser Glu Thr Val Arg Ala
                325                 330                 335

Val Leu Asp Ser Leu Ser Glu Lys Lys Ser Ser Pro
            340                 345

<210> SEQ ID NO 191
<211> LENGTH: 349
<212> TYPE: PRT
<213> ORGANISM: artificial sequence
<220> FEATURE:
<223> OTHER INFORMATION: SCOH-SH112-pCLS7529

<400> SEQUENCE: 191

Met Ala Asn Thr Lys Tyr Asn Glu Glu Phe Leu Leu Tyr Leu Ala Gly
1               5                   10                  15

```
Phe Val Asp Gly Asp Gly Ser Ile Ile Ala Gln Ile Lys Pro Asn Gln
             20                  25                  30

Ser Cys Lys Phe Lys His Tyr Leu Ser Leu Thr Phe Asp Val Thr Gln
         35                  40                  45

Lys Thr Gln Arg Arg Trp Phe Leu Asp Lys Leu Val Asp Glu Ile Gly
     50                  55                  60

Val Gly Tyr Val Ala Asp Ser Gly Ser Val Ser Lys Tyr Arg Leu Ser
 65                  70                  75                  80

Glu Ile Lys Pro Leu His Asn Phe Leu Thr Gln Leu Gln Pro Phe Leu
                 85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Asp Ser Ser Val Ser Asn Ser Glu His
                165                 170                 175

Ile Ala Pro Leu Ser Leu Pro Ser Ser Pro Ser Val Gly Ser Asn
            180                 185                 190

Lys Lys Phe Leu Leu Tyr Leu Ala Gly Phe Val Asp Ser Asp Gly Ser
        195                 200                 205

Ile Ile Ala Gln Ile Lys Pro Asn Gln Ser Tyr Lys Phe Lys His Gln
    210                 215                 220

Leu Arg Leu Thr Phe Ser Val Gly Gln Lys Thr Gln Arg Arg Trp Phe
225                 230                 235                 240

Leu Asp Lys Leu Val Asp Arg Ile Gly Val Gly Tyr Val Arg Asp Ser
                245                 250                 255

Gly Ser Met Ser Glu Tyr Cys Leu Ser Glu Ile Lys Pro Leu His Asn
            260                 265                 270

Phe Leu Thr Gln Leu Gln Pro Phe Leu Lys Leu Lys Gln Lys Gln Ala
        275                 280                 285

Asn Leu Val Leu Lys Ile Ile Glu Gln Leu Pro Ser Ala Lys Glu Ser
    290                 295                 300

Pro Asp Lys Phe Leu Glu Val Cys Thr Trp Val Asp Gln Val Ala Ala
305                 310                 315                 320

Leu Asn Asp Ser Lys Thr Arg Lys Thr Thr Ser Glu Thr Val Arg Ala
                325                 330                 335

Val Leu Asp Ser Leu Ser Glu Lys Lys Lys Ser Ser Pro
            340                 345
```

<210> SEQ ID NO 192
<211> LENGTH: 349
<212> TYPE: PRT
<213> ORGANISM: artificial sequence
<220> FEATURE:
<223> OTHER INFORMATION: SCOH-SH108-pCLS7525

<400> SEQUENCE: 192

```
Met Ala Asn Thr Lys Tyr Asn Glu Glu Phe Leu Leu Tyr Leu Ala Gly
 1               5                  10                  15

Phe Val Asp Gly Asp Gly Ser Ile Ile Ala Gln Ile Lys Pro Asn Gln
             20                  25                  30
```

Ser Tyr Lys Phe Lys His Gln Leu Ala Leu Thr Phe Gln Val Thr Gln
                 35                  40                  45

Lys Thr Gln Arg Arg Trp Phe Leu Asp Lys Leu Val Asp Glu Ile Gly
     50                  55                  60

Val Gly Tyr Val Arg Asp Ser Gly Ser Val Ser Asn Tyr Ile Leu Ser
 65                  70                  75                  80

Glu Ile Lys Pro Leu His Asn Phe Leu Thr Gln Leu Gln Pro Phe Leu
                 85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Asp Ser Ser Val Ser Asn Ser Glu His
                165                 170                 175

Ile Ala Pro Leu Ser Leu Pro Ser Ser Pro Ser Val Gly Ser Asn
            180                 185                 190

Lys Lys Phe Leu Leu Tyr Leu Ala Gly Phe Val Asp Ser Asp Gly Ser
        195                 200                 205

Ile Ile Ala Gln Ile Lys Pro Asn Gln Thr Cys Lys Phe Lys His Gln
210                 215                 220

Leu Ser Leu Thr Phe Ala Val Thr Gln Lys Thr Gln Arg Arg Trp Phe
225                 230                 235                 240

Leu Asp Lys Leu Val Asp Arg Ile Gly Val Gly Tyr Val Tyr Asp Ser
                245                 250                 255

Gly Ser Val Ser Tyr Tyr Lys Leu Ser Glu Ile Lys Pro Leu His Asn
            260                 265                 270

Phe Leu Thr Gln Leu Gln Pro Phe Leu Lys Leu Lys Gln Lys Gln Ala
        275                 280                 285

Asn Leu Val Leu Lys Ile Ile Glu Gln Leu Pro Ser Ala Lys Glu Ser
290                 295                 300

Pro Asp Lys Phe Leu Glu Val Cys Thr Trp Val Asp Gln Val Ala Ala
305                 310                 315                 320

Leu Asn Asp Ser Lys Thr Arg Lys Thr Thr Ser Glu Thr Val Arg Ala
                325                 330                 335

Val Leu Asp Ser Leu Ser Glu Lys Lys Ser Ser Pro
            340                 345

<210> SEQ ID NO 193
<211> LENGTH: 349
<212> TYPE: PRT
<213> ORGANISM: artificial sequence
<220> FEATURE:
<223> OTHER INFORMATION: SCOH-SH110-pCLS7527

<400> SEQUENCE: 193

Met Ala Asn Ile Lys Tyr Asn Glu Glu Phe Leu Leu Tyr Leu Ala Gly
 1               5                  10                  15

Phe Val Asp Gly Asp Gly Ser Ile Ile Ala Gln Ile Lys Pro Asn Gln
                 20                  25                  30

Thr Tyr Arg Tyr Lys His Trp Leu Cys Leu Thr Phe Ala Val Thr Gln
             35                  40                  45

Lys Thr Gln Arg Arg Trp Phe Leu Asp Lys Leu Val Asp Glu Ile Gly
 50                  55                  60

Val Gly Tyr Val Arg Asp Ser Gly Ser Val Ser Tyr Tyr Thr Leu Ser
 65                  70                  75                  80

Glu Ile Lys Pro Leu His Asn Phe Leu Thr Gln Leu Gln Pro Phe Leu
                 85                  90                  95

Glu Leu Lys Gln Lys Gln Ala Asn Leu Val Leu Lys Ile Ile Glu His
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Thr
145                 150                 155                 160

Lys Ser Ser Pro Ala Ala Gly Asp Ser Ser Val Ser Asn Ser Glu His
                165                 170                 175

Ile Ala Pro Leu Ser Leu Pro Ser Ser Pro Ser Val Gly Ser Asn
            180                 185                 190

Lys Lys Phe Leu Leu Tyr Leu Ala Gly Phe Val Asp Ser Asp Gly Ser
        195                 200                 205

Ile Ile Ala Gln Ile Lys Pro Asp Gln Ser Arg Lys Phe Lys His Ser
210                 215                 220

Leu Ser Leu Thr Phe Lys Val Thr Gln Lys Thr Gln Arg Arg Trp Phe
225                 230                 235                 240

Leu Asp Lys Leu Val Asp Arg Ile Gly Val Gly Tyr Val Ala Asp Ser
                245                 250                 255

Gly Ser Val Ser Asp Tyr Lys Leu Ser Glu Ile Lys Pro Leu His Asn
            260                 265                 270

Phe Leu Thr Gln Leu Gln Pro Phe Leu Lys Leu Lys Gln Lys Gln Ala
        275                 280                 285

Asn Leu Val Leu Lys Ile Ile Glu Gln Leu Pro Ser Ala Lys Glu Ser
290                 295                 300

Pro Asp Lys Phe Leu Glu Val Cys Thr Trp Val Asp Gln Val Ala Ala
305                 310                 315                 320

Leu Asn Asp Ser Lys Thr Arg Lys Thr Thr Ser Glu Thr Val Arg Ala
                325                 330                 335

Val Leu Asp Ser Leu Ser Glu Lys Lys Ser Ser Pro
            340                 345

<210> SEQ ID NO 194
<211> LENGTH: 349
<212> TYPE: PRT
<213> ORGANISM: artificial sequence
<220> FEATURE:
<223> OTHER INFORMATION: SCOH-SH114-pCLS7531

<400> SEQUENCE: 194

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Cys Gln
            20                  25                  30

Ser Cys Lys Phe Lys His Gln Leu Ser Leu Thr Phe Lys Val Thr Gln
        35                  40                  45

Lys Thr Gln Arg Arg Trp Leu Leu Asp Lys Leu Val Asp Glu Ile Gly
    50                  55                  60

Val Gly Tyr Val Ala Asp Ser Gly Ser Val Ser Asp Tyr Lys Leu Ser
65                  70                  75                  80

Glu Val Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Val Asp Gln Val Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Gly Asp Ser Val Ser Asn Ser Glu His
                165                 170                 175

Ile Ala Pro Leu Ser Leu Pro Ser Ser Pro Ser Val Gly Ser Asn
            180                 185                 190

Lys Lys Phe Leu Leu Tyr Leu Ala Gly Phe Val Asp Ser Asp Gly Ser
            195                 200                 205

Ile Ile Ala Gln Ile Lys Pro Asn Gln Ser Cys Lys Phe Lys His Ala
210                 215                 220

Leu Ser Leu Thr Phe Val Val Thr Gln Lys Thr Gln Arg Arg Trp Phe
225                 230                 235                 240

Leu Asp Lys Leu Val Asp Arg Ile Gly Val Gly Tyr Val Arg Asp Arg
                245                 250                 255

Gly Ser Val Ser Asp Tyr Lys Leu Ser Glu Ile Lys Pro Leu His Asn
            260                 265                 270

Phe Leu Thr Gln Leu Gln Pro Phe Leu Lys Leu Lys Gln Lys Gln Ala
            275                 280                 285

Asn Leu Val Leu Lys Ile Ile Glu Gln Leu Pro Ser Ala Lys Glu Ser
290                 295                 300

Pro Asp Lys Phe Leu Glu Val Cys Thr Trp Val Asp Gln Val Ala Ala
305                 310                 315                 320

Leu Asn Asp Ser Lys Thr Arg Lys Thr Thr Ser Glu Thr Val Arg Ala
                325                 330                 335

Val Leu Asp Ser Leu Ser Glu Lys Lys Ser Ser Pro
            340                 345

<210> SEQ ID NO 195
<211> LENGTH: 349
<212> TYPE: PRT
<213> ORGANISM: artificial sequence
<220> FEATURE:
<223> OTHER INFORMATION: SCOH-SH116-pCLS7533

<400> SEQUENCE: 195

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
                20                  25                  30

Ser His Lys Phe Lys His Ala Leu Gln Leu Thr Phe Lys Val Thr Gln
            35                  40                  45

Lys Thr Gln Arg Arg Trp Phe Leu Asp Lys Leu Val Asp Glu Ile Gly
        50                  55                  60

Val Gly Tyr Val Gln Asp Ser Gly Ser Val Ser Asn Tyr Ile Leu Ser
65                  70                  75                  80

Glu Ile Lys Pro Leu His Asn Phe Leu Thr Gln Leu Gln Pro Phe Leu
            85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Asp Ser Ser Val Ser Asn Ser Glu His
                165                 170                 175

Ile Ala Pro Leu Ser Leu Pro Ser Ser Pro Ser Val Gly Ser Asn
            180                 185                 190

Lys Lys Phe Leu Leu Tyr Leu Ala Gly Phe Val Asp Ser Asp Gly Ser
            195                 200                 205

Ile Val Ala Gln Ile Lys Pro Asn Gln Ser Tyr Lys Phe Lys His Gln
            210                 215                 220

Leu Ser Leu Thr Phe Ala Val Thr Gln Lys Thr Gln Arg Arg Trp Phe
225                 230                 235                 240

Leu Asp Lys Leu Val Asp Arg Ile Gly Val Gly Tyr Val Tyr Asp Ser
            245                 250                 255

Gly Ser Val Ser Tyr Tyr Arg Leu Ser Glu Ile Lys Pro Leu His Asn
            260                 265                 270

Phe Leu Thr Gln Leu Gln Pro Phe Leu Lys Leu Lys Gln Lys Gln Ala
            275                 280                 285

Asn Leu Val Leu Lys Ile Ile Glu Gln Leu Pro Ser Ala Lys Glu Ser
290                 295                 300

Pro Asp Lys Phe Leu Glu Val Cys Thr Trp Val Asp Gln Val Ala Ala
305                 310                 315                 320

Leu Asn Asp Ser Lys Thr Arg Lys Thr Thr Ser Glu Thr Val Arg Ala
            325                 330                 335

Val Leu Asp Ser Leu Ser Glu Lys Lys Lys Ser Ser Pro
            340                 345

<210> SEQ ID NO 196
<211> LENGTH: 349
<212> TYPE: PRT
<213> ORGANISM: artificial sequence
<220> FEATURE:
<223> OTHER INFORMATION: SCOH-SH111-pCLS7528

<400> SEQUENCE: 196

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Arg Pro Asn Gln
            20                  25                  30

Ser Ser Lys Phe Lys His Tyr Leu Gln Leu Thr Phe Arg Val Thr Gln
            35                  40                  45

Lys Thr Gln Arg Arg Trp Phe Leu Asp Lys Leu Val Asp Glu Ile Gly
            50                  55                  60

Val Gly Tyr Val Ala Asp Ser Gly Ser Val Ser Asn Tyr Asn Leu Ser
65                  70                  75                  80

Glu Ile Lys Pro Leu His Asn Phe Leu Thr Gln Leu Gln Pro Phe Leu
            85                  90                  95

```
Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Asp Ser Val Ser Asn Ser Glu His
                165                 170                 175

Ile Ala Pro Leu Ser Leu Pro Ser Ser Pro Ser Val Gly Ser Asn
            180                 185                 190

Lys Lys Phe Leu Leu Tyr Leu Ala Gly Phe Val Asp Ser Asp Gly Ser
        195                 200                 205

Ile Ile Ala Gln Ile Arg Pro Asn Gln Ser Ser Lys Phe Lys His Ser
    210                 215                 220

Leu Ser Leu Thr Phe Gln Val Thr Gln Lys Thr Gln Arg Arg Trp Phe
225                 230                 235                 240

Leu Asp Lys Leu Val Asp Arg Ile Gly Val Gly Tyr Val Ala Asp Ser
                245                 250                 255

Gly Ser Val Ser Asn Tyr Arg Leu Gly Glu Ile Lys Pro Leu His Asn
            260                 265                 270

Phe Leu Thr Gln Leu Gln Pro Phe Leu Lys Leu Lys Gln Lys Gln Ala
        275                 280                 285

Asn Leu Val Leu Lys Ile Ile Glu Gln Leu Pro Ser Ala Lys Lys Ser
290                 295                 300

Pro Asp Lys Phe Leu Glu Val Cys Thr Trp Val Asp Gln Val Ala Ala
305                 310                 315                 320

Leu Asn Asp Ser Lys Thr Arg Lys Thr Thr Ser Glu Thr Val Arg Ala
                325                 330                 335

Val Leu Asp Ser Leu Ser Glu Lys Lys Ser Ser Pro
            340                 345
```

<210> SEQ ID NO 197
<211> LENGTH: 349
<212> TYPE: PRT
<213> ORGANISM: artificial sequence
<220> FEATURE:
<223> OTHER INFORMATION: SCOH-SH115-pCLS7532

<400> SEQUENCE: 197

```
Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Cys Lys Phe Lys His Ala Leu Ser Leu Thr Phe Gln Val Thr Gln
        35                  40                  45

Lys Thr Gln Arg Arg Trp Leu Leu Asp Lys Leu Val Asp Glu Ile Gly
    50                  55                  60

Val Gly Tyr Val Arg Asp Ser Gly Ser Val Ser His Tyr Tyr Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110
```

Leu Pro Ser Ala Lys Glu Ser Pro Asp Lys Phe Leu Glu Val Cys Thr
            115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Asp Ser Ser Val Ser Asn Ser Glu His
                165                 170                 175

Ile Ala Pro Leu Ser Leu Pro Ser Pro Ser Val Gly Ser Asn
            180                 185                 190

Lys Lys Phe Leu Leu Tyr Leu Ala Gly Phe Val Asp Ser Asp Gly Ser
    195                 200                 205

Ile Val Ala Gln Ile Lys Pro Asn Gln Ser Cys Lys Phe Lys His Ser
    210                 215                 220

Leu Ser Leu Thr Phe Ile Val Thr Gln Lys Thr Arg Arg Trp Phe
225                 230                 235                 240

Leu Asp Lys Leu Val Asp Arg Ile Gly Val Gly Tyr Val Arg Asp Ser
                245                 250                 255

Gly Ser Val Ser Asn Tyr Arg Leu Gly Glu Ile Lys Pro Leu His Asn
                260                 265                 270

Phe Leu Thr Gln Leu Gln Pro Phe Leu Lys Leu Lys Gln Lys Gln Ala
    275                 280                 285

Asn Leu Ala Leu Lys Ile Ile Glu Gln Leu Pro Ser Ala Lys Glu Ser
290                 295                 300

Pro Asp Lys Phe Leu Glu Val Cys Thr Trp Val Asp Gln Val Ala Ala
305                 310                 315                 320

Leu Asn Asp Ser Lys Thr Arg Lys Thr Thr Ser Glu Thr Val Arg Ala
                325                 330                 335

Val Leu Asp Ser Leu Ser Glu Lys Lys Ser Ser Pro
                340                 345

<210> SEQ ID NO 198
<211> LENGTH: 349
<212> TYPE: PRT
<213> ORGANISM: artificial sequence
<220> FEATURE:
<223> OTHER INFORMATION: SCOH-SH121-pCLS7538

<400> SEQUENCE: 198

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
                20                  25                  30

Ser His Lys Phe Lys His Ala Leu Ser Leu Thr Phe Gln Val Thr Gln
            35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser His Tyr Tyr Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

```
Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Asp Ser Val Ser Asn Ser Glu His
                165                 170                 175

Ile Ala Pro Leu Ser Leu Pro Ser Ser Pro Ser Val Gly Ser Asn
            180                 185                 190

Lys Lys Phe Leu Leu Tyr Leu Ala Gly Phe Val Asp Ser Asp Gly Ser
        195                 200                 205

Ile Ile Ala Gln Ile Lys Pro Asn Gln Ser Ser Lys Phe Lys His Ser
    210                 215                 220

Leu Ser Leu Thr Phe Asn Val Thr Gln Lys Thr Gln Arg Arg Trp Phe
225                 230                 235                 240

Leu Asp Lys Leu Val Asp Arg Ile Gly Val Gly Tyr Val Tyr Asp Ser
            245                 250                 255

Gly Ser Val Ser Tyr Tyr Asn Leu Ser Glu Ile Lys Pro Leu His Asn
                260                 265                 270

Phe Leu Thr Gln Leu Gln Pro Phe Leu Lys Leu Lys Gln Lys Gln Ala
            275                 280                 285

Asn Leu Val Leu Lys Ile Ile Glu Gln Leu Pro Ser Ala Lys Glu Ser
    290                 295                 300

Pro Asp Lys Phe Leu Glu Val Cys Thr Trp Val Asp Gln Val Ala Ala
305                 310                 315                 320

Leu Asn Asp Ser Lys Thr Arg Lys Thr Thr Ser Glu Thr Val Arg Ala
            325                 330                 335

Val Leu Asp Ser Leu Ser Glu Lys Lys Lys Ser Ser Pro
                340                 345
```

<210> SEQ ID NO 199
<211> LENGTH: 349
<212> TYPE: PRT
<213> ORGANISM: artificial sequence
<220> FEATURE:
<223> OTHER INFORMATION: SCOH-SH120-pCLS7537

<400> SEQUENCE: 199

```
Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
                20                  25                  30

Ser Cys Lys Phe Lys His Ala Leu Ser Leu Thr Phe Gln Val Thr Gln
            35                  40                  45

Lys Thr Gln Arg Arg Trp Phe Leu Asp Lys Leu Val Asp Glu Ile Gly
50                  55                  60

Val Gly Tyr Val Thr Asp Arg Gly Ser Val Ser Asp Tyr His Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
            130                 135                 140
```

```
Thr Ser Glu Thr Val Arg Ala Val Leu Asp Ser Leu Ser Glu Lys Lys
145                 150                 155                 160

Lys Ser Ser Pro Ala Ala Gly Asp Ser Ser Val Ser Asn Ser Glu His
                165                 170                 175

Ile Ala Pro Leu Ser Leu Pro Ser Ser Pro Ser Val Gly Ser Asn
            180                 185                 190

Lys Lys Phe Leu Leu Tyr Leu Ala Gly Phe Val Asp Ser Asp Gly Ser
        195                 200                 205

Ile Ile Ala Gln Ile Lys Pro Gly Gln Ser Tyr Lys Phe Lys His Gln
            210                 215                 220

Leu Tyr Leu Thr Phe Gln Val Thr Gln Lys Thr Gln Arg Arg Trp Leu
225                 230                 235                 240

Leu Asp Lys Leu Val Asp Arg Ile Gly Val Gly Tyr Val Arg Asp Ser
                245                 250                 255

Gly Ser Val Ser Asn Tyr Ile Leu Ser Glu Ile Lys Pro Leu His Asn
                260                 265                 270

Phe Leu Thr Gln Leu Gln Pro Phe Leu Lys Leu Lys Gln Lys Gln Ala
            275                 280                 285

Asn Leu Val Leu Lys Ile Ile Glu Gln Leu Pro Ser Ala Lys Glu Ser
290                 295                 300

Pro Asp Lys Phe Leu Glu Val Cys Thr Trp Val Asp Gln Val Ala Ala
305                 310                 315                 320

Leu Asn Asp Ser Lys Thr Arg Lys Thr Thr Ser Glu Thr Val Arg Ala
                325                 330                 335

Val Leu Asp Ser Leu Ser Glu Lys Lys Ser Ser Pro
                340                 345

<210> SEQ ID NO 200
<211> LENGTH: 349
<212> TYPE: PRT
<213> ORGANISM: artificial sequence
<220> FEATURE:
<223> OTHER INFORMATION: SCOH-SH122-pCLS7539

<400> SEQUENCE: 200

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Gly Gln
                20                  25                  30

Ser Tyr Lys Phe Lys His Arg Leu Ser Leu Thr Phe Gln Val Thr Gln
            35                  40                  45

Lys Thr Gln Arg Arg Trp Phe Leu Asp Lys Leu Val Asp Glu Ile Gly
        50                  55                  60

Val Gly Tyr Val Arg Asp Asp Gly Ser Val Ser Asn Tyr Ile Leu Ser
65                  70                  75                  80

Glu Thr Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Gly Leu Ser Glu Lys Lys
145                 150                 155                 160
```

```
Lys Ser Ser Pro Ala Ala Gly Asp Ser Ser Val Ser Asn Ser Glu His
            165                 170                 175

Ile Ala Pro Leu Ser Leu Pro Ser Ser Pro Ser Val Gly Ser Asn
        180                 185                 190

Lys Lys Phe Leu Leu Tyr Leu Ala Gly Phe Val Asp Ser Asp Gly Ser
        195                 200                 205

Ile Ile Ala Gln Ile Lys Pro Asn Gln Ser His Lys Phe Lys His Gln
210                 215                 220

Leu Ser Leu Thr Phe Ala Val Thr Gln Lys Thr Gln Arg Arg Trp Phe
225                 230                 235                 240

Leu Asp Lys Leu Val Asp Arg Ile Gly Val Gly Tyr Val Arg Asp Ser
                245                 250                 255

Gly Ser Val Ser Tyr Tyr Val Leu Ser Glu Ile Lys Pro Leu His Asn
                260                 265                 270

Phe Leu Thr Gln Leu Gln Pro Phe Leu Lys Leu Lys Gln Lys Gln Ala
            275                 280                 285

Asn Leu Val Leu Lys Ile Ile Glu Gln Leu Pro Ser Ala Lys Glu Ser
            290                 295                 300

Pro Asp Lys Phe Leu Glu Val Cys Thr Trp Val Asp Gln Val Ala Ala
305                 310                 315                 320

Leu Asn Asp Ser Lys Thr Arg Lys Thr Thr Ser Glu Thr Val Arg Ala
                325                 330                 335

Val Leu Asp Ser Leu Ser Glu Lys Lys Ser Ser Pro
            340                 345

<210> SEQ ID NO 201
<211> LENGTH: 349
<212> TYPE: PRT
<213> ORGANISM: artificial sequence
<220> FEATURE:
<223> OTHER INFORMATION: SCOH-SH117-pCLS7534

<400> SEQUENCE: 201

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Thr Lys Phe Lys His Ala Leu Ser Leu Thr Phe Gln Val Thr Gln
        35                  40                  45

Lys Ala Gln Arg Arg Trp Phe Leu Asp Lys Leu Val Asp Glu Ile Gly
    50                  55                  60

Val Gly His Val Tyr Asp Ser Gly Ser Val Ser Tyr Tyr Arg Leu Ser
65                  70                  75                  80

Glu Ile Lys Pro Gln His Asn Phe Leu Thr Gln Leu Gln Pro Phe Leu
                85                  90                  95

Glu Leu Lys Gln Lys Gln Ala Asn Leu Ala Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Asp Ser Ser Val Ser Asn Ser Glu His
                165                 170                 175
```

Ile Ala Pro Leu Ser Leu Pro Ser Ser Pro Ser Val Gly Ser Asn
            180                 185                 190

Lys Lys Phe Leu Leu Tyr Leu Ala Gly Phe Val Asp Ser Asp Gly Ser
        195                 200                 205

Ile Ile Ala Gln Ile Lys Pro Arg Gln Thr Tyr Lys Phe Lys His Gln
        210                 215                 220

Leu Ser Leu Thr Phe Lys Val Thr Gln Lys Thr Gln Arg Arg Trp Leu
225                 230                 235                 240

Leu Asp Lys Leu Val Asp Arg Ile Gly Val Gly Tyr Val Ser Asp Ser
                245                 250                 255

Gly Ser Val Ser Asn Tyr Val Leu Ser Glu Ile Lys Pro Leu His Asn
            260                 265                 270

Phe Leu Thr Gln Leu Gln Pro Phe Leu Lys Leu Lys Gln Lys Gln Ala
        275                 280                 285

Asn Leu Val Leu Lys Ile Ile Glu Gln Leu Pro Ser Ala Lys Glu Ser
    290                 295                 300

Pro Asp Lys Phe Leu Glu Val Cys Thr Trp Val Asp Gln Val Ala Ala
305                 310                 315                 320

Leu Asn Asp Ser Lys Thr Arg Lys Thr Thr Ser Glu Thr Val Arg Ala
                325                 330                 335

Val Leu Asp Ser Leu Gly Glu Lys Lys Lys Ser Ser Pro
            340                 345

<210> SEQ ID NO 202
<211> LENGTH: 349
<212> TYPE: PRT
<213> ORGANISM: artificial sequence
<220> FEATURE:
<223> OTHER INFORMATION: SCOH-SH118-pCLS7535

<400> SEQUENCE: 202

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Asn Gly Lys Phe Lys His Gln Leu Ser Leu Thr Phe Lys Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Asp Tyr Thr Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Asp Ser Ser Val Ser Asn Ser Glu His
                165                 170                 175

Ile Ala Pro Leu Ser Leu Pro Ser Ser Pro Ser Val Gly Ser Asn
            180                 185                 190

```
Lys Lys Phe Leu Leu Tyr Leu Ala Gly Phe Val Asp Ser Asp Gly Ser
            195                 200                 205

Ile Ile Ala Gln Ile Arg Pro Asn Arg Ser Ser Lys Phe Lys His Ser
210                 215                 220

Leu Ser Leu Thr Phe Gln Val Thr Gln Lys Thr Gln Arg Arg Trp Phe
225                 230                 235                 240

Leu Asp Lys Leu Val Asp Arg Ile Gly Val Gly Tyr Val Ala Asp Ser
            245                 250                 255

Gly Ser Val Ser Asn Tyr Arg Leu Gly Glu Ile Lys Pro Leu His Asn
            260                 265                 270

Phe Leu Thr Gln Leu Gln Pro Phe Leu Lys Leu Lys Gln Lys Gln Ala
            275                 280                 285

Asn Leu Val Leu Lys Ile Ile Glu Gln Leu Pro Ser Ala Lys Lys Ser
            290                 295                 300

Pro Asp Lys Phe Leu Glu Val Cys Thr Trp Val Asp Gln Val Ala Ala
305                 310                 315                 320

Leu Asn Asp Ser Lys Thr Arg Lys Thr Thr Ser Glu Thr Val Arg Ala
            325                 330                 335

Val Leu Asp Ser Leu Ser Glu Lys Lys Lys Ser Ser Pro
            340                 345

<210> SEQ ID NO 203
<211> LENGTH: 349
<212> TYPE: PRT
<213> ORGANISM: artificial sequence
<220> FEATURE:
<223> OTHER INFORMATION: SCOH-SH119-pCLS7536

<400> SEQUENCE: 203

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Cys Lys Phe Lys His Tyr Leu Ser Leu Thr Phe Ala Val Thr Gln
        35                  40                  45

Lys Thr Gln Arg Arg Trp Phe Leu Asp Lys Leu Val Asp Glu Ile Gly
50                  55                  60

Val Gly Tyr Val Arg Asp Ser Gly Ser Val Ser Tyr Tyr Val Leu Ser
65                  70                  75                  80

Glu Ile Lys Pro Leu His Asn Phe Leu Thr Gln Leu Gln Pro Phe Leu
            85                  90                  95

Glu Leu Lys Gln Lys Gln Ala Asn Leu Val Leu Lys Ile Ile Glu Gln
        100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Asp Ser Ser Val Ser Asn Ser Glu His
                165                 170                 175

Ile Ala Pro Leu Ser Leu Pro Ser Ser Pro Ser Val Gly Ser Asn
            180                 185                 190

Lys Lys Phe Leu Leu Tyr Leu Ala Gly Phe Val Asp Ser Asp Gly Ser
            195                 200                 205
```

Ile Ile Ala Gln Ile Lys Pro Asn Gln Ser Cys Lys Phe Lys His Arg
210                 215                 220

Leu Ser Leu Thr Phe Lys Val Thr Gln Lys Thr Gln Arg Arg Trp Phe
225                 230                 235                 240

Leu Asp Lys Leu Val Asp Arg Ile Gly Val Gly Tyr Val Tyr Asp Ser
            245                 250                 255

Gly Ser Val Ser Asn Tyr Gln Leu Ser Glu Ile Lys Pro Leu His Asn
            260                 265                 270

Phe Leu Thr Gln Leu Gln Pro Phe Leu Lys Leu Lys Gln Lys Gln Ala
        275                 280                 285

Asn Leu Val Leu Lys Ile Ile Glu Gln Leu Pro Ser Ala Lys Glu Ser
290                 295                 300

Pro Asp Lys Phe Leu Glu Val Cys Thr Trp Val Asp Gln Val Ala Ala
305                 310                 315                 320

Leu Asn Asp Ser Lys Thr Arg Lys Thr Thr Ser Glu Thr Val Arg Ala
            325                 330                 335

Val Leu Asp Ser Leu Ser Glu Lys Lys Ser Ser Pro
            340                 345

<210> SEQ ID NO 204
<211> LENGTH: 349
<212> TYPE: PRT
<213> ORGANISM: artificial sequence
<220> FEATURE:
<223> OTHER INFORMATION: SCOH-SH123-pCLS7540

<400> SEQUENCE: 204

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Cys Lys Phe Lys His Tyr Leu Ser Leu Thr Phe Arg Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Asp Tyr Thr Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Asp Ser Ser Val Ser Asn Ser Glu His
                165                 170                 175

Ile Ala Pro Leu Ser Leu Pro Ser Ser Pro Ser Val Gly Ser Asn
            180                 185                 190

Lys Lys Phe Leu Leu Tyr Leu Ala Gly Phe Val Asp Ser Asp Gly Ser
        195                 200                 205

Ile Ile Ala Gln Ile Lys Pro Asn Gln Asp Tyr Lys Phe Lys His Tyr
    210                 215                 220

```
Leu Ser Leu Thr Phe Ala Val Thr Gln Lys Thr Gln Arg Arg Trp Phe
225                 230                 235                 240

Leu Asp Lys Leu Val Asp Arg Ile Gly Val Gly Tyr Val Tyr Gly Ser
                245                 250                 255

Gly Ser Val Ser Tyr Tyr Lys Leu Ser Ala Ile Lys Pro Leu His Asn
            260                 265                 270

Phe Leu Thr Gln Leu Gln Pro Phe Leu Lys Leu Lys Gln Lys Gln Ala
            275                 280                 285

Asn Leu Ala Leu Lys Ile Ile Glu Gln Leu Pro Ser Ala Lys Glu Ser
290                 295                 300

Pro Asp Lys Phe Leu Glu Val Cys Thr Trp Val Asp Gln Val Ala Ala
305                 310                 315                 320

Leu Asn Asp Ser Lys Thr Arg Lys Thr Thr Ser Glu Thr Val Arg Ala
                325                 330                 335

Val Leu Asp Ser Leu Ser Glu Lys Lys Lys Ser Pro Pro
                340                 345
```

<210> SEQ ID NO 205
<211> LENGTH: 349
<212> TYPE: PRT
<213> ORGANISM: artificial sequence
<220> FEATURE:
<223> OTHER INFORMATION: SCOH-SH126-pCLS7543

<400> SEQUENCE: 205

```
Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
                20                  25                  30

Ser Cys Lys Phe Lys His Ala Leu Ser Leu Thr Phe Lys Val Thr Gln
            35                  40                  45

Lys Thr Gln Arg Arg Trp Leu Leu Asp Lys Leu Val Asp Glu Ile Gly
        50                  55                  60

Val Gly Tyr Val Gln Asp Arg Gly Ser Val Ser Asp Tyr Ile Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Asp Ser Val Ser Asn Ser Glu His
            165                 170                 175

Ile Ala Pro Leu Ser Leu Pro Ser Pro Ser Val Gly Ser Asn
        180                 185                 190

Lys Lys Phe Leu Leu Tyr Leu Ala Gly Phe Val Asp Ser Asp Gly Ser
            195                 200                 205

Ile Ile Ala Gln Ile Lys Pro Asn Gln Ser Tyr Lys Phe Lys His Gln
        210                 215                 220

Leu Ser Leu Thr Phe Lys Val Thr Gln Lys Thr Gln Arg Arg Trp Phe
225                 230                 235                 240
```

```
Leu Asp Lys Leu Val Asp Arg Ile Gly Val Gly Tyr Val Tyr Asp Ser
                245                 250                 255

Gly Ser Val Ser Asp Tyr Thr Leu Ser Glu Ile Lys Pro Leu His Asn
            260                 265                 270

Phe Leu Thr Gln Leu Gln Pro Phe Leu Lys Leu Lys Gln Lys Gln Ala
            275                 280                 285

Asn Leu Val Leu Lys Ile Ile Glu Gln Leu Pro Ser Ala Lys Glu Ser
            290                 295                 300

Pro Asp Lys Phe Leu Glu Val Cys Thr Trp Val Asp Gln Val Ala Ala
305                 310                 315                 320

Leu Asn Asp Ser Lys Thr Arg Lys Thr Thr Ser Glu Thr Val Arg Ala
                325                 330                 335

Val Leu Asp Ser Leu Ser Glu Lys Lys Lys Ser Ser Pro
                340                 345
```

<210> SEQ ID NO 206
<211> LENGTH: 349
<212> TYPE: PRT
<213> ORGANISM: artificial sequence
<220> FEATURE:
<223> OTHER INFORMATION: SCOH-SH128-pCLS7545

<400> SEQUENCE: 206

```
Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Thr Cys Lys Phe Lys His Gln Leu Ser Leu Thr Phe Lys Val Thr Gln
        35                  40                  45

Lys Thr Gln Arg Arg Trp Phe Leu Asp Lys Leu Val Asp Glu Ile Gly
 50                  55                  60

Val Gly Tyr Val Gly Asp Arg Gly Ser Val Ser Asp Tyr Tyr Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Asp Ser Ser Val Ser Asn Ser Glu His
                165                 170                 175

Ile Ala Pro Leu Ser Leu Pro Ser Ser Pro Ser Val Gly Ser Asn
            180                 185                 190

Lys Lys Phe Leu Leu Tyr Leu Ala Gly Phe Val Asp Ser Asp Gly Ser
        195                 200                 205

Ile Ile Ala Gln Ile Lys Pro Asn Gln Ser Cys Lys Phe Lys His Tyr
210                 215                 220

Leu Ser Leu Thr Phe Arg Val Thr Gln Lys Thr Gln Arg Arg Trp Phe
225                 230                 235                 240

Leu Asp Lys Leu Val Asp Arg Ile Gly Val Gly Tyr Val Ser Asp Ser
                245                 250                 255
```

```
Gly Ser Val Ser Asn Tyr Asn Leu Ser Glu Ile Lys Pro Leu His Asn
            260                 265                 270

Phe Leu Thr Gln Leu Gln Pro Phe Leu Lys Leu Lys Gln Lys Gln Ala
            275                 280                 285

Asn Leu Val Leu Lys Ile Ile Glu Gln Leu Pro Ser Ala Lys Glu Ser
            290                 295                 300

Pro Asp Lys Phe Leu Glu Val Cys Thr Trp Val Asp Gln Val Ala Ala
305                 310                 315                 320

Leu Asn Asp Ser Lys Thr Arg Lys Thr Thr Ser Glu Thr Val Arg Ala
            325                 330                 335

Val Leu Asp Ser Leu Ser Glu Lys Lys Lys Ser Ser Pro
            340                 345
```

<210> SEQ ID NO 207
<211> LENGTH: 349
<212> TYPE: PRT
<213> ORGANISM: artificial sequence
<220> FEATURE:
<223> OTHER INFORMATION: SCOH-SH129.2-pCLS7547

<400> SEQUENCE: 207

```
Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Thr Cys Lys Phe Lys His Gln Leu Trp Leu Thr Phe Gln Val Thr Gln
            35                  40                  45

Lys Thr Gln Arg Arg Trp Phe Leu Asp Lys Leu Val Asp Glu Ile Gly
    50                  55                  60

Val Gly Tyr Val Arg Asp Arg Gly Ser Val Ser Asp Tyr Ile Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Asp Ser Ser Val Ser Asn Ser Glu His
                165                 170                 175

Ile Ala Pro Leu Ser Leu Pro Ser Ser Pro Ser Val Gly Ser Asn
            180                 185                 190

Lys Lys Phe Leu Leu Tyr Leu Ala Gly Phe Val Asp Ser Asp Gly Ser
            195                 200                 205

Ile Ile Ala Gln Ile Lys Pro Asn Gln Gly Cys Lys Phe Lys His Gln
    210                 215                 220

Leu Ser Leu Thr Phe Gln Val Thr Gln Lys Thr Gln Arg Arg Trp Phe
225                 230                 235                 240

Leu Asp Lys Leu Val Asp Arg Ile Gly Val Gly Tyr Val Arg Asp Arg
                245                 250                 255

Gly Ser Val Ser Asp Tyr Ile Leu Ser Glu Ile Lys Pro Leu His Asn
            260                 265                 270
```

```
Phe Leu Thr Gln Leu Gln Pro Phe Leu Lys Leu Lys Gln Lys Gln Ala
            275                 280                 285

Asn Leu Val Leu Lys Ile Ile Glu Gln Leu Pro Ser Ala Lys Glu Ser
        290                 295                 300

Pro Asp Lys Phe Leu Glu Val Cys Thr Trp Val Asp Gln Val Ala Ala
305                 310                 315                 320

Leu Asn Asp Ser Lys Thr Arg Lys Thr Thr Ser Glu Thr Val Arg Ala
                325                 330                 335

Val Leu Asp Ser Leu Ser Glu Lys Lys Ser Ser Pro
            340                 345
```

<210> SEQ ID NO 208
<211> LENGTH: 349
<212> TYPE: PRT
<213> ORGANISM: artificial sequence
<220> FEATURE:
<223> OTHER INFORMATION: SCOH-SH129-pCLS7546

<400> SEQUENCE: 208

```
Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Thr Cys Lys Phe Lys His Gln Leu Trp Leu Thr Phe Gln Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Arg Gly Ser Val Ser Asp Tyr Ile Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Asp Ser Ser Val Ser Asn Ser Glu His
                165                 170                 175

Ile Ala Pro Leu Ser Leu Pro Ser Pro Ser Val Gly Ser Asn
                180                 185                 190

Lys Lys Phe Leu Leu Tyr Leu Ala Gly Phe Val Asp Ser Asp Gly Ser
            195                 200                 205

Ile Ile Ala Gln Ile Lys Pro Asn Gln Gly Cys Lys Phe Lys His Gln
210                 215                 220

Leu Ser Leu Thr Phe Gln Val Thr Gln Lys Thr Gln Arg Arg Trp Phe
225                 230                 235                 240

Leu Asp Lys Leu Val Asp Arg Ile Gly Val Gly Tyr Val Arg Asp Arg
                245                 250                 255

Gly Ser Val Ser Asn Tyr Ile Leu Ser Glu Ile Lys Pro Leu His Asn
            260                 265                 270

Phe Leu Thr Gln Leu Gln Pro Phe Leu Lys Leu Lys Gln Lys Gln Ala
        275                 280                 285
```

```
Asn Leu Val Leu Lys Ile Ile Glu Gln Leu Pro Ser Ala Lys Glu Ser
    290                 295                 300

Pro Asp Lys Phe Leu Glu Val Cys Thr Trp Val Asp Gln Val Ala Ala
305                 310                 315                 320

Leu Asn Asp Ser Lys Thr Arg Lys Thr Thr Ser Glu Thr Val Arg Ala
                325                 330                 335

Val Leu Asp Ser Leu Ser Glu Lys Lys Lys Ser Ser Pro
                340                 345

<210> SEQ ID NO 209
<211> LENGTH: 349
<212> TYPE: PRT
<213> ORGANISM: artificial sequence
<220> FEATURE:
<223> OTHER INFORMATION: SCOH-SH124-pCLS7541

<400> SEQUENCE: 209

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
                20                  25                  30

Ser Tyr Lys Phe Lys His Gln Leu Ser Leu Thr Phe Gln Val Thr Gln
            35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Asp Ser Ser Val Ser Asn Ser Glu His
                165                 170                 175

Ile Ala Pro Leu Ser Leu Pro Ser Ser Pro Ser Val Gly Ser Asn
            180                 185                 190

Lys Lys Phe Leu Leu Tyr Leu Ala Gly Phe Val Asp Ser Asp Gly Ser
    195                 200                 205

Ile Ile Ala Gln Ile Lys Pro Arg Gln Ser Tyr Lys Phe Lys His Gln
    210                 215                 220

Leu Arg Leu Thr Phe Asn Val Thr Gln Lys Thr Gln Arg Arg Trp Phe
225                 230                 235                 240

Leu Asp Lys Leu Val Asp Arg Ile Gly Val Gly Tyr Val Arg Asp Ser
                245                 250                 255

Gly Ser Val Ser Tyr Tyr Ser Leu Ser Glu Ile Lys Pro Leu His Asn
            260                 265                 270

Phe Leu Thr Gln Leu Gln Pro Phe Leu Lys Leu Lys Gln Lys Gln Ala
        275                 280                 285

Asn Leu Val Leu Lys Ile Ile Glu Gln Leu Pro Ser Ala Lys Glu Ser
    290                 295                 300
```

```
Pro Asp Lys Phe Leu Glu Val Cys Thr Trp Val Asp Gln Val Ala Ala
305                 310                 315                 320

Leu Asn Asp Ser Lys Thr Arg Lys Thr Thr Ser Glu Thr Val Arg Ala
            325                 330                 335

Val Leu Asp Ser Leu Ser Glu Lys Lys Lys Ser Ser Pro
            340                 345
```

<210> SEQ ID NO 210
<211> LENGTH: 349
<212> TYPE: PRT
<213> ORGANISM: artificial sequence
<220> FEATURE:
<223> OTHER INFORMATION: SCOH-SH131-pCLS7549

<400> SEQUENCE: 210

```
Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
                20                  25                  30

Ser Tyr Lys Phe Lys His Gln Leu Ser Leu Thr Phe Ala Val Thr Gln
            35                  40                  45

Lys Thr Gln Arg Arg Trp Phe Leu Asp Lys Leu Val Asp Glu Ile Gly
50                  55                  60

Val Gly Tyr Val Arg Asp Ser Gly Ser Val Ser Tyr Tyr Ile Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Asp Ser Ser Val Ser Asn Ser Glu His
                165                 170                 175

Ile Ala Pro Leu Ser Leu Pro Ser Ser Pro Ser Val Gly Ser Asn
            180                 185                 190

Lys Lys Phe Leu Leu Tyr Leu Ala Gly Phe Val Asp Ser Asp Gly Ser
        195                 200                 205

Ile Ile Ala Gln Ile Lys Pro Asn Gln Gly His Lys Phe Lys His Gln
210                 215                 220

Leu Ser Leu Thr Phe Lys Val Thr Gln Lys Thr Gln Arg Arg Trp Leu
225                 230                 235                 240

Leu Asp Lys Leu Val Asp Arg Ile Gly Val Gly Tyr Val Tyr Asp Ser
                245                 250                 255

Gly Ser Val Ser Tyr Tyr Asn Leu Ser Glu Ile Lys Pro Leu His Asn
            260                 265                 270

Phe Leu Thr Gln Leu Gln Pro Phe Leu Lys Lys Gln Lys Gln Ala
        275                 280                 285

Asn Leu Val Leu Lys Ile Ile Glu His Leu Pro Ser Ala Lys Glu Ser
    290                 295                 300

Pro Asp Lys Phe Leu Glu Val Cys Thr Trp Val Asp Gln Val Ala Ala
305                 310                 315                 320
```

```
Leu Asn Asp Ser Lys Thr Arg Lys Thr Thr Ser Glu Thr Val Arg Ala
            325                 330                 335

Val Leu Asp Ser Leu Ser Glu Lys Lys Ser Ser Pro
        340                 345

<210> SEQ ID NO 211
<211> LENGTH: 349
<212> TYPE: PRT
<213> ORGANISM: artificial sequence
<220> FEATURE:
<223> OTHER INFORMATION: SCOH-SH125-pCLS7542

<400> SEQUENCE: 211

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Ala Gln
            20                  25                  30

Ser Asp Lys Phe Lys His His Leu Ser Leu Thr Phe Lys Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Glu Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Asp Ser Ser Val Ser Asn Ser Glu His
                165                 170                 175

Ile Ala Pro Leu Ser Leu Pro Ser Ser Pro Ser Val Gly Ser Asn
            180                 185                 190

Lys Lys Phe Leu Leu Tyr Leu Ala Gly Phe Val Asp Ser Asp Gly Ser
        195                 200                 205

Ile Ile Ala Gln Ile Glu Pro Asn Gln Ser Tyr Lys Phe Lys His Arg
210                 215                 220

Leu Lys Leu Thr Phe Lys Val Thr Gln Lys Thr Gln Arg Arg Trp Leu
225                 230                 235                 240

Leu Asp Lys Leu Val Asp Arg Ile Gly Val Gly Tyr Val Arg Asp Glu
                245                 250                 255

Gly Ser Val Ser Asn Tyr Ile Leu Ser Glu Val Lys Pro Leu His Asn
            260                 265                 270

Phe Leu Thr Gln Leu Gln Pro Phe Leu Arg Leu Lys Gln Lys Gln Ala
        275                 280                 285

Asn Leu Val Leu Lys Ile Ile Glu Gln Leu Pro Ser Ala Lys Glu Ser
290                 295                 300

Pro Asp Lys Phe Leu Glu Val Cys Thr Trp Val Asp Gln Val Ala Ala
305                 310                 315                 320

Leu Asn Asp Ser Lys Thr Arg Lys Thr Thr Ser Glu Thr Val Arg Ala
            325                 330                 335
```

Val Leu Val Ser Leu Ser Glu Lys Lys Arg Ser Ser Pro
            340                 345

<210> SEQ ID NO 212
<211> LENGTH: 349
<212> TYPE: PRT
<213> ORGANISM: artificial sequence
<220> FEATURE:
<223> OTHER INFORMATION: SCOH-SH127-pCLS7544

<400> SEQUENCE: 212

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Cys Lys Phe Lys His Ala Leu Ser Leu Thr Phe Lys Val Thr Gln
        35                  40                  45

Lys Thr Gln Arg Arg Trp Leu Leu Asp Lys Leu Val Asp Glu Ile Gly
    50                  55                  60

Val Gly Tyr Val Gln Asp Arg Gly Ser Val Ser Asp Tyr Ile Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Asp Ser Val Ser Asn Ser Glu His
                165                 170                 175

Ile Ala Pro Leu Ser Leu Pro Ser Ser Pro Ser Val Gly Ser Asn
        180                 185                 190

Lys Lys Phe Leu Leu Tyr Leu Ala Gly Phe Val Asp Ser Asp Gly Ser
    195                 200                 205

Ile Ile Ala Gln Ile Lys Pro Asn Gln Thr Cys Lys Phe Lys His Gln
    210                 215                 220

Leu Ser Leu Thr Phe Ala Val Thr Gln Lys Thr Gln Arg Arg Trp Phe
225                 230                 235                 240

Leu Asp Lys Leu Val Asp Arg Ile Gly Val Gly Tyr Val Arg Asp Ser
                245                 250                 255

Gly Ser Val Ser Tyr Tyr Thr Leu Ser Glu Ile Lys Pro Leu His Asn
            260                 265                 270

Phe Leu Thr Gln Leu Gln Pro Phe Leu Lys Leu Lys Gln Lys Gln Ala
        275                 280                 285

Asn Leu Val Leu Lys Ile Ile Glu Gln Leu Pro Ser Ala Lys Glu Ser
    290                 295                 300

Pro Asp Lys Phe Leu Glu Val Cys Thr Trp Val Asp Gln Val Ala Ala
305                 310                 315                 320

Leu Asn Asp Ser Lys Thr Arg Lys Thr Thr Ser Glu Thr Val Arg Ala
                325                 330                 335

Val Leu Asp Ser Leu Ser Glu Lys Lys Lys Ser Ser Pro
            340                 345

<210> SEQ ID NO 213
<211> LENGTH: 349
<212> TYPE: PRT
<213> ORGANISM: artificial sequence
<220> FEATURE:
<223> OTHER INFORMATION: SCOH-SH130-pCLS7548

<400> SEQUENCE: 213

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Tyr Lys Phe Lys His Gln Leu Ser Leu Thr Phe Gln Val Thr Gln
        35                  40                  45

Lys Thr Gln Arg Arg Trp Phe Leu Asp Lys Leu Val Asp Glu Ile Gly
    50                  55                  60

Val Gly Tyr Val Asn Asp Asn Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Asp Ser Ser Val Ser Asn Ser Glu His
                165                 170                 175

Ile Ala Pro Leu Ser Leu Pro Ser Ser Pro Ser Val Gly Ser Asn
            180                 185                 190

Lys Lys Phe Leu Leu Tyr Leu Ala Gly Phe Val Asp Ser Asp Gly Ser
        195                 200                 205

Ile Ile Ala Gln Ile Lys Pro Asn Gln Ser His Lys Phe Lys His Gln
    210                 215                 220

Leu Thr Leu Thr Phe Gln Val Thr Gln Lys Thr Gln Arg Arg Trp Phe
225                 230                 235                 240

Leu Asp Lys Leu Val Asp Arg Ile Gly Val Gly Tyr Val Arg Asp Arg
                245                 250                 255

Gly Ser Val Ser Asp Tyr Ile Leu Ser Glu Ile Lys Pro Leu His Asn
            260                 265                 270

Phe Leu Thr Gln Leu Gln Pro Phe Leu Lys Leu Lys Gln Lys Gln Ala
        275                 280                 285

Asn Leu Val Leu Lys Ile Ile Glu Gln Leu Pro Ser Ala Lys Glu Ser
    290                 295                 300

Pro Asp Lys Phe Leu Glu Val Cys Thr Trp Val Asp Gln Val Ala Ala
305                 310                 315                 320

Leu Asn Asp Ser Lys Thr Arg Lys Thr Thr Ser Glu Thr Val Arg Ala
                325                 330                 335

Val Leu Asp Ser Leu Ser Glu Lys Lys Lys Ser Ser Pro
            340                 345

<210> SEQ ID NO 214
<211> LENGTH: 24

-continued

```
<212> TYPE: DNA
<213> ORGANISM: Artificial
<220> FEATURE:
<223> OTHER INFORMATION: SH11

<400> SEQUENCE: 214
agaagcccag gtaaaacagc ctgg                                           24

<210> SEQ ID NO 215
<211> LENGTH: 24
<212> TYPE: DNA
<213> ORGANISM: Artificial
<220> FEATURE:
<223> OTHER INFORMATION: SH12

<400> SEQUENCE: 215
ataaaacaag tcacgttatt ttgg                                           24

<210> SEQ ID NO 216
<211> LENGTH: 24
<212> TYPE: DNA
<213> ORGANISM: Artificial
<220> FEATURE:
<223> OTHER INFORMATION: SH13

<400> SEQUENCE: 216
attacactct ttaagtgatt ttaa                                           24

<210> SEQ ID NO 217
<211> LENGTH: 24
<212> TYPE: DNA
<213> ORGANISM: Artificial
<220> FEATURE:
<223> OTHER INFORMATION: SH17

<400> SEQUENCE: 217
ctaggctgga ttacagcggc ttga                                           24

<210> SEQ ID NO 218
<211> LENGTH: 24
<212> TYPE: DNA
<213> ORGANISM: Artificial
<220> FEATURE:
<223> OTHER INFORMATION: SH19

<400> SEQUENCE: 218
gcaaaacatt gtaagacatg ccaa                                           24

<210> SEQ ID NO 219
<211> LENGTH: 24
<212> TYPE: DNA
<213> ORGANISM: Artificial
<220> FEATURE:
<223> OTHER INFORMATION: SH20

<400> SEQUENCE: 219
gctggctgct tcacattgga gaga                                           24

<210> SEQ ID NO 220
<211> LENGTH: 24
<212> TYPE: DNA
<213> ORGANISM: Artificial
<220> FEATURE:
<223> OTHER INFORMATION: SH21

<400> SEQUENCE: 220
```

```
tagaaatctg ttaaaagaga tgat                                          24

<210> SEQ ID NO 221
<211> LENGTH: 24
<212> TYPE: DNA
<213> ORGANISM: Artificial
<220> FEATURE:
<223> OTHER INFORMATION: SH23

<400> SEQUENCE: 221
tcaaaccatt gtactccagc ctgg                                          24

<210> SEQ ID NO 222
<211> LENGTH: 24
<212> TYPE: DNA
<213> ORGANISM: Artificial
<220> FEATURE:
<223> OTHER INFORMATION: SH33

<400> SEQUENCE: 222
ttttcatcac ttaaagtgtt ttaa                                          24

<210> SEQ ID NO 223
<211> LENGTH: 24
<212> TYPE: DNA
<213> ORGANISM: Artificial
<220> FEATURE:
<223> OTHER INFORMATION: SH34

<400> SEQUENCE: 223
ttttcctgtc ttaccaggtt ttgt                                          24

<210> SEQ ID NO 224
<211> LENGTH: 24
<212> TYPE: DNA
<213> ORGANISM: Artificial
<220> FEATURE:
<223> OTHER INFORMATION: SH40

<400> SEQUENCE: 224
gtcttctgtc ttaagacata aaat                                          24

<210> SEQ ID NO 225
<211> LENGTH: 24
<212> TYPE: DNA
<213> ORGANISM: Artificial
<220> FEATURE:
<223> OTHER INFORMATION: SH53

<400> SEQUENCE: 225 gtaaatgga ttaaagagg gaag                                            24

<210> SEQ ID NO 226
<211> LENGTH: 24
<212> TYPE: DNA
<213> ORGANISM: Artificial
<220> FEATURE:
<223> OTHER INFORMATION: SH54

<400> SEQUENCE: 226
ccaaaacacg ttaaaaagt ttaa                                           24

<210> SEQ ID NO 227
<211> LENGTH: 24
<212> TYPE: DNA
<213> ORGANISM: Artificial
```

<220> FEATURE:
<223> OTHER INFORMATION: SH55

<400> SEQUENCE: 227
ataatattct gtgactcatg gcaa                                              24

<210> SEQ ID NO 228
<211> LENGTH: 24
<212> TYPE: DNA
<213> ORGANISM: Artificial
<220> FEATURE:
<223> OTHER INFORMATION: SH56

<400> SEQUENCE: 228
agtagatctt ttaaaagatt ttaa                                              24

<210> SEQ ID NO 229
<211> LENGTH: 24
<212> TYPE: DNA
<213> ORGANISM: Artificial
<220> FEATURE:
<223> OTHER INFORMATION: SH57

<400> SEQUENCE: 229
ataaaaccac ttaagacata ggaa                                              24

<210> SEQ ID NO 230
<211> LENGTH: 24
<212> TYPE: DNA
<213> ORGANISM: Artificial
<220> FEATURE:
<223> OTHER INFORMATION: SH58

<400> SEQUENCE: 230
acttgctgtc ttaacagaga agat                                              24

<210> SEQ ID NO 231
<211> LENGTH: 24
<212> TYPE: DNA
<213> ORGANISM: Artificial
<220> FEATURE:
<223> OTHER INFORMATION: SH59

<400> SEQUENCE: 231
atgtacctct ttaaaacaga tgaa                                              24

<210> SEQ ID NO 232
<211> LENGTH: 24
<212> TYPE: DNA
<213> ORGANISM: Artificial
<220> FEATURE:
<223> OTHER INFORMATION: SH60

<400> SEQUENCE: 232
ctcttctcct gtgacagagt tctg                                              24

<210> SEQ ID NO 233
<211> LENGTH: 24
<212> TYPE: DNA
<213> ORGANISM: Artificial
<220> FEATURE:
<223> OTHER INFORMATION: SH61

<400> SEQUENCE: 233
tccagcccct gtgacagagt gaga                                              24

<210> SEQ ID NO 234
<211> LENGTH: 24
<212> TYPE: DNA
<213> ORGANISM: Artificial
<220> FEATURE:
<223> OTHER INFORMATION: SH62

<400> SEQUENCE: 234 acaaatatt ttaagggagc caaa                                            24

<210> SEQ ID NO 235
<211> LENGTH: 354
<212> TYPE: PRT
<213> ORGANISM: artificial sequence
<220> FEATURE:
<223> OTHER INFORMATION: SC-SH11-pCLS3895

<400> SEQUENCE: 235

```
Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Glu Pro Asn Gln
            20                  25                  30

Ser Arg Lys Phe Lys His Arg Leu Lys Leu Thr Phe Gln Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Ile Ala Gln Ile Lys Pro Asn Gln His Tyr
    210                 215                 220

Lys Phe Lys His Gln Leu Arg Leu Thr Phe Asn Val Thr Gln Lys Thr
225                 230                 235                 240

Gln Arg Arg Trp Phe Leu Asp Lys Leu Val Asp Arg Ile Gly Val Gly
                245                 250                 255

Tyr Val Tyr Asp Ser Gly Ser Val Ser Tyr Tyr Asn Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300
```

```
Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
            325                 330                 335

Glu Thr Val Arg Ala Val Leu Asp Ser Leu Ser Glu Lys Lys Lys Ser
            340                 345                 350

Ser Pro

<210> SEQ ID NO 236
<211> LENGTH: 354
<212> TYPE: PRT
<213> ORGANISM: artificial sequence
<220> FEATURE:
<223> OTHER INFORMATION: SC-SH11v2-pCLS4664

<400> SEQUENCE: 236

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Glu Pro Asn Gln
            20                  25                  30

Ser Arg Lys Phe Lys His Arg Leu Lys Leu Thr Phe Gln Val Thr Gln
        35                  40                  45

Lys Thr Gln Arg Arg Trp Phe Leu Asp Lys Leu Val Asp Glu Ile Gly
50                  55                  60

Val Gly Tyr Val Arg Asp Ser Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Ile Ala Gln Ile Lys Pro Asn Gln His Tyr
210                 215                 220

Lys Phe Lys His Gln Leu Arg Leu Thr Phe Ala Val Thr Gln Lys Thr
225                 230                 235                 240

Gln Arg Arg Trp Phe Leu Asp Lys Leu Val Asp Arg Ile Gly Val Gly
                245                 250                 255

Tyr Val Tyr Asp Ser Gly Ser Val Ser Tyr Tyr Ile Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
```

```
305                 310                 315                 320
Asp Gln Val Ala Ala Leu Asn Asp Ser Lys Thr Arg Lys Thr Thr Ser
                325                 330                 335
Glu Thr Val Arg Ala Val Leu Gly Ser Leu Ser Glu Lys Lys Lys Ser
                340                 345                 350
Ser Pro

<210> SEQ ID NO 237
<211> LENGTH: 354
<212> TYPE: PRT
<213> ORGANISM: artificial sequence
<220> FEATURE:
<223> OTHER INFORMATION: SC-SH12-pCLS3896

<400> SEQUENCE: 237

Met Ala Asn Thr Lys Tyr Asn Glu Glu Phe Leu Leu Tyr Leu Ala Gly
1               5                   10                  15
Phe Val Asp Gly Asp Gly Ser Ile Val Ala Gln Ile Lys Pro Asn Gln
                20                  25                  30
Ser Tyr Lys Phe Lys His Gln Leu Ser Leu Thr Phe Ala Val Thr Gln
                35                  40                  45
Lys Thr Gln Arg Arg Trp Phe Leu Asp Lys Leu Val Asp Glu Ile Gly
        50                  55                  60
Val Gly Tyr Val Arg Asp Ser Gly Ser Val Ser Tyr Tyr Ile Leu Ser
65              70                  75                  80
Glu Ile Lys Pro Leu His Asn Phe Leu Thr Gln Leu Gln Pro Phe Leu
                85                  90                  95
Glu Leu Lys Gln Lys Gln Ala Asn Leu Val Leu Lys Ile Ile Glu Gln
                100                 105                 110
Leu Pro Ser Ala Lys Glu Ser Pro Asp Lys Phe Leu Glu Val Cys Thr
                115                 120                 125
Trp Val Asp Gln Val Ala Ala Leu Asn Asp Ser Lys Thr Arg Lys Thr
        130                 135                 140
Thr Ser Glu Thr Val Arg Ala Val Leu Asp Ser Leu Ser Glu Lys Lys
145             150                 155                 160
Lys Ser Ser Pro Ala Ala Gly Gly Ser Asp Lys Tyr Asn Gln Ala Leu
                165                 170                 175
Ser Lys Tyr Asn Gln Ala Leu Ser Lys Tyr Asn Gln Ala Leu Ser Gly
                180                 185                 190
Gly Gly Gly Ser Asn Lys Lys Phe Leu Leu Tyr Leu Ala Gly Phe Val
                195                 200                 205
Asp Ser Asp Gly Ser Ile Ile Ala Gln Ile Lys Pro Asn Gln Ser Tyr
        210                 215                 220
Lys Phe Lys His Gln Leu Ser Leu Thr Phe Ile Val Thr Gln Lys Thr
225             230                 235                 240
Gln Arg Arg Trp Phe Leu Asp Lys Leu Val Asp Arg Ile Gly Val Gly
                245                 250                 255
Tyr Val Ser Asp Arg Gly Ser Val Ser Asp Tyr Lys Leu Ser Glu Ile
                260                 265                 270
Lys Pro Leu His Asn Phe Leu Thr Gln Leu Gln Pro Phe Leu Lys Leu
                275                 280                 285
Lys Gln Lys Gln Ala Asn Leu Val Leu Lys Ile Ile Glu Gln Leu Pro
                290                 295                 300
Ser Ala Lys Glu Ser Pro Asp Lys Phe Leu Glu Val Cys Thr Trp Val
305             310                 315                 320
```

```
Asp Gln Val Ala Ala Leu Asn Asp Ser Lys Thr Arg Lys Thr Thr Ser
            325                 330                 335

Glu Thr Val Arg Ala Val Leu Asp Ser Leu Ser Glu Lys Lys Ser
            340                 345                 350

Ser Pro

<210> SEQ ID NO 238
<211> LENGTH: 354
<212> TYPE: PRT
<213> ORGANISM: artificial sequence
<220> FEATURE:
<223> OTHER INFORMATION: SC-SH12-pCLS3915

<400> SEQUENCE: 238

Met Ala Asn Thr Lys Tyr Asn Glu Glu Phe Leu Leu Tyr Leu Ala Gly
1               5                   10                  15

Phe Val Asp Gly Asp Gly Ser Ile Val Ala Gln Ile Lys Pro Asn Gln
            20                  25                  30

Ser Tyr Lys Phe Lys His Gln Leu Ser Leu Thr Phe Ala Val Thr Gln
        35                  40                  45

Lys Thr Gln Arg Arg Trp Phe Leu Asp Lys Leu Val Asp Glu Ile Gly
50                  55                  60

Val Gly Tyr Val Tyr Asp Ser Gly Ser Val Ser Tyr Tyr Ile Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Ile Ala Gln Ile Lys Pro Asn Gln Ser Tyr
210                 215                 220

Lys Phe Lys His Gln Leu Ser Leu Thr Phe Cys Val Thr Gln Lys Thr
225                 230                 235                 240

Gln Arg Arg Trp Phe Leu Asp Lys Leu Val Asp Arg Ile Gly Val Gly
                245                 250                 255

Tyr Val Ser Asp Arg Gly Ser Val Ser Asp Tyr Arg Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320
```

Asp Gln Val Ala Ala Leu Asn Asp Ser Lys Thr Arg Lys Thr Thr Ser
            325                 330                 335

Glu Thr Val Arg Ala Val Leu Asp Ser Leu Ser Glu Lys Lys Ser
            340                 345                 350

Ser Pro

<210> SEQ ID NO 239
<211> LENGTH: 349
<212> TYPE: PRT
<213> ORGANISM: artificial sequence
<220> FEATURE:
<223> OTHER INFORMATION: SCOH SH12-Linker-BQY-pCLS6445

<400> SEQUENCE: 239

Met Ala Asn Thr Lys Tyr Asn Glu Glu Phe Leu Leu Tyr Leu Ala Gly
1               5                   10                  15

Phe Val Asp Gly Asp Gly Ser Ile Val Ala Gln Ile Lys Pro Asn Gln
            20                  25                  30

Ser Tyr Lys Phe Lys His Gln Leu Ser Leu Thr Phe Ala Val Thr Gln
        35                  40                  45

Lys Thr Gln Arg Arg Trp Phe Leu Asp Lys Leu Val Asp Glu Ile Gly
50                  55                  60

Val Gly Tyr Val Arg Asp Ser Gly Ser Val Ser Tyr Tyr Ile Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Asp Ser Ser Val Ser Asn Ser Glu His
                165                 170                 175

Ile Ala Pro Leu Ser Leu Pro Ser Ser Pro Ser Val Gly Ser Asn
            180                 185                 190

Lys Lys Phe Leu Leu Tyr Leu Ala Gly Phe Val Asp Ser Asp Gly Ser
        195                 200                 205

Ile Ile Ala Gln Ile Lys Pro Asn Gln Ser Tyr Lys Phe Lys His Gln
210                 215                 220

Leu Ser Leu Thr Phe Ile Val Thr Gln Lys Thr Gln Arg Arg Trp Phe
225                 230                 235                 240

Leu Asp Lys Leu Val Asp Arg Ile Gly Val Gly Tyr Val Ser Asp Arg
                245                 250                 255

Gly Ser Val Ser Asp Tyr Lys Leu Ser Glu Ile Lys Pro Leu His Asn
            260                 265                 270

Phe Leu Thr Gln Leu Gln Pro Phe Leu Lys Leu Lys Gln Lys Gln Ala
        275                 280                 285

Asn Leu Val Leu Lys Ile Ile Glu Gln Leu Pro Ser Ala Lys Glu Ser
290                 295                 300

Pro Asp Lys Phe Leu Glu Val Cys Thr Trp Val Asp Gln Val Ala Ala
305                 310                 315                 320

Leu Asn Asp Ser Lys Thr Arg Lys Thr Thr Ser Glu Thr Val Arg Ala

Val Leu Asp Ser Leu Ser Glu Lys Lys Lys Ser Ser Pro
         340                 345

<210> SEQ ID NO 240
<211> LENGTH: 354
<212> TYPE: PRT
<213> ORGANISM: artificial sequence
<220> FEATURE:
<223> OTHER INFORMATION: SC-SH13-pCLS3897

<400> SEQUENCE: 240

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Arg Pro Asn Gln
            20                  25                  30

Ser Ser Lys Phe Lys His Tyr Leu Gln Leu Thr Phe Lys Val Thr Gln
        35                  40                  45

Lys Thr Gln Arg Arg Trp Phe Leu Asp Lys Leu Val Asp Glu Ile Gly
    50                  55                  60

Val Gly Tyr Val Gly Asp Thr Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Ser Asn Lys Lys Phe Leu Leu Tyr Leu Ala Gly Phe Val
        195                 200                 205

Asp Ser Asp Gly Ser Ile Ile Ala Gln Ile Lys Pro Asn Gln Ser Tyr
    210                 215                 220

Lys Phe Lys His Gln Leu Ser Leu Thr Phe Cys Val Thr Gln Lys Thr
225                 230                 235                 240

Gln Arg Arg Trp Phe Leu Asp Lys Leu Val Asp Arg Ile Gly Val Gly
                245                 250                 255

Tyr Val Ser Asp Arg Gly Ser Val Ser Asp Tyr Arg Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser

Ser Pro

<210> SEQ ID NO 241
<211> LENGTH: 349
<212> TYPE: PRT
<213> ORGANISM: artificial sequence
<220> FEATURE:
<223> OTHER INFORMATION: SCOH SH13-Linker-BQY-p1853-pCLS6446

<400> SEQUENCE: 241

```
Met Ala Asn Thr Lys Tyr Asn Glu Glu Phe Leu Leu Tyr Leu Ala Gly
1               5                  10                  15

Phe Val Asp Gly Asp Gly Ser Ile Ile Ala Gln Ile Arg Pro Asn Gln
            20                  25                  30

Ser Ser Lys Phe Lys His Tyr Leu Gln Leu Thr Phe Lys Val Thr Gln
        35                  40                  45

Lys Thr Gln Arg Arg Trp Phe Leu Asp Lys Leu Val Asp Glu Ile Gly
    50                  55                  60

Val Gly Tyr Val Gly Asp Thr Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Asp Ser Ser Val Ser Asn Ser Glu His
                165                 170                 175

Ile Ala Pro Leu Ser Leu Pro Ser Ser Pro Ser Val Gly Ser Asn
            180                 185                 190

Lys Lys Phe Leu Leu Tyr Leu Ala Gly Phe Val Asp Ser Asp Gly Ser
        195                 200                 205

Ile Ile Ala Gln Ile Lys Pro Asn Gln Ser Tyr Lys Phe Lys His Gln
    210                 215                 220

Leu Ser Leu Thr Phe Cys Val Thr Gln Lys Thr Gln Arg Arg Trp Phe
225                 230                 235                 240

Leu Asp Lys Leu Val Asp Arg Ile Gly Val Gly Tyr Val Ser Asp Arg
                245                 250                 255

Gly Ser Val Ser Asp Tyr Arg Leu Ser Glu Ile Lys Pro Leu His Asn
            260                 265                 270

Phe Leu Thr Gln Leu Gln Pro Phe Leu Lys Leu Lys Gln Lys Gln Ala
        275                 280                 285

Asn Leu Val Leu Lys Ile Ile Glu Gln Leu Pro Ser Ala Lys Glu Ser
    290                 295                 300

Pro Asp Lys Phe Leu Glu Val Cys Thr Trp Val Asp Gln Val Ala Ala
305                 310                 315                 320

Leu Asn Asp Ser Lys Thr Arg Lys Thr Thr Ser Glu Thr Val Arg Ala
                325                 330                 335

Val Leu Asp Ser Leu Ser Glu Lys Lys Ser Ser Pro
            340                 345
```

<210> SEQ ID NO 242
<211> LENGTH: 354
<212> TYPE: PRT
<213> ORGANISM: artificial sequence
<220> FEATURE:
<223> OTHER INFORMATION: SC-SH17-pCLS3898

<400> SEQUENCE: 242

```
Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Gly Gln
                20                  25                  30

Ser Tyr Lys Phe Lys His Arg Leu Ser Leu Thr Phe Ser Val Gly Gln
            35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Met Ser Glu Tyr Cys Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
            115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
                180                 185                 190

Gly Gly Gly Ser Asn Lys Lys Phe Leu Leu Tyr Leu Ala Gly Phe Val
            195                 200                 205

Asp Ser Asp Gly Ser Ile Ile Ala Gln Ile Lys Pro Asn Gln Ser Tyr
    210                 215                 220

Lys Phe Lys His Gln Leu Ser Leu Thr Phe Arg Val Thr Gln Lys Thr
225                 230                 235                 240

Gln Arg Arg Trp Phe Leu Asp Lys Leu Val Asp Arg Ile Gly Val Gly
                245                 250                 255

Tyr Val Tyr Asp Ser Gly Ser Val Ser Asn Tyr Asn Leu Ser Glu Ile
                260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Gly Leu Gly Glu Lys Lys Lys Ser
            340                 345                 350

Ser Pro
```

```
<210> SEQ ID NO 243
<211> LENGTH: 354
<212> TYPE: PRT
<213> ORGANISM: artificial sequence
<220> FEATURE:
<223> OTHER INFORMATION: SC-SH19-pCLS3899

<400> SEQUENCE: 243

Met Ala Asn Thr Lys Tyr Asn Glu Glu Phe Leu Leu Tyr Leu Ala Gly
1               5                   10                  15

Phe Val Asp Gly Asp Gly Ser Ile Val Ala Gln Ile Lys Pro Asn Gln
                20                  25                  30

Ser Tyr Lys Phe Lys His Gln Leu Ser Leu Thr Phe Leu Val Thr Gln
            35                  40                  45

Lys Thr Gln Arg Arg Trp Phe Leu Asp Lys Leu Val Asp Glu Ile Gly
    50                  55                  60

Val Gly Tyr Val Arg Asp Asn Gly Ser Val Ser Asn Tyr Ile Leu Ser
65                  70                  75                  80

Lys Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
            115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
                180                 185                 190

Gly Gly Gly Ser Asn Lys Lys Phe Leu Leu Tyr Leu Ala Gly Phe Val
            195                 200                 205

Asp Ser Asp Gly Ser Ile Ile Ala Gln Ile Lys Pro Asn Gln Thr His
    210                 215                 220

Lys Phe Lys His Gln Leu Ser Leu Thr Phe Gln Val Thr Gln Lys Thr
225                 230                 235                 240

Gln Arg Arg Trp Phe Leu Asp Lys Leu Val Asp Arg Ile Gly Val Gly
                245                 250                 255

Tyr Val Arg Asp Arg Gly Ser Val Ser Asp Tyr Ile Leu Ser Glu Ile
                260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
                340                 345                 350

Ser Pro
```

```
<210> SEQ ID NO 244
<211> LENGTH: 354
<212> TYPE: PRT
<213> ORGANISM: artificial sequence
<220> FEATURE:
<223> OTHER INFORMATION: SC-SH19-5new-pCLS7278

<400> SEQUENCE: 244

Met Ala Asn Thr Lys Tyr Asn Glu Glu Phe Leu Leu Tyr Leu Ala Gly
1               5                   10                  15

Phe Val Asp Gly Asp Gly Ser Ile Val Ala Gln Ile Lys Pro Asn Gln
            20                  25                  30

Ser Tyr Lys Phe Lys His Gln Leu Ser Leu Thr Phe Ile Val Thr Gln
        35                  40                  45

Lys Thr Gln Arg Arg Trp Phe Leu Asp Lys Leu Val Asp Glu Ile Gly
50                  55                  60

Val Gly Tyr Val Arg Asp Ser Gly Ser Val Ser Asn Tyr Arg Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Ile Ala Gln Ile Lys Pro Asn Gln Thr His
210                 215                 220

Lys Phe Lys His Gln Leu Ser Leu Thr Phe Gln Val Thr Gln Lys Thr
225                 230                 235                 240

Gln Arg Arg Trp Phe Leu Asp Lys Leu Val Asp Arg Ile Gly Val Gly
                245                 250                 255

Tyr Val Arg Asp Arg Gly Ser Val Ser Asp Tyr Ile Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 245
```

<211> LENGTH: 354
<212> TYPE: PRT
<213> ORGANISM: artificial sequence
<220> FEATURE:
<223> OTHER INFORMATION: SC-SH19-10new-pCLS7279

<400> SEQUENCE: 245

Met Ala Asn Thr Lys Tyr Asn Glu Glu Phe Leu Leu Tyr Leu Ala Gly
1               5                   10                  15

Phe Val Asp Gly Asp Gly Ser Ile Val Ala Gln Ile Lys Pro Asn Gln
            20                  25                  30

Ser Tyr Lys Phe Lys His Gln Leu Ser Leu Thr Phe Leu Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Asn Gly Ser Val Ser Asn Tyr Ile Leu Ser
65                  70                  75                  80

Lys Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Ile Ala Gln Ile Lys Pro Asn Gln Ser His
    210                 215                 220

Lys Phe Lys His Gln Leu Glu Leu Thr Phe Gln Val Thr Gln Lys Thr
225                 230                 235                 240

Gln Arg Arg Trp Phe Leu Asp Lys Leu Val Asp Arg Ile Gly Val Gly
                245                 250                 255

Tyr Val Arg Asp Arg Gly Ser Val Ser Asp Tyr Ile Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 246
<211> LENGTH: 354

```
<212> TYPE: PRT
<213> ORGANISM: artificial sequence
<220> FEATURE:
<223> OTHER INFORMATION: SC-SH20-pCLS3900

<400> SEQUENCE: 246
```

| | | | | | | | | | | | | | | |
|---|---|---|---|---|---|---|---|---|---|---|---|---|---|---|
| Met | Ala | Asn | Thr | Lys | Tyr | Asn | Glu | Glu | Phe | Leu | Leu | Tyr | Leu | Ala | Gly |
| 1 | | | | 5 | | | | | 10 | | | | | 15 | |
| Phe | Val | Asp | Gly | Asp | Gly | Ser | Ile | Ile | Ala | Gln | Ile | Lys | Pro | Asn | Gln |
| | | | 20 | | | | | 25 | | | | | 30 | | |
| Ser | Cys | Lys | Phe | Lys | His | Tyr | Leu | Ser | Leu | Thr | Phe | Asn | Val | Thr | Gln |
| | | 35 | | | | | 40 | | | | | 45 | | | |
| Lys | Thr | Gln | Arg | Arg | Trp | Phe | Leu | Asp | Lys | Leu | Val | Asp | Glu | Ile | Gly |
| 50 | | | | | 55 | | | | | 60 | | | | | |
| Val | Gly | Tyr | Val | Tyr | Asp | Ser | Gly | Ser | Val | Ser | Tyr | Tyr | Asn | Leu | Ser |
| 65 | | | | | 70 | | | | | 75 | | | | | 80 |
| Glu | Ile | Lys | Pro | Leu | His | Asn | Phe | Leu | Thr | Gln | Leu | Gln | Pro | Phe | Leu |
| | | | | 85 | | | | | 90 | | | | | 95 | |
| Glu | Leu | Lys | Gln | Lys | Gln | Ala | Asn | Leu | Val | Leu | Lys | Ile | Ile | Glu | Gln |
| | | | 100 | | | | | 105 | | | | | 110 | | |
| Leu | Pro | Ser | Ala | Lys | Glu | Ser | Pro | Asp | Lys | Phe | Leu | Glu | Val | Cys | Thr |
| | | | 115 | | | | | 120 | | | | | 125 | | |
| Trp | Val | Asp | Gln | Val | Ala | Ala | Leu | Asn | Asp | Ser | Lys | Thr | Arg | Lys | Thr |
| 130 | | | | | 135 | | | | | 140 | | | | | |
| Thr | Ser | Glu | Thr | Val | Arg | Ala | Val | Leu | Asp | Ser | Leu | Ser | Glu | Lys | Lys |
| 145 | | | | | 150 | | | | | 155 | | | | | 160 |
| Lys | Ser | Ser | Pro | Ala | Ala | Gly | Gly | Ser | Asp | Lys | Tyr | Asn | Gln | Ala | Leu |
| | | | | 165 | | | | | 170 | | | | | 175 | |
| Ser | Lys | Tyr | Asn | Gln | Ala | Leu | Ser | Lys | Tyr | Asn | Gln | Ala | Leu | Ser | Gly |
| | | | 180 | | | | | 185 | | | | | 190 | | |
| Gly | Gly | Gly | Ser | Asn | Lys | Lys | Phe | Leu | Leu | Tyr | Leu | Ala | Gly | Phe | Val |
| | | | 195 | | | | | 200 | | | | | 205 | | |
| Asp | Ser | Asp | Gly | Ser | Ile | Ile | Ala | Gln | Ile | Lys | Pro | Asn | Gln | Ser | Cys |
| | | 210 | | | | | 215 | | | | | 220 | | | |
| Lys | Phe | Lys | His | Ser | Leu | Ser | Leu | Thr | Phe | Arg | Val | Thr | Gln | Lys | Thr |
| 225 | | | | | 230 | | | | | 235 | | | | | 240 |
| Gln | Arg | Arg | Trp | Phe | Leu | Asp | Lys | Leu | Val | Asp | Arg | Ile | Gly | Val | Gly |
| | | | | 245 | | | | | 250 | | | | | 255 | |
| Tyr | Val | Tyr | Asp | Ser | Gly | Ser | Val | Ser | Asn | Tyr | Asn | Leu | Ser | Glu | Ile |
| | | | 260 | | | | | 265 | | | | | 270 | | |
| Lys | Pro | Leu | His | Asn | Phe | Leu | Thr | Gln | Leu | Gln | Pro | Phe | Leu | Lys | Leu |
| | | | | 275 | | | | | 280 | | | | | 285 | |
| Lys | Gln | Lys | Gln | Ala | Asn | Leu | Val | Leu | Lys | Ile | Ile | Glu | Gln | Leu | Pro |
| | | 290 | | | | | 295 | | | | | 300 | | | |
| Ser | Ala | Lys | Glu | Ser | Pro | Asp | Lys | Phe | Leu | Glu | Val | Cys | Thr | Trp | Val |
| 305 | | | | | 310 | | | | | 315 | | | | | 320 |
| Asp | Gln | Val | Ala | Ala | Leu | Asn | Asp | Ser | Lys | Thr | Arg | Lys | Thr | Thr | Ser |
| | | | | 325 | | | | | 330 | | | | | 335 | |
| Glu | Thr | Val | Arg | Ala | Val | Leu | Asp | Ser | Leu | Ser | Glu | Lys | Lys | Lys | Ser |
| | | | 340 | | | | | 345 | | | | | 350 | | |
| Ser | Pro | | | | | | | | | | | | | | |

```
<210> SEQ ID NO 247
<211> LENGTH: 354
<212> TYPE: PRT
```

<213> ORGANISM: artificial sequence
<220> FEATURE:
<223> OTHER INFORMATION: SC-SH21-pCLS3901

<400> SEQUENCE: 247

```
Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Thr Cys Lys Phe Lys His Gln Leu Ser Leu Thr Phe Arg Val Thr Gln
        35                  40                  45

Lys Thr Gln Arg Arg Trp Phe Leu Asp Lys Leu Val Asp Glu Ile Gly
50                  55                  60

Val Gly Tyr Val Tyr Asp Ser Gly Ser Val Ser Asn Tyr Asn Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Ile Ala Gln Ile Lys Pro Asn Arg Ser His
210                 215                 220

Lys Phe Lys His Gln Leu Gln Leu Thr Phe Lys Val Thr Gln Lys Thr
225                 230                 235                 240

Gln Arg Arg Trp Phe Leu Asp Lys Leu Val Asp Arg Ile Gly Val Gly
                245                 250                 255

Tyr Val Tyr Asp Ser Gly Ser Val Ser Glu Tyr Val Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
290                 295                 300

Ser Ala Lys Gly Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Asn Leu Ser Glu Lys Lys Lys Ser
            340                 345                 350

Ser Pro
```

<210> SEQ ID NO 248
<211> LENGTH: 354
<212> TYPE: PRT
<213> ORGANISM: artificial sequence

```
<220> FEATURE:
<223> OTHER INFORMATION: SC-SH21v2-pCLS4666

<400> SEQUENCE: 248

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Thr Cys Lys Phe Lys His Gln Leu Ser Leu Thr Phe Arg Val Thr Gln
        35                  40                  45

Lys Thr Gln Arg Arg Trp Leu Leu Asp Lys Leu Val Asp Glu Ile Gly
    50                  55                  60

Val Gly Tyr Val Tyr Asp Ser Gly Ser Val Ser Asn Tyr Asn Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Ile Ala Gln Ile Lys Pro Asn Arg Ser His
    210                 215                 220

Lys Phe Lys His Gln Leu Gln Leu Thr Phe Lys Val Thr Gln Lys Thr
225                 230                 235                 240

Gln Arg Arg Trp Phe Leu Asp Lys Leu Val Asp Arg Ile Gly Val Gly
                245                 250                 255

Tyr Val Tyr Asp Ser Gly Ser Val Ser Glu Tyr Val Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Gly Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Asn Leu Ser Glu Lys Lys Lys Ser
            340                 345                 350

Ser Pro

<210> SEQ ID NO 249
<211> LENGTH: 354
<212> TYPE: PRT
<213> ORGANISM: artificial sequence
<220> FEATURE:
```

<223> OTHER INFORMATION: SC-SH21v3-pCLS4667

<400> SEQUENCE: 249

```
Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Thr Cys Lys Phe Lys His Gln Leu Ser Leu Thr Phe Arg Val Thr Gln
        35                  40                  45

Lys Thr Gln Arg Arg Trp Leu Leu Asp Lys Leu Val Asp Glu Ile Gly
    50                  55                  60

Val Gly Tyr Val Tyr Asp Ser Gly Ser Val Ser Asn Tyr Asn Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Ile Ala Gln Ile Lys Pro Asn Gln Ser His
210                 215                 220

Lys Phe Lys His Gln Leu Gln Leu Thr Phe Lys Val Thr Gln Lys Thr
225                 230                 235                 240

Gln Arg Arg Trp Phe Leu Asp Lys Leu Val Asp Arg Ile Gly Val Gly
                245                 250                 255

Tyr Val Tyr Asp Ser Gly Ser Val Ser Glu Tyr Val Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Gly Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Asn Leu Ser Glu Lys Lys Lys Ser
            340                 345                 350

Ser Pro
```

<210> SEQ ID NO 250
<211> LENGTH: 354
<212> TYPE: PRT
<213> ORGANISM: artificial sequence
<220> FEATURE:
<223> OTHER INFORMATION: SC-SH23-pCLS3902

<400> SEQUENCE: 250

```
Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Gly Gln
                20                  25                  30

Ser Tyr Lys Phe Lys His Arg Leu Ser Leu Thr Phe Ser Val Gly Gln
            35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Met Ser Glu Tyr Cys Leu Ser
65              70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Val Ala Gln Ile Lys Pro Asn Gln Ser Tyr
    210                 215                 220

Lys Phe Lys His Gln Leu Ser Leu Thr Phe Leu Val Thr Gln Lys Thr
225                 230                 235                 240

Gln Arg Arg Trp Phe Leu Asp Lys Leu Val Asp Arg Ile Gly Val Gly
                245                 250                 255

Tyr Val Arg Asp Asn Gly Ser Val Ser Asn Tyr Ile Leu Ser Lys Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro
```

<210> SEQ ID NO 251
<211> LENGTH: 349
<212> TYPE: PRT
<213> ORGANISM: artificial sequence
<220> FEATURE:
<223> OTHER INFORMATION: SCOH SH23-Linker-BQY-p1853-pCLS6447

<400> SEQUENCE: 251

```
Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Gly Gln
            20                  25                  30

Ser Tyr Lys Phe Lys His Arg Leu Ser Leu Thr Phe Ser Val Gly Gln
        35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Met Ser Glu Tyr Cys Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Asp Ser Ser Val Ser Asn Ser Glu His
                165                 170                 175

Ile Ala Pro Leu Ser Leu Pro Ser Ser Pro Ser Val Gly Ser Asn
            180                 185                 190

Lys Lys Phe Leu Leu Tyr Leu Ala Gly Phe Val Asp Ser Asp Gly Ser
        195                 200                 205

Ile Val Ala Gln Ile Lys Pro Asn Gln Ser Tyr Lys Phe Lys His Gln
    210                 215                 220

Leu Ser Leu Thr Phe Leu Val Thr Gln Lys Thr Gln Arg Arg Trp Phe
225                 230                 235                 240

Leu Asp Lys Leu Val Asp Arg Ile Gly Val Gly Tyr Val Arg Asp Asn
                245                 250                 255

Gly Ser Val Ser Asn Tyr Ile Leu Ser Lys Ile Lys Pro Leu His Asn
            260                 265                 270

Phe Leu Thr Gln Leu Gln Pro Phe Leu Lys Leu Lys Gln Lys Gln Ala
        275                 280                 285

Asn Leu Val Leu Lys Ile Ile Glu Gln Leu Pro Ser Ala Lys Glu Ser
    290                 295                 300

Pro Asp Lys Phe Leu Glu Val Cys Thr Trp Val Asp Gln Val Ala Ala
305                 310                 315                 320

Leu Asn Asp Ser Lys Thr Arg Lys Thr Thr Ser Glu Thr Val Arg Ala
                325                 330                 335

Val Leu Asp Ser Leu Ser Glu Lys Lys Lys Ser Ser Pro
            340                 345
```

<210> SEQ ID NO 252
<211> LENGTH: 354
<212> TYPE: PRT
<213> ORGANISM: artificial sequence
<220> FEATURE:
<223> OTHER INFORMATION: SC-SH33-pCLS3905

<400> SEQUENCE: 252

Met Ala Asn Thr Lys Tyr Asn Glu Glu Phe Leu Leu Tyr Leu Ala Gly

```
  1               5                   10                  15
Phe Val Asp Gly Asp Gly Ser Ile Ile Ala Gln Ile Lys Pro Cys Gln
                20                  25                  30

Ser Cys Lys Phe Lys His Asn Leu Ser Leu Thr Phe Ala Val Thr Gln
            35                  40                  45

Lys Thr Gln Arg Arg Trp Phe Leu Asp Lys Leu Val Asp Glu Ile Gly
        50                  55                  60

Val Gly Cys Val Tyr Asp Ser Gly Ser Val Ser Tyr Tyr Lys Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Ala Leu Lys Ile Ile Glu Gln
                100                 105                 110

Leu Pro Ser Ala Lys Glu Ser Pro Asp Lys Phe Leu Glu Val Cys Thr
            115                 120                 125

Trp Val Asp Gln Val Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
                180                 185                 190

Gly Gly Gly Ser Asn Lys Lys Phe Leu Leu Tyr Leu Ala Gly Phe Val
            195                 200                 205

Asp Ser Asp Gly Ser Ile Val Ala Gln Ile Lys Pro Asn Gln Ser Tyr
        210                 215                 220

Lys Phe Lys His Gln Leu Ser Leu Thr Phe Arg Val Thr Gln Lys Thr
225                 230                 235                 240

Gln Arg Arg Trp Phe Leu Asp Lys Leu Val Asp Arg Ile Gly Val Gly
                245                 250                 255

Tyr Val Tyr Asp Ser Gly Ser Val Ser Tyr Tyr Asn Leu Ser Glu Ile
                260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
        290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
                340                 345                 350

Ser Pro

<210> SEQ ID NO 253
<211> LENGTH: 354
<212> TYPE: PRT
<213> ORGANISM: artificial sequence
<220> FEATURE:
<223> OTHER INFORMATION: SC-SH33.2-pCLS4077

<400> SEQUENCE: 253

Met Ala Asn Thr Lys Tyr Asn Glu Glu Phe Leu Leu Tyr Leu Ala Gly
1               5                   10                  15
```

Phe Val Asp Gly Asp Gly Ser Ile Ile Ala Gln Ile Lys Pro Cys Gln
            20                  25                  30

Ser Cys Lys Phe Lys His Asn Leu Ser Leu Thr Phe Ala Val Thr Gln
        35                  40                  45

Lys Thr Gln Arg Arg Trp Phe Leu Asp Lys Leu Val Asp Glu Ile Gly
50                  55                  60

Val Gly Cys Val Tyr Asp Arg Gly Ser Val Ser Asp Tyr Lys Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Ala Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Val Ala Gln Ile Lys Pro Asn Gln Ser Tyr
210                 215                 220

Lys Phe Lys His Gln Leu Ser Leu Thr Phe Arg Val Thr Gln Lys Thr
225                 230                 235                 240

Gln Arg Arg Trp Phe Leu Asp Lys Leu Val Asp Arg Ile Gly Val Gly
                245                 250                 255

Tyr Val Tyr Asp Ser Gly Ser Val Ser Tyr Tyr Asn Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 254
<211> LENGTH: 354
<212> TYPE: PRT
<213> ORGANISM: artificial sequence
<220> FEATURE:
<223> OTHER INFORMATION: SC-SH33v2-pCLS4668

<400> SEQUENCE: 254

Met Ala Ser Thr Lys Tyr Asn Glu Glu Phe Leu Leu Tyr Leu Ala Gly
1               5                   10                  15

```
Phe Val Asp Ser Asp Gly Ser Ile Ile Ala Gln Ile Lys Pro Asn Gln
            20                  25                  30

Thr Cys Lys Phe Lys His His Leu Ser Leu Thr Phe Val Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Arg Tyr Val Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Gly Asp Gly Ser Ile Val Ala Gln Ile Lys Pro Asn Gln Ser Tyr
    210                 215                 220

Lys Phe Lys His Gln Leu Ser Leu Thr Phe Arg Val Thr Gln Lys Thr
225                 230                 235                 240

Gln Arg Arg Trp Phe Leu Asp Lys Leu Val Asp Arg Ile Gly Val Gly
                245                 250                 255

Tyr Val Tyr Asp Ser Gly Ser Val Ser Tyr Tyr Asn Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 255
<211> LENGTH: 354
<212> TYPE: PRT
<213> ORGANISM: artificial sequence
<220> FEATURE:
<223> OTHER INFORMATION: SC-SH33v2.2-pCLS4669

<400> SEQUENCE: 255

Met Ala Ser Thr Lys Tyr Asn Glu Glu Phe Leu Leu Tyr Leu Ala Gly
1               5                   10                  15

Phe Val Asp Ser Asp Gly Ser Ile Ile Ala Gln Ile Lys Pro Asn Gln
```

```
                20              25              30
Thr Cys Lys Phe Lys His His Leu Ser Leu Thr Phe Val Val Thr Gln
         35                  40                  45

Lys Thr Gln Arg Arg Trp Phe Leu Asp Lys Leu Val Asp Glu Ile Gly
 50                  55                  60

Val Gly Tyr Val Tyr Asp Arg Gly Ser Val Ser Asp Tyr Val Leu Ser
 65                  70                  75                  80

Glu Ile Lys Pro Leu His Asn Phe Leu Thr Gln Leu Gln Pro Phe Leu
                 85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Tyr Leu Ala Gly Phe Val
        195                 200                 205

Asp Gly Asp Gly Ser Ile Val Ala Gln Ile Lys Pro Asn Gln Ser Tyr
    210                 215                 220

Lys Phe Lys His Gln Leu Ser Leu Thr Phe Arg Val Thr Gln Lys Thr
225                 230                 235                 240

Gln Arg Arg Trp Phe Leu Asp Lys Leu Val Asp Arg Ile Gly Val Gly
                245                 250                 255

Tyr Val Tyr Asp Ser Gly Ser Val Ser Tyr Tyr Asn Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 256
<211> LENGTH: 354
<212> TYPE: PRT
<213> ORGANISM: artificial sequence
<220> FEATURE:
<223> OTHER INFORMATION: SC-SH34-pCLS3906

<400> SEQUENCE: 256

Met Thr Asn Thr Lys Tyr Asn Glu Glu Phe Leu Leu Tyr Leu Ala Gly
1               5                   10                  15

Phe Val Asp Gly Asp Gly Ser Ile Val Ala Gln Ile Lys Pro Asn Gln
                20                  25                  30
```

```
Ser Tyr Lys Phe Lys His Gln Leu Ser Leu Thr Phe Arg Val Thr Gln
        35                  40                  45

Lys Thr Gln Arg Arg Trp Phe Leu Asp Lys Leu Val Asp Glu Ile Gly
50                  55                  60

Val Gly Tyr Val Tyr Asp Ser Gly Ser Val Ser Glu Tyr Tyr Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Ile Ala Gln Ile Lys Pro Asn Gln Thr Thr
210                 215                 220

Lys Phe Lys His Gln Leu Ser Leu Thr Phe Gln Val Thr Gln Lys Thr
225                 230                 235                 240

Gln Arg Arg Trp Phe Leu Asp Lys Leu Val Asp Arg Ile Gly Val Gly
                245                 250                 255

Tyr Val Arg Asp Arg Gly Ser Val Ser Asp Tyr Ile Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 257
<211> LENGTH: 354
<212> TYPE: PRT
<213> ORGANISM: artificial sequence
<220> FEATURE:
<223> OTHER INFORMATION: SCOH-SH40-b1-C-pCLS5427

<400> SEQUENCE: 257

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30
```

```
Ser Ser Lys Phe Lys His Asp Leu Ser Leu Thr Phe Gln Val Thr Gln
            35                  40                  45

Lys Thr Gln Arg Arg Trp Phe Leu Asp Lys Leu Val Asp Glu Ile Gly
 50                  55                  60

Val Gly Tyr Val Arg Asp Arg Gly Ser Val Ser Asp Tyr Ile Leu Ser
 65                  70                  75                  80

Glu Ile Lys Pro Leu His Asn Phe Leu Thr Gln Leu Gln Pro Phe Leu
                 85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Val Asp Gln Val Ala Ala Leu Asn Asp Ser Lys Thr Arg Lys Thr
            130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
            195                 200                 205

Asp Ser Asp Gly Ser Ile Ile Ala Gln Ile Lys Pro Asn Gln Ser Tyr
            210                 215                 220

Lys Phe Lys His Gln Leu Ser Leu Thr Phe Arg Val Thr Gln Lys Thr
225                 230                 235                 240

Gln Arg Arg Trp Phe Leu Asp Lys Leu Val Asp Arg Ile Gly Val Gly
            245                 250                 255

Tyr Val Ser Asp Arg Gly Ser Val Ser Asp Tyr Phe Leu Ser Glu Ile
            260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
            325                 330                 335

Glu Thr Val Arg Ala Val Leu Asp Ser Leu Ser Glu Lys Lys Lys Ser
            340                 345                 350

Ser Pro

<210> SEQ ID NO 258
<211> LENGTH: 167
<212> TYPE: PRT
<213> ORGANISM: artificial sequence
<220> FEATURE:
<223> OTHER INFORMATION: SH40-homodimer33S38D-pCLS5565

<400> SEQUENCE: 258

Met Ala Asn Thr Lys Tyr Asn Lys Glu Phe Leu Leu Tyr Leu Ala Gly
  1               5                  10                  15

Phe Val Asp Gly Asp Gly Ser Ile Ile Ala Gln Ile Lys Pro Asn Gln
             20                  25                  30

Ser Ser Lys Phe Lys His Asp Leu Ser Leu Thr Phe Gln Val Thr Gln
```

35                  40                  45

Lys Thr Gln Arg Arg Trp Phe Leu Asp Lys Leu Val Asp Glu Ile Gly
 50                  55                  60

Val Gly Tyr Val Arg Asp Arg Gly Ser Val Ser Asp Tyr Ile Leu Ser
 65                  70                  75                  80

Glu Ile Lys Pro Leu His Asn Phe Leu Thr Gln Leu Gln Pro Phe Leu
                 85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
                115                 120                 125

Trp Val Asp Gln Ile Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 259
<211> LENGTH: 167
<212> TYPE: PRT
<213> ORGANISM: artificial sequence
<220> FEATURE:
<223> OTHER INFORMATION: SH40-homodimer33S38D132V-pCLS5566

<400> SEQUENCE: 259

Met Ala Asn Thr Lys Tyr Asn Lys Glu Phe Leu Leu Tyr Leu Ala Gly
 1               5                  10                  15

Phe Val Asp Gly Asp Gly Ser Ile Ile Ala Gln Ile Lys Pro Asn Gln
                20                  25                  30

Ser Ser Lys Phe Lys His Asp Leu Ser Leu Thr Phe Gln Val Thr Gln
                35                  40                  45

Lys Thr Gln Arg Arg Trp Phe Leu Asp Lys Leu Val Asp Glu Ile Gly
 50                  55                  60

Val Gly Tyr Val Arg Asp Arg Gly Ser Val Ser Asp Tyr Ile Leu Ser
 65                  70                  75                  80

Glu Ile Lys Pro Leu His Asn Phe Leu Thr Gln Leu Gln Pro Phe Leu
                 85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
                115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 260
<211> LENGTH: 354
<212> TYPE: PRT
<213> ORGANISM: artificial sequence
<220> FEATURE:
<223> OTHER INFORMATION: SCOH-SH53-pCLS4773

<400> SEQUENCE: 260

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Tyr Lys Phe Lys His Gln Leu Ser Leu Thr Phe Glu Val Gly Gln
        35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Met Ser Arg Tyr Ile Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Ile Ala Gln Ile Arg Pro Asn Gln Ser Ala
    210                 215                 220

Lys Phe Lys His Tyr Leu Gln Leu Thr Phe Arg Val Thr Gln Lys Thr
225                 230                 235                 240

Gln Arg Arg Trp Phe Leu Asp Lys Leu Val Asp Arg Ile Gly Val Gly
                245                 250                 255

Tyr Val Ser Asp Ser Gly Ser Val Ser Asn Tyr Asn Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 261
<211> LENGTH: 354
<212> TYPE: PRT
<213> ORGANISM: artificial sequence
<220> FEATURE:
<223> OTHER INFORMATION: SCOH-SH54-pCLS4774

<400> SEQUENCE: 261

Met Ala Asn Thr Lys Tyr Asn Glu Glu Phe Leu Leu Tyr Leu Ala Gly

-continued

```
            1               5                  10                 15
        Phe Val Asp Gly Asp Gly Ser Ile Val Ala Gln Ile Lys Pro Asn Gln
                        20                  25                  30

Ser Tyr Lys Phe Lys His Gln Leu Ser Leu Thr Phe Lys Val Thr Gln
                        35                  40                  45

Lys Thr Gln Arg Arg Trp Phe Leu Asp Lys Leu Val Asp Glu Ile Gly
                        50                  55                  60

Val Gly Tyr Val Tyr Asp Ser Gly Ser Val Ser Asp Tyr Thr Leu Ser
         65                 70                  75                  80

Glu Ile Lys Pro Leu His Asn Phe Leu Thr Gln Leu Gln Pro Phe Leu
                        85                  90                  95

Glu Leu Lys Gln Lys Gln Ala Asn Leu Val Leu Lys Ile Ile Glu Gln
                       100                 105                 110

Leu Pro Ser Ala Lys Glu Ser Pro Asp Lys Phe Leu Glu Val Cys Thr
                       115                 120                 125

Trp Val Asp Gln Val Ala Ala Leu Asn Asp Ser Lys Thr Arg Lys Thr
                 130                 135                 140

Thr Ser Glu Thr Val Arg Ala Val Leu Asp Ser Leu Ser Glu Lys Lys
        145                 150                 155                 160

Lys Ser Ser Pro Ala Ala Gly Gly Ser Asp Lys Tyr Asn Gln Ala Leu
                       165                 170                 175

Ser Lys Tyr Asn Gln Ala Leu Ser Lys Tyr Asn Gln Ala Leu Ser Gly
                       180                 185                 190

Gly Gly Gly Ser Asn Lys Lys Phe Leu Leu Tyr Leu Ala Gly Phe Val
                       195                 200                 205

Asp Ser Asp Gly Ser Ile Ile Ala Gln Ile Lys Pro Asn Gln Ser Tyr
                 210                 215                 220

Lys Phe Lys His Gln Leu Ser Leu Thr Phe Gln Val Thr Gln Lys Thr
        225                 230                 235                 240

Gln Arg Arg Trp Phe Leu Asp Lys Leu Val Asp Arg Ile Gly Val Gly
                       245                 250                 255

Tyr Val Arg Asp Tyr Gly Ser Val Ser Asn Tyr Ile Leu Ser Glu Ile
                       260                 265                 270

Lys Pro Leu His Asn Phe Leu Thr Gln Leu Gln Pro Phe Leu Lys Leu
                       275                 280                 285

Lys Gln Lys Gln Ala Asn Leu Val Leu Lys Ile Ile Glu Gln Leu Pro
                 290                 295                 300

Ser Ala Lys Glu Ser Pro Asp Lys Phe Leu Glu Val Cys Thr Trp Val
        305                 310                 315                 320

Asp Gln Val Ala Ala Leu Asn Asp Ser Lys Thr Arg Lys Thr Thr Ser
                       325                 330                 335

Glu Thr Val Arg Ala Val Leu Asp Ser Leu Ser Glu Lys Lys Lys Ser
                       340                 345                 350

Ser Pro

<210> SEQ ID NO 262
<211> LENGTH: 354
<212> TYPE: PRT
<213> ORGANISM: artificial sequence
<220> FEATURE:
<223> OTHER INFORMATION: SCOH-SH55-pCLS4775

<400> SEQUENCE: 262

Met Ala Asn Thr Lys Tyr Ser Glu Glu Phe Leu Leu Tyr Leu Ala Gly
        1               5                  10                 15
```

Phe Val Asp Gly Asp Gly Ser Ile Ile Ala Gln Ile Lys Pro Asn Gln
                20                  25                  30

Ser Arg Lys Phe Lys His Glu Leu Ser Leu Thr Phe Asn Val Thr Gln
            35                  40                  45

Lys Thr Gln Arg Arg Trp Phe Leu Asp Lys Leu Val Asp Glu Ile Gly
 50                  55                  60

Val Gly His Val His Asp Ser Gly Ser Val Ser Tyr Tyr Asn Leu Arg
 65                  70                  75                  80

Lys Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Ile Ala Gln Ile Lys Pro Asn Gln Ser Tyr
210                 215                 220

Lys Phe Lys His Gln Leu Ser Leu Thr Phe Lys Val Thr Gln Lys Thr
225                 230                 235                 240

Gln Arg Arg Trp Phe Leu Asp Lys Leu Val Asp Arg Ile Gly Val Gly
                245                 250                 255

Tyr Val Gly Asp Ser Gly Ser Val Ser Asn Tyr Ile Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 263
<211> LENGTH: 354
<212> TYPE: PRT
<213> ORGANISM: artificial sequence
<220> FEATURE:
<223> OTHER INFORMATION: SCOH-SH56-pCLS4776

<400> SEQUENCE: 263

Met Ala Asn Thr Lys Tyr Asn Glu Glu Phe Leu Leu Tyr Leu Ala Gly
 1               5                  10                  15

```
Phe Val Asp Gly Asp Gly Ser Ile Ile Ala Gln Ile Lys Pro Asn Gln
             20                  25                  30

Ser Tyr Lys Phe Lys His Gln Leu Ser Leu Thr Phe Val Thr Gln
         35                  40                  45

Lys Thr Gln Arg Arg Trp Phe Leu Asp Lys Leu Val Asp Glu Ile Gly
 50                  55                  60

Val Gly Tyr Val Arg Asp Asn Gly Ser Val Ser Asp Tyr Ile Leu Ser
 65                  70                  75                  80

Glu Ile Lys Pro Leu His Asn Phe Leu Thr Gln Leu Gln Pro Phe Leu
                 85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
            195                 200                 205

Asp Ser Asp Gly Ser Ile Ile Ala Gln Ile Lys Pro Asn Gln His Cys
210                 215                 220

Lys Phe Lys His Gln Leu Ser Leu Thr Phe Arg Val Thr Gln Lys Thr
225                 230                 235                 240

Gln Arg Arg Trp Phe Leu Asp Lys Leu Val Asp Arg Ile Gly Val Gly
                245                 250                 255

Tyr Val Tyr Asp Ser Gly Ser Val Ser Tyr Tyr Asn Leu Ser Glu Ile
            260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 264
<211> LENGTH: 354
<212> TYPE: PRT
<213> ORGANISM: artificial sequence
<220> FEATURE:
<223> OTHER INFORMATION: SCOH-SH57-pCLS4777

<400> SEQUENCE: 264

Met Ala Asn Thr Lys Tyr Asn Glu Glu Phe Leu Leu Tyr Leu Ala Gly
 1                5                  10                  15

Phe Val Asp Gly Asp Gly Ser Ile Ile Ala Gln Ile Lys Pro Asn Gln
```

```
              20                  25                  30
Thr Tyr Lys Phe Lys His Trp Leu Ser Leu Thr Phe Gln Val Thr Gln
         35                  40                  45
Lys Thr Gln Arg Arg Trp Phe Leu Asp Lys Leu Val Asp Glu Ile Gly
 50                  55                  60
Val Gly Tyr Val Arg Asp Arg Gly Ser Val Ser Asp Tyr Ile Leu Ser
 65                  70                  75                  80
Glu Ile Lys Pro Leu His Asn Phe Leu Thr Gln Leu Gln Pro Phe Leu
                 85                  90                  95
Glu Leu Lys Gln Lys Gln Ala Asn Leu Val Leu Lys Ile Ile Glu Gln
            100                 105                 110
Leu Pro Ser Ala Lys Glu Ser Pro Asp Lys Phe Leu Glu Val Cys Thr
        115                 120                 125
Trp Val Asp Gln Val Ala Ala Leu Asn Asp Ser Lys Thr Arg Lys Thr
130                 135                 140
Thr Ser Glu Thr Val Arg Ala Val Leu Asp Ser Leu Ser Glu Lys Lys
145                 150                 155                 160
Lys Ser Ser Pro Ala Ala Gly Gly Ser Asp Lys Tyr Asn Gln Ala Leu
                165                 170                 175
Ser Lys Tyr Asn Gln Ala Leu Ser Lys Tyr Asn Gln Ala Leu Ser Gly
            180                 185                 190
Gly Gly Gly Ser Asn Lys Lys Phe Leu Leu Tyr Leu Ala Gly Phe Val
        195                 200                 205
Asp Ser Asp Gly Ser Ile Ile Ala Gln Ile Lys Pro Asn Gln Ser Tyr
210                 215                 220
Lys Phe Lys His Gln Leu Ser Leu Thr Phe Arg Val Thr Gln Lys Thr
225                 230                 235                 240
Gln Arg Arg Trp Phe Leu Asp Lys Leu Val Asp Arg Ile Gly Val Gly
                245                 250                 255
Tyr Val Ser Asp Arg Gly Ser Val Ser Asp Tyr Trp Leu Ser Glu Ile
            260                 265                 270
Lys Pro Leu His Asn Phe Leu Thr Gln Leu Gln Pro Phe Leu Lys Leu
        275                 280                 285
Lys Gln Lys Gln Ala Asn Leu Val Leu Lys Ile Ile Glu Gln Leu Pro
290                 295                 300
Ser Ala Lys Glu Ser Pro Asp Lys Phe Leu Glu Val Cys Thr Trp Val
305                 310                 315                 320
Asp Gln Val Ala Ala Leu Asn Asp Ser Lys Thr Arg Lys Thr Thr Ser
                325                 330                 335
Glu Thr Val Arg Ala Val Leu Asp Ser Leu Ser Glu Lys Lys Lys Ser
            340                 345                 350
Ser Pro

<210> SEQ ID NO 265
<211> LENGTH: 354
<212> TYPE: PRT
<213> ORGANISM: artificial sequence
<220> FEATURE:
<223> OTHER INFORMATION: SCOH-SH58-pCLS4778

<400> SEQUENCE: 265

Met Ala Asn Thr Lys Tyr Asn Glu Glu Phe Leu Leu Tyr Leu Ala Gly
 1               5                  10                  15
Phe Val Asp Gly Asp Gly Ser Ile Ile Ala Gln Ile Lys Pro Ser Gln
            20                  25                  30
```

-continued

```
Ser Ser Lys Phe Lys His Gln Leu Ser Leu Thr Phe Arg Val Thr Gln
        35                  40                  45

Lys Thr Gln Arg Arg Trp Phe Leu Asp Lys Leu Val Asp Glu Ile Gly
 50                  55                  60

Val Gly His Val Tyr Asp Ser Gly Ser Val Ser Asp Tyr Thr Leu Ser
 65                  70                  75                  80

Glu Ile Lys Pro Leu His Asn Phe Leu Thr Gln Leu Gln Pro Phe Leu
                 85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Ile Ala Gln Ile Lys Pro Ala Gln Ser Thr
210                 215                 220

Lys Phe Lys His Gln Leu Ser Leu Thr Phe Gln Val Thr Gln Lys Thr
225                 230                 235                 240

Gln Arg Arg Trp Phe Leu Asp Lys Leu Val Asp Arg Ile Gly Val Gly
                245                 250                 255

Tyr Val Arg Asp Arg Gly Ser Val Ser Asp Tyr Ile Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro
```

<210> SEQ ID NO 266
<211> LENGTH: 354
<212> TYPE: PRT
<213> ORGANISM: artificial sequence
<220> FEATURE:
<223> OTHER INFORMATION: SCOH-SH59-pCLS4779

<400> SEQUENCE: 266

```
Met Ala Asn Thr Lys Tyr Asn Glu Glu Phe Leu Leu Tyr Leu Ala Gly
 1               5                  10                  15

Phe Val Asp Gly Asp Gly Ser Ile Ile Ala Gln Ile Lys Pro Cys Gln
             20                  25                  30
```

Ser Cys Lys Phe Lys His Gln Leu Ser Leu Thr Phe Gln Val Thr Gln
        35                  40                  45

Lys Thr Gln Arg Arg Trp Leu Leu Asp Lys Leu Val Asp Glu Ile Gly
 50                  55                  60

Val Gly Tyr Val Arg Asp Ser Gly Ser Val Ser His Tyr Tyr Leu Ser
 65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
            195                 200                 205

Asp Ser Asp Gly Ser Ile Ile Ala Gln Ile Lys Pro Asn Gln Ser Arg
            210                 215                 220

Lys Phe Lys His Ala Leu Gln Leu Thr Phe Gln Val Thr Gln Lys Thr
225                 230                 235                 240

Gln Arg Arg Trp Phe Leu Asp Lys Leu Val Asp Arg Ile Gly Val Gly
                245                 250                 255

Tyr Val Arg Asp Ser Gly Ser Val Ser Asn Tyr Ile Leu Ser Glu Ile
            260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 267
<211> LENGTH: 354
<212> TYPE: PRT
<213> ORGANISM: artificial sequence
<220> FEATURE:
<223> OTHER INFORMATION: SCOH-SH60-pCLS4780

<400> SEQUENCE: 267

Met Ala Asn Thr Lys Tyr Asn Glu Glu Phe Leu Leu Tyr Leu Ala Gly
 1               5                  10                  15

Phe Val Asp Gly Asp Gly Ser Ile Ile Ala Gln Ile Lys Pro Asn Gln
                20                  25                  30

Asn Gly Lys Phe Lys His Gln Leu Ser Leu Thr Phe Lys Val Thr Gln

```
            35                  40                  45
Lys Thr Gln Arg Arg Trp Phe Leu Asp Lys Leu Val Asp Glu Ile Gly
 50                  55                  60

Val Gly His Val Tyr Asp Ser Gly Ser Val Ser Asp Tyr Thr Leu Ser
 65                  70                  75                  80

Glu Ile Lys Pro Leu His Asn Phe Leu Thr Gln Leu Gln Pro Phe Leu
                 85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Ile Ala Gln Ile Lys Pro Asn Arg Ser His
210                 215                 220

Lys Phe Lys His Gln Leu Gln Leu Thr Phe Lys Val Thr Gln Lys Thr
225                 230                 235                 240

Gln Arg Arg Trp Phe Leu Asp Lys Leu Val Asp Arg Ile Gly Val Gly
                245                 250                 255

Tyr Val Tyr Asp Ser Gly Ser Val Ser Glu Tyr Val Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
290                 295                 300

Ser Ala Lys Gly Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Asn Leu Ser Glu Lys Lys Lys Ser
            340                 345                 350

Ser Pro

<210> SEQ ID NO 268
<211> LENGTH: 354
<212> TYPE: PRT
<213> ORGANISM: artificial sequence
<220> FEATURE:
<223> OTHER INFORMATION: SC-SH61-pCLS5333

<400> SEQUENCE: 268

Met Ala Asn Thr Lys Tyr Asn Glu Glu Phe Leu Leu Tyr Leu Ala Gly
 1               5                  10                  15

Phe Val Asp Gly Asp Gly Ser Ile Ile Ala Gln Ile Lys Pro Asn Gln
            20                  25                  30

Ser Cys Lys Tyr Lys His Cys Leu Ser Leu Thr Phe Arg Val Thr Gln
        35                  40                  45
```

```
Lys Thr Gln Arg Arg Trp Phe Leu Asp Lys Leu Val Asp Glu Ile Gly
 50                  55                  60

Val Gly Tyr Val Tyr Asp Ser Gly Ser Val Ser Asp Tyr Gln Leu Ser
 65                  70                  75                  80

Glu Ile Lys Pro Leu His Asn Phe Leu Thr Gln Leu Gln Pro Phe Leu
                 85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Phe Leu Leu Tyr Leu Ala Gly Phe Val
            195                 200                 205

Asp Ser Asp Gly Ser Ile Ile Ala Gln Ile Lys Pro Asn Gln Lys Ala
210                 215                 220

Lys Phe Lys His Gln Leu Ser Leu Thr Phe Lys Val Thr Gln Lys Thr
225                 230                 235                 240

Gln Arg Arg Trp Phe Leu Asp Lys Leu Val Asp Arg Ile Gly Val Gly
                245                 250                 255

Tyr Val Glu Asp Ser Gly Ser Val Ser Asn Tyr Arg Leu Ser Lys Ile
            260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Arg Leu Ser Glu Lys Lys Lys Ser
            340                 345                 350

Ser Pro

<210> SEQ ID NO 269
<211> LENGTH: 354
<212> TYPE: PRT
<213> ORGANISM: artificial sequence
<220> FEATURE:
<223> OTHER INFORMATION: SC-SH62-pCLS5334

<400> SEQUENCE: 269

Met Ala Asn Thr Lys Tyr Asn Glu Glu Phe Leu Leu Tyr Leu Ala Gly
 1               5                  10                  15

Phe Val Asp Gly Asp Gly Ser Ile Ile Ala Gln Ile Lys Pro Asn Gln
                20                  25                  30

Ser Cys Lys Phe Lys His His Leu Ser Leu Thr Phe Asp Val Thr Gln
            35                  40                  45
```

```
Lys Thr Gln Arg Arg Trp Phe Leu Asp Lys Leu Val Asp Glu Ile Gly
            50                  55                  60

Val Gly Tyr Val Ala Asp Ser Gly Ser Val Ser Lys Tyr Arg Leu Ser
 65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
               100                 105                 110

Leu Pro Ser Ala Lys Glu Ser Pro Asp Lys Phe Leu Glu Val Cys Thr
               115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
               165                 170                 175

Ser Lys Tyr Asn Gln Ala Leu Ser Lys Tyr Asn Gln Ala Leu Ser Gly
               180                 185                 190

Gly Gly Gly Ser Asn Lys Lys Phe Leu Leu Tyr Leu Ala Gly Phe Val
               195                 200                 205

Asp Ser Asp Gly Ser Ile Val Ala Gln Ile Lys Pro Asn Gln Ser Tyr
210                 215                 220

Lys Phe Lys His Gln Leu Ser Leu Thr Phe Leu Val Thr Gln Lys Thr
225                 230                 235                 240

Gln Arg Arg Trp Phe Leu Asp Lys Leu Val Asp Arg Ile Gly Val Gly
               245                 250                 255

Tyr Val Arg Asp Asn Gly Ser Val Ser Asn Tyr Ile Leu Ser Lys Ile
               260                 265                 270

Lys Pro Leu His Asn Phe Leu Thr Gln Leu Gln Pro Phe Leu Lys Leu
               275                 280                 285

Lys Gln Lys Gln Ala Asn Leu Val Leu Lys Ile Ile Glu Gln Leu Pro
               290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                   325                 330                 335

Glu Thr Val Arg Ala Val Leu Asp Ser Leu Ser Glu Lys Lys Lys Ser
               340                 345                 350

Ser Pro

<210> SEQ ID NO 270
<211> LENGTH: 354
<212> TYPE: PRT
<213> ORGANISM: artificial sequence
<220> FEATURE:
<223> OTHER INFORMATION: SC-SH62.2-pCLS5335

<400> SEQUENCE: 270

Met Ala Asn Thr Lys Tyr Asn Glu Glu Phe Leu Leu Tyr Leu Ala Gly
 1               5                  10                  15

Phe Val Asp Gly Asp Gly Ser Ile Ile Ala Gln Ile Lys Pro Asn Gln
                20                  25                  30

Ser Cys Lys Phe Lys His His Leu Ser Leu Thr Phe Asp Val Thr Gln
                35                  40                  45

Lys Thr Gln Arg Arg Trp Phe Leu Asp Lys Leu Val Asp Glu Ile Gly
```

```
            50                  55                  60
Val Gly Tyr Val Ala Asp Arg Gly Ser Val Ser Asp Tyr Arg Leu Ser
 65                  70                  75                  80

Glu Ile Lys Pro Leu His Asn Phe Leu Thr Gln Leu Gln Pro Phe Leu
                 85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Val Asp Gln Val Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Val Ala Gln Ile Lys Pro Asn Gln Ser Tyr
    210                 215                 220

Lys Phe Lys His Gln Leu Ser Leu Thr Phe Leu Val Thr Gln Lys Thr
225                 230                 235                 240

Gln Arg Arg Trp Phe Leu Asp Lys Leu Val Asp Arg Ile Gly Val Gly
                245                 250                 255

Tyr Val Arg Asp Asn Gly Ser Val Ser Asn Tyr Ile Leu Ser Lys Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 271
<211> LENGTH: 24
<212> TYPE: DNA
<213> ORGANISM: Artificial
<220> FEATURE:
<223> OTHER INFORMATION: SH65

<400> SEQUENCE: 271
ctcacctgtc tcacaaggga ggga                                          24

<210> SEQ ID NO 272
<211> LENGTH: 24
<212> TYPE: DNA
<213> ORGANISM: Artificial
<220> FEATURE:
<223> OTHER INFORMATION: SH67

<400> SEQUENCE: 272
```

-continued

```
ctactaccat gtgactggtt gtag                                    24

<210> SEQ ID NO 273
<211> LENGTH: 24
<212> TYPE: DNA
<213> ORGANISM: Artificial
<220> FEATURE:
<223> OTHER INFORMATION: SH68

<400> SEQUENCE: 273
gctgcacgtt ttacatgaga gtaa                                    24

<210> SEQ ID NO 274
<211> LENGTH: 24
<212> TYPE: DNA
<213> ORGANISM: Artificial
<220> FEATURE:
<223> OTHER INFORMATION: SH69

<400> SEQUENCE: 274
tcagacttct ttacctcatt tgat                                    24

<210> SEQ ID NO 275
<211> LENGTH: 354
<212> TYPE: PRT
<213> ORGANISM: artificial sequence
<220> FEATURE:
<223> OTHER INFORMATION: SC-SH65-pCLS5336

<400> SEQUENCE: 275
```

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Thr Lys Phe Lys His Gln Leu Gln Leu Thr Phe Gln Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Arg Gly Ser Val Ser Asp Tyr Ile Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Ile Ala Gln Ile Lys Pro Asn Gln Ser Ser
    210                 215                 220

```
Lys Phe Lys His Tyr Leu Ser Leu Thr Leu Arg Val Thr Gln Lys Thr
225                 230                 235                 240

Gln Arg Arg Trp Phe Leu Asp Lys Leu Val Asp Arg Ile Gly Val Gly
            245                 250                 255

Tyr Val Tyr Asp Ser Gly Ser Val Ser Asp Tyr Asn Leu Ser Glu Ile
        260                 265                 270

Lys Pro Leu His Asn Phe Leu Thr Gln Leu Gln Pro Phe Leu Lys Leu
    275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Gly Lys Lys Lys Ser
            340                 345                 350

Ser Pro

<210> SEQ ID NO 276
<211> LENGTH: 354
<212> TYPE: PRT
<213> ORGANISM: artificial sequence
<220> FEATURE:
<223> OTHER INFORMATION: SC-SH67-pCLS5337

<400> SEQUENCE: 276

Met Ala Asn Ile Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Thr Tyr Lys Tyr Lys His Trp Leu Cys Leu Thr Phe Ala Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Tyr Tyr Thr Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu His
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Thr
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Ile Ala Gln Ile Lys Pro Arg Gln Ser Tyr
    210                 215                 220

Lys Phe Lys His Glu Leu Ser Leu Thr Phe Val Val Thr Gln Lys Thr
```

Gln Arg Arg Trp Phe Leu Asp Lys Leu Val Asp Arg Ile Gly Val Gly
            245                 250                 255

Tyr Val Glu Asp Arg Gly Ser Val Ser Asn Tyr Arg Leu Ser Lys Ile
            260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
            290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
            325                 330                 335

Glu Thr Val Arg Ala Val Leu Asp Ser Leu Ser Glu Lys Lys Lys Ser
            340                 345                 350

Ser Pro

<210> SEQ ID NO 277
<211> LENGTH: 354
<212> TYPE: PRT
<213> ORGANISM: artificial sequence
<220> FEATURE:
<223> OTHER INFORMATION: SCOH-SH68-pCLS5955

<400> SEQUENCE: 277

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Cys Lys Phe Lys His Ala Leu Ser Leu Thr Phe Gln Val Thr Gln
            35                  40                  45

Lys Thr Gln Arg Arg Trp Phe Leu Asp Lys Leu Val Asp Glu Ile Gly
        50                  55                  60

Val Gly Tyr Val Arg Asp Ser Gly Ser Val Ser His Tyr Tyr Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Phe Leu Leu Tyr Leu Ala Gly Phe Val
        195                 200                 205

Asp Ser Asp Gly Ser Ile Ile Ala Gln Ile Lys Pro Asn Gln Thr Tyr
        210                 215                 220

Lys Tyr Lys His Trp Leu Cys Leu Thr Phe Ala Val Thr Gln Lys Thr
225                 230                 235                 240

```
Gln Arg Arg Trp Phe Leu Asp Lys Leu Val Asp Arg Ile Gly Val Gly
                245                 250                 255

Tyr Val Arg Asp Ser Gly Ser Val Ser Tyr Tyr Thr Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Ala Leu Lys Ile Ile Glu His Leu Pro
    290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 278
<211> LENGTH: 354
<212> TYPE: PRT
<213> ORGANISM: artificial sequence
<220> FEATURE:
<223> OTHER INFORMATION: SCOH-SH69-pCLS5956

<400> SEQUENCE: 278

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asp Gln
            20                  25                  30

Ser Cys Lys Phe Lys His Tyr Leu Ser Leu Thr Phe Ala Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Tyr Tyr Val Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Ile Ala Gln Ile Lys Pro Asn Gln Ser Gly
    210                 215                 220

Lys Phe Lys His Lys Leu Ser Leu Thr Phe Lys Val Thr Gln Lys Thr
225                 230                 235                 240
```

```
Gln Arg Arg Trp Leu Leu Asp Lys Leu Val Asp Arg Ile Gly Val Gly
                245                 250                 255
Tyr Val Tyr Asp Ser Gly Ser Val Ser Asn Tyr Tyr Leu Ser Glu Ile
            260                 265                 270
Lys Pro Leu His Asn Phe Leu Thr Gln Leu Gln Pro Phe Leu Lys Leu
        275                 280                 285
Lys Gln Lys Gln Ala Asn Leu Val Leu Lys Ile Ile Glu Gln Leu Pro
    290                 295                 300
Ser Ala Lys Glu Ser Pro Asp Lys Phe Leu Glu Val Cys Thr Trp Val
305                 310                 315                 320
Asp Gln Val Ala Ala Leu Asn Asp Ser Lys Thr Arg Lys Thr Thr Ser
                325                 330                 335
Glu Thr Val Arg Ala Val Leu Asp Ser Leu Ser Glu Lys Lys Lys Ser
            340                 345                 350
Ser Pro

<210> SEQ ID NO 279
<211> LENGTH: 10217
<212> TYPE: DNA
<213> ORGANISM: Artificial
<220> FEATURE:
<223> OTHER INFORMATION: pCLS3779

<400> SEQUENCE: 279
```

| | | |
|---|---|---|
| ggatctgcga tcgctccggt gcccgtcagt gggcagagcg cacatcgccc acagtccccg | 60 |
| agaagttggg gggaggggtc ggcaattgaa ccggtgccta gagaaggtgg cgcggggtaa | 120 |
| actgggaaag tgatgtcgtg tactggctcc gcctttttcc cgagggtggg ggagaaccgt | 180 |
| atataagtgc agtagtcgcc gtgaacgttc tttttcgcaa cgggtttgcc gccagaacac | 240 |
| agctgaagct tcgaggggct cgcatctctc cttcacgcgc ccgccgccct acctgaggcc | 300 |
| gccatccacg ccggttgagt cgcgttctgc cgcctcccgc tgtggtgcc tcctgaactg | 360 |
| cgtccgccgt ctaggtaagt ttaaagctca ggtcgagacc gggcctttgt ccggcgctcc | 420 |
| cttggagcct acctagactc agccggctct ccacgctttg cctgaccctg cttgctcaac | 480 |
| tctacgtctt tgtttcgttt tctgttctgc gccgttacag atccaagctg tgaccggcgc | 540 |
| ctacgtaagt gatatctact agatttatca aaagagtgt tgacttgtga gcgctcacaa | 600 |
| ttgatactta gattcatcga gagggacacg tcgactacta accttcttct ctttcctaca | 660 |
| gctgagatca ccggcgaagg agggccacca tggcttctta ccctggacac cagcatgctt | 720 |
| ctgcctttga ccaggctgcc agatccaggg ccactccaa caggagaact gccctaagac | 780 |
| ccagaagaca gcaggaagcc actgaggtga ggcctgagca aagatgccaa ccctgctga | 840 |
| gggtgtacat tgatggacct catggcatgg gcaagaccac caccactcaa ctgctggtgg | 900 |
| cactgggctc cagggatgac attgtgtatg tgcctgagcc aatgacctac tggagagtgc | 960 |
| taggagcctc tgagaccatt gccaacatct acaccaccca gcacaggctg gaccaggag | 1020 |
| aaatctctgc tggagatgct gctgtggtga tgacctctgc ccagatcaca atgggaatgc | 1080 |
| cctatgctgt gactgatgct gttctggctc tcacattgg aggagaggct ggctcttctc | 1140 |
| atgcccctcc acctgccctg accctgatct ttgacagaca ccccattgca gccctgctgt | 1200 |
| gctacccagc agcaaggtac ctcatgggct ccatgaccc acaggctgtg ctggcttttg | 1260 |
| tggccctgat ccctccaacc ctccctggca ccaacattgt tctgggagca ctgcctgaag | 1320 |
| acagacacat tgacaggctg gcaaagaggc agagacctgg agagagactg gacctggcca | 1380 |

```
tgctggctgc aatcagaagg gtgtatggac tgctggcaaa cactgtgaga tacctccagt  1440
gtggaggctc ttggagagag gactggggac agctctctgg aacagcagtg cccccctcaag 1500
gagctgagcc ccagtccaat gctggtccaa gacccacat  tggggacacc ctgttcaccc  1560
tgttcagagc ccctgagctg ctggctccca atggagacct gtacaatgtg tttgcctggg  1620
ctctggatgt tctagccaag aggctgaggt ccatgcatgt gttcatcctg gactatgacc  1680
agtcccctgc tggatgcaga gatgctctgc tgcaactaac ctctggcatg gtgcagaccc  1740
atgtgaccac ccctggcagc atccccacca tctgtgacct agccagaacc tttgccaggg  1800
agatggggaga ggccaactaa acctgagcta gctcgacatg ataagataca ttgatgagtt  1860
tggacaaacc acaactagaa tgcagtgaaa aaaatgcttt atttgtgaaa tttgtgatgc  1920
tattgcttta tttgtgaaat ttgtgatgct attgctttat ttgtaaccat tataagctgc  1980
aataaacaag ttaacaacaa caattgcatt cattttatgt ttcaggttca ggggagggtg  2040
tgggaggttt tttaaagcaa gtaaaacctc tacaaatgtg gtagatcatt taaatgttaa  2100
ttaagaacat gtgagcaaaa ggccagcaaa aggccaggaa ccgtaaaaag gccgcgttgc  2160
tggcgttttt ccataggctc cgcccccctg acgagcatca caaaaatcga cgctcaagtc  2220
agaggtggcg aaacccgaca ggactataaa gataccaggc gtttccccct ggaagctccc  2280
tcgtgcgctc tcctgttccg accctgccgc ttaccggata cctgtccgcc tttctccctt  2340
cgggaagcgt ggcgctttct caatgctcac gctgtaggta tctcagttcg gtgtaggtcg  2400
ttcgctccaa gctgggctgt gtgcacgaac cccccgttca gcccgaccgc tgcgccttat  2460
ccggtaacta tcgtcttgag tccaacccgg taagacacga cttatcgcca ctggcagcag  2520
ccactggtaa caggattagc agagcgaggt atgtaggcgg tgctacagag ttcttgaagt  2580
ggtggcctaa ctacggctac actagaagaa cagtatttgg tatctgcgct ctgctgaagc  2640
cagttacctt cggaaaaaga gttggtagct cttgatccgg caaacaaacc accgctggta  2700
gcggtggttt ttttgtttgc aagcagcaga ttacgcgcag aaaaaaagga tctcaagaag  2760
atcctttgat cttttctacg ggtctgacg  ctcagtggaa cgaaaactca cgttaaggga  2820
ttttggtcat gagattatca aaaaggatct cacctagat  ccttttaaat taaaaatgaa  2880
gttttaaatc aatctaaagt atatatgagt aaacttggtc tgacagttac caatgcttaa  2940
tcagtgaggc acctatctca gcgatctgtc tatttcgttc atccatagtt gcctgactcc  3000
ccgtcgtgta gataactacg atacgggagg gcttaccatc tggccccagt gctgcaatga  3060
taccgcgaga cccacgctca ccggctccag atttatcagc aataaaccag ccagccggaa  3120
gggccgagcg cagaagtggt cctgcaactt tatccgcctc catccagtct attaattgtt  3180
gccgggaagc tagagtaagt agttcgccag ttaatagttt gcgcaacgtt gttgccattg  3240
ctacaggcat cgtggtgtca cgctcgtcgt ttggtatggc ttcattcagc tccggttccc  3300
aacgatcaag gcgagttaca tgatccccca tgttgtgcaa aaaagcggtt agctccttcg  3360
gtcctccgat cgttgtcaga agtaagttgg ccgcagtgtt atcactcatg gttatggcag  3420
cactgcataa ttctcttact gtcatgccat ccgtaagatg cttttctgtg actggtgagt  3480
actcaaccaa gtcattctga gaatagtgta tgcggcgacc gagttgctct tgcccggcgt  3540
caatacggga taataccgcg ccacatagca gaactttaaa agtgctcatc attggaaaac  3600
gttcttcggg gcgaaaactc tcaaggatct taccgctgtt gagatccagt tcgatgtaac  3660
ccactcgtgc acccaactga tcttcagcat cttttacttt caccagcgtt tctgggtgag  3720
caaaaacagg aaggcaaaat gccgcaaaaa agggaataag ggcgacacgg aaatgttgaa  3780
```

```
tactcatact cttccttttt caatattatt gaagcattta tcagggttat tgtctcatga    3840
gcggatacat atttgaatgt atttagaaaa ataaacaaat aggggttccg cgcacatttc    3900
cccgaaaagt gccacctgac gtctaagaaa ccattattat catgacatta acctataaaa    3960
ataggcgtat cacgaggccc tttcgtctcg cgcgtttcgg tgatgacggt gaaaacctct    4020
gacacatgca gctcccggag acggtcacag cttgtctgta agcggatgcc gggagcagac    4080
aagcccgtca gggcgcgtca gcgggtgttg gcgggtgtcg gggctggctt aactatgcgg    4140
catcagagca gattgtactg agagtgcacc atatggatct cgagcggccg cggcgcgccg    4200
cactcttatg ccttatctaa tttaaattga tgagttagtt tctcctacaa attctctatg    4260
gcatactaga aattacatta aattgtaagt caaaccccaa tgatttggct acaattaaga    4320
aagcccactc acaccactaa agtgtgtgac acagaatatt gtttcatctt tgtgtaattg    4380
taaaattgga aagaatctta gatgtcctcc agcccagagg tttcaatccc ttctccccag    4440
ggacttcagg gggtatattc tttcctaggg aggggctggt gttgagaaga tgcaactttc    4500
ctcccctaac tccatttaat cagaggccac taattcgttc tgttttacaa attggtacaa    4560
tctgagtatc ttccccaatt ctctgtctct gttcttcagc atgagaggct gtgtatcaga    4620
taatattttt tactcagtta aagcatctga atccccaccc tgaatgacta aagaaaaat    4680 ccatttggaa tcatgtttct ctatcttagt attttcaaga atttccagag gatgcttaca    4740
tatctcacaa ttgtgctgtg gttttgattt actgtcttat catagacatc tcctccaaac    4800
tatgacttct ttcaacataa ctctatctca aacatggatt cagtgcagtc tcagtacttc    4860
tgaaagtaaa cactgagaat actgtttaac aaaactttac taaaggtttg tgagccattg    4920
agttttccaa gcctcccaaa gacattccaa gggcatgtta gcaccatatg ttagtgttct    4980
tgacagtgtg ttaaatgctg tatcctgaaa aagcatatcc ataaattttc ccttttctgg    5040
ctttatttcc caccccctctt aatcttccat cctgagaatg taatcccaat atcctatccc    5100
atgtatttta cattctcttt ccagtacatc tgagctaggt cttgtatctc aggtctccac    5160
tagtgcaata atacacttag ttatttggct taactttagt taattgtctt agtggccagg    5220
acatacggta gacacaaatg ctgaggggga catctgctgt cttacgcggt agtgcctctg    5280
tgtcaccttc aagccaggct actcttaaag gagtggtggg cacttctgca ggctcaaagg    5340
gtccaggaaa tctgagggga ccagattttc aaatgcatca acaagtgtc ttcatccaat    5400 aactttgggt ctcatttatt gcagccaggg ccctactctt gtcatggcag acctaactag    5460
ttggggaatt ttactttctc tggaggtctg ctgtccttag ttcctgagcc tgatcctcag    5520 cctttttctgt cctccagctg caagaaatag gaatctctct ttgtgtttcc aaagagttcc    5580
tttggctttc acatttagcc ttttattgat ggttaatctt tttcagtctt tcattttgc    5640 ttcccacagc attaattgcc cccagcaagt actgtccaat accattgccc ttataataac    5700
tacttgcctc atttacggcg cgccgttgac attgattatt gactagttat taatagtaat    5760
caattacggg gtcattagtt catagcccat atatggagtt ccgcgttaca taacttacgg    5820
taaatggccc gcctggctga ccgcccaacg accccgccc attgacgtca ataatgacgt    5880
atgttcccat agtaacgcca atagggactt tccattgacg tcaatgggtg gagtatttac    5940
ggtaaactgc ccacttggca gtacatcaag tgtatcatat gccaagtacg ccccctattg    6000
acgtcaatga cggtaaatgg cccgcctggc attatgccca gtacatgacc ttatgggact    6060
ttcctacttg gcagtacatc tacgtattag tcatcgctat taccatggtg atgcggtttt    6120
```

```
ggcagtacat caatgggcgt ggatagcggt ttgactcacg gggatttcca agtctccacc    6180
ccattgacgt caatgggagt ttgttttggc accaaaatca acgggacttt ccaaaatgtc    6240
gtaacaactc cgcccattg acgcaaatgg gcggtaggcg tgtacggtgg gaggtctata    6300
taagcagagc tccccgggag cttgtatatc cattttcgga tctgatcaag agacaggatg    6360
aggatcgttt cgcatgattg aacaagatgg attgcacgca ggttctccgg ccgcttgggt    6420
ggagaggcta ttcggctatg actgggcaca acagacaatc ggctgctctg atgccgccgt    6480
gttccggctg tcagcgcagg ggcgcccggt tctttttgtc aagaccgacc tgtccggtgc    6540
cctgaatgaa ctgcaggacg aggcagcgcg gctatcgtgg ctggccacga cgggcgttcc    6600
ttgcgcagct gtgctcgacg ttgtcactga agcgggaagg gactggctgc tattgggcga    6660
agtgccgggg caggatctcc tgtcatctca ccttgctcct gccgagaaag tatccatcat    6720
ggctgatgca atgcggcggc tgcatacgct tgatccggct acctgcccat tcgaccacca    6780
agcgaaacat cgcatcgagc gagcacgtac tcggatggaa gccggtcttg tcgatcagga    6840
tgatctggac gaagagcatc aggggctcgc gccagccgaa ctgttcgcca ggctcaaggc    6900
gcgcatgccc gacggcgagg atctcgtcgt gacccatggc gatgcctgct tgccgaatat    6960
catggtggaa aatggccgct tttctggatt catcgactgt ggccggctgg gtgtggcgga    7020
ccgctatcag gacatagcgt tggctacccg tgatattgct gaagagcttg gcggcgaatg    7080
ggctgaccgc ttcctcgtgc tttacggtat cgccgctccc gattcgcagc gcatcgcctt    7140
ctatcgcctt cttgacgagt tcttctgatt aattaacagg actgacacgt gctacgagat    7200
ttcgattcca ccgccgcctt ctatgaaagg ttgggcttcg aatcgttttc cgggacgcc    7260 ggctggatga tcctccagcg cggggatctc atgctggagt tcttcgccca ccccaacttg    7320
tttattgcag cttataatgg ttacaaataa agcaatagca tcacaaattt cacaaataaa    7380 gcatttttt cactgcattc tagttgtggt ttgtccaaac tcatcaatgt atcttatcat    7440
gtctgacgcg aattcgccct gcgcgcgat gtacgggcca gatatacgcg ttgacattga    7500
ttattgacta gttattaata gtaatcaatt acggggtcat tagttcatag cccatatatg    7560
gagttccgcg ttacataact tacggtaaat ggcccgcctg gctgaccgcc caacgacccc    7620
cgcccattga cgtcaataat gacgtatgtt cccatagtaa cgccaatagg gactttccat    7680
tgacgtcaat gggtggagta tttacggtaa actgcccact tggcagtaca tcaagtgtat    7740
catatgccaa gtacgccccc tattgacgtc aatgacggta aatggcccgc ctggcattat    7800
gcccagtaca tgaccttatg ggactttcct acttggcagt acatctacgt attagtcatc    7860
gctattacca tggtgatgcg gttttggcag tacatcaatg ggcgtggata gcggtttgac    7920
tcacggggat ttccaagtct ccaccccatt gacgtcaatg ggagtttgtt ttggcaccaa    7980
aatcaacggg actttccaaa atgtcgtaac aactccgccc cattgacgca aatgggcggt    8040
aggcgtgtac ggtgggaggt ctatataagc agagctctct ggctaactag agaacccact    8100
gcttactggc ttatcgaaat taatacgact cactataggg agacccaagc tggctagcct    8160
taggcgcggc tagggataac agggtaatat cgcgccagat ctgtacattc gaagatatct    8220
taattaagcg gccgctcgag tctagagggc ccgtttaaac ccgctgatca gcctcgactg    8280
tgccttctag ttgccagcca tctgttgttt gcccctcccc cgtgccttcc ttgaccctgg    8340
aaggtgccac tcccactgtc ctttcctaat aaaatgagga aattgcatcg cattgtctga    8400
gtaggtgtca ttctattctg gggggtgggg tggggcagga cagcaagggg gaggattggg    8460
aagacaatag caggcatgct ggggaggccg gcctgcaggt cccagtttac ctatgatgaa    8520
```

```
agctttataa tttccatctt gtgtcacaga atctttgttc tctacctcat tgtccactga   8580
ataatgggtg atccagcttc aaaatctcat ttaacctctc cattttcaga ccattctcag   8640
atcaactgtc aggcctactt ctgtagtaag taggctcaga tgacatttag aaaattgagg   8700
gttcattaag aaatgctctt gggatcaaca actgtgggag aaggaaacaa agcaaattg    8760 aggtggtgtg tgaaatcaca acaagccctc agccaaattt acaggatgct ctgaagctgg   8820
caaatatctt cagaattaaa gaaagggtc aagcctttaa tatgccatga ttaaccagtc    8880
attggttgca agctaccacc tctcccacag ggaacccaat cccagagaag gggtatgatc   8940
ttgaatgagg cagctactgt ccatcgagga caagtttcca aatgggtaga cagctaagaa   9000
attttaaccc tcaacctttg ggataactga ggataaaatc ctttagtctt aaagtggaga   9060
tctgagtggc aaaggccgcc ctccattgca aaggattaa gtactgatga ggacatgtct    9120
aaaagatgca ggaaccagtt tgaaagaggc tcactagtta attttggct aatgtaaata    9180 tcaaaaagaa taatgatgac agtgagtttt caaatattga atgagaaaat aatttgacta   9240
aatatattct gaatacgttt agtatatcca tcggtgtcct gaaagaaga gtggatggaa    9300 gctcttttt gtagaataat gccagttcct taatgtgaaa tgaccaaatt aaagaacta    9360 gatcattttc aaacatcaat gtatgaattg atttagttat caatagttgc aaaaaccttt   9420
agctgataat ttgttgagga tcaggatttc acatacatta caaagtatca acatacagaa   9480
tacacattaa tgacaaaggg gaagaaaaca cctttacaat ggggggtgt tgtagatact    9540 accttaaccg agagatcaaa cttgacatca ccaataagag aaggaaaaaa aaacagact    9600 tcattagctt tctaatttaa tgcaatggga agtacatctg tattattctt gacaaaatgt   9660
ttaacttgag tctgatcata ggaagcaatt tgacaaatct ggattgtgag tgagcttgta   9720
agacaaccag cctggattat ttaaaaatat cagaatcatg aaaacaaagt gtaaagagac   9780
tgtcctaaat taaagatgtt tttaaaaatg acaaatatac tatgagatca ttaatcagat   9840
cctgaattga acataaaaat agctaaaaag aacattgtgg gctcaactga gtaaatacga   9900
gtataaatta tatatcagat attactgtat caatattaaa ttttctgagt tcgatcatgc   9960
atttgtgatt atatcatggc tacctactaa aatactaaag gaccctgcag gttcgaaaag  10020
ggcgaattcg cgtttaaagc ttgtacatcg atgcggccgc aataaaatat ctttattttc  10080
attacatctg tgtgttggtt ttttgtgtga atcgtaacta acatacgctc tccatcaaaa  10140
caaaacgaaa caaaacaaac tagcaaaata ggctgtcccc agtgcaagtg caggtgccag  10200
aacatttctc tatcgaa                                                 10217
```

<210> SEQ ID NO 280
<211> LENGTH: 20
<212> TYPE: DNA
<213> ORGANISM: Artificial
<220> FEATURE:
<223> OTHER INFORMATION: PCR primer SH6GHGF3

<400> SEQUENCE: 280
caatggagtt ttggagccac                                                   20

<210> SEQ ID NO 281
<211> LENGTH: 20
<212> TYPE: DNA
<213> ORGANISM: Artificial
<220> FEATURE:
<223> OTHER INFORMATION: PCR primer NeoR9

<400> SEQUENCE: 281
atcagagcag ccgattgtct                                          20

<210> SEQ ID NO 282
<211> LENGTH: 20
<212> TYPE: DNA
<213> ORGANISM: Artificial
<220> FEATURE:
<223> OTHER INFORMATION: PCR forward primer HPRT

<400> SEQUENCE: 282
gccagacttt gttggatttg                                          20

<210> SEQ ID NO 283
<211> LENGTH: 25
<212> TYPE: DNA
<213> ORGANISM: Artificial
<220> FEATURE:
<223> OTHER INFORMATION: PCR reverse primer HPRT

<400> SEQUENCE: 283
ctctcatctt aggctttgta ttttg                                    25

<210> SEQ ID NO 284
<211> LENGTH: 23
<212> TYPE: DNA
<213> ORGANISM: Artificial
<220> FEATURE:
<223> OTHER INFORMATION: PCR forward primer USP25

<400> SEQUENCE: 284
cagaggacat gatgaagaat tga                                      23

<210> SEQ ID NO 285
<211> LENGTH: 20
<212> TYPE: DNA
<213> ORGANISM: Artificial
<220> FEATURE:
<223> OTHER INFORMATION: PCR reverse primer USP25

<400> SEQUENCE: 285
ctcgatcctc tccagattcg                                          20

<210> SEQ ID NO 286
<211> LENGTH: 20
<212> TYPE: DNA
<213> ORGANISM: Artificial
<220> FEATURE:
<223> OTHER INFORMATION: PCR forward primer NRIP1

<400> SEQUENCE: 286
gcactgtggt cagactgcat                                          20

<210> SEQ ID NO 287
<211> LENGTH: 20
<212> TYPE: DNA
<213> ORGANISM: Artificial
<220> FEATURE:
<223> OTHER INFORMATION: PCR reverse primer NRIP1

<400> SEQUENCE: 287
ttccatcgca atcagagaga                                          20

<210> SEQ ID NO 288
<211> LENGTH: 20

-continued

```
<212> TYPE: DNA
<213> ORGANISM: Artificial
<220> FEATURE:
<223> OTHER INFORMATION: PCR forward primer CXADR

<400> SEQUENCE: 288
cttatcatct tttgctgtcg                                              20

<210> SEQ ID NO 289
<211> LENGTH: 20
<212> TYPE: DNA
<213> ORGANISM: Artificial
<220> FEATURE:
<223> OTHER INFORMATION: PCR reverse primer CXADR

<400> SEQUENCE: 289
tactgccgat gtagcttctg                                              20

<210> SEQ ID NO 290
<211> LENGTH: 20
<212> TYPE: DNA
<213> ORGANISM: Artificial
<220> FEATURE:
<223> OTHER INFORMATION: PCR forward primer BTG3

<400> SEQUENCE: 290
ccagaaaaac catcgaaagg                                              20

<210> SEQ ID NO 291
<211> LENGTH: 21
<212> TYPE: DNA
<213> ORGANISM: Artificial
<220> FEATURE:
<223> OTHER INFORMATION: PCR reverse primer BTG3

<400> SEQUENCE: 291
ggtcactata caagatgcag c                                            21

<210> SEQ ID NO 292
<211> LENGTH: 21
<212> TYPE: DNA
<213> ORGANISM: Artificial
<220> FEATURE:
<223> OTHER INFORMATION: PCR forward primer C21orf91

<400> SEQUENCE: 292
aaacactctc cttctgccac a                                            21

<210> SEQ ID NO 293
<211> LENGTH: 20
<212> TYPE: DNA
<213> ORGANISM: Artificial
<220> FEATURE:
<223> OTHER INFORMATION: PCR reverse primer C21orf91

<400> SEQUENCE: 293 atggccoctt aatgatttgg                                              20

<210> SEQ ID NO 294
<211> LENGTH: 349
<212> TYPE: PRT
<213> ORGANISM: artificial sequence
<220> FEATURE:
<223> OTHER INFORMATION: SCOH-SH6-b12-G2-linker-BQY-pCLS6567

<400> SEQUENCE: 294
```

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Tyr Lys Phe Lys His Gln Leu Ser Leu Thr Phe Lys Val Thr Gln
        35                  40                  45

Lys Thr Gln Arg Arg Trp Leu Leu Asp Lys Leu Val Asp Glu Ile Gly
    50                  55                  60

Val Gly Tyr Val Arg Gly Ser Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Asp Ser Ser Val Ser Asn Ser Glu His
                165                 170                 175

Ile Ala Pro Leu Ser Leu Pro Ser Ser Pro Ser Val Gly Ser Asn
            180                 185                 190

Lys Lys Phe Leu Leu Tyr Leu Ala Gly Phe Val Asp Ser Asp Gly Ser
        195                 200                 205

Ile Phe Ala Gln Ile Gln Pro Asn Gln Ser Tyr Lys Phe Lys His Gln
    210                 215                 220

Leu Arg Leu Thr Phe Ala Val Thr Gln Lys Thr Gln Arg Arg Trp Phe
225                 230                 235                 240

Leu Asp Lys Leu Val Asp Arg Ile Gly Val Gly Tyr Val Arg Asp Leu
                245                 250                 255

Gly Ser Val Ser Asn Tyr Ile Leu Ser Glu Ile Lys Pro Leu His Asn
            260                 265                 270

Phe Leu Thr Gln Leu Gln Pro Phe Leu Arg Leu Lys Gln Lys Gln Ala
        275                 280                 285

Asn Leu Val Leu Lys Ile Ile Glu His Leu Pro Ser Ala Lys Glu Ser
    290                 295                 300

Pro Asp Lys Phe Leu Glu Val Cys Thr Trp Val Asp Gln Val Ala Ala
305                 310                 315                 320

Leu Asn Asp Ser Lys Thr Arg Lys Thr Ser Glu Thr Val Arg Ala
                325                 330                 335

Val Leu Asp Ser Leu Ser Glu Lys Lys Ser Ser Pro
            340                 345

<210> SEQ ID NO 295
<211> LENGTH: 349
<212> TYPE: PRT
<213> ORGANISM: artificial sequence
<220> FEATURE:
<223> OTHER INFORMATION: SCOH-SH6-b11-G2.2-linker-BQY-pCLS6570

<400> SEQUENCE: 295

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Tyr Lys Phe Lys His Gln Leu Ser Leu Thr Phe Val Thr Gln
        35                  40                  45

Lys Thr Gln Arg Arg Trp Leu Leu Asp Lys Leu Val Asp Glu Ile Gly
50                  55                  60

Val Gly Tyr Val Arg Asp Arg Gly Ser Val Ser Asp Tyr Ile Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Asp Ser Ser Val Ser Asn Ser Glu His
                165                 170                 175

Ile Ala Pro Leu Ser Leu Pro Ser Ser Pro Ser Val Gly Ser Asn
            180                 185                 190

Lys Lys Phe Leu Leu Tyr Leu Ala Gly Phe Val Asp Ser Asp Gly Ser
        195                 200                 205

Ile Phe Ala Gln Ile Gln Pro Asn Gln Ser Tyr Lys Phe Lys His Gln
210                 215                 220

Leu Arg Leu Thr Phe Ala Val Thr Gln Lys Thr Gln Arg Arg Trp Phe
225                 230                 235                 240

Leu Asp Lys Leu Val Asp Arg Ile Gly Val Gly Tyr Val Arg Asp Leu
                245                 250                 255

Gly Ser Val Ser Asn Tyr Ile Leu Ser Glu Ile Lys Pro Leu His Asn
            260                 265                 270

Phe Leu Thr Gln Leu Gln Pro Phe Leu Arg Leu Lys Gln Lys Gln Ala
        275                 280                 285

Asn Leu Val Leu Lys Ile Ile Glu His Leu Pro Ser Ala Lys Glu Ser
290                 295                 300

Pro Asp Lys Phe Leu Glu Val Cys Thr Trp Val Asp Gln Val Ala Ala
305                 310                 315                 320

Leu Asn Asp Ser Lys Thr Arg Lys Thr Ser Glu Thr Val Arg Ala
                325                 330                 335

Val Leu Asp Ser Leu Ser Glu Lys Lys Lys Ser Ser Pro
            340                 345

<210> SEQ ID NO 296
<211> LENGTH: 24
<212> TYPE: DNA
<213> ORGANISM: Artificial
<220> FEATURE:
<223> OTHER INFORMATION: Deep sequencing forward primer SH3

<400> SEQUENCE: 296
tgggggtctt actctgtttc ccag          24

<210> SEQ ID NO 297
<211> LENGTH: 22
<212> TYPE: DNA

```
<213> ORGANISM: Artificial
<220> FEATURE:
<223> OTHER INFORMATION: Deep sequencing reverse primer SH3

<400> SEQUENCE: 297
aggagagtcc ttctttggcc aa                                              22

<210> SEQ ID NO 298
<211> LENGTH: 24
<212> TYPE: DNA
<213> ORGANISM: Artificial
<220> FEATURE:
<223> OTHER INFORMATION: Deep sequencing forward primer SH4

<400> SEQUENCE: 298
gagtgatagc ataatgaaaa ccca                                            24

<210> SEQ ID NO 299
<211> LENGTH: 24
<212> TYPE: DNA
<213> ORGANISM: Artificial
<220> FEATURE:
<223> OTHER INFORMATION: Deep sequencing reverse primer SH4

<400> SEQUENCE: 299
ctcaccataa gtcaactgtc tcag                                            24

<210> SEQ ID NO 300
<211> LENGTH: 35
<212> TYPE: DNA
<213> ORGANISM: Artificial
<220> FEATURE:
<223> OTHER INFORMATION: Deep sequencing forward primer SH6

<400> SEQUENCE: 300
tctttgtgtt tccaaagagt tcctttggct ttcac                                35

<210> SEQ ID NO 301
<211> LENGTH: 35
<212> TYPE: DNA
<213> ORGANISM: Artificial
<220> FEATURE:
<223> OTHER INFORMATION: Deep sequencing reverse primer SH6

<400> SEQUENCE: 301
gaatggtctg aaaatggaga ggttaaatga gattt                                35

<210> SEQ ID NO 302
<211> LENGTH: 35
<212> TYPE: DNA
<213> ORGANISM: Artificial
<220> FEATURE:
<223> OTHER INFORMATION: Deep sequencing forward primer SH8

<400> SEQUENCE: 302
actaaatatg ttaattgtgt gtatacagtt tttgt                                35

<210> SEQ ID NO 303
<211> LENGTH: 35
<212> TYPE: DNA
<213> ORGANISM: Artificial
<220> FEATURE:
<223> OTHER INFORMATION: Deep sequencing reverse primer SH8

<400> SEQUENCE: 303
attgctactt catttgttat gttaactatg acatg                                35
```

<210> SEQ ID NO 304
<211> LENGTH: 36
<212> TYPE: DNA
<213> ORGANISM: Artificial
<220> FEATURE:
<223> OTHER INFORMATION: Deep sequencing forward primer SH13

<400> SEQUENCE: 304
tttttgtggg tccacagtag gtgtatatat ttatgg                              36

<210> SEQ ID NO 305
<211> LENGTH: 35
<212> TYPE: DNA
<213> ORGANISM: Artificial
<220> FEATURE:
<223> OTHER INFORMATION: Deep sequencing reverse primer SH13

<400> SEQUENCE: 305
cagttgaact catggatgta gagagtagaa gaatg                               35

<210> SEQ ID NO 306
<211> LENGTH: 20
<212> TYPE: DNA
<213> ORGANISM: Artificial
<220> FEATURE:
<223> OTHER INFORMATION: Deep sequencing forward primer SH18

<400> SEQUENCE: 306
gacctgaagc tcaggtactt                                                20

<210> SEQ ID NO 307
<211> LENGTH: 20
<212> TYPE: DNA
<213> ORGANISM: Artificial
<220> FEATURE:
<223> OTHER INFORMATION: Deep sequencing reverse primer SH18

<400> SEQUENCE: 307
agtggtggta ggcaggacat                                                20

<210> SEQ ID NO 308
<211> LENGTH: 35
<212> TYPE: DNA
<213> ORGANISM: Artificial
<220> FEATURE:
<223> OTHER INFORMATION: Deep sequencing forward primer SH19

<400> SEQUENCE: 308
cttaggtaaa cctcaaaaca acaagagagg agcaa                               35

<210> SEQ ID NO 309
<211> LENGTH: 35
<212> TYPE: DNA
<213> ORGANISM: Artificial
<220> FEATURE:
<223> OTHER INFORMATION: Deep sequencing reverse primer SH19

<400> SEQUENCE: 309
ctgctagagc ccgtaatgtt tcaatcatag ttatt                               35

<210> SEQ ID NO 310
<211> LENGTH: 24
<212> TYPE: DNA
<213> ORGANISM: Artificial
<220> FEATURE:

<223> OTHER INFORMATION: Deep sequencing forward primer SH31

<400> SEQUENCE: 310
ttcaggttag gtgaccttca aact                                          24

<210> SEQ ID NO 311
<211> LENGTH: 24
<212> TYPE: DNA
<213> ORGANISM: Artificial
<220> FEATURE:
<223> OTHER INFORMATION: Deep sequencing reverse primer SH31

<400> SEQUENCE: 311
aagaccaggc tgggcaacca tagc                                          24

<210> SEQ ID NO 312
<211> LENGTH: 32
<212> TYPE: DNA
<213> ORGANISM: Artificial
<220> FEATURE:
<223> OTHER INFORMATION: Deep sequencing forward primer SH39

<400> SEQUENCE: 312
gaataatgga ataaacccag agagaaacag ag                                 32

<210> SEQ ID NO 313
<211> LENGTH: 32
<212> TYPE: DNA
<213> ORGANISM: Artificial
<220> FEATURE:
<223> OTHER INFORMATION: Deep sequencing reverse primer SH39

<400> SEQUENCE: 313
gtgttcaagg aaaatggagt gatattagga at                                 32

<210> SEQ ID NO 314
<211> LENGTH: 24
<212> TYPE: DNA
<213> ORGANISM: Artificial
<220> FEATURE:
<223> OTHER INFORMATION: Deep sequencing forward primer SH41

<400> SEQUENCE: 314
ggagatatca ttaaaagagg catt                                          24

<210> SEQ ID NO 315
<211> LENGTH: 24
<212> TYPE: DNA
<213> ORGANISM: Artificial
<220> FEATURE:
<223> OTHER INFORMATION: Deep sequencing reverse primer SH41

<400> SEQUENCE: 315
attacaatag ccttaggaaa ctag                                          24

<210> SEQ ID NO 316
<211> LENGTH: 30
<212> TYPE: DNA
<213> ORGANISM: Artificial
<220> FEATURE:
<223> OTHER INFORMATION: Deep sequencing forward primer SH42

<400> SEQUENCE: 316
gagtcacagc caccttacat tttactttc                                     30

```
<210> SEQ ID NO 317
<211> LENGTH: 30
<212> TYPE: DNA
<213> ORGANISM: Artificial
<220> FEATURE:
<223> OTHER INFORMATION: Deep sequencing reverse primer SH42

<400> SEQUENCE: 317
aagtagaaca cattcctatt tccattaagt                                    30

<210> SEQ ID NO 318
<211> LENGTH: 24
<212> TYPE: DNA
<213> ORGANISM: Artificial
<220> FEATURE:
<223> OTHER INFORMATION: Deep sequencing forward primer SH43

<400> SEQUENCE: 318
attaagtaca aaatttggtc caat                                          24

<210> SEQ ID NO 319
<211> LENGTH: 23
<212> TYPE: DNA
<213> ORGANISM: Artificial
<220> FEATURE:
<223> OTHER INFORMATION: Deep sequencing reverse primer SH43

<400> SEQUENCE: 319
aaagttgatt catctgaaac atg                                           23

<210> SEQ ID NO 320
<211> LENGTH: 20
<212> TYPE: DNA
<213> ORGANISM: Artificial
<220> FEATURE:
<223> OTHER INFORMATION: Deep sequencing forward primer SH44

<400> SEQUENCE: 320
gcagcgatcc atggtggaga                                               20

<210> SEQ ID NO 321
<211> LENGTH: 20
<212> TYPE: DNA
<213> ORGANISM: Artificial
<220> FEATURE:
<223> OTHER INFORMATION: Deep sequencing reverse primer SH44

<400> SEQUENCE: 321
taacacaggc tcatgtaggt                                               20

<210> SEQ ID NO 322
<211> LENGTH: 20
<212> TYPE: DNA
<213> ORGANISM: Artificial
<220> FEATURE:
<223> OTHER INFORMATION: Deep sequencing forward primer SH52

<400> SEQUENCE: 322
atgttattcg aggacccact                                               20

<210> SEQ ID NO 323
<211> LENGTH: 20
<212> TYPE: DNA
<213> ORGANISM: Artificial
<220> FEATURE:
<223> OTHER INFORMATION: Deep sequencing reverse primer SH52
```

-continued

```
<400> SEQUENCE: 323
gtgacaactc tgctagaaga                                              20

<210> SEQ ID NO 324
<211> LENGTH: 30
<212> TYPE: DNA
<213> ORGANISM: Artificial
<220> FEATURE:
<223> OTHER INFORMATION: Deep sequencing adaptor primer

<400> SEQUENCE: 324
ccatctcatc cctgcgtgtc tccgactcag                                   30

<210> SEQ ID NO 325
<211> LENGTH: 30
<212> TYPE: DNA
<213> ORGANISM: Artificial
<220> FEATURE:
<223> OTHER INFORMATION: Deep sequencing adaptor primer

<400> SEQUENCE: 325
cctatcccct gtgtgccttg gcagtctcag                                   30

<210> SEQ ID NO 326
<211> LENGTH: 27
<212> TYPE: PRT
<213> ORGANISM: artificial sequence
<220> FEATURE:
<223> OTHER INFORMATION: BQY peptide linker

<400> SEQUENCE: 326

Ala Ala Gly Asp Ser Ser Val Ser Asn Ser Glu His Ile Ala Pro Leu
1               5                   10                  15

Ser Leu Pro Ser Ser Pro Pro Ser Val Gly Ser
            20                  25
```

USE OF ENDONUCLEASES FOR INSERTING TRANSGENES INTO SAFE HARBOR LOCI

CROSS REFERENCE TO RELATED APPLICATIONS

This application claims benefit of U.S. Provisional Application No. 61/308,509, filed Feb. 26, 2010 (which is hereby incorporated by reference).

The present invention concerns the endonucleases capable of cleaving a target sequence located in a "safe harbor loci", i.e. a loci allowing safe expression of a transgene. The present invention further concerns the use of such endonucleases for inserting transgenes into a cell, tissue or organism.

Meganucleases

Meganucleases, also referred to as homing endonucleases, were the first endonucleases used to induce double-strand breaks and recombination in living cells (Rouet et al. PNAS 1994 91:6064-6068; Rouet et al. Mol Cell Biol. 1994 14:8096-8106; Choulika et al. Mol Cell Biol. 1995 15:1968-1973; Puchta et al. PNAS 1996 93:5055-5060). However, their use has long been limited by their narrow specificity. Although several hundred natural meganucleases had been identified over the past years, this diversity was still largely insufficient to address genome complexity, and the probability of finding a meganuclease cleavage site within a gene of interest is still extremely low. These findings highlighted the need for artificial endonucleases with tailored specificities, cleaving chosen sequences with the same selectivity as natural endonucleases.

Meganucleases have emerged as scaffolds of choice for deriving genome engineering tools cutting a desired target sequence (Paques et al. Curr Gen Ther. 2007 7:49-66). Combinatorial assembly processes allowing to engineer meganucleases with modified specificities has been described by Arnould et al. J Mol. Biol. 2006 355:443-458; Arnould et al. J Mol. Biol. 2007 371:49-65; Smith et al. NAR 2006 34:e149; Grizot et al. NAR 2009 37:5405). Briefly, these processes rely on the identifications of locally engineered variants with a substrate specificity that differs from the substrate specificity of the wild-type meganuclease by only a few nucleotides. Up to four sets of mutations identified in such proteins can then be assembled in new proteins in order to generate new meganucleases with entirely redesigned binding interface.

These processes require two steps, wherein different sets of mutations are first assembled into homodimeric variants cleaving palindromic targets. Two homodimers can then be co-expressed in order to generate heterodimeric meganucleases cleaving the chosen non palindromic target. The first step of this process remains the most challenging one, and one cannot know in advance whether a meganuclease cleaving a given locus could be obtained with absolute certainty. Indeed, not all sequences are equally likely to be cleaved by engineered meganucleases, and in certain cases, meganuclease engineering could prove difficult (Galetto et al. Expert Opin Biol Ther. 2009 9:1289-303).

Other Enzymes Suitable for Site-specific Genome Modifications

Specialized enzymes like integrases, recombinases, transposases and endonucleases have been proposed for site-specific genome modifications. For years, the use of these enzymes remained limited, due to the challenge of retargeting their natural specificities towards desired target sites. Indeed, the target sites of these proteins, or sequences with a sufficient degree of sequence identity, should be present in the sequences neighboring the mutations to be corrected, or within the gene to be inactivated, which is usually not the case, except in the case of pre-engineered sequences. The main challenge that would allow the use of these DNA modifying enzymes in gene therapy relies on the possibility of redesigning their DNA binding properties. Many strategies have been developed, aiming to obtain artificial proteins with tailored substrate specificities, The integrase from the *Streptomyces* phage PhiC31 was used early for targeted gene transfer in an endogenous locus. This enzyme mediates recombination of the phage genome into the bacterial chromosome through a site-specific reaction between the phage attachment site (attP) and the bacterial attachment site (attB) (Kuhstoss et al. J Mol Biol 1991 222: 897-908; Rausch et al. NAR 1991 19:5187-5189). This can occur from plasmids carrying attB sites into native genomic sequences harboring partial identity with attP, called pseudo attP sites (attP'). The PhiC31 integrase has been used to transfer several transgenes, including hFIX, in the human genome (Olivares et al. Nat Biotech 2002 20:1124-1128; Ginsburg et al. Adv Genet. 2005 54:179-187; Calos Curr Gene Ther 2006 6:633-645; Chalberg et al. J Mol Biol 2006 357:28-48; Aneja et al. J Gene Med 2007 9:967-975). The drawback here is that the site where integration can occur cannot be chosen (Chalberg et al. J Mol Biol 2006 357:28-48), and one has to rely on pseudo attP sites within the human genome loci, for precise integration. Whereas a major integration site is found on chromosome 19, hundreds other integration loci have been identified (Chalberg et al. J Mol Biol 2006 357:28-48). In recent work, the PhiC31 integrase was mutated in order to increase efficiency and specificity for integration at an attP' site, paving the way for the development of engineered integrases that target chosen sites (Keravala et al. Mol Ther 2009 17:112-120). However, development of engineered integrases has lagged behind similar efforts focused on targeted recombinase and endonuclease systems.

Site-specific recombinases, such as the Cre recombinase from bacteriophage P1, or the Flp protein from *Saccharomyces cerevisiae* have been used to induce recombination between pre-engineered sequences containing their cognate sites. The Cre recombinase recognizes and mediates recombination between two identical 34 bp sites known as loxP (Abremski et al. Cell 1983 32:1301-1311). For many years, a limitation of Cre derived recombinases has been that repeated loxP, or pseudo loxP sites, must be present in order to allow DNA integration between these two sites. However, directed evolution of the DNA binding interface of this molecule has been used to create recombinases with new specificities (Buchholz et al. Nat Biotech 2001 19:1047-1052; Santoro et al. PNAS 2002 99:4185-4190). The Cre recombinase system has also been useful in providing a framework for the use of DNA targeting enzymes to induce the excision of viral sequences. Indeed, work with a retroviral Moloney murine leukemia virus vector system has shown that, when loxP sites are introduced in the LTR of an integrative retroviral vector, the expression of Cre can result in the deletion of all the sequences between the two loxP sites (Choulika et al. J Virol 1996 70:1792-1798). More recently, an engineered Cre recombinase variant has been used to excise an HIV type 1 provirus (Sarkar et al. Science 2007 316:1912-1915) from cells. The recombinase was redesigned to target the proviral LTRs, and used to induce the excision of all intervening sequences. Engineering attempts have also been made with the Flp recombinase, targeting the FRT (Flp Recombination Target) sequence (Buchholzt et al. Nat Biotech 1998 16:657-662), and variants recognizing non-native Flp recombination targets have been obtained (Voziyanov et al. J Mol Biol 2003 326:65-76). However, there is no example of targeted insertion in a non-pre-engineered locus with such enzymes today.

Transposons such as Piggy Back and Sleeping Beauty can provide efficient tools for insertion of sequences into vertebrate cells and have been proposed as an alternative to viral mediated gene delivery to achieve long-lasting expression (lzsvak et al. Mol ther 2004 9:147-156; Ivics et al. Curr Gene Ther 2006 6:593-607; Mates et al. Nat Genet. 2009 41:753-761).Transposons are a natural means of gene delivery in which a DNA sequence present in a DNA molecule is inserted in another location, through the action of the transposase. An engineered SB transposase, called SB100X was recently shown to increase the efficiency of the process (Mates et al. Nat Genet. 2009 41:753-761). Transposition is random on a genomic level (for example, SB integrates into TA dinucleotides (Vigdal et al. J Mol Biol 2002 323:441-452), and should therefore not be considered as tools for targeted approaches. However, further work has shown the possibility of chromosomal transposition mediated by engineered transposases in human cells, by fusing the transposase catalytic domain to specific DNA binding domains (Ivics, et al. Mol Ther 2007 15:1137-1144), paving the way for the development of a new category of targeted tools.

Gene Therapy

The successful treatment of several X-SCID patients by gene therapy nearly 10 years ago was one of the most significant milestones in the field of gene therapy. This tremendous achievement was followed by significant success in other clinical trials addressing different diseases, including another form of SCID, Epidermolysis Bullosa and Leber Amaurosis and others. However, these initial successes have long been overshadowed by a series of serious adverse events, i.e. the appearance of leukemia in X-SCID treated patients (Hacein-Bey-Abina et al. Science 2003 302:415-419; Hacein-Bey-Abina et al. J Clin Invest. 2008 118:3132-3142; Howe et al. J Clin Invest. 2008 118:3143-3150). All cases of leukemia, but one, could eventually be treated by chemotherapy, and the approach appears globally as a success, but these serious adverse effects highlighted the major risks of current gene therapy approaches.

There is thus a need in the art for a safe method for inserting a gene into the genome of a subject.

Most of the gene therapy protocols that are being developed these days for the treatment of inherited diseases are based on the complementation of a variant allele by an additional and functional copy of the disease-causing gene. In non-dividing tissues, such as retina, delivering this copy can be accomplished using a non integrative vector, derived for example, from an Adeno Associated Virus (AAV). However, when targeting stem cells, such as hematopoietic stem cells (HSCs), whose fate is to proliferate, persistent expression becomes an issue, and there is a need for integrative vectors. Retroviral vectors, which integrate in the genome and replicate with the hosts' chromosomes, have proved efficient for this purpose, but the random nature of their insertion has raised various concerns, all linked with gene expression. The cases of leukemia observed in the X-SCID trials were clearly linked to the activation of a proto-oncogene in the vicinity of the integration sites. In addition, inappropriate expression of the transgene could result in metabolic or immunological problems. Finally, insertion could result in the knock-out of endogenous genes.

Site-specific integration would be a promising alternative to random integration of viral vectors since it could alleviate the risks of insertional mutagenesis (Kolb et al. Trends Biotechnol. 2005 23:399-406; Porteus et al. Nat. Biotechnol. 2005 23:967-973; Paques et al. Curr Gen Ther. 2007 7:49-66). However, it is relatively tedious to engineer tools for targeted recombination. In addition, each tool has its intrinsic properties in terms of activity and specificity.

Therefore, there is a need in the art for a tool allowing the targeted insertion of transgenes into loci of the genome that can be considered as "safe harbors" for gene addition. In addition, it would be extremely advantageous if this tool could be used for inserting transgenes irrespective of their sequences, thereby allowing the treatment of numerous diseases by gene therapy using a same tool. Moreover, it would be extremely advantageous if this tool allowed inserting transgenes into the genome with a high efficacy, and led to stable expression of the transgene at high levels.

SUMMARY OF THE INVENTION

The invention is notably drawn to the following embodiments:

Embodiment 1: A variant endonuclease capable of cleaving a target sequence for use in inserting a transgene into the genome of an individual, wherein
  i. said genome comprises a locus comprising said target sequence; and
  ii. said target sequence is located at a distance of at most 200 kb from a retroviral insertion site (RIS), wherein said RIS is neither associated with cancer nor with abnormal cell proliferation.

Embodiment 2: The endonuclease according to embodiment 1, wherein insertion of said transgene does not substantially modify expression of genes located in the vicinity of the target sequence.

Embodiment 3: The endonuclease according to embodiment 1 or 2, wherein said target sequence is located at a distance of at least 100 kb from the nearest genes.

Embodiment 4: The endonuclease according to any one of embodiments 1 to 3, wherein said RIS has been identified in cells from a patient treated by gene therapy by transduction of stem cells.

Embodiment 5: The endonuclease according to any one of embodiments 1 to 3, wherein said RIS has been identified in cells from a patient treated by gene therapy by transduction of hematopoietic stem cells.

Embodiment 6: The endonuclease according to any one of embodiments 1 to 5, wherein said endonuclease is a homing endonuclease.

Embodiment 7: The endonuclease according to embodiment 6, wherein said homing endonuclease is a member of the family of LAGLIDADG endonucleases.

Embodiment 8: The endonuclease according to embodiment 7, wherein said member of the family of LAGLIDADG endonucleases is I-CreI.

Embodiment 9: The endonuclease according to any one of embodiments 1 to 8, wherein said locus is selected from the SH3 locus on human chromosome 6p25.1, the SH4 locus on human chromosome 7q31.2, the SH6 locus on human chromosome 21q21.1, the SH12 locus on human chromosome 13q34, the SH13 locus on human chromosome 3p12.2, the SH19 locus on human chromosome 22, the SH20 locus on human chromosome 12q21.2, the SH21 locus on human chromosome 3p24.1, the SH33 locus on human chromosome 6p12.2, the SH7 locus on human chromosome 2p16.1 and the SH8 locus on human chromosome 5.

Embodiment 10: In vitro or ex vivo use of an endonuclease as defined in any one of embodiments 1 to 9 for inserting a transgene into the genome of a cell or a tissue.

Embodiment 11: A variant dimeric I-CreI protein comprising two monomers that comprise a sequence at least 80% identical to SEQ ID NO: 1 or SEQ ID NO: 42, wherein:
  i. said dimeric I-CreI protein is capable of cleaving a target sequence located within a locus of an individual, said target sequence being located at a distance of at most 200 kb from a retroviral insertion site (RIS), and said RIS being neither associated with cancer nor with abnormal cell proliferation; and
  ii. said target sequence does not comprise a sequence of SEQ ID NO: 4.

Embodiment 12: The dimeric I-CreI protein according to embodiment 11, wherein said dimeric I-CreI protein is capable of cleaving a target sequence located within the SH3 locus on human chromosome 6p25.1.

Embodiment 13: The dimeric I-CreI protein according to embodiment 12, wherein said target sequence comprises the sequence of SEQ ID NO: 2.

Embodiment 14: The dimeric I-CreI protein according to embodiment 12 or 13, wherein said protein comprises:
  a) a first monomer that comprises amino acid substitutions at positions 30, 38, 70 and 75 of SEQ ID NO: 1; and
  b) a second monomer that comprises amino acid substitutions at positions 44, 54, 70 and 75 of SEQ ID NO: 1.

Embodiment 15: The dimeric I-CreI protein according to embodiment 14, wherein said polypeptide comprises:
  a) a first monomer comprising 30G 38R 70D 75N 86D mutations;
  b) a second monomer selected from the group consisting of:
    i. a monomer comprising 44A 54L 64A 70Q 75N 158R 162A mutations;
    ii. a monomer comprising 44A 54L 70Q 75Y 92R 158R 162A mutations;
    iii. a monomer comprising 4E 44A 54L 64A 70Q 75N 158R 162A mutations;
    iv. a monomer comprising 44A 54L 64A 70Q 75N 158W 162A mutations;
    v. a monomer comprising 44A 54L 70Q 75N mutations;
    vi. a monomer comprising 44A 54L 57E 70Q 75N 158R 162A mutations; and
    vii. a monomer comprising 44V 54L 70Q 75N 77V mutations;

Embodiment 16: The dimeric I-CreI protein according to embodiment 14, wherein said polypeptide comprises:
  a) a first monomer comprising 30G 38R 70D 75N 81T 154G mutations;
  b) a second monomer selected from the group consisting of:
    i. a monomer comprising 44A 54L 70Q 75N 105A 158R 162A mutations;
    ii. a monomer comprising 44A 54L 64A 70Q 75N 158R 162A mutations;
    iii. a monomer comprising 4E 44A 54L 64A 70Q 75N 158R 162A mutations;
    iv. a monomer comprising 44A 54L 64A 70Q 75N 158W 162A mutations;
    v. a monomer comprising 44A 54L 70Q 75N mutations; and
    vi. a monomer comprising 44V 54L 70Q 75N 77V mutations;

Embodiment 17: The dimeric I-CreI protein according to embodiment 14, wherein said polypeptide comprises:
  a) a first monomer comprising 30G 38R, 50R 70D 75N 142R mutations;
  b) a second monomer selected from the group consisting of:
    i. a monomer comprising 44A 54L 70Q 75N 105A 158R 162A mutations;
    ii. a monomer comprising 44A 54L 64A 70Q 75N 158R 162A mutations;
    iii. a monomer comprising 44A 54L 70Q 75Y 92R 158R 162A mutations;
    iv. a monomer comprising 4E 44A 54L 64A 70Q 75N 158R 162A mutations;
    v. a monomer comprising 44A 54L 64A 70Q 75N 158W 162A mutations;
    vi. a monomer comprising 44A 54L 66C 70Q 71 R 75N 151 A 158R 162A mutations;
    vii. a monomer comprising 44A 54L 70Q 75N mutations;
    viii. a monomer comprising 44A 54L 57E 70Q 75N 158R 162A mutations; and
    ix. a monomer comprising 44V 54L 70Q 75N 77V mutations;

Embodiment 18: The dimeric I-CreI protein according to embodiment 11, wherein said dimeric I-CreI protein is capable of cleaving a target sequence located within the SH4 locus on human chromosome 7q31.2.

Embodiment 19: The dimeric I-CreI protein according to embodiment 18, wherein said target sequence comprises the sequence of SEQ ID NO: 3.

Embodiment 20: The dimeric I-CreI protein according to embodiment 18 or 19, wherein said protein comprises:
  a) a first monomer that comprises amino acid substitutions at positions 24, 70, 75 and 77 of SEQ ID NO: 1; and
  b) a second monomer that comprises amino acid substitutions at positions 24, 44 and 70 of SEQ ID NO: 1.

Embodiment 21: The dimeric I-CreI protein according to embodiment 20, wherein said polypeptide comprises:
  a) a first monomer selected from the group consisting of:
    i. a monomer comprising 24V 44R 68Y 70S 75Y 77N mutations;
    ii. a monomer comprising 24V 68A 70S 75N 77R mutations; and
    iii. a monomer comprising 24V 70D 75N 77R mutations;
  b) a second monomer selected from the group consisting of:
    i. a monomer comprising 24V 44Y 70S mutations; and
    ii. a monomer comprising 24V 44Y 70S 77V mutations.

Embodiment 22: The dimeric I-CreI protein according to embodiment 11, wherein said dimeric I-CreI protein is capable of cleaving a target sequence located within the SH6 locus on human chromosome 21q21.1.

Embodiment 23: The dimeric I-CreI protein according to embodiment 22, wherein said target sequence comprises the sequence of SEQ ID NO: 59.

Embodiment 24: The dimeric I-CreI protein according to embodiment 22 or 23, wherein said protein comprises:
  a) a first monomer that comprises amino acid substitutions at positions 44, and optionally at positions 70 and/or 75 of SEQ ID NO: 1; and
  b) a second monomer that comprises amino acid substitutions at positions 28, 40, 44, 70 and 75 of SEQ ID NO: 1.

Embodiment 25: The dimeric I-CreI protein according to embodiment 24, wherein said polypeptide comprises:
  a) a first monomer comprising 44K 68T 70G 75N mutations; and
  b) a second monomer selected from the group consisting of:
    i. a monomer comprising 28Q 40R 44A 70L 75N 96R 111H 144S mutations;

ii. a monomer comprising 7R 28Q 40R 44A 70L 75N 85R 103T mutations;
iii. a monomer comprising 28Q 40R 44A 70L 75N 103S mutations;
iv. a monomer comprising 24F 27V 28Q 40R 44A 70L 75N 99R mutations;
v. a monomer comprising 7R 28Q 40R 44A 70L 75N 81T mutations;
vi. a monomer comprising 7R 28Q 40R 44A 70L 75N 77V mutations;
vii. a monomer comprising 7R 28Q 40R 44A 70L 75N 103T 121E 132V 160R mutations;
viii. a monomer comprising 28Q 40R 44A 70L 75N mutations;
ix. a monomer comprising 7R 28Q 40R 44A 70L 75N 103T mutations; and
x. a monomer comprising 28Q 34R 40R 44A 70L 75N 81V 103T 108V 160E mutations.

Embodiment 26: The dimeric I-CreI protein according to embodiment 24, wherein said polypeptide comprises:
a) a first monomer comprising a 44K mutation, and optionally 70S and/or 75N mutations; and
b) a second monomer selected from the group consisting of:
i. a monomer comprising 28Q 40R 44A 70L 75N 96R 111H 144S mutations;
ii. a monomer comprising 7R 28Q 40R 44A 70L 75N 85R 103T mutations;
iii. a monomer comprising 28Q 40R 44A 70L 75N 103S mutations;
iv. a monomer comprising 24F 27V 28Q 40R 44A 70L 75N 99R mutations;
v. a monomer comprising 7R 28Q 40R 44A 70L 75N 81T mutations;
vi. a monomer comprising 7R 28Q 40R 44A 70L 75N 103T 121E 132V 160R mutations;
vii. a monomer comprising 7R 28Q 40R 44A 70L 75N 103T mutations; and
viii. a monomer comprising 28Q 34R 40R 44A 70L 75N 81V 103T 108V 160E mutations.

Embodiment 27: A fusion protein comprising the monomers of the dimeric I-CreI protein according to any one of embodiments 11 to 26.

Embodiment 28: The fusion protein according to embodiment 27, wherein said monomers are connected by a peptidic linker comprising a sequence of SEQ ID NO: 43.

Embodiment 29: The fusion protein according to embodiment 27 or 28, wherein the C-terminal monomer further comprises K7E and K96E mutations, and wherein the N-terminal monomer further comprises E8K, E61R and G19S mutations.

Embodiment 30: The fusion protein according to any one of embodiments 27 to 29, wherein said fusion protein comprises a sequence selected from the group consisting of SEQ ID Nos. 25-40 and 76-96.

Embodiment 31: A nucleic acid encoding the endonuclease according to any one of embodiments 1-9 or the protein according to any one of embodiments 11 to 30.

Embodiment 32: An expression vector comprising the nucleic acid according to embodiment 31.

Embodiment 33: The expression vector according to embodiment 32, further comprising a targeting construct comprising a transgene and two sequences homologous to the genomic sequence flanking a target sequence recognized by the endonuclease as defined in one of embodiments 1-9 or by the protein as defined in any one of embodiments 11 to 30.

Embodiment 34: The expression vector of embodiment 33, wherein said transgene encodes a therapeutic polypeptide.

Embodiment 35: The expression vector according to any one of embodiments 32 to 34 for use in gene therapy.

Embodiment 36: A combination of:
an expression vector according to embodiment 32; and
a vector comprising a targeting construct comprising a transgene and two sequences homologous to the genomic sequence of a target sequence a recognized by the endonuclease as defined in one of embodiments 1-9 or by the protein as defined in any one of embodiments 11 to 30.

Embodiment 37: A pharmaceutical composition comprising the expression vector as defined in any one of embodiments 32 to 34 or the combination as defined in embodiment 36 and a pharmaceutically active carrier.

Embodiment 38: A method of treating an individual by gene therapy comprising administering an effective amount of the expression vector as defined in any one of embodiments 32 to 34 or of the combination as defined in embodiment 36 to an individual in need thereof.

Embodiment 39: A method for obtaining an endonuclease suitable for inserting a transgene into the genome of an individual, comprising the step of:
a) selecting, within the genome of said individual, a retroviral insertion site (RIS) that is neither associated with cancer nor with abnormal cell proliferation;
b) defining a genomic region extending 200 kb upstream and 200 kb downstream of said RIS; and
c) identifying a wild-type endonuclease or constructing a variant endonuclease capable of cleaving a target sequence located within said genomic region.

Embodiment 40: Use of the endonuclease according to any one of embodiments 1 to 9, or of the protein according to any one of embodiments 11 to 30, or of the nucleic acid according to embodiment 31, or of the expression vector according to any one of embodiments 32 to 34, or of the combination according to embodiment 36, for inserting a transgene into the genome of a cell, tissue or non-human animal, wherein said use is not therapeutic.

Embodiment 41: The use of embodiment 40, for making a non-human animal model of a hereditary disorder.

Embodiment 42: The use of embodiment 40, for producing a recombinant protein.

Embodiment 43: A non-human transgenic animal comprising a nucleic acid according to embodiment 31, or an expression vector according to any one of embodiments 32-34, or a combination according to embodiment 36 in its genome.

DETAILED DESCRIPTION OF THE INVENTION

The inventors have identified "safe harbors" loci within the genome allowing safe expression of a transgene through targeted insertion wherein (i) said loci are close to a retroviral insertion site identified in a cell from a patient treated by gene therapy, and (ii) said retroviral insertion are not associated with cancer or abnormal cell proliferation. As immediately apparent from the following description and examples, the safe harbor loci according to the invention may either be located within the intron of a gene, or within an intergenic region.

In particular, the inventors have found that endonucleases could be engineered in such a way as to target said safe harbors for gene addition.

More specifically, the inventors have engineered several I-CreI meganucleases that are capable of recognizing and cleaving target sequences located within different safe harbors loci, for instance the SH6, the SH3 locus, the SH4 locus, the SH12 locus, the SH13 locus, the SH19 locus, the SH20 locus, the SH21 locus, the SH33 locus, the SH7 locus, the SH8 locus, the SH18 locus, the SH31 locus, the SH38 locus, the SH39 locus, the SH41 locus, the SH42 locus, the SH43 locus, the SH44 locus, the SH45 locus, the SH46 locus, the SH47 locus, the SH48 locus, the SH49 locus, the SH50 locus, the SH51 locus, the SH52 locus, the SH70 locus, the SH71 locus, the SH72 locus, the SH73 locus, the SH74 locus, the SH75 locus, the SH101 locus, the SH106 locus, the SH107 locus, the SH102 locus, the SH105 locus, the SH103 locus, the SH104 locus, the SH113 locus, the SH109 locus, the SH112 locus, the SH108 locus, the SH110 locus, the SH114 locus, the SH116 locus, the SH111 locus, the SH115 locus, the SH121 locus, the SH120 locus, the SH122 locus, the SH117 locus, the SH118 locus, the SH119 locus, the SH123 locus, the SH126 locus, the SH128 locus, the SH129 locus, the SH124 locus, the SH131 locus, the SH125 locus, the SH127 locus, the SH130 locus, the SH11 locus, the SH17 locus, the SH23 locus, the SH34 locus, the SH40 locus, the SH53 locus, the SH54 locus, the SH55 locus, the SH56 locus, the SH57 locus, the SH58 locus, the SH59 locus, the SH60 locus, the SH61 locus, the SH62 locus, the SH65 locus, the SH67 locus, the SH68 locus and the SH69 locus that are further described herein.

It has further been shown that these meganucleases can cleave their target sequences efficiently.

These meganucleases, as well as other enymes like integrases, recombinases and transposases, can therefore be used as a tool for inserting a transgene into safe harbors, thereby avoiding the appearance of adverse events such as leukemia in the frame of gene therapy. In addition, these meganucleases, as well as other enymes like integrases, recombinases and transposases can be used for inserting any transgene into the safe harbor starting from a single targeting construct irrespective of the sequence of the transgene.

Endonucleases According to the Invention and Uses Thereof

The invention therefore relates to:
an endonuclease capable of cleaving a target sequence for use in inserting a transgene into the genome of an individual, wherein (i) said genome comprises a locus comprising said target sequence, and (ii) said target sequence is located at a distance of at most 200 kb from a retroviral insertion site (RIS), wherein said RIS is neither associated with cancer nor with abnormal cell proliferation.

an in vitro or ex vivo use of an endonuclease capable of cleaving a target sequence for inserting a transgene into the genome of a cell or a tissue, (i) said genome comprises a locus comprising said target sequence, and (ii) said target sequence is located at a distance of at most 200 kb from a retroviral insertion site (RIS), wherein said RIS is neither associated with cancer nor with abnormal cell proliferation.

a method for inserting a transgene into the genome of an individual comprising the steps of (i) providing an endonuclease capable of cleaving a target sequence, wherein said genome comprises a locus comprising said target sequence, and said target sequence is located at a distance of at most 200 kb from a retroviral insertion site (RIS) that is neither associated with cancer nor with abnormal cell proliferation; (ii) contacting an individual with a transgene and with said endonuclease, whereby said transgene is inserted into said locus of the genome of the individual.

As used herein, the term "endonuclease" refers to any wild-type or variant enzyme capable of catalyzing the hydrolysis (cleavage) of bonds between nucleic acids within of a DNA or RNA molecule, preferably a DNA molecule. The endonucleases according to the present invention do not cleave the DNA or RNA molecule irrespective of its sequence, but recognize and cleave the DNA or RNA molecule at specific polynucleotide sequences, further referred to as "target sequences" or "target sites". Target sequences recognized and cleaved by an endonuclease according to the invention are referred to as target sequences according to the invention.

The endonuclease according to the invention can for example be a homing endonuclease (Paques et al. Curr Gen Ther. 2007 7:49-66), a chimeric Zinc-Finger nuclease (ZFN) resulting from the fusion of engineered zinc-finger domains with the catalytic domain of a restriction enzyme such as FokI (Porteus et al. Nat. Biotechnol. 2005 23:967-973) or a chemical endonuclease (Arimondo et al. Mol Cell Biol. 2006 26:324-333; Simon et al. NAR 2008 36:3531-3538; Eisenschmidt et al. NAR 2005 33:7039-7047; Cannata et al. PNAS 2008 105:9576-9581). In chemical endonucleases, a chemical or peptidic cleaver is conjugated either to a polymer of nucleic acids or to another DNA recognizing a specific target sequence, thereby targeting the cleavage activity to a specific sequence.

The endonuclease according to the invention is preferably a homing endonuclease, also known under the name of meganuclease. Such homing endonucleases are well-known to the art (see e.g. Stoddard, Quarterly Reviews of Biophysics, 2006, 38:49-95). Homing endonucleases recognize a DNA target sequence and generate a single- or double-strand break. Homing endonucleases are highly specific, recognizing DNA target sites ranging from 12 to 45 base pairs (bp) in length, usually ranging from 14 to 40 bp in length. The homing endonuclease according to the invention may for example correspond to a LAGLIDADG endonuclease, to a HNH endonuclease, or to a GIY-YIG endonuclease. Examples of such endonuclease include I-Sce I, I-Chu I, I-Cre I, I-Csm I, PI-Sce I, PI-Tli I, PI-Mtu I, I-Ceu I, I-Sce II, I-Sce III, HO, PI-Civ I, PI-Ctr I, PI-Aae I, PI-Bsu I, PI-Dha I, PI-Dra I, PI-May I, PI-Mch I, PI-Mfu I, PI-Mfl I, PI-Mga I, PI-Mgo I, PI-Min I, PI-Mka I, PI-Mle I, PI-Mma I, PI-Msh I, PI-Msm I, PI-Mth I, PI-Mtu I, PI-Mxe I, PI-Npu I, PI-Pfu I, PI-Rma I, PI-Spb I, PI-Ssp I, PI-Fac I, PI-Mja I, PI-Pho I, PI-Tag I, PI-Thy I, PI-Tko I, PI-Tsp I, I-Msol.

In a preferred embodiment, the homing endonuclease according to the invention is a LAGLIDADG endonuclease such as I-Scel, I-Crel, I-Ceul, I-Msol, and I-Dmol.

In a most preferred embodiment, said LAGLIDADG endonuclease is I-Crel. Wild-type I-Crel is a homodimeric homing endonuclease that is capable of cleaving a 22 to 24 bp double-stranded target sequence. The sequence of a wild-type monomer of I-Crel includes the sequence shown as SEQ ID NO: 1 (which corresponds to the I-Crel sequence of pdb accession number 1g9y) and the sequence shown in SwissProt Accession n° P05725 (in particular the sequence shown in version 73, last modified Nov. 3, 2009).

In the present patent application, the I-Crel variants may comprise an additional alanine after the first methionine of the wild type I-Crel sequence, and three additional amino acid residues at the C-terminal extremity (see sequence of SEQ ID NO: 42 and FIG. 11). These three additional amino acid residues consist of two additional alanine residues and one aspartic acid residue after the final proline of the wild type I-Crel sequence. These additional residues do not affect the properties of the enzyme. For the sake of clarity, these additional residues do not affect the numbering of the residues in I-Crel or variants thereof. More specifically, the numbering used herein exclusively refers to the position of residues in the wild type I-CreI enzyme of SEQ ID NO: 1. For instance, the second residue of wild-type I-CreI is in fact the third residue of a variant of SEQ ID NO: 42 since this variant comprises an additional alanine after the first methionine.

In the present application, I-CreI variants may be homodimers (meganuclease comprising two identical monomers), heterodimers (meganuclease comprising two non-identical monomers) and single-chains.

The invention encompasses both wild-type (naturally-occurring) and variant endonucleases. In a preferred embodiment, the endonuclease according to the invention is a "variant" endonuclease, i.e. an endonuclease that does not naturally exist in nature and that is obtained by genetic engineering or by random mutagenesis. The variant endonuclease according to the invention can for example be obtained by substitution of at least one residue in the amino acid sequence of a wild-type, naturally-occurring, endonuclease with a different amino acid. Said substitution(s) can for example be introduced by site-directed mutagenesis and/or by random mutagenesis. In the frame of the present invention, such variant endonucleases remain functional, i.e. they retain the capacity of recognizing and specifically cleaving a target sequence.

The variant endonuclease according to the invention cleaves a target sequence that is different from the target sequence of the corresponding wild-type endonuclease. For example, the target sequence of a variant I-CreI endonuclease is different from the sequence of SEQ ID NO: 4. Methods for obtaining such variant endonucleases with novel specificities are well-known in the art.

The present invention is based on the finding that such variant endonucleases with novel specificities can be used for inserting a gene into a "safe harbor" locus of the genome of a cell, tissue or individual.

As used herein, the term "locus" is the specific physical location of a DNA sequence (e.g. of a gene) on a chromosome. As used in this specification, the term "locus" usually refers to the specific physical location of an endonuclease's target sequence on a chromosome. Such a locus, which comprises a target sequence that is recognized and cleaved by an endonuclease according to the invention, is referred to as "locus according to the invention".

Ideally, insertion into a safe harbor locus should have no impact on the expression of other genes. Testing these properties is a multi-step process, and a first pre-screening of candidate safe harbor loci by bioinformatic means is desirable. One can thus first identify loci in which targeted insertion is unlikely to result in insertional mutagenesis.

One of the major features of a locus according to the invention is that (i) it is located in a region wherein retroviral insertion was observed in a cell from a patient, in a gene therapy clinical trial, and (ii) said retroviral insertion has not been associated with a cancer or an abnormal cell proliferation.

Indeed, one way to identify safe habor loci according to the invention is to use the data generated by former gene therapy trials. In the X-SCID trial, insertions of retroviral vector-borne transgenes next to the LMO2 and CCND2 genes have been shown to be associated with leukemia. The follow up of vector insertions in patients have clearly demonstrated that cells carrying this insertion had outnumbered the other modified cells after a several years process (Hacein-Bey-Abina et al. Science 2003 302:415-9; Deichmann et al. J. of Clin. Invest. 2007 117:2225-32, Cavazzana-Calvo et al. Blood 2007 109:4575-4581). In another clinical trial, insertion in several loci were found to trigger a high proliferation rate in two patients (Ott et al. Nat Med 2006 12:401-9). In these cases, proliferation seemed to be a consequence of the insertional activation of the MDS1-EVI1, PRDM16, or SETBP1 genes. Although malignancy was not observed initially, EVI1 activation eventually resulted in myelodysplasia in both patients (Stein et al., Nat. Med. 2010 16: 198-205). More generally, even if non oncogenic, cell proliferation resulting from activation of a gene close to the insert could represent a first step towards malignancy, and therefore lead to potential problems in terms of safety. In order to better understand the pattern of viral vector integration, and its potential consequences on the fate of transformed cells, several large scale studies of Retroviral Insertion Sites (RIS) have been conducted in patients from gene therapy trials (Mavilio et al., Nat Med 2006:1397-1402; Recchia et al. PNAS 2006:1457-62; Aiuti, et al. J Clin Invest 2007:2233-40; Schwarzwaelder et al. J Clin Invest 2007:2241-9; Deichmann et al. J Clin Invest 2007:2225-32). RIS which are not associated with leukemia or with abnormal cell proliferation can be considered as safe harbors. Therefore, the locus according to the invention preferably overlaps or is close to a RIS identified in a clinical trial, and yet not associated with cancer or abnormal cell proliferation.

More specifically, the locus according to the invention is defined as a locus comprising a target sequence that is located at a distance of at most 200, 180, 150, 100 or 50 kb from a retroviral insertion site (RIS), said RIS being neither associated with cancer nor with abnormal cell proliferation. Such loci are referred to as "safe harbor" loci according to the invention (or loci according to the invention), i.e. loci that are safe for insertion of transgenes.

By "Retroviral insertion sites" (RIS) is meant a genomic site which was identified as an insertion site for a retroviral vector in a cell from a patient treated by gene therapy with said retroviral vector. Such RIS are well-known to the art. They include but are not limited to those described in Schwarzwaelder et al. (J. Clin. Invest. 2007 117:2241), Deichmann et al. (J. of Clin. Invest. 2007 117:2225), Aiuti et al. (J. Clin. Invest. 2007 117:2233), Recchia et al. (PNAS 2006 103:1457) and Mavilio et al. (Nature Medicine 12:1397, 2006).

By "retroviral vector" is meant any vector derived from a virus from the retroviridae family.

The RIS according to the invention is neither associated with cancer nor with abnormal cell proliferation. RIS known to be associated with leukemia or with abnormal cell proliferation are well known in the art and can easily be excluded by the skilled in the art. Such RIS known to be associated with leukemia or with abnormal cell proliferation include, e.g., insertion sites next to the LMO2, CCND2, MDS1-EVI1, PRDM16, and SETBP1 genes.

In a more preferred embodiment according to the invention, the RIS used to define safe harbor loci have been identified in a clinical trial, with the transduced cells being stem cells. The RIS can thus have been identified in cells from a patient treated by gene therapy by transduction of stem cells.

In another most preferred embodiment according to the invention, the RIS used to define safe harbor loci have been identified in a clinical trial for SCID patients, with the transduced cells being hematopoietic stem cells (HSCs). The RIS can thus have been identified in cells from a patient treated by gene therapy by transduction of hematopoietic stem cells.

Furthermore, more stringent criteria for definition of a RIS according to the invention can be used.

Among RIS, Common Integration sites (CIS) are loci in which the statistical over representation of RIS could be interpreted as the consequence of cell high proliferation rate upon insertion. (Mikkers et al., 2003, Nat. Genet. 32:153; Lund et al., 2002, Nat. Genet. 32:160; Hemati et al. 2004, PLOS Biol. 2:e423; Suzuki et al., 2002, Nat. Genet. 32:166-174; Deichman et al. J. of Clin. Invest. 2007 117:2225-32). For example, Deichman et al. (J. of Clin. Invest. 2007 117: 2225-32) made a survey of RIS from 9 X-SCID patients treated by gene therapy, and found 572 unique RIS that could be mapped unequivocally to the human genome. Among them, they defined CIS of second, third, fourth, fifth, and higher order. CIS of second orders were defined by the occurrence of two retroviral insertions within a 30 kb distance, CIS of third, fourth and fifth order by the occurrence of 3, 4 or 5 insertions within 50, 100 or 200 kb, respectively. 122 RIS were found in 47 different CIS loci, 33-fold the value expected under random distribution of the RIS. Eleven CIS were found to localize next to proto-oncogenes, including ZNF217, VAV-3, CCND2, LMO2, MDS1, BCL2L1, NOTCH2, SOCS2, RUNX1, RUNX3, and SEPT6.

To ensure maximal safety, it could be preferred to avoid RIS located within CIS. Therefore, in a preferred embodiment according to the invention, the target sequence according to the invention is not located in a CIS, In addition, said target sequence or locus is preferably located at a distance of at least 50, 100 or 200 kb from a RIS being part of a common integration site (CIS).

By "Common Integration site" (CIS) is meant a genomic region of 30 kb, 50 kb, 100 kb or 200 kb wherein RIS identified in clinical trials are overrepresented (assuming a random distribution of insertions). Such CIS are well known in the art and are described in Schwarzwaelder et al. (J. Clin. Invest. 2007 117:2241), Deichmann et al. (J. of Clin. Invest. 2007 117:2225), Aiuti et al. (J. Clin. Invest. 2007 117:2233), Recchia et al. (PNAS 2006 103:1457), Mavilio et al. (Nature Medicine 12:1397, 2006) and Gabriel et al. (Nat. Med. 2009 15(12):143.

In addition to be close to a RIS, targeted integration into the locus according to the invention should not result in the disruption of essential functions in the targeted cell.

Therefore, in a specific embodiment according to the invention, insertion into the locus according to the invention does preferably not substantially modify expression of genes located in the vicinity of the target sequence, for example of the nearest genes.

In addition, in another specific embodiment, insertion of a genetic element into said locus does preferably not substantially modify the phenotype of said cell, tissue or individual (except for the phenotype due to expression of the genetic element). By "phenotype" is meant a cell's, a tissue's or an individual's observable traits. The phenotype includes e.g. the viability, the cellular proliferation and/or the growth rate. The skilled in the art can easily verify that a locus is a safe harbor locus according to the invention e.g. by analyzing the expression pattern of adjacent genes, by carrying out microarray studies of transcriptome and/or by characterizing proliferation and/or differentiation abnormalities (if any).

In still another specific embodiment, the locus according to the invention does not comprise any gene. A locus that does not comprise any gene refers to a locus that does not comprise any referenced or known gene. In other terms, such a locus does not comprise any known gene according to sequence databases such as those available on the National Center for Biotechnology Information (NCBI) website. Therefore, the target sequence according to the invention and/or the locus according to the invention can advantageously be located at a distance of at least 1, 5, 10, 25, 50, 100, 180, 200, 250, 300, 400 or 500 kb from the nearest genes.

By "gene" is meant the basic unit of heredity, consisting of a segment of DNA arranged in a linear manner along a chromosome, which codes for a specific protein or segment of protein. A gene typically includes a promoter, a 5' untranslated region, one or more coding sequences (exons), optionally introns, a 3' untranslated region. The gene may further comprise a terminator, enhancers and/or silencers.

By "nearest genes" is meant the one, two or three genes that are located the closest to the target sequence, centromeric and telomeric to the target sequence respectively.

In a preferred embodiment, the locus according to the invention further allows stable expression of the transgene.

In another preferred embodiment, the target sequence according to the invention is only present once within the genome of said cell, tissue or individual.

Once such a safe harbor locus according to the invention has been selected, one can then (i) either construct a variant endonuclease specifically recognizing and cleaving a target sequence located within said locus, e.g. as described in Examples 1, 2 and 5, or (ii) determine whether a known wild-type endonuclease is capable of cleaving a target sequence located within said locus. Alternatively, once a safe harbor locus according to the invention has been selected, the skilled in the art can insert therein a target sequence that is recognized and cleaved by a known wild-type or variant endonuclease.

Therefore, the invention is drawn to a method for obtaining an endonuclease suitable for inserting a transgene into the genome of an individual, comprising the step of:

a) selecting and/or identifying, within the genome of said individual, a retroviral insertion site (RIS) that is neither associated with cancer nor with abnormal cell proliferation;

b) defining a genomic region extending 200 kb upstream and 200 kb downstream of said RIS; and c) identifying a wild-type endonuclease or constructing a variant endonuclease capable of cleaving a target sequence located within said genomic region.

Such an endonuclease allows safely inserting a transgene into the genome of the cell, tissue or individual, for example without substantially modifying (i) expression of the nearest genes, and/or (ii) the cellular proliferation and/or the growth rate of the cell, tissue or individual.

All criteria presented hereabove in connection with the locus according to the invention can of course be applied when carried out the above method. For example, RIS being part of a CIS may be excluded, and/or the genomic region defined at step (b) may only extend 50 kb upstream and 50 kb downstream of said RIS, and/or the locus comprising the target sequence may not comprise any gene.

The locus according to the invention may for example correspond to any one of the SH3, SH4, SH6, SH12, SH13, SH19, $SH_{20}$, SH21, SH33, SH7 or SH8 loci which are described in Tables A to C below.

Table A provides the location of the locus within the human genome, a target sequence comprised within the locus, the location of the closest RIS as well as the reference to a publication describing the RIS, and examples of endonucleases according to the invention that cleave the locus.

Table B provides information about the nearest genes that are located immediately upstream (at 5') and downstream (at 3') of the locus according to the invention. The distance indicates the distance between the target sequence and the nearest coding sequence of the gene.

Table C and D provide similar information as Table B, but for the second nearest genes and for the third nearest genes, respectively.

Tables A', B', C' and D' provide updated information similar to that in Tables A, B, C and D, respectively, for some loci and associated examples of target sequences within these loci, namely SH3, SH4, SH6, SH8 and SH19. Updated localization information is given by reference to GRCh37/hg19 version of the human genome assembly.

The locus according to the invention may also correspond to any one of the SH18, SH31, SH38, SH39, SH41, SH42, SH43, SH44, SH45, SH46, SH47, SH48, SH49, SH50, SH51, SH52, SH70, SH71, SH72, SH73, SH74 and SH75 which are described in Tables A" to D" below.

Table A" provides the location of the locus within the human genome, a target sequence comprised within the locus, the location of the closest RIS as well as the reference to a publication describing the RIS, the distance between said target and the closest RIS and examples of endonucleases according to the invention that cleave the locus.

Table B" provides information about the nearest genes that are located immediately upstream (at 5') and downstream (at 3') of the locus according to the invention. The distance indicates the distance between the target sequence and the nearest coding sequence of the gene.

Table C" and D" provide similar information as Table B", but for the second nearest genes and for the third nearest genes, respectively.

Locations of loci, targets in this loci and genes are given according to GRCh37/hg19 version of the human genome assembly.

TABLE A

| Name | Human chromo-some | locus | Example of Target Sequence Comprised within the locus: | SEQ ID NO: | Close to a RIS at position: | RIS described in: | Cleaved by mega-nucleases (examples) of SEQ ID NO: |
|---|---|---|---|---|---|---|---|
| SH3 | 6 | 6p25.1 | CCAATACAAGGTACAAAGTCCTGA | 54 | 6837845 | Deichmann, 2007 | 25-32 |
| SH4 | 7 | 7q31.2 | TTAAAACACTGTACACCATTTTGA | 55 | 114606124 | Schwarzwaelder, 2007 | 33-40 |
| SH6 | 21 | 21q21.1 | TTAATACCCCGTACCTAATATTGC | 59 | 17265069 | Schwarzwaelder, 2007 | 76-85 |
| SH12 | 13 | 13q34 | ATAAAACAAGTCACGTTATTTTGG | 97 | 109463429 | Mavilio, 2006 | 89 |
| SH13 | 3 | 3p12.2 | ATTACACTCTTTAAGTGATTTTAA | 98 | 80607284 | Recchia, 2006 | 90 |
| SH19 | 22 | chr22 | GCAAAACATTGTAAGACATGCCAA | 99 | 46815611 | Aiuti, 2007 | 91 |
| SH20 | 12 | 12q21.2 | GCTGGCTGCTTCACATTGGAGAGA | 100 | 74339720 | Mavilio, 2006 | 92 |
| SH21 | 3 | 3p24.1 | TAGAAATCTGTTAAAAGAGATGAT | 101 | 31235316 | Deichmann, 2007 | 93-95 |
| SH33 | 6 | 6p12.2 | TTTTCATCACTTAAAGTGTTTTAA | 102 | 50055278 | Recchia, 2006 | 96 |
| SH7 | 2 | 2p16.1 | ACAACACTTTGTGAGACGTCTAAG | 103 | 58962165 | Deichmann, 2007 | 86-87 |
| SH8 | 5 | chr5 | ACAATCTGAGGTAAGTAATACTGA | 104 | 20572231 | Aiuti, 2007 | 88 |

TABLE A'

| Name | Human chromo-some | locus | Example of Target Sequence Comprised within the locus: | SEQ ID NO: | Close to a RIS at position: | RIS position according to GRCh37/hg19 | RIS Dis-tance (bases) | RIS described in: | Cleaved by mega-nucleases (examples) of SEQ ID NO: |
|---|---|---|---|---|---|---|---|---|---|
| SH3 | 6 | 6p25.1 | CCAATACAAGGTACAAAGTCCTGA | 54 | 6837845 | 6892846 | 40782 | Deichmann, 2007 | 25-32 |
| SH4 | 7 | 7q31.2 | TTAAAACACTGTACACCATTTTGA | 55 | 114606124 | 115051621 | 77337 | Schwarzwaelder, 2007 | 33-40 |
| SH6 | 21 | 21q21.1 | TTAATACCCCGTACCTAATATTGC | 59 | 17265069 | 18343198 | 96099 | Schwarzwaelder, 2007 | 76-85 |

TABLE A'-continued

| Name | Human chromo- some | locus | Example of Target Sequence Comprised within the locus: | SEQ ID NO: | Close to a RIS at position: | RIS position according to GRCh37/ hg19 | RIS Dis- tance (bases) | RIS described in: | Cleaved by mega- nucleases (examples) of SEQ ID NO: |
|---|---|---|---|---|---|---|---|---|---|
| SH8 | 5 | chr5 | ACAATCTGAGGTAA GTAATACTGA | 104 | 20572231 | 20536474 | 50714 | Aiuti, 2007 | 88 |
| SH19 | 22 | chr22 | GCAAAACATTGTAA GACATGCCAA | 99 | 46815611 | 20536474 | 97664 | Aiuti, 2007 | 91 |

TABLE A"

| Name | Human chromo- some | Target position on chromo- some | Example of Target Sequence Comprised within the locus: | SEQ ID NO: |
|---|---|---|---|---|
| SH18 | 5 | 20634138 | CTTACCCCACGTACC ACAGACTGT | 105 |
| SH31 | 14 | 65874037 | TTGTAATGTCTTACA AGGTTTTAA | 106 |
| SH38 | 10 | 3983262 | CTGGGATGTCTCAC GACAGCATGG | 107 |
| SH39 | 11 | 104531937 | TCCTTCTGTCTTAAG AGATTTATC | 108 |
| SH41 | 5 | 18182572 | CCTCTCTTAGGTGAG ACGGTACAT | 109 |
| SH42 | 5 | 20466837 | TATATCCCATGTGAG ACATGCAGT | 110 |
| SH43 | 18 | 37446750 | TAAATACGTCTTACA TTATTTTGC | 111 |
| SH44 | 6 | 147302518 | AAGAAATGTCTCACA GAATTTTAC | 112 |
| SH45 | 8 | 24854461 | CAGATATGTCTTAAA ATGTCACTG | 113 |
| SH46 | 19 | 12036102 | ACCAGATGTCGTGA GACGGGGGAG | 114 |
| SH47 | 8 | 25002335 | GCAGGCTTATTCACC AGGGTTTAC | 115 |
| SH48 | 10 | 101896036 | TTGAAATTAGTTACA GGAGGTTAT | 116 |
| SH49 | 13 | 68191409 | ATAATACAATTTACC TAATCCTAT | 117 |
| SH50 | 1 | 47411545 | CCCGGCCCCTTTAAT CCATCTTAA | 118 |
| SH51 | 21 | 30011146 | TTGAGCTCACTCACA TGGTCTCAG | 119 |
| SH52 | 12 | 76131166 | CTCCACTGTCTTACC TAATCCAGC | 120 |
| SH70 | 12 | 796917 | CATGTATGATTTACA TCGGTTTGA | 121 |
| SH71 | 2 | 231579954 | GTTGTATTATTTACC TCAGATGAA | 122 |
| SH72 | 6 | 25192217 | TTTGGATGCTGTAAA GAATTTCCT | 123 |

TABLE A"-continued

| Name | | | | | |
|------|---|---|---|---|---|
| SH73 | 8 | 78807830 | ATAAAACGACTTACAAGGTCTGAA | | 124 |
| SH74 | 19 | 29033855 | TTCAGATCTCGTACAGGGGATGAC | | 125 |
| SH75 | 8 | 114771707 | CTGCCATAGGGTAACTGAGTCAAT | | 126 |

| Name | Close to a RIS at position: | RIS position according to GRCh37/hg19 | RIS distance | RIS described in: | Cleaved by meganucleases (examples) of SEQ ID NO: | Plasmids |
|------|---|---|---|---|---|---|
| SH18 | 20536474 | 20536474 | 97664 | Aiuti, 2007 | 127 | pCLS5518 |
|      |          |          |       |             | 128 | pCLS5519 |
|      |          |          |       |             | 129 | pCLS5520 |
|      |          |          |       |             | 130 | pCLS5521 |
| SH31 | 64841555 | 65771802 | 102235 | Recchia, 2006 | 131 | pCLS3904 |
|      |          |          |       |             | 132 | pCLS4076 |
| SH38 | 3929865 | 3939865 | 43397 | Mavilio F, 2006 | | |
| SH39 | 104003035 | 104465318 | 66619 | Schwartzwaelder, 2007 | 133 | pCLS6038 |
|      |          |          |       |             | 134 | pCLS6039 |
| SH41 | 18180277 | 18134776 | 47796 | Schwartzwaelder, 2007 | 135 | pCLS5187 |
|      |          |          |       |             | 136 | pCLS5188 |
| SH42 | 20581361 | 20535860 | 69023 | Schwartzwaelder, 2007 | 137 | pCLS5549 |
|      |          |          |       |             | 138 | pCLS5550 |
| SH43 | 35630950 | 37378963 | 67787 | Schwartzwaelder, 2007 | 139 | pCLS5594 |
|      |          |          |       |             | 140 | pCLS5595 |
| SH44 | 147201063 | 147220493 | 82025 | Schwartzwaelder, 2007 | 141 | pCLS5868 |
|      |          |          |       |             | 142 | pCLS5869 |
| SH45 | 24923302 | 24867385 | 12924 | Mavilio F, 2006 | | |
| SH46 | 11713157 | 11852157 | 183945 | Mavilio F, 2006 | | |
| SH47 | 24923302 | 24867385 | 134950 | Mavilio F, 2006 | | |
| SH48 | 101755754 | 101765764 | 130272 | Mavilio F, 2006 | | |
| SH49 | 65947183 | 68149182 | 42227 | Schwartzwaelder, 2007 | | |
| SH50 | 46928138 | 47216118 | 195427 | Mavilio F, 2006 | | |
| SH51 | 28929744 | 30007873 | 3273 | Mavilio F, 2006 | | |
| SH52 | 74339720 | 76053453 | 77713 | Mavilio F, 2006 | 143 | pCLS5870 |
|      |          |          |       |             | 144 | pCLS5871 |
| SH70 | 708202 | 837941 | 41024 | Recchia, 2006 | 145 | pCLS5957 |
| SH71 | 231351771 | 231526266 | 53688 | Recchia, 2006 | 146 | pCLS5958 |
| SH72 | 25101289 | 24993310 | 198907 | Recchia, 2006 | 147 | pCLS5959 |
| SH73 | 78989339 | 78939377 | 131547 | Deichmann, 2007 | 148 | pCLS5960 |
| SH74 | 33661180 | 28969340 | 64515 | Deichmann, 2007 | 149 | pCLS5961 |
| SH75 | 114711413 | 114754830 | 16877 | Deichmann, 2007 | 150 | pCLS5962 |

TABLE B

| Name | Left Gene1 | Left Gene Description1 | Dist Left Kb1 | Right Gene1 | Right Gene Description1 | Dist Right Kb1 |
|---|---|---|---|---|---|---|
| SH3 | LY86 | MD-1, RP105-associated | 197 | RREB1 | ras responsive element binding protein 1 isoform 1 | 330 |
| SH4 | MDFIC | MyoD family inhibitor domain containing protein isoform p40 | 318 | TFEC | transcription factor EC isoform b | 606 |
| SH6 | C21orf34 | hypothetical protein LOC388815 isoform b | 675 | CXADR | coxsackie virus and adenovirus receptor precursor | 446 |
| SH12 | LOC728767 | hypothetical protein | 41 | COL4A1 | alpha 1 type IV collagen preproprotein preproprotein | 302 |
| SH13 | ROBO1 | roundabout 1 isoform a | 919 | LOC728290 | hypothetical protein | 484 |
| SH19 | LOC100289420 | hypothetical protein XP_002343824 | 1106 | FAM19A5 | family with sequence similarity 19 (chemokine (C-C motif)-like), member A5 isoform 1 | 208 |
| SH20 | KRR1 | HIV-1 rev binding protein 2 | 120 | LOC100289143 | hypothetical protein XP_002343241 | 307 |
| SH21 | GADL1 | glutamate decarboxylase-like 1 | 236 | STT3B | source of immunodominant MHC-associated peptides | 402 |
| SH33 | DEFB133 | beta-defensin 133 | 7 | DEFB114 | beta-defensin 114 | 4 |
| SH7 | FANCL | Fanconi anemia, complementation group L isoform 2 | 685 | LOC730134 | similar to hCG1815165 | 312 |
| SH8 | CDH18 | cadherin 18, type 2 preproprotein preproprotein | 647 | LOC100288118 | hypothetical protein XP_002342537 | 988 |

TABLE B'

| Name | Left Gene1 | Left Gene Description1 | Dist Left Kb1 | Right Gene1 | Right Gene Description1 | Dist Right Kb1 |
|---|---|---|---|---|---|---|
| SH3 | LOC652960 | na | 56 | RREB1 | ras responsive element binding protein 1 isoform 2 | 256 |
| SH4 | MDFIC | MyoD family inhibitor domain containing protein isoform p40 | 315 | LOC100287693 | na | 162 |
| SH6 | RPS26P5 | na | 945 | RPL39P40 | na | 433 |
| SH8 | NUP50P3 | na | 179 | LOC728411 | na | 973 |
| SH19 | LOC100289420 | hypothetical protein XP_002343824 | 1105 | FAM19A5 | family with sequence similarity 19 (chemokine (C-C motif)-like), member A5 isoform 2 | 208 |

TABLE B"

| Name | Left Gene1 | Left Gene Description1 | Dist Left Kb1 | Right Gene1 | Right Gene Description1 | Dist Right Kb1 |
|---|---|---|---|---|---|---|
| SH18 | NUP50P3 | na | 328 | LOC728411 | na | 825 |
| SH31 | PTBP1P | na | 127 | LOC645431 | na | 3 |
| SH38 | LOC727894 | hypothetical protein | 5 | LOC100128356 | na | 498 |
| SH39 | DDI1 | DDI1, DNA-damage inducible 1, homolog 1 | 622 | CASP12 | na | 225 |
| SH41 | RPL36AP21 | na | 132 | RPL32P14 | na | 858 |
| SH42 | NUP50P3 | na | 160 | LOC728411 | na | 992 |
| SH43 | RPL7AP66 | na | 531 | RPL17P45 | na | 277 |
| SH44 | LOC729176 | na | 177 | STXBP5 | syntaxin binding protein 5 (tomosyn) isoform a | 222 |
| SH45 | NEFL | neurofilament, light polypeptide 68 kDa | 40 | DOCK5 | dedicator of cytokinesis 5 | 187 |
| SH46 | VN2R15P | na | 9 | VN2R21P | na | 27 |
| SH47 | NEFL | neurofilament, light polypeptide 68 kDa | 188 | DOCK5 | dedicator of cytokinesis 5 | 39 |
| SH48 | LOC644566 | na | 18 | LOC644573 | na | 6 |
| SH49 | RPSAP53 | na | 349 | LOC390411 | na | 214 |
| SH50 | CYP4A11 | cytochrome P450, family 4, subfamily A, polypeptide 11 | 4 | CYP4X1 | cytochrome P450, family 4, subfamily X, polypeptide 1 | 77 |
| SH51 | NCRNA00161 | na | 98 | N6AMT1 | N-6 adenine-specific DNA methyltransferase 1 isoform 1 | 233 |
| SH52 | RPL10P13 | na | 48 | LOC100289143 | hypothetical protein XP_002343241 | 201 |
| SH70 | LOC100049716 | na | 41 | LOC100132369 | hypothetical protein | 64 |
| SH71 | LOC646839 | na | 141 | ITM2C | integral membrane protein 2C isoform 3 | 149 |
| SH72 | LOC100132239 | na | 38 | LOC100129757 | na | 26 |
| SH73 | LOC100289199 | na | 878 | PKIA | cAMP-dependent protein kinase inhibitor alpha isoform 7 | 620 |
| SH74 | LOC100131694 | na | 558 | LOC100129507 | na | 184 |
| SH75 | RPL18P7 | na | 382 | TRPS1 | zinc finger transcription factor TRPS1 | 1648 |

TABLE C

| Name | Left Gene2 | Left Gene Description2 | Dist Left Kb2 | Right Gene2 | Right Gene Description2 | Dist Right Kb2 |
|---|---|---|---|---|---|---|
| SH3 | F13A1 | coagulation factor XIII A1 subunit precursor | 533 | LOC100288758 | hypothetical protein XP_002342653 | 378 |
| SH4 | FOXP2 | forkhead box P2 isoform III | 644 | TES | testin isoform 1 | 876 |
| SH6 | C21orf34 | hypothetical protein LOC388815 isoform a | 996 | BTG3 | B-cell translocation gene 3 isoform b | 527 |
| SH12 | IRS2 | insulin receptor substrate 2 | 63 | COL4A2 | alpha 2 type IV collagen preproprotein preproprotein | 459 |
| SH13 | ROBO2 | roundabout, axon guidance receptor, homolog 2 isoform ROBO2a | 2863 | GBE1 | glucan (1,4-alpha-), branching enzyme 1 | 982 |

TABLE C-continued

| Name | Left Gene2 | Left Gene Description2 | Dist Left Kb2 | Right Gene2 | Right Gene Description2 | Dist Right Kb2 |
|---|---|---|---|---|---|---|
| SH19 | TBC1D22A | TBC1 domain family, member 22A | 1108 | FAM19A5 | family with sequence similarity 19 (chemokine (C-C motif)-like), member A5 isoform 2 | 295 |
| SH20 | GLIPR1 | GLI pathogenesis-related 1 precursor | 133 | LOC100131830 | hypothetical protein | 382 |
| SH21 | TGFBR2 | transforming growth factor, beta receptor II isoform A precursor | 439 | OSBPL10 | oxysterol-binding protein-like protein 10 | 532 |
| SH33 | CRISP1 | acidic epididymal glycoprotein-like 1 isoform 2 precursor | 99 | DEFB113 | beta-defensin 113 | 13 |
| SH7 | VRK2 | vaccinia related kinase 2 isoform 6 | 767 | BCL11A | B-cell CLL/lymphoma 11A isoform 3 | 1526 |
| SH8 | LOC391769 | similar to HIStone family member (his-72) | 2830 | CDH12 | cadherin 12, type 2 preproprotein preproprotein | 1266 |

TABLE C'

| Name | Left Gene2 | Left Gene Description2 | Dist Left Kb2 | Right Gene2 | Right Gene Description2 | Dist Right Kb2 |
|---|---|---|---|---|---|---|
| SH3 | LY86 | MD-1, RP105-associated | 196 | LOC100288758 | hypothetical protein XP_002342653 | 376 |
| SH4 | FOXP2 | forkhead box P2 isoform III | 643 | TFEC | transcription factor EC isoform a | 600 |
| SH6 | VDAC2P | na | 971 | CXADR | coxsackie virus and adenovirus receptor precursor | 446 |
| SH8 | CDH18 | cadherin 18, type 2 preproprotein preproprotein | 646 | LOC100288118 | hypothetical protein XP_002342537 | 987 |
| SH19 | TBC1D22A | TBC1 domain family, member 22A | 1107 | LOC100128946 | hypothetical protein | 614 |

TABLE C"

| Name | Left Gene2 | Left Gene Description2 | Dist Left Kb2 | Right Gene2 | Right Gene Description2 | Dist Right Kb2 |
|---|---|---|---|---|---|---|
| SH18 | CDH18 | cadherin 18, type 2 preproprotein preproprotein | 794 | LOC100288118 | hypothetical protein XP_002342537 | 839 |
| SH31 | RPL36AP2 | na | 137 | FUT8 | fucosyltransferase 8 isoform c | 3 |
| SH38 | LOC100130652 | hypothetical protein | 112 | LOC100216001 | na | 709 |
| SH39 | PDGFD | platelet derived growth factor D isoform 1 precursor | 496 | LOC643733 | na | 242 |
| SH41 | LOC100133112 | na | 488 | LOC646273 | na | 1050 |
| SH42 | CDH18 | cadherin 18, type 2 preproprotein preproprotein | 627 | LOC100288118 | hypothetical protein XP_002342537 | 1006 |
| SH43 | LOC647946 | na | 114 | KC6 | na | 1613 |
| SH44 | C6orf103 | hypothetical protein LOC79747 | 165 | LOC442266 | na | 425 |

TABLE C"-continued

| Name | Left Gene2 | Left Gene Description2 | Dist Left Kb2 | Right Gene2 | Right Gene Description2 | Dist Right Kb2 |
|---|---|---|---|---|---|---|
| SH45 | LOC100129717 | na | 40 | GNRH1 | gonadotropin-releasing hormone 1 precursor | 422 |
| SH46 | ZNF69 | zinc finger protein 69 | 10 | ZNF763 | zinc finger protein 440 like | 39 |
| SH47 | LOC100129717 | na | 188 | GNRH1 | gonadotropin-releasing hormone 1 precursor | 274 |
| SH48 | CPN1 | carboxypeptidase N, polypeptide 1 precursor | 54 | ERLIN1 | ER lipid raft associated 1 | 13 |
| SH49 | LOC730236 | hypothetical protein | 385 | OR7E111P | na | 284 |
| SH50 | CYP4Z2P | na | 45 | CYP4Z1 | cytochrome P450 4Z1 | 121 |
| SH51 | C21orf94 | na | 615 | HSPD1P7 | na | 248 |
| SH52 | LOC100129649 | na | 135 | LOC100131830 | hypothetical protein | 276 |
| SH70 | NINJ2 | ninjurin 2 | 24 | WNK1 | WNK lysine deficient protein kinase 1 | 65 |
| SH71 | HMGB1L3 | na | 199 | GPR55 | G protein-coupled receptor 55 | 192 |
| SH72 | NUP50P2 | na | 50 | RPL21P68 | na | 69 |
| SH73 | PXMP3 | peroxin 2 | 895 | FAM164A | hypothetical protein LOC51101 | 770 |
| SH74 | LOC100132081 | na | 640 | LOC148145 | na | 422 |
| SH75 | LOC100289099 | na | 1220 | EIF3H | eukaryotic translation initiation factors, subunit 3 gamma, 40 kDa | 2885 |

TABLE D

| Name | Left Gene3 | Left Gene Description3 | Dist Left Kb3 | Right Gene3 | Right Gene Description3 | Dist Right Kb3 |
|---|---|---|---|---|---|---|
| SH3 | NRN1 | neuritin precursor | 845 | LOC100288790 | hypothetical protein XP_002342654 | 417 |
| SH4 | FOXP2 | forkhead box P2 isoform II | 644 | TES | testin isoform 2 | 900 |
| SH6 | USP25 | ubiquitin specific peptidase 25 | 1189 | C21orf91 | early undifferentiated retina and lens isoform 2 | 726 |
| SH12 | MY016 | myosin heavy chain Myr 8 | 642 | RAB20 | RAB20, member RAS oncogene family | 675 |
| SH13 | ROBO2 | roundabout, axon guidance receptor, homolog 2 isoform ROBO2b | 2863 | LOC100289598 | hypothetical protein XP_002342405 | 4448 |
| SH19 | CERK | ceramide kinase | 1543 | LOC100128946 | hypothetical protein | 616 |
| SH20 | GLIPR1L2 | GLI pathogenesis-related 1 like 2 | 209 | PHLDA1 | pleckstrin homology-like domain, family A, member 1 | 398 |
| SH21 | RBMS3 | RNA binding motif, single stranded interacting protein 3 isoform 1 | 1127 | ZNF860 | zinc finger protein 860 | 859 |
| SH33 | CRISP1 | acidic epididymal glycoprotein-like 1 isoform 1 precursor | 99 | DEFB110 | beta-defensin 110 | 53 |

TABLE D-continued

| Name | Left Gene3 | Left Gene Description3 | Dist Left Kb3 | Right Gene3 | Right Gene Description3 | Dist Right Kb3 |
|---|---|---|---|---|---|---|
| SH7 | VRK2 | vaccinia related kinase 2 isoform 2 | 767 | BCL11A | B-cell CLL/lymphoma 11A isoform 2 | 1526 |
| SH8 | LOC391767 | similar to TBP-associated factor 11 | 2851 | PRDM9 | PR domain containing 9 | 3023 |

TABLE D'

| Name | Left Gene3 | Left Gene Description3 | Dist Left Kb3 | Right Gene3 | Right Gene Description3 | Dist Right Kb3 |
|---|---|---|---|---|---|---|
| SH3 | LOC643875 | na | 316 | LOC100288790 | hypothetical protein XP_002342654 | 416 |
| SH4 | RPL36P13 | na | 1036 | TES | testin isoform 2 | 876 |
| SH6 | C21orf34 | hypothetical protein LOC388815 isoform b | 459 | BTG3 | B-cell translocation gene 3 isoform a | 526 |
| SH8 | LOC646273 | na | 1251 | GUSBP1 | na | 1005 |
| SH19 | CERK | ceramide kinase | 1542 | LOC100287247 | hypothetical protein XP_002343807 | 768 |

TABLE D"

| Name | Left Gene3 | Left Gene Description3 | Dist Left Kb3 | Right Gene3 | Right Gene Description3 | Dist Right Kb3 |
|---|---|---|---|---|---|---|
| SH18 | LOC646273 | na | 1399 | GUSBP1 | na | 857 |
| SH31 | RPL21P7 | na | 139 | RPL21P8 | na | 60 |
| SH38 | KLF6 | Kruppel-like factor 6 | 155 | LOC338588 | na | 715 |
| SH39 | LOC100190922 | na | 1031 | CASP4 | caspase 4 isoform gamma precursor | 281 |
| SH41 | LOC391769 | similar to HIStone family member (his-72) | 526 | CDH18 | cadherin 18, type 2 preproprotein preproprotein | 1290 |
| SH42 | LOC646273 | na | 1232 | GUSBP1 | na | 1024 |
| SH43 | RPL12P40 | na | 2193 | NPM1P1 | na | 1922 |
| SH44 | RAB32 | RAB32, member RAS oncogene family | 426 | SAMD5 | sterile alpha motif domain containing 5 | 527 |
| SH45 | LOC100289018 | hypothetical protein XP_002342868 | 81 | KCTD9 | potassium channel tetramerisation domain containing 9 | 430 |
| SH46 | VN2R14P | na | 53 | ZNF433 | zinc finger protein 433 | 89 |
| SH47 | LOC100289018 | hypothetical protein XP_002342868 | 229 | KCTD9 | potassium channel tetramerisation domain containing 9 | 283 |
| SH48 | NCRNA00093 | na | 177 | CHUK | conserved helix-loop-helix ubiquitous kinase | 52 |
| SH49 | PCDH9 | protocadherin 9 isoform 1 precursor | 386 | OR7E33P | na | 293 |
| SH50 | LOC100132680 | na | 45 | LOC100132432 | na | 123 |
| SH51 | NCRNA00113 | na | 887 | LOC391276 | na | 262 |
| SH52 | KRR1 | HIV-1 rev binding protein 2 | 225 | PHLDA1 | pleckstrin homology-like domain, family A, member 1 | 288 |
| SH70 | B4GALNT3 | beta 1,4-N-acetyl-galactosaminyl-transferase-transferase-III | 125 | HSN2 | hereditary sensory neuropathy, type II | 179 |
| SH71 | SP100 | nuclear antigen Sp100 isoform 2 | 169 | LOC100289170 | na | 232 |
| SH72 | CMAH | na | 54 | LOC100128495 | na | 80 |
| SH73 | ZFHX4 | zinc finger homeodomain 4 | 1028 | IL7 | interleukin 7 precursor | 837 |

TABLE D"-continued

| Name | Left Gene3 | Left Gene Description3 | Dist Left Kb3 | Right Gene3 | Right Gene Description3 | Dist Right Kb3 |
|---|---|---|---|---|---|---|
| SH74 | LOC642290 | na | 715 | UQCRFS1 | ubiquinol-cytochrome c reductase, Rieske iron-sulfur polypeptide 1 | 664 |
| SH75 | CSMD3 | CUB and Sushi multiple domains 3 isoform 2 | 322 | UTP23 | UTP23, small subunit (SSU) processome component, homolog | 3007 |

The locus according to the invention may also correspond to any one of the SH101, SH106, SH107, SH102, SH105, SH103, SH104, SH113, SH109, SH112, SH108, SH110, SH114, SH116, SH111, SH115, SH121, SH120, SH122, SH117, SH118, SH119, SH123, SH126, SH128, SH129, SH124, SH131, SH125, SH127 and SH130 which are described in Tables E and F below.

Table E provides the location of the locus within the human genome, a target sequence comprised within the locus, the location of the closest RIS as well as the reference to a publication describing the RIS, the distance between said target and the closest RIS and examples of endonucleases according to the invention that cleave the locus.

Table F provides information about the nearest genes that are located immediately upstream (at 5') and downstream (at 3') of the locus according to the invention. The distance indicates the distance between the target sequence and the nearest coding sequence of the gene.

Locations of loci, targets in this loci and genes are given in Tables E and F according to GRCh36.3/hg19 version of the human genome assembly.

TABLE E

| Name | Human chromo- some | Target position on chromo- some (start; V36.3) | Example of Target Sequence Comprised within the locus: | SEQ ID NO: |
|---|---|---|---|---|
| SH101 | 3 | 72293606 | CCTACACCCTGTAAGATGGCTAGT | 151 |
| SH106 | 13 | 103230446 | CTAAAATCATGTAAGTTGTATTAT | 152 |
| SH107 | 13 | 103240747 | TAAACATTTTGTACAGAATCTCAG | 153 |
| SH102 | 4 | 143846381 | ATGAGATAATGTACAAGGTTTTGT | 154 |
| SH105 | 12 | 64610385 | CAGGGACTATTTACAAAAGATTGA | 155 |
| SH103 | 4 | 143907910 | CCAAACCTAGGTAAGAGATATGAA | 156 |
| SH104 | 7 | 131856646 | TATAGATCAAGTAACAAGTGTAAT | 157 |
| SH113 | 8 | 66935276 | TTTTACTGTCTTACCTAGTTTTGC | 158 |
| SH109 | 3 | 72674929 | TCAATCTCACTTACAAAGTTGTGA | 159 |
| SH112 | 7 | 127627660 | CTAGGATGTAGTACAGGGTGCTAT | 160 |
| SH108 | 3 | 173734739 | AATATCTCATGTAACACATATTGC | 161 |
| SH110 | 5 | 14051421 | TTACTCCCATTTACAAGAGCAGAG | 162 |
| SH114 | 10 | 11537739 | ACCAGACCTTGTAAGTTATACAGA | 163 |
| SH116 | 21 | 14663030 | ATAAAATAAGTTACAGAGTTACAA | 164 |
| SH111 | 7 | 127808719 | ACTTCCTGTTTTACAAGGTGTAAT | 165 |
| SH115 | 12 | 95084648 | CCTGGATATGTTACAACAGAAAGC | 166 |
| SH121 | 8 | 8897353 | TTTCTCTCAGGTAAAACAGTCCAC | 167 |
| SH120 | 8 | 24344273 | GTAAGCTATTGTAAGAAATGCAAG | 168 |
| SH122 | 17 | 58931643 | ATGAGATGATGTACAAAGTCCTAG | 169 |
| SH117 | 1 | 223618330 | ACTGTATTTTGTAAAGTGTCCCTC | 170 |

TABLE E-continued

| Name | | | | SEQ ID NO: |
|---|---|---|---|---|
| SH118 | 4 | 8209666 | TCTTCATGTTGTACCTTGTCCCCT | 171 |
| SH119 | 5 | 138660535 | ATCATCTGAGGTAAAGAGTTCTGA | 172 |
| SH123 | 19 | 40227362 | GCTCTCTCTGGTACCTGATAGTGA | 173 |
| SH126 | 2 | 194307577 | ACAAACTCTTTTACGGGATTCAGG | 174 |
| SH128 | 2 | 193954229 | TTCACATGCTTTACGAAAGTTAGC | 175 |
| SH129 | 2 | 194043922 | CCTACATTTCGTAAGACATCTATT | 176 |
| SH124 | 4 | 159540469 | GCAAACTGTGGTACCTAGGCCCGT | 177 |
| SH131 | 1 | 201630446 | TCGAGCCACTGTACCTAGTTTTGT | 178 |
| SH125 | 17 | 10025853 | ACAGGATCCAGTAAAGGAGCCGGC | 179 |
| SH127 | 2 | 20001992 | GCTGTACTATTTACGGTATTCAAT | 180 |
| SH130 | 16 | 56151416 | ATAAACTTCGGTAAGACATCTCAA | 181 |

| Name | RIS position according to GRCh36.3/hg19 | RIS distance (bases) | RIS described in: | Cleaved by meganucleases (examples) of SEQ ID NO: | Plasmids |
|---|---|---|---|---|---|
| SH101 | 72478871 | 185265 | Gabriel et al, 2009 | 182 | pCLS7518 |
| SH106 | 103311358 | 80912 | Gabriel et al, 2009 | 183 | pCLS7523 |
| SH107 | 103311358 | 70611 | Gabriel et al, 2009 | 184 | pCLS7524 |
| SH102 | 143708544 | 137837 | Gabriel et al, 2009 | 185 | pCLS7519 |
| SH105 | 64560662 | 49723 | Gabriel et al, 2009 | 186 | pCLS7522 |
| SH103 | 143708544 | 199366 | Gabriel et al, 2009 | 187 | pCLS7520 |
| SH104 | 131765633 | 91013 | Gabriel et al, 2009 | 188 | pCLS7521 |
| SH113 | 67019410 | 84134 | Gabriel et al, 2009 | 189 | pCLS7530 |
| SH109 | 72478871 | 196058 | Gabriel et al, 2009 | 190 | pCLS7526 |
| SH112 | 127698957 | 71297 | Gabriel et al, 2009 | 191 | pCLS7529 |
| SH108 | 173720808 | 13931 | Gabriel et al, 2009 | 192 | pCLS7525 |
| SH110 | 14197567 | 146146 | Gabriel et al, 2009 | 193 | pCLS7527 |
| SH114 | 11694871 | 157132 | Gabriel et al, 2009 | 194 | pCLS7531 |
| SH116 | 14814623 | 151593 | Gabriel et al, 2009 | 195 | pCLS7533 |
| SH111 | 127698957 | 109762 | Gabriel et al, 2009 | 196 | pCLS7528 |
| SH115 | 95131508 | 46860 | Gabriel et al, 2009 | 197 | pCLS7532 |
| SH121 | 8837115 | 60238 | Gabriel et al, 2009 | 198 | pCLS7538 |
| SH120 | 24200341 | 143932 | Gabriel et al, 2009 | 199 | pCLS7537 |
| SH122 | 59056021 | 124378 | Gabriel et al, 2009 | 200 | pCLS7539 |
| SH117 | 223700385 | 82055 | Gabriel et al, 2009 | 201 | pCLS7534 |
| SH118 | 8250751 | 41085 | Gabriel et al, 2009 | 202 | pCLS7535 |
| SH119 | 138751654 | 91119 | Gabriel et al, 2009 | 203 | pCLS7536 |
| SH123 | 40144506 | 82856 | Gabriel et al, 2009 | 204 | pCLS7540 |
| SH126 | 194148379 | 159198 | Gabriel et al, 2009 | 205 | pCLS7543 |
| SH128 | 194148379 | 194150 | Gabriel et al, 2009 | 206 | pCLS7545 |

TABLE E-continued

| SH129 | 194148379 | 104457 | Gabriel et al, 2009 | 207 | pCLS7546 |
|---|---|---|---|---|---|
|  |  |  |  | 208 | pCLS7547 |
| SH124 | 159391564 | 148905 | Gabriel et al, 2009 | 209 | pCLS7541 |
| SH131 | 201525001 | 105445 | Gabriel et al, 2009 | 210 | pCLS7549 |
| SH125 | 9964030 | 61823 | Gabriel et al, 2009 | 211 | pCLS7542 |
| SH127 | 20112551 | 110559 | Gabriel et al, 2009 | 212 | pCLS7544 |
| SH130 | 56136054 | 15362 | Gabriel et al, 2009 | 213 | pCLS7548 |

TABLE F

| Name | Left Gene1 | Dist Left Kb1 | Right Gene1 | Dist Right Kb1 |
|---|---|---|---|---|
| SH101 | PROK2 | 380 | RYPB | 213 |
| SH106 | SLC10A2 | 713 | DAOA | 1500 |
| SH107 | SLC10A2 | 724 | DAOA | 1500 |
| SH113 | PDE7A | 19 | DNAJC5B | 161 |
| SH109 | RYBP | 96 | SHQ1 | 208 |
| SH112 | SND1 | 100 | LEP | 41 |
| SH108 | TNFSF10 | 11 | AADACL1 | 96 |
| SH110 | DNAH5 | 54 | TRIO | 146 |
| SH114 | CUGBP2 | 120 | USP6NL | 5 |
| SH116 | ABCC13 | 66 | HSPA13 | 3 |
| SH111 | PRRT4 | 25 | IMPDH1 | 11 |
| SH115 | LTA4H | 151 | ELK3 | 27 |
| SH121 | MFHAS1 | 110 | ERI1 | 0.37 |
| SH120 | ADAMDEC1 | 25 | ADAM7 | 10 |
| SH122 | ACE | 3 | KCNH6 | 24 |
| SH126 | TMEFF2 | 1500 | SLC39A10 | 2000 |
| SH128 | TMEFF2 | 1400 | SLC39A10 | 2100 |
| SH129 | TMEFF2 | 1300 | SLC39A10 | 2200 |
| SH124 | TMEM144 | 145 | RXFP1 | 122 |
| SH131 | FMOD | 44 | PRELP | 81 |

The locus according to the invention may also correspond to any one of the SH125, SH127, SH130, SH102, SH105, SH103, SH104, SH117, SH118, SH119 and SH123 which are described in Table G below.

Table G provides examples of target sequences located in introns of genes which are mentioned and examples of endonucleases according to the invention that cleave said intronic locus.

TABLE G

| Name | Example of Target Sequence Comprised within the locus: | Hit position | Gene | Intron |
|---|---|---|---|---|
| SH125 | ACAGGATCCAGTAA AGGAGCCGGC | intronic | GAS7 | 1 |
| SH127 | GCTGTACTATTTACG GTATTCAAT | intronic | WDR35 | 18 |
| SH130 | ATAAACTTCGGTAAG ACATCTCAA | intronic | GPR114 | 1 |
| SH102 | ATGAGATAATGTACA AGGTTTTGT | intronic | INPP4B | 2 |
| SH105 | CAGGGACTATTTACA AAAGATTGA | intronic | HMGA2 | 3 |
| SH103 | CCAAACCTAGGTAA GAGATATGAA | intronic | INPP4B | 1 |

TABLE G-continued

| Name | Example of Target Sequence Comprised within the locus: | Hit position | Gene | Intron |
|---|---|---|---|---|
| SH104 | TATAGATCAAGTAAC AAGTGTAAT | intronic | PLXNA4 | 1 |
| SH117 | ACTGTATTTTGTAAA GTGTCCCTC | intronic | DNAH14 | 76 |
| SH118 | TCTTCATGTTGTACC TTGTCCCCT | intronic | ABLIM2 | 1 |
| SH119 | ATCATCTGAGGTAAA GAGTTCTGA | intronic | MATR3 | 5 |
| SH123 | GCTCTCTCTGGTAC CTGATAGTGA | intronic | HPN | 3 |

The locus according to the invention may also contains any one of the SH11, SH12, SH13, SH17, SH19, SH20, SH21, SH23, SH33, SH34, SH40, SH53, SH54, SH55, SH56, SH57, SH58, SH59, SH60, SH61, SH62, SH65, SH67, SH68 and SH69 which are given in Tables H below.

Table H provides target sequences comprised within these loci as well as examples of endonucleases according to the invention that cleave these target sequences.

TABLE H

| Name | Sequence | SEQ ID NO: | Cleaved by meganucleases (examples) of SEQ ID NO: | Plasmids |
|---|---|---|---|---|
| SH11 | AGAAGCCCAGGTAA AACAGCCTGG | 214 | 235 | pCLS3895 |
|  |  |  | 236 | pCLS4664 |
| SH12 | ATAAACAAGTCAC GTTATTTTGG | 215 | 237 | pCLS3896 |
|  |  |  | 238 | pCLS3915 |
|  |  |  | 239 | pCLS6445 |
| SH13 | ATTACACTCTTTAA GTGATTTTAA | 216 | 240 | pCLS3897 |
|  |  |  | 241 | pCLS6446 |
| SH17 | CTAGGCTGGATTAC AGCGGCTTGA | 217 | 242 | pCLS3898 |
| SH19 | GCAAAACATTGTAA GACATGCCAA | 218 | 243 | pCLS3899 |

TABLE H-continued

| Name | Sequence | SEQ ID NO: | Cleaved by meganucleases (examples) of SEQ ID NO: | Plasmids |
|---|---|---|---|---|
| | | | 244 | pCLS7278 |
| | | | 245 | pCLS7279 |
| SH20 | GCTGGCTGCTTCACATTGGAGAGA | 219 | 246 | pCLS3900 |
| SH21 | TAGAAATCTGTTAAAAGAGATGAT | 220 | 247 | pCLS3901 |
| | | | 248 | pCLS4666 |
| | | | 249 | pCLS4667 |
| SH23 | TCAAACCATTGTACTCCAGCCTGG | 221 | 250 | pCLS3902 |
| | | | 251 | pCLS6447 |
| SH33 | TTTTCATCACTTAAAGTGTTTTAA | 222 | 252 | pCLS3905 |
| | | | 253 | pCLS4077 |
| | | | 254 | pCLS4668 |
| | | | 255 | pCLS4669 |
| SH34 | TTTTCCTGTCTTACCAGGTTTTGT | 223 | 256 | pCLS3906 |
| SH40 | GTCTTCTGTCTTAAGACATAAAAT | 224 | 257 | pCLS5427 |
| | | | 258 | pCLS5565 |
| | | | 259 | pCLS5566 |
| SH53 | GTAAAATGGATTAAAAGAGGGAAG | 225 | 260 | pCLS4773 |
| SH54 | CCAAAACACGTTAAAAAAGTTTAA | 226 | 261 | pCLS4774 |
| SH55 | ATAATATTCTGTGACTCATGGCAA | 227 | 262 | pCLS4775 |
| SH56 | AGTAGATCTTTTAAAAGATTTTAA | 228 | 263 | pCLS4776 |
| SH57 | ATAAAACCACTTAAGACATAGGAA | 229 | 264 | pCLS4777 |
| SH58 | ACTTGCTGTCTTAACAGAGAAGAT | 230 | 265 | pCLS4778 |
| SH59 | ATGTACCTCTTTAAAACAGATGAA | 231 | 266 | pCLS4779 |
| SH60 | CTCTTCTCCTGTGACAGAGTTCTG | 232 | 267 | pCLS4780 |
| SH61 | TCCAGCCCTGTGACAGAGTGAGA | 233 | 268 | pCLS5333 |
| SH62 | ACAAAATATTTTAAGGGAGCCAAA | 234 | 269 | pCLS5334 |
| | | | 270 | pCLS5335 |
| SH65 | CTCACCTGTCTCACAAGGGAGGGA | 271 | 275 | pCLS5336 |
| SH67 | CTACTACCATGTGACTGGTTGTAG | 272 | 276 | pCLS5337 |
| SH68 | GCTGCACGTTTTACATGAGAGTAA | 273 | 277 | pCLS5955 |
| SH69 | TCAGACTTCTTTACCTCATTTGAT | 274 | 278 | pCLS5956 |

In a specific embodiment, the locus according to the invention is the SH3 locus. The term "SH3 locus" refers to the region of human chromosome 6 that is located at about 120 kb centromeric to the gene encoding the lymphocyte antigen 86 (see e.g. the world wide web site ncbi.nlm.nih.gov/projects/mapview/maps.cgi?TAXID=9606&CHR=6&MAPS=ideogr%2Ccntg-r%2CugHs%2Cgenes&BEG=6432845&END=7232845&thmb=on, which shows the 6,430K-7,230K region of chromosome 6), and to homologous regions in other species. More precisely, the SH3 locus extends from position 6850510 to 6853677 of the sequence shown in NC_000006.11. It comprises a sequence of SEQ ID NO: 54.

In another specific embodiment, the locus according to the invention is the SH4 locus. The SH4 locus is defined herein as the region of human chromosome 7 that is located at about 320 kb telomeric to MyoD family inhibitor domain containing locus (MDFIC), or to the homologous region in another species (see e.g. the world wide web site ncbi.nlm.nih.gov/projects/mapview/maps.cgi?TAXID=9606&CHR=7&MAPS=ideogr,cntg-r,ugHs,genes[113908811.00%3A114908811.00]&CMD=DN, which shows the 114,660K-115,660K region of chromosome 7). More precisely, the SH4 locus extends from position 114972751 to 114976380 of the sequence shown in NC_000007.13. It comprises a sequence of SEQ ID NO: 55.

As used herein, the term "transgene" refers to a sequence encoding a polypeptide. Preferably, the polypeptide encoded by the transgene is either not expressed, or expressed but not biologically active, in the cell, tissue or individual in which the transgene is inserted. Most preferably, the transgene encodes a therapeutic polypeptide useful for the treatment of an individual.

In the frame of the present invention, the individual may be a human or non-human animal. The individual is preferably a human. Alternatively, the individual can be a non-human animal, preferably a vertebrate and/or a mammalian animal such as e.g. a mouse, a rat, a rabbit, a Chinese hamster, a Guinea pig or a monkey. The cells and tissues according to the invention are preferably derived from such human or non-human animals.

Endonucleases According to the Invention that are Derived from I-CreI

The variant endonuclease according to the invention can for example be derived:

either from the wild-type I-CreI meganuclease, which is a homodimeric protein comprising two monomers, each of these monomers comprising a sequence of SEQ ID NO: 1 or the sequence shown in shown SwissProt Accession n° P05725;

or from a I-CreI meganuclease comprising two monomers, each of these monomers comprising a sequence of SEQ ID NO: 42 Such a I-CreI meganuclease, which recognizes the wild-type target sequence, has been shown to be suitable for engineering endonucleases with novel specificities.

Therefore, the invention pertains to a dimeric I-CreI protein comprising or consisting of two monomers, each monomer comprising or consisting of a sequence at least 80%, 85%, 86%, 87%, 88%, 89%, 90%, 91%, 92%, 93%, 94%, 95%, 96%, 97%, 98% or 99% identical to SEQ ID NO: 1 or to SEQ ID NO: 42, wherein said dimeric I-CreI protein is capable of cleaving a target sequence located within a safe harbor locus.

Preferably, the target sequence neither comprises nor consists of a sequence of SEQ ID NO: 4.

Most preferably, the dimeric I-CreI protein according to the invention is a heterodimeric protein.

By a protein having a sequence at least, for example, 95% "identical" to a query sequence of the present invention, it is intended that the sequence of the protein is identical to the query sequence except that the sequence may include up to five nucleotide mutations per each 100 amino acids of the query sequence. In other words, to obtain a protein having a sequence at least 95% identical to a query sequence, up to 5% (5 of 100) of the amino acids of the sequence may be inserted, deleted, or replaced with another nucleotide. The <<needle>> program, which uses the Needleman-Wunsch global alignment algorithm (Needleman and Wunsch, 1970 J. Mol. Biol. 48:443-453) to find the optimum alignment (including gaps) of two sequences when considering their entire length, may for example be used. The needle program is for example available on the ebi.ac.uk world wide web site. The percentage of identity in accordance with the invention can thus be calculated using the EMBOSS::needle (global) program with a "Gap Open" parameter equal to 10.0, a "Gap Extend" parameter equal to 0.5, and a Blosum62 matrix.

Each monomer of the dimeric I-CreI protein according to the invention may for example comprise at least, at most or about 2, 5, 8, 10, 12, 15, 18, 20 or 25 mutations compared with the sequence of a wild-type monomer (SEQ ID NO: 1) or with a monomer of SEQ ID NO: 42. In other terms, the monomer according to the invention comprises a sequence that differs from SEQ ID NO: 1 or SEQ ID NO: 42 by at least, at most or about 2, 5, 8, 10, 12, 15, 18, 20, 25 or 30 mutations.

In the frame of the present invention, the mutation preferably corresponds to a substitution of one amino acid with another amino acid. Therefore, a preferred embodiment according to the invention is directed to a dimeric I-CreI protein comprising or consisting of two monomers comprising a sequence at least 80%, identical to SEQ ID NO: 1 or SEQ ID NO: 42, wherein said sequence only differs from SEQ ID NO: 1 or SEQ ID NO: 42 by the presence of amino acid substitutions.

The monomers of the dimeric I-CreI protein according to the invention are preferably derived from monomers comprising or consisting of the sequence of SEQ ID NO: 42.

The mutations are preferably located at positions of the I-CreI sequence that are involved in recognition of the target sequence. Indeed, introducing such mutations allow designing meganucleases with novel specificities.

In addition to such mutations, the monomers may also have mutations corresponding to:
 mutations that improve the binding and/or the cleavage properties of the protein towards the target site, such as e.g. G19S, G19A, F54L, S79G, E80K, F87L, V105A and/or I132V (see for example WO 2008/152524); and/or
 mutations leading to the obtention of an obligate heterodimer (see for example WO 2008/093249 and Fajardo-Sanchez et al., Nucleic Acids Res. 2008 36:2163-73); and/or
 mutations suitable for the generation of a fusion protein such as, e.g., the deletion of the five most N-terminal amino acid residues of SEQ ID NO: 1 in the C-terminal monomer of a fusion protein; and/or
 a mutation consisting of the insertion of an alanine between the first and the second residue of SEQ ID NO: 1, as is the case in a monomer of SEQ ID NO: 42.

In addition to the sequence homologous to SEQ ID NO: 1 or SEQ ID NO: 42, the monomers of the protein according to the invention may comprise one or more amino acids added at the NH$_2$ terminus and/or COOH terminus of the sequence, such as a Tag useful in purification of the protein, a propeptide and/or a nuclear localization signal. In particular, the monomers of the protein according to the invention may comprise AAD amino acids added at the COOH terminus of the sequence of SEQ ID NO: 1, as is the case in a monomer of SEQ ID NO: 42.

In the present specification, the mutations are indicated by the position on SEQ ID NO: 1 followed by the nature of the amino acid replacing the amino acid located at this position in SEQ ID NO: 1. For example, a monomer comprising a 44A mutation refers to a I-CreI monomer in which the amino acid at position 44 of SEQ ID NO: 1 (i.e. a glutamine, Q) is replaced with an alanine (A). Thus this monomer differs from the wild-type I-CreI monomer of SEQ ID NO: 1 by at least the following amino acid substitution: Q44A. As explained hereabove, the I-CreI monomer of SEQ ID NO: 42 comprises some additional amino acid residues compared to the I-CreI monomer of SEQ ID NO: 1 (see FIG. 11). Therefore, on SEQ ID NO: 42, the 44A mutation corresponds to a replacement of the glutamine at position 45 of SEQ ID NO: 42 with an alanine.

For the purpose of illustration, a monomer comprising 44A 54L 64A 70Q 75N 158R 162A mutations may for example have the sequence of SEQ ID NO: 57 (when this monomer is directly derived from a I-CreI monomer of SEQ ID NO: 1) or the sequence of SEQ ID NO: 58 (when this monomer is directly derived from a I-CreI monomer of SEQ ID NO: 42). FIG. 12 shows an alignment between two such monomers, and indicates the position of the 44A 54L 64A 70Q 75N 158R and 162A mutations on these monomers.

Examples of dimeric I-CreI proteins according to the invention, capable of cleaving target sequences located in the SH3, SH4 or SH6 locus, are further described below.

Dimeric I-CreI Protein According to the Invention Capable of Cleaving the SH3 Locus In a preferred embodiment, the target sequence is located within the SH3 locus (defined hereabove). The target sequence located within SH3 may for example comprise or consist of SEQ ID NO: 2, or of nucleotides 2 to 23 of SEQ ID NO: 2. Example 1 discloses several examples of heterodimeric I-CreI proteins according to the invention capable of cleaving such a target sequence. In addition, methods for constructing other such proteins are well-known in the art and include e.g. those described in PCT applications WO 2006/097784, WO 2006/097853 and WO 2009019614, and in Arnould et al. (J. Mol. Biol., 2006, 355:443-458).

The monomers of such a dimeric protein preferably comprise at least one, preferably at least 3, 4, 5 or 6, amino acid substitutions located at a position selected from the group consisting of positions 4, 24, 26, 28, 30, 32, 33, 38, 44, 50, 54, 57, 64, 66, 70, 71, 75, 77, 81, 86, 92, 105, 142, 151, 154, 158 and 162 of SEQ ID NO: 1, preferably positions 4, 30, 38, 44, 50, 54, 57, 64, 66, 70, 71, 75, 77, 81, 86, 92, 105, 142, 151, 154, 158 and 162 of SEQ ID NO: 1. Said substitutions may for example be selected from the following substitutions: 4E, 30G, 38R, 44A, 50R, 54L, 57E, 64A, 66C, 70Q, 70D, 71R, 75N, 75Y, 77V, 81T, 86D, 92R, 105A, 142R, 151A, 154G, 158R, 158W and 162A. The dimeric protein may optionally comprise a mutation at position 1, however, such a mutation has no influence on cleavage activity or on cleavage specificity.

Such dimeric I-CreI proteins may for example comprise or consist of:
 a first monomer comprising at least one amino acid substitution compared to SEQ ID NO: 1, wherein said at least one amino acid substitution is located at a position selected from the group consisting of positions 30, 38, 50, 70, 75, 81, 86, 142 and 154 of SEQ ID NO: 1.

Preferably, said first monomer comprises substitutions at positions 30, 38, 70 and 75 of SEQ ID NO: 1. Most preferably, said substitutions are selected from the following substitutions: 30G, 38R, 50R, 70D, 75N, 81T, 86D, 142R and 154G. Such a monomer may for example comprise at least 4, 5 or 6 mutations compared to SEQ ID NO: 1, and/or at most 4, 5, 6, 8, 10, 12 or 15 amino acid mutations compared to SEQ ID NO: 1; and a second monomer comprising at least one amino acid substitution compared to SEQ ID NO: 1, wherein said at least one amino acid substitution is located at a position selected from the group consisting of positions 4, 44, 54, 57, 64, 66, 70, 71, 75, 77, 92, 105, 151, 158 and 162 of SEQ ID NO: 1. Preferably, said second monomer comprises substitutions at positions 44, 54, 70 and 75 of SEQ ID NO: 1. Most preferably, said substitutions are selected from the following substitutions: 4E, 44A, 54L, 57E, 64A, 66C, 70Q, 71R, 75N, 75Y, 77V, 92R, 105A, 151A 158R, 158W and 162A. Such a monomer may for example comprise at least 4, 5 or 6 mutations compared to SEQ ID NO: 1, and/or at most 4, 6, 8, 10, 12 or 15 amino acid mutations compared to SEQ ID NO: 1.

In a specific embodiment, the dimeric I-CreI protein according the invention comprises or consists of:
a) a first monomer comprising 30G 38R 70D 75N 86D mutations;
b) a second monomer selected from the group consisting of:
i. a monomer comprising 44A 54L 64A 70Q 75N 158R 162A mutations;
ii. a monomer comprising 44A 54L 70Q 75Y 92R 158R 162A mutations;
iii. a monomer comprising 4E 44A 54L 64A 70Q 75N 158R 162A mutations;
iv. a monomer comprising 44A 54L 64A 70Q 75N 158W 162A mutations;
v. a monomer comprising 44A 54L 70Q 75N mutations;
vi. a monomer comprising 44A 54L 57E 70Q 75N 158R 162A mutations; and
vii. a monomer comprising 44V 54L 70Q 75N 77V mutations;

In another specific embodiment, the dimeric I-CreI protein according the invention comprises or consists of:
a) a first monomer comprising 30G 38R 70D 75N 81T 154G mutations;
b) a second monomer selected from the group consisting of:
i. a monomer comprising 44A 54L 70Q 75N 105A 158R 162A mutations;
ii. a monomer comprising 44A 54L 64A 70Q 75N 158R 162A mutations;
iii. a monomer comprising 4E 44A 54L 64A 70Q 75N 158R 162A mutations;
iv. a monomer comprising 44A 54L 64A 70Q 75N 158W 162A mutations;
v. a monomer comprising 44A 54L 70Q 75N mutations; and
vi. a monomer comprising 44V 54L 70Q 75N 77V mutations;

In still another specific embodiment, the dimeric I-CreI protein according the invention comprises or consists of:
a) a first monomer comprising 30G 38R, 50R 70D 75N 142R mutations;
b) a second monomer selected from the group consisting of:
i. a monomer comprising 44A 54L 70Q 75N 105A 158R 162A mutations;
ii. a monomer comprising 44A 54L 64A 70Q 75N 158R 162A mutations;
iii. a monomer comprising 44A 54L 70Q 75Y 92R 158R 162A mutations;
iv. a monomer comprising 4E 44A 54L 64A 70Q 75N 158R 162A mutations;
v. a monomer comprising 44A 54L 64A 70Q 75N 158W 162A mutations;
vi. a monomer comprising 44A 54L 66C 70Q 71R 75N 151 A 158R 162A mutations;
vii. a monomer comprising 44A 54L 70Q 75N mutations;
viii. a monomer comprising 44A 54L 57E 70Q 75N 158R 162A mutations; and
ix. a monomer comprising 44V 54L 70Q 75N 77V mutations.

The monomers of the dimeric I-CreI protein may also comprise additional mutations, for example allowing the obtention of an obligate heterodimer. Such mutations are known to the skilled in the art and include those described in Fajardo-Sanchez et al. (Nucleic Acids Res. 2008 36:2163-73).

In a specific embodiment, the above monomers are directly derived from a monomer of SEQ ID NO: 42, and differ from the sequence of SEQ ID NO: 42 only by the presence of the indicated mutations.

Dimeric I-CreI Protein According to the Invention Capable of Cleaving the SH4 Locus In a preferred embodiment, the target sequence is located within the SH4 locus (defined hereabove). The target sequence located within SH4 may for example comprise or consist of SEQ ID NO: 3, or of nucleotides 2 to 23 of SEQ ID NO: 3. Example 2 discloses several examples of dimeric I-CreI proteins according to the invention capable of cleaving such a target sequence.

The monomers of such a dimeric protein preferably comprise at least one, preferably at least 3, 4, 5 or 6, amino acid substitutions located at a position selected from the group consisting of positions 24, 44, 68, 70, 75 and 77 of SEQ ID NO: 1. Said substitutions may for example be selected from the following substitutions: 24V, 44R, 44Y, 68Y, 68A, 70S, 70D, 75Y, 75N, 77R, 77N and 77V.

Such dimeric I-CreI proteins may for example comprise or consist of:
a first monomer comprising at least one amino acid substitution compared to SEQ ID NO: 1, wherein said at least one amino acid substitution is located at a position selected from the group consisting of positions 24, 44, 68, 70, 75 and 77 of SEQ ID NO: 1. Preferably, the first monomer comprises substitutions at positions 24, 70, 75 and 77 of SEQ ID NO: 1. Most preferably, said substitutions are selected from the following substitutions: 24V, 44R, 68Y, 68A, 70D, 70S, 75Y, 75N, 77N and 77R. Such a monomer may for example comprise at least 4, 5 or 6 mutations compared to SEQ ID NO: 1, and/or at most 4, 5, 6, 8, 10, 12 or 15 amino acid mutations compared to SEQ ID NO: 1; and a second monomer comprising at least one amino acid substitution compared to SEQ ID NO: 1, wherein said at least one amino acid substitution is located at a position selected from the group consisting of positions 24, 44, 70 and 77 of SEQ ID NO: 1. Preferably, the second monomer comprises substitutions at positions 24, 44 and 70 of SEQ ID NO: 1. Most preferably, said substitutions are selected from the following substitutions: 24V, 44Y, 70S and 77V. Such a monomer may for example comprise at least 3 or 4 mutations compared to SEQ ID NO: 1, and/or at most 3, 4, 6, 8, 10, 12 or 15 amino acid mutations compared to SEQ ID NO: 1.

In a specific embodiment, the dimeric I-CreI protein according to the invention comprises or consists of:
a) a first monomer selected from the group consisting of:
  i. a monomer comprising 24V 44R 68Y 70S 75Y 77N mutations;
  ii. a monomer comprising 24V 68A 70S 75N 77R mutations; and
  iii. a monomer comprising 24V 70D 75N 77R mutations;
b) a second monomer selected from the group consisting of:
  i. a monomer comprising 24V 44Y 70S mutations; and
  ii. a monomer comprising 24V 44Y 70S 77V mutations.

The monomers of the dimeric I-CreI protein may also comprise additional mutations, for example allowing the obtention of an obligate heterodimer. Such mutations are known to the skilled in the art and include those described in Fajardo-Sanchez et al. (Nucleic Acids Res. 2008 36:2163-73).

In a specific embodiment, the above monomers are directly derived from a monomer of SEQ ID NO: 42, and differ from the sequence of SEQ ID NO: 42 only by the presence of the indicated mutations.

Dimeric I-CreI Protein According to the Invention Capable of Cleaving the SH6 Locus In a preferred embodiment, the target sequence is located within the SH6 locus (defined hereabove). The target sequence located within SH6 may for example comprise or consist of SEQ ID NO: 59, or of nucleotides 2 to 23 of SEQ ID NO: 59. Example 5 discloses several examples of dimeric I-CreI proteins according to the invention capable of cleaving such a target sequence.

The monomers of such a dimeric protein preferably comprise at least one, preferably at least 3, 4, 5 or 6, amino acid substitutions located at a position selected from the group consisting of positions 7, 24, 27, 28, 34, 40, 44, 68, 70, 75, 77, 81, 85, 96, 99, 103, 108, 111, 121, 132, 144 and 160 of SEQ ID NO: 1. Said substitutions may for example be selected from the following substitutions: 7R, 24F, 27V, 28Q, 34R, 40R, 44A, 44K, 68T, 70L, 70G, 70S, 75N, 77V, 81T, 81V, 85R, 96R, 99R, 103T, 103S, 108V, 111H, 121E, 132V, 144S, 160R and 160E.

Such dimeric I-CreI proteins may for example comprise or consist of:
a first monomer comprising at least one amino acid substitution compared to SEQ ID NO: 1, wherein said at least one amino acid substitution is located at a position selected from the group consisting of positions 7, 24, 27, 28, 34, 40, 44, 70, 75, 77, 81, 85, 96, 99, 103, 108, 111, 121, 132, 144 and 160 of SEQ ID NO: 1. Preferably, the first monomer comprises substitutions at positions 28, 40, 44, 70 and 75 of SEQ ID NO: 1. Most preferably, said substitutions are selected from the following substitutions: 7R, 24F, 27V, 28Q, 34R, 40R, 44A, 70L, 75N, 77V, 81T, 81V, 85R, 96R, 99R, 103T, 103S, 108V, 111H, 121E, 132V, 144S and 160R et 160E. Such a monomer may for example comprise at least 5 or 6 mutations compared to SEQ ID NO: 1, and/or at most 5, 6, 8, 10, 12, 15 or 20 amino acid mutations compared to SEQ ID NO: 1; and
a second monomer comprising at least one amino acid substitution compared to SEQ ID NO: 1, wherein said at least one amino acid substitution is located at a position selected from the group consisting of positions 44, 68, 70 and 75 of SEQ ID NO: 1. Preferably, the second monomer comprises substitutions at positions 44, 70 and 75 of SEQ ID NO: 1. Most preferably, said substitutions are selected from the following substitutions: 44K, 68T, 70G, 70S and 75N. Such a monomer may for example comprise at least 3 or 4 mutations compared to SEQ ID NO: 1, and/or at most 3, 4, 6, 8, 10, 12 or 15 amino acid mutations compared to SEQ ID NO: 1.

In a specific embodiment, the dimeric I-CreI protein according the invention comprises or consists of:
a) a first monomer comprising 44K 68T 70G 75N mutations; and
b) a second monomer selected from the group consisting of:
  i. a monomer comprising 28Q 40R 44A 70L 75N 96R 111H 144S mutations;
  ii. a monomer comprising 7R 28Q 40R 44A 70L 75N 85R 103T mutations;
  iii. a monomer comprising 28Q 40R 44A 70L 75N 103S mutations;
  iv. a monomer comprising 24F 27V 28Q 40R 44A 70L 75N 99R mutations;
  v. a monomer comprising 7R 28Q 40R 44A 70L 75N 81T mutations;
  vi. a monomer comprising 7R 28Q 40R 44A 70L 75N 77V mutations;
  vii. a monomer comprising 7R 28Q 40R 44A 70L 75N 103T 121E 132V 160R mutations;
  viii. a monomer comprising 28Q 40R 44A 70L 75N mutations;
  ix. a monomer comprising 7R 28Q 40R 44A 70L 75N 103T mutations; and
  x. a monomer comprising 28Q 34R, 40R 44A 70L 75N 81V 103T 108V 160E mutations.

In another specific embodiment, the dimeric I-CreI protein according the invention comprises or consists of:
a) a first monomer comprising 44K 70S 75N mutations; and
b) a second monomer selected from the group consisting of:
  i. a monomer comprising 28Q 40R 44A 70L 75N 96R 111H 144S mutations;
  ii. a monomer comprising 7R 28Q 40R 44A 70L 75N 85R 103T mutations;
  iii. a monomer comprising 28Q 40R 44A 70L 75N 103S mutations;
  iv. a monomer comprising 24F 27V 28Q 40R 44A 70L 75N 99R mutations;
  v. a monomer comprising 7R 28Q 40R 44A 70L 75N 81T mutations;
  vi. a monomer comprising 7R 28Q 40R 44A 70L 75N 103T 121E 132V 160R mutations;
  vii. a monomer comprising 7R 28Q 40R 44A 70L 75N 103T mutations; and
  viii. a monomer comprising 28Q 34R, 40R 44A 70L 75N 81V 103T 108V 160E mutations.

The monomers of the dimeric I-CreI protein may also comprise additional mutations, for example allowing the obtention of an obligate heterodimer. Such mutations are known to the skilled in the art and include those described in Fajardo-Sanchez et al. (Nucleic Acids Res. 2008 36:2163-73).

In a specific embodiment, the above monomers are directly derived from a monomer of SEQ ID NO: 42, and differ from the sequence of SEQ ID NO: 42 only by the presence of the indicated mutations.

Fusion Proteins According to the Invention

Fusion proteins comprising the two monomers of a dimeric I-CreI protein fused together and retaining the biological activity of the parent dimeric I-CreI protein can be constructed (Grizot et al. NAR 2009 37:5405; Li et al. Nucleic Acids Res. 2009 37:1650-62; Epinat et al. Nucleic Acids Res. 2003 31:2952-62). Such fusion proteins are commonly referred to as "single-chain meganucleases".

Therefore, the invention further relates to a fusion protein comprising the two monomers of the dimeric I-CreI protein as defined hereabove, or biologically active fragments of such monomers. In such a fusion protein, the first and second monomers of a dimeric I-CreI protein as defined hereabove are fused together and are optionally connected to each other by a linker such as a peptidic linker. The linker may for example comprise or consist of SEQ ID NO: 43 or SEQ ID NO: 326.

In the frame of the present invention, it is understood that such a fusion protein according to the invention is capable of cleaving a target sequence according to the invention, i.e., it is capable of cleaving the same target sequence as the dimeric I-CreI protein from which it is derived. The single chain meganuclease of the present invention further comprises obligate heterodimer mutations as described above so as to obtain single chain obligate heterodimer meganuclease variants.

In the first version of I-CreI single chain (Epinat et al. NAR 2003 3:2952-2962; WO 03/078619), the N-terminal monomer of the single-chain meganuclease consisted essentially of positions 1 to 93 of I-CreI amino acid sequence whereas the C-terminal (positions 8 to 163 of I-CreI amino acid sequence) was a nearly complete I-CreI monomer. More recently, a new way to design a single chain molecule derived from the I-CreI homodimeric meganuclease consisted in two nearly complete C-terminal and N-terminal I-CreI monomers (see, e.g. WO 2009/095793). This design greatly decreases off-site cleavage and toxicity while enhancing efficacy. The structure and stability of this single-chain molecule are very similar to those of the dimeric variants and this molecule appears to be monomeric in solution. In all respects, this single-chain molecule performs as well as I-SceI considered to be gold standard in terms of specificity. These properties place this new generation of meganucleases among the best molecular scissors available for genome surgery strategies and should facilitate gene correction therapy for monogenetic diseases, such as for example severe combined immunodeficiency (SCID), while potentially avoiding the deleterious effects of previous gene therapy approaches.

In addition to the mutations described hereabove, additional mutations may be introduced into the sequence of each of the two monomers of the fusion protein. For example, the C-terminal monomer may comprise the K7E and K96E mutations, and the N-terminal monomer may comprise the E8K, E61R and G19S mutations.

Examples 1, 2 and 5 disclose several examples of such fusion proteins according to the invention.

In a specific embodiment, the fusion protein according to the invention comprises or consists of a sequence at least 80%, 85%, 90%, 95%, 96%, 97%, 98%, 99% or 100% identical to any one of SEQ ID Nos. 25-40 and 76-96, or to a fragment of at least 50, 100, 150 or 200 amino acids thereof.

Nucleic Acids, Vectors and Combinations According to the Invention

When inserting a transgene into the genome of a cell, tissue or animal, the endonuclease according to the invention is preferably introduced to said cell, tissue or animal as a nucleic acid molecule rather than as a protein.

Therefore, the invention pertains to a nucleic acid encoding the endonuclease according to the invention, e.g. encoding a dimeric I-CreI protein or a fusion protein described hereabove. When the endonuclease is a dimeric I-CreI protein, said nucleic acid comprises at least two coding sequences, one for each monomer. When the endonuclease is a fusion protein, said nucleic acid comprises at least one coding sequence. The endonuclease protein can be combined with a variety of cell-penetrating peptide leading to a recombinant protein; such combined molecules are able to enter target cells at much higher levels of efficiency than the endonuclease alone. These cell-penetrating peptides were developed by Diatos S. A. (WO01/64738; WO05/016960; WO03/018636; WO05/018650; WO07/069,068). The applicant has previously shown that endonuclease cell-penetrating peptides combinations can enter target cells efficiently and that the internalized endonuclease can act upon the target cell genome so as to generate a DSB and in turn stimulate a homologous recombination event. The applicant has shown that the complex three dimensional structure of the endonuclease is not affected by the presence of the cell-penetrating peptide and that the all important specificity of the endonuclease also remains unaffected (data not shown).

Another aspect of the invention is a vector comprising such a nucleic acid according to the invention. By "vector" is meant a nucleic acid molecule capable of transporting another nucleic acid to which it has been linked.

Vectors which can be used in the present invention includes but is not limited to viral vectors, plasmids and YACs, which may consist of chromosomal, non chromosomal, semisynthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available.

In a preferred embodiment, the vector is a viral vector such as e.g. a vector derived from a retrovirus, an adenovirus, a parvovirus (e.g. an adeno-associated viruses), a coronavirus, a negative strand RNA virus (e.g. an orthomyxovirus such as influenza virus, a rhabdovirus such as rabies and vesicular stomatitis virus, a paramyxovirus such as measles and Sendai virus), a positive strand RNA virus such as picornavirus and alphavirus, or a double-stranded DNA virus such as adenovirus, herpesvirus (e.g. Herpes Simplex virus types 1 and 2, Epstein-Barr virus, cytomegalovirus) and poxvirus (e.g. vaccinia, fowlpox and canarypox). Preferred vectors include lentiviral vectors, and particularly self-inactivacting lentiviral vectors.

In addition to the sequence coding for the endonuclease according to the invention, the vector can also comprise elements such as:
- transcriptional and translational control elements such as promoters, enhancers, polyadenylation sites, terminations signals, introns, etc.;
- a multiple cloning site;
- a replication origin;
- selection markers;
- a transgene; and/or
- a targeting construct comprising sequences sharing homologies with the region surrounding the genomic target site as defined herein.

In a preferred embodiment, said vector is an "expression vector", i.e. a vector in which at least one coding sequence is operatively linked to transcriptional and translational control elements. In the frame of this embodiment, the nucleic acid encoding the endonuclease according to the invention (e.g. encoding the dimeric I-CreI protein or the fusion protein described hereabove) is operatively linked to transcriptional and translational control elements.

In a preferred embodiment, the vector according to the invention comprises a targeting construct comprising a transgene and two sequences homologous to the genomic sequence flanking the target sequence as defined herein (e.g. the target sequence of SEQ ID NO: 2 or 3). The genomic sequences flanking the target sequence are preferably immediately adjacent to the target site.

Such targeting constructs are well-known to the skilled in the art. For insertion of a transgene, such constructs typically comprise a first sequence that is homologous to the upstream (5') genomic sequence flanking the target sequence, the transgene to be inserted, and a second fragment that is homologous to the downstream (3') genomic sequence flanking the target sequence.

By "homologous" is intended a sequence with enough identity to another one to lead to a homologous recombination between sequences, more particularly having at least 95% identity, preferably 97% identity and more preferably 99% identity to each other.

Preferably, homologous sequences of at least 50 bp, preferably more than 100 bp and more preferably more than 200 bp are used. Therefore, the targeting DNA construct is preferably from 200 pb to 6000 pb, more preferably from 1000 pb to 2000 pb. Indeed, shared DNA homologies are located in regions flanking upstream and downstream the site of the break and the DNA sequence to be introduced should be located between the two arms.

The targeting construct may also comprise a positive selection marker between the two homology arms and eventually a negative selection marker upstream of the first homology arm or downstream of the second homology arm. The marker(s) allow(s) the selection of cells having inserted the sequence of interest by homologous recombination at the target site.

Methods for constructing targeting constructs suitable for inserting a transgene into the SH3 or SH4 locus are given in Example 4.

The nucleic acid encoding the endonuclease according to the invention and the targeting construct can also be located on two separate vectors. Therefore, the invention also pertains to a combination of two vectors, namely:
an expression vector according the invention; and
a vector comprising a targeting construct comprising a transgene and two sequences homologous to the genomic sequence of the target sequence according to the invention.

Pharmaceutical Uses According to the Invention

The vectors and combinations described hereabove can for example be used as a medicament. In particular, these vectors and combinations can be used in gene therapy.

Therefore, the invention relates to a vector or combination according to the invention for use as a medicament. In such vectors and combinations, the transgene encodes a therapeutic polypeptide.

In particular, diseases that may be treated by gene therapy using the vectors and combinations according to the invention include but are not limited to X-SCID, SCID, epidermolysis bullosa, leber amaurosis, hemophilia, thalassemia, fanconi anemia and muscular dystrophy.

In these diseases, the transgene encodes the following therapeutic polypeptides, respectively: IL2RG, GI7A1, Rp 65, Blood factors VIII and IX, haemoglobin A and B, Fanc-A, Fanc-C (or other Fanconi Anemia related genes), Dystrophine.

The invention further relates to a pharmaceutical composition comprising the vectors and combinations according to the invention and a pharmaceutically active carrier.

The invention also relates to a method of treating an individual by gene therapy comprising administering an effective amount of a vector or combination according to the invention to an individual in need thereof.

By "effective amount" is meant an amount sufficient to achieve insertion of the transgene into the genome of the individual to be treated. Such concentrations can be routinely determined by those of skilled in the art.

By "subject in need thereof" is meant an individual suffering from or susceptible of suffering from a genetic disease that can be treated or prevented by insertion of the transgene. The individuals to be treated in the frame of the invention are preferably human beings.

Non Pharmaceutical Uses According to the Invention

The vectors and combinations described hereabove not only find use in gene therapy but also in non pharmaceutical uses such as, e.g., production of animal models and production of recombinant cell lines expressing a protein of interest.

Therefore, the invention relates to:
the use of an endonuclease, nucleic acid, expression vector or combination according to the invention for inserting a transgene into the genome of a cell, tissue or non-human animal, wherein said use is not therapeutic.
a method of inserting a transgene into the genome of a cell, tissue or non-human animal, comprising the step of bringing said cell, tissue or non-human animal in contact with an endonuclease, nucleic acid, expression vector or combination according to the invention, thereby inserting said transgene into said genome.

In a preferred embodiment, the above use or method aims at inserting a transgene encoding a protein of interest into the genome of a cell order to obtain a recombinant cell line for protein production. Suitable cells for constructing recombinant cell lines for protein production include but are not limited to human (e.g. PER.C6 or HEK), Chinese Ovary hamster (CHO) and mouse (NSE0) cells.

In another preferred embodiment, the above use aims at making a non-human animal model of a hereditary disorder.

The invention is also directed to a non-human transgenic animal comprising a nucleic acid, an expression vector or a combination according to the invention in its genome.

All references cited herein, including journal articles or abstracts, published patent applications, issued patents or any other references, are entirely incorporated by reference herein, including all data, tables, figures and text presented in the cited references.

The invention will be further evaluated in view of the following examples and figures.

BRIEF DESCRIPTION OF THE FIGURES

FIG. 1 represents target sequences of meganucleases described in Example 1.

FIG. 4 represents target sequences of meganucleases described in Example 2.

FIG. 9 represents target sequences of meganucleases described in Example 5.

FIG. 11 represents a sequence alignment between a I-CreI monomer of SEQ ID NO: 1 and a I-CreI monomer of SEQ ID NO: 42.

FIG. 12 represents a sequence alignment between a I-CreI monomer of SEQ ID NO: 1 and two I-CreI monomers comprising 44A 54L 64A 70Q 75N 158R and 162A mutations. The first one (SEQ ID NO: 57) is directly derived from SEQ ID NO: 1 and the second one (SEQ ID NO: 58) is directly derived from SEQ ID NO: 42.

BRIEF DESCRIPTION OF THE SEQUENCES

Figure 2:
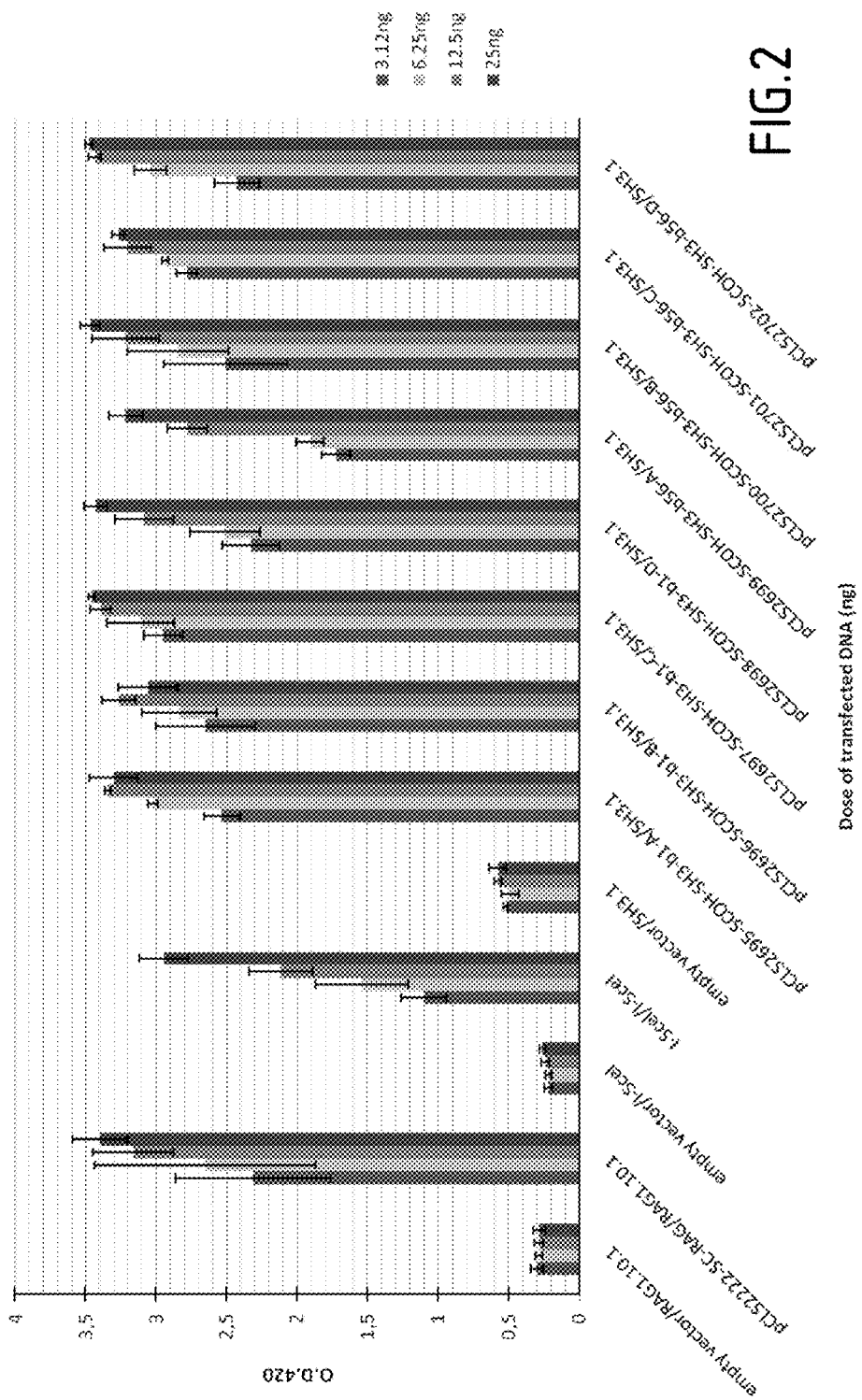
FIGS. 2 and 3 represent SCOH SH3 meganucleases vs. I-SceI and SCOH-RAG DNA dose response in CHO.

SEQ ID NO: 1 shows the amino acid sequence of a wild-type I-CreI monomer.

SEQ ID NO: 2 shows the sequence of a target sequence according to the invention that is located within the SH3 locus.

SEQ ID NO: 3 shows the sequence of a target sequence according to the invention that is located within the SH4 locus.

SEQ ID NO: 4 shows the sequence of the target sequence of the wild-type I-CreI homodimeric protein.

SEQ ID Nos. 5 to 10 represent sequences shown on FIG. 1.

SEQ ID Nos. 11 to 15 represent oligonucleotides, primers and linkers used in Example 1.

SEQ ID Nos. 16 to 19 represent sequences shown on FIG. 4.

SEQ ID Nos. 20 to 24 represent oligonucleotides, primers and linkers used in Example 2.

SEQ ID Nos. 25 to 32 represent the single-chain meganucleases constructed in Example 1, referred to as SCOH-SH3-b56-A, SCOH-SH3-b56-B, SCOH-SH3-b56-C, SCOH-SH3-b56-D, SCOH-SH3-b1-A, SCOH-SH3-b1-B, SCOH-SH3-b1-C and SCOH-SH3-b1-D respectively.

SEQ ID Nos. 33 to 40 represent the single-chain meganucleases constructed in Example 2, referred to as SCOH-SH4-b56-A, SCOH-SH4-b56-B, SCOH-SH4-b56-C, SCOH-SH4-b56-D, SCOH-SH4-b1-A, SCOH-SH4-b1-B, SCOH-SH4-b1-C and SCOH-SH4-b1-D respectively.

SEQ ID NO: 41 represents the positive control SCOH-RAG.

SEQ ID NO: 42 shows the amino acid sequence of a I-CreI monomer with an additional alanine at position 2, and with three additional residues after the final proline.

SEQ ID NO: 43 shows the amino acid sequence of the RM2 linker.

SEQ ID Nos. 44 to 49 represent oligonucleotides, primers and linkers used in Example 3.

SEQ ID Nos. 50 to 53 represent oligonucleotides, primers and linkers used in Example 4.

SEQ ID Nos. 54 to 55 show sequences comprised in the SH3, SH4 and SH6 loci, respectively.

SEQ ID NO: 57 shows a monomer derived from a monomer of SEQ ID NO: 1 that comprises 44A 54L 64A 70Q 75N 158R 162A mutations.

SEQ ID NO: 58 shows a monomer derived from a monomer of SEQ ID NO: 42 that comprises 44A 54L 64A 70Q 75N 158R 162A mutations.

SEQ ID NO: 59 shows the sequence of a target sequence according to the invention that is located within the SH6 locus.

SEQ ID Nos. 60 to 64 represent sequences shown on FIG. 9.

SEQ ID Nos. 65 to 75 represent oligonucleotides, primers and linkers used in Example 5.

SEQ ID Nos. 76 to 85 represent the single-chain meganucleases constructed in Example 5, referred to as SCOH-SH6-b1-B, SCOH-SH6-b1-C, SCOH-SH6-b1-C, QCSH61-A01, QCSH61-E01, QCSH61-HO, QCSH62-A02, QCSH61-H01b, QCSH61-H01c) and QCSH61-H01d respectively.

SEQ ID Nos. 86 to 96 represent the single-chain meganucleases capable of cleaving the SH7 locus (SEQ ID Nos. 86 and 87), SH8 locus (SEQ ID NO: 88), the SH12 locus (SEQ ID NO: 89), the SH13 locus (SEQ ID NO: 90), the SH19 locus (SEQ ID NO: 91), the $SH_{20}$ locus (SEQ ID NO: 92), the SH21 locus (SEQ ID Nos. 93 to 95) and the SH33 locus (SEQ ID NO: 96).

SEQ ID Nos. 97 to 104 represent sequences comprised within the SH12, SH13, SH19, $SH_{20}$, SH21, SH33, SH7 and SH8 loci, respectively.

SEQ ID Nos. 105 to 325 represent sequences disclosed in Examples 6 to 9 and/or in any one of Tables A', A", E, G and H.

SEQ ID NO: 326 shows the amino acid sequence of the BQY linker.

EXAMPLES

In the following examples, all the I-CreI variants were constructed by genetic engineering of I-CreI monomers of SEQ ID NO: 42.

Example 1

Engineering Meganucleases Targeting the SH3 Locus

SH3 is a locus comprising a 24 bp non-palindromic target (SEQ ID NO: 2) that is present on chromosome 6. As shown in Table A, SH3 is located in the vicinity of a RIS disclosed in Deichmann et al. (J. of Clin. Invest. 2007 117:2225). The SH3 sequence is not included in any of the CIS described in Deichmann et al.

I-CreI heterodimers capable of cleaving a target sequence of SEQ ID NO: 2 were identified using methods derived from those described in Chames et al. (Nucleic Acids Res., 2005, 33, e178), Arnould et al. (J. Mol. Biol., 2006, 355, 443-458), Smith et al. (Nucleic Acids Res., 2006, 34, e149), Arnould et al. (Arnould et al. J Mol. Biol. 2007 371:49-65). Some of these heterodimers were then cloned into mammalian expression vectors for assessing SH3 cleavage in CHO cells. These results were then utilized to design single-chain meganucleases directed against the target sequence of SEQ ID NO: 2. These single-chain meganucleases were cloned into mammalian expression vectors and tested for SH3 cleavage in CHO cells. Strong cleavage activity of the SH3 target could be observed for these single chain molecules in mammalian cells.

Example 1.1

Identification of Meganucleases Cleaving SH3

I-CreI variants potentially cleaving the SH3 target sequence in heterodimeric form were constructed by genetic engineering. Pairs of such variants were then co-expressed in yeast. Upon co-expression, one obtains three molecular species, namely two homodimers and one heterodimer. It was then determined whether the heterodimers were capable of cutting the SH3 target sequence of SEQ ID NO: 2.

a) Construction of Variants of the I-CreI Meganuclease Cleaving Palindromic Sequences Derived from the SH3 Target Sequence The SH3 sequence is partially a combination of the 10AAT_P (SEQ ID NO: 5), 5AAG_P (SEQ ID NO: 6), 10AGG_P (SEQ ID NO: 7) and 5TTT_P (SEQ ID NO: 8) target sequences which are shown on FIG. 1. These sequences are cleaved by meganucleases obtained as described in International PCT applications WO 2006/097784 and WO 2006/097853, Arnould et al. (J. Mol. Biol., 2006, 355, 443-458) and Smith et al. (Nucleic Acids Res., 2006). Thus, SH3 should be cleaved by combinatorial variants resulting from these previously identified meganucleases.

Two palindromic targets, SH3.3 and SH3.4, were derived from SH3 (FIG. 1). Since SH3.3 and SH3.4 are palindromic, they should be cleaved by homodimeric proteins. Therefore, homodimeric I-CreI variants cleaving either the SH3.3 palindromic target sequence of SEQ ID NO: 9 or the SH3.4 palindromic target sequence of SEQ ID NO: 10 were constructed using methods derived from those described in Chames et al. (Nucleic Acids Res., 2005, 33, e178), Arnould et al. (J. Mol. Biol., 2006, 355, 443-458), Smith et al. (Nucleic Acids Res., 2006, 34, e149) and Arnould et al. (Arnould et al. J Mol. Biol. 2007 371:49-65).

b) Construction of Target Vector

An oligonucleotide of SEQ ID NO: 11, corresponding to the SH3 target sequence flanked y gateway cloning sequences, was ordered from PROLIGO. This oligo has the following sequence: TGGCATACAAGTTTCCAATACAAGGTA-CAAAGTCCTGACAATCGTCTGTCA). Double-stranded target DNA, generated by PCR amplification of the single stranded oligonucleotide, was cloned into the pCLS1055 yeast reporter vector using the Gateway protocol (INVITROGEN).

Yeast reporter vector was transformed into the FYBL2-7B Saccharomyces cerevisiae strain having the following genotype: MAT a, ura3Δ851, trp1Δ63, leu2Δ1, lys2Δ202. The resulting strain corresponds to a reporter strain (MilleGen).

c) Co-expression of Variants

The open reading frames coding for the variants cleaving the SH3.4 or the SH3.3 sequence were cloned in the pCLS542 expression vector and in the pCLS1107 expression vector, respectively. Yeast DNA from these variants was extracted using standard protocols and was used to transform E. coli. The resulting plasmids were then used to co-transform yeast. Transformants were selected on synthetic medium lacking leucine and containing G418.

d) Mating of Meganucleases Coexpressing Clones and Screening in Yeast

Mating was performed using a colony gridder (QpixII, Genetix). Variants were gridded on nylon filters covering YPD plates, using a low gridding density (4-6 spots/cm$^2$). A second gridding process was performed on the same filters to spot a second layer consisting of different reporter-harboring yeast strains for each target. Membranes were placed on solid agar YPD rich medium, and incubated at 30° C. for one night, to allow mating. Next, filters were transferred to synthetic medium, lacking leucine and tryptophan, adding G418, with galactose (2%) as a carbon source, and incubated for five days at 37° C., to select for diploids carrying the expression and target vectors. After 5 days, filters were placed on solid agarose medium with 0.02% X-Gal in 0.5 M sodium phosphate buffer, pH 7.0, 0.1% SDS, 6% dimethyl formamide (DMF), 7 mM β-mercaptoethanol, 1% agarose, and incubated at 37° C., to monitor β-galactosidase activity. Results were analyzed by scanning and quantification was performed using an appropriate software.

e) Results

Co-expression of different variants resulted in cleavage of the SH3 target in 58 tested combinations. Functional combinations are summarized in Table I herebelow. In this table, "+" indicates a functional combination on the SH3 target sequence, i.e., the heterodimer is capable of cleaving the SH3 target sequence.

TABLE I

| | | Amino acids positions and residues of the I-CreI variants cleaving the SH3.3 target | | | | | | | |
|---|---|---|---|---|---|---|---|---|---|
| | | 44A 54L 70Q 75N 105A 158R 162A | 44A 54L 64A 70Q 75N 158R 162A | 44A 54L 70Q 75Y 92R 158R 162A | 4E 44A 54L 64A 70Q 75N 158R 162A | 1V 44A 54L 64A 70Q 75N 158W 162A | 44A 54L 66C 70Q 71R 75N 151A 158R 162A | 44A 54L 70Q 75N 158R 162A | 44A 54L 57E 70Q 75N 158R 162A | 44V 54L 70Q 75N 158R 162A |
| Amino acids positions and resdidues of the I-CreI variants cleaving the SH3.4 target | 30G 38R 70D 75N 86D | | + | + | + | + | | | + | + | + |
| | 30G 38R 70D 75N 81T 154G | + | + | | + | + | | + | | + | |
| | 30G 38R 50R 70D 75N 142R | + | + | + | + | + | + | + | + | + |

In conclusion, several heterodimeric I-CreI variants, capable of cleaving the SH3 target sequence in yeast, were identified.

Example 1.2

Validation of SH3 Target Cleavage in an Extrachromosomal Model in CHO Cells

I-CreI variants able to efficiently cleave the SH3 target in yeast when forming heterodimers are described hereabove in example 1.1. In order to identify heterodimers displaying maximal cleavage activity for the SH3 target in CHO cells, the efficiency of some of these variants was compared using an extrachromosomal assay in CHO cells. The screen in CHO cells is a single-strand annealing (SSA) based assay where cleavage of the target by the meganucleases induces homologous recombination and expression of a LagoZ reporter gene (a derivative of the bacterial lacZ gene).

a) Cloning of SH3 Target in a Vector for CHO Screen

An oligonucleotide corresponding to the SH3 target sequence flanked by gateway cloning sequences, was ordered from PROLIGO (SEQ ID NO: 12; TGGCATACAAGTTTC-CAATACAAGGTACAAAGTCCTGA-CAATCGTCTGTCA). Double-stranded target DNA, generated by PCR amplification of the single stranded oligonucleotide, was cloned using the Gateway protocol (IN-VITROGEN) into the pCLS1058 CHO reporter vector. Cloned target was verified by sequencing (MILLEGEN).

b) Re-cloning of Meganucleases

The open-reading frames coding for these variants identified in Table I hereabove sub-cloned into the pCLS2437 expression vector. ORFs were amplified by PCR on yeast DNA using primers of SEQ ID Nos. 13 and 14 (5'-AAAAAG-CAGGCTGGCGCGCCTACACAGCGGCCT-TGCCACCATG-3' and 5'-AGAAAGCTGGGT-GCTAGCGCTCGAGTTATCAGTCGG-3'). PCR products were cloned in the CHO expression vector pCLS2437 using the AscI and XhoI restriction enzymes for internal fragment replacement. Selected clones resulting from ligation and *E. coli* transformation steps were verified by sequencing (MILLEGEN).

c) Extrachromosomal Assay in Mammalian Cells

CHO K1 cells were transfected with Polyfect® transfection reagent according to the supplier's protocol (QIAGEN). 72 hours after transfection, culture medium was removed and 150 µl of lysis/revelation buffer for β-galactosidase liquid assay was added (typically 1 liter of buffer contained 100 ml of lysis buffer (Tris-HCl 10 mM pH7.5, NaCl 150 mM, Triton X100 0.1%, BSA 0.1 mg/ml, protease inhibitors), 10 ml of Mg 100X buffer (MgCl$_2$ 100 mM, β-mercaptoethanol 35%), 110 ml ONPG 8 mg/ml and 780 ml of sodium phosphate 0.1M pH7.5). After incubation at 37° C., OD was measured at 420 nm. The entire process was performed on an automated Velocity11 BioCel platform.

Per assay, 150 ng of target vector was cotransfected with 12.5 ng of each one of both variants.

d) Results

The four following variants described in Table I were re-cloned into pCLS2437:

44A 54L 70Q 75Y 92R 158R 162A (referred to as SH3.3-MA);
1V 44A 54L 64A 70Q 75N 158W 162A (referred to as SH3.3-MB);
30G 38R 70D 75N 86D (referred to as SH3.4-M1); and
30G 38R 70D 75N 81T 154G (referred to as SH3.4-M2).

These I-CreI variants were assayed together as heterodimers against the SH3 target in the CHO extrachromosomal assay.

Table II shows the functional combinations obtained for nine heterodimers.

TABLE II

|  |  | Optimized variants cleaving SH3.3 | |
|---|---|---|---|
|  |  | 44A 54L 70Q 75Y 92R 158R 162A | 1V 44A 54L 64A 70Q 75N 158W 162A |
| Optimized variants cleaving SH3.4 | 30G 38R 70D 75N 86D | + | + |
|  | 30G38R70D75N81T 154G | + | + |

Analysis of the efficiencies of cleavage and recombination of the SH3 sequence demonstrates that all of the four tested combinations of I-CreI variants were capable to transpose their cleavage activity from yeast to CHO cells without additional mutation.

Example 1.3

Covalent Assembly as Single Chain and Improvement of Meganucleases Cleaving SH3

Co-expression of the variants identified in example 1.1. leads to a high cleavage activity of the SH3 target in yeast. Some of the heterodimers have been validated for SH3 cleavage in a mammalian expression system (example 1.2.). One of them, shown in Table III, was selected for further optimization.

TABLE III

| SH3 variant | Amino acids positions and residues of the I-CreI variants |
|---|---|
| SH3.3-MA | 44A 54L 70Q 75Y 92R 158R 162A |
| SH3.4-M1 | 30G 38R 70D 75N 86D |

The MA×M1 SH3 heterodimer gives high cleavage activity in yeast. SH3.3-MA is a SH3.3 cutter that bears the following mutations in comparison with the I-CreI wild type sequence: 44A 54L 70Q 75Y 92R 158R 162A. SH3.4-M1 is a SH3.4 cutter that bears the following mutations in comparison with the I-CreI wild type sequence: 30G 38R 70D 75N 86D.

Single chain constructs were engineered using the linker RM2 of SEQ ID NO: 15 (AAGGSDKYNQALSKYNQAL-SKYNQALSGGGGS), thus resulting in the production of the single chain molecule: MA-linkerRM2-M1. During this design step, the G195 mutation was introduced in the C-terminal M1 variant. In addition, mutations K7E, K96E were introduced into the MA variant and mutations E8K, E61R into the M1 variant to create the single chain molecule: MA (K7E K96E)-linkerRM2-M1 (E8K E61R G195) that is further called SCOH-SH3-b1 scaffold. Some additional amino-acid substitutions have been found in previous studies to enhance the activity of I-CreI derivatives: the replacement of Isoleucine 132 with Valine (I132V) is one of them. The I132V mutation was introduced into either one, both or none of the coding sequence of N-terminal and C-terminal protein fragments.

The same strategy was applied to a second scaffold, termed SCOH-SH3-b56 scaffold, based on the best variants cleaving SH3.3 (44A 54L 70Q 75Y 92R 158R 162A) and SH3.4 (30G 38R 50R 70D 75N 142R) as homodimers, respectively.

The resulting proteins are shown in Table IV below. All the single chain molecules were assayed in CHO for cleavage of the SH3 target.

a) Cloning of the Single Chain Molecule

A series of synthetic gene assembly was ordered to MWG-EUROFINS. Synthetic genes coding for the different single chain variants targeting SH3 were cloned in pCLS1853 using AscI and XhoI restriction sites.

b) Extrachromosomal Assay in Mammalian Cells

CHO K1 cells were transfected as described in example 1.2. 72 hours after transfection, culture medium was removed and 150 μl of lysis/revelation buffer for β-galactosidase liquid assay was added. After incubation at 37° C., OD was measured at 420 nm. The entire process is performed on an automated Velocity11 BioCel platform. Per assay, 150 ng of target vector was cotransfected with an increasing quantity of variant DNA from 3.12 to 25 ng (25 ng of single chain DNA corresponding to 12.5 ng+12.5 ng of heterodimer DNA). Finally, the transfected DNA variant DNA quantity was 3.12 ng, 6.25 ng, 12.5 ng and 25 ng. The total amount of transfected DNA was completed to 175 ng (target DNA, variant DNA, carrier DNA) using an empty vector (pCLS0002).

d) Results

Figure 3:
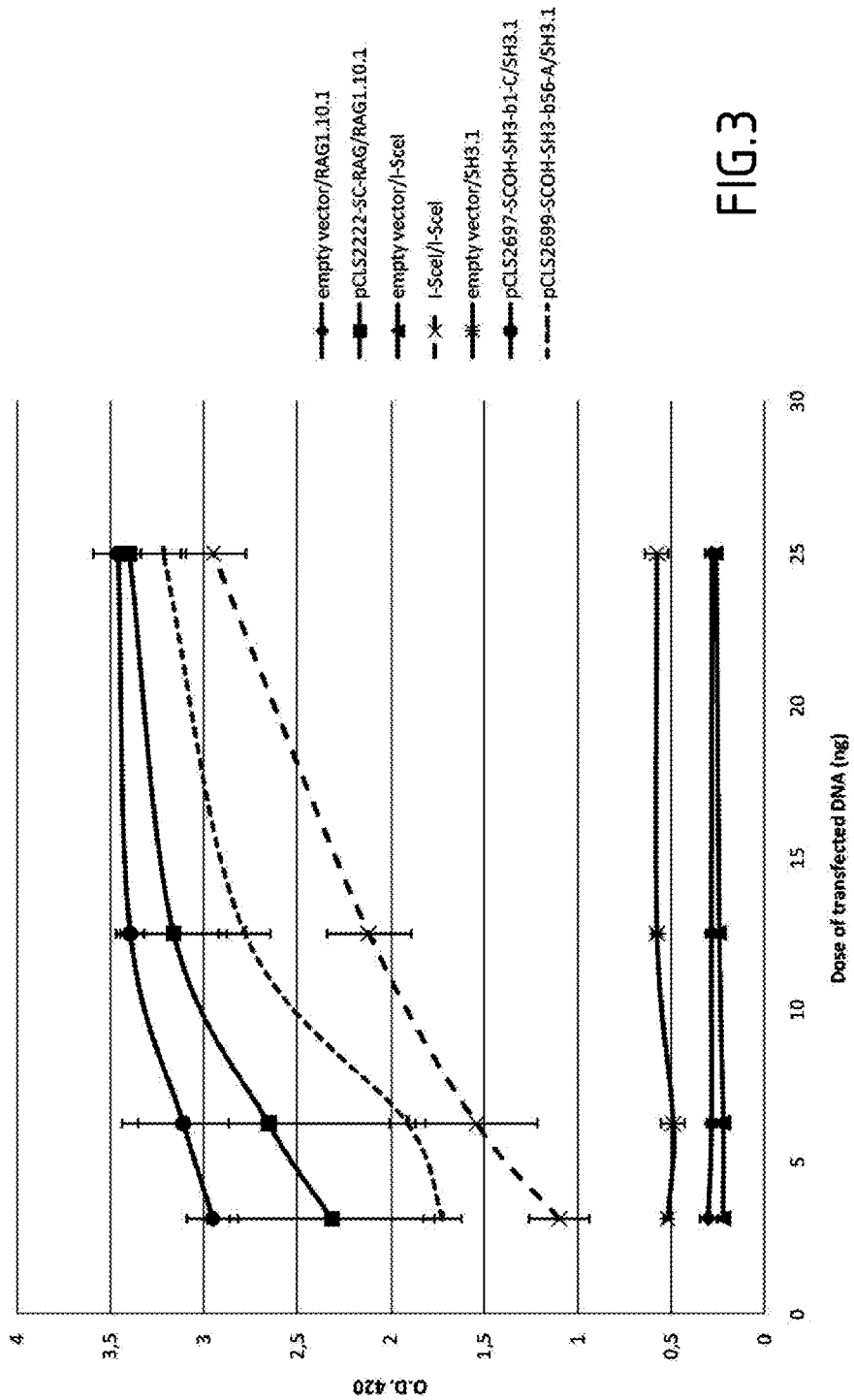

The activity of the single chain molecules against the SH3 target was monitored using the previously described CHO assay along with our internal control SCOH-RAG and I-SceI meganucleases. All comparisons were done at 3.12 ng, 6.25 ng, 12.5 ng, and 25 ng transfected variant DNA (FIGS. 2 and 3). All the single molecules displayed SH3 target cleavage activity in CHO assay as listed in Table IV.

TABLE IV

| Name | Mutations on N-terminal monomer | Mutations on C-terminal monomer | SEQ ID No. | Cleavage of SH3 in CHO cells |
| --- | --- | --- | --- | --- |
| SCOH-SH3-b56-A | 7E 44A 54L 70Q 75Y 92R 96E 158R 162A | 8K 19S 30G 38R 50R 61R 70D 75N 142R | 25 | + |
| SCOH-SH3-b56-B | 7E 44A 54L 70Q 75Y 92R 96E 132V 158R 162A | 8K 19S 30G 38R 50R 61R 70D 75N 142R | 26 | + |
| SCOH-SH3-b56-C | 7E 44A 54L 70Q 75Y 92R 96E 132V 158R 162A | 8K 19S 30G 38R 50R 61R 70D 75N 132V 142R | 27 | + |
| SCOH-SH3-b56-D | 7E 44A 54L 70Q 75Y 92R 96E 158R 162A | 8K 19S 30G 38R 50R 61R 70D 75N 132V 142R | 28 | + |
| SCOH-SH3-b1-A | 7E 44A 54L 70Q 75Y 92R 96E 158R 162A | 8K 19S 30G 38R 61R 70D 75N 86D | 29 | + |
| SCOH-SH3-b1-B | 7E 44A 54L 70Q 75Y 92R 96E 132V 158R 162A | 8K 19S 30G 38R 61R 70D 75N 86D | 30 | + |
| SCOH-SH3-b1-C | 7E 44A 54L 70Q 75Y 92R 96E 132V 158R 162A | 8K 19S 30G 38R 61R 70D 75N 86D 132V | 31 | + |
| SCOH-SH3-b1-D | 7E 44A 54L 70Q 75Y 92R 96E 158R 162A | 8K 19S 30G 38R 61R 70D 75N 86D 132V | 32 | + |

Variants shared specific behaviour upon assayed dose depending on the mutation profile they bear (FIGS. 2 and 3). For example, SCOH-SH3-b1-C has a similar profile, and is even more active than. Its activity reaches the maxima at the lowest DNA quantity transfected from low quantity to high quantity. In comparison with SCOH-SH3-b1-C, the molecule SCOH-SH3-b56-A has a maximal activity at higher DNA doses but reaches equivalent level of activity of SCOH-SH3-b1-C and our internal standard.

All of the variants described are active and can be used for inserting transgenes into the SH3 locus.

Example 2

Engineering meganucleases targeting the SH4 locus

SH4 is a locus that is present on chromosome 7. The SH4 locus comprises a 24 bp non-palindromic sequence of SEQ ID NO: 3. As shown in Table A, SH4 is located in the vicinity a RIS disclosed in Schwarzwaelder et al. (J. Clin. Invest. 2007 117:2241). The SH4 sequence is not included in any of the CIS described in Deichman et al.

Experiments similar to those described hereabove in Example 1 were carried out to identify I-CreI heterodimers and single-chain meganucleases capable of cleaving a target sequence of SEQ ID NO: 3.

Example 2.1

Identification of Meganucleases Cleaving SH4

I-CreI variants potentially cleaving the SH4 target sequence in heterodimeric form were constructed by genetic engineering. Pairs of such variants were then co-expressed in yeast. Upon co-expression, one obtains three molecular species, namely two homodimers and one heterodimer. It was then determined whether the heterodimers were capable of cutting the SH4 target sequence of SEQ ID NO: 3.

a) Construction of Variants of the I-CreI Meganuclease Cleaving Palindromic Sequences Derived from the SH4 Target Sequence The SH4 sequence is partially a combination of the 10AAA_P (SEQ ID NO: 4), 5ACT_P (SEQ ID NO: 16), 10AAA_P (SEQ ID NO: 4), 5GGT_P (SEQ ID NO: 17) targets shown on FIG. 4. These sequences are cleaved by previously identified meganucleases, obtained as described in International PCT Applications WO 2006/097784 and WO 2006/097853; Arnould et al., J. Mol. Biol., 2006, 355, 443-458; Smith et al., Nucleic Acids Res., 2006. Thus, SH4 should be cleaved by combinatorial variants resulting from these previously identified meganucleases.

The screening procedure was performed using methods derived from those described in Chames et al. (Nucleic Acids Res., 2005, 33, e178), Arnould et al. (J. Mol. Biol., 2006, 355, 443-458), Smith et al. (Nucleic Acids Res., 2006, 34, e149) and Arnould et al. (Arnould et al. J Mol. Biol. 2007 371:49-65) on the two following palindromic sequences: the SH4.3 sequence of SEQ ID NO: 18 and the SH4.4 sequence of SEQ ID NO: 19.

b) Construction of Target Vector

The experimental procedure is as described in Example 1.1, with the exception that an oligonucleotide corresponding to the SH4 target sequence of SEQ ID NO: 20 (5'-TGGCATA-CAAGTTTTTAAAACACTGTACAC-CATTTTGACAATCGTCTGTCA-3') was used.

c) Co-expression of Variants

Yeast DNA from variants cleaving the SH4.3 and SH4.4 target in the pCLS542 and pCLS1107 expression vectors was extracted using standard protocols and was used to transform *E. coli*. The resulting plasmid DNA was then used to co-transform yeast strain. Transformants were selected on synthetic medium lacking leucine and containing G418.

d) Mating of Meganucleases Coexpressing Clones and Screening in Yeast

Mating was performed using a colony gridder (QpixII, Genetix). Variants were gridded on nylon filters covering YPD plates, using a low gridding density (4-6 spots/cm$^2$). A second gridding process was performed on the same filters to spot a second layer consisting of different reporter-harboring yeast strains for each target. Membranes were placed on solid agar YPD rich medium, and incubated at 30° C. for one night, to allow mating. Next, filters were transferred to synthetic medium, lacking leucine and tryptophan, adding G418, with galactose (2%) as a carbon source, and incubated for five days at 37° C., to select for diploids carrying the expression and target vectors. After 5 days, filters were placed on solid agarose medium with 0.02% X-Gal in 0.5 M sodium phosphate buffer, pH 7.0, 0.1% SDS, 6% dimethyl formamide (DMF), 7 mM β-mercaptoethanol, 1% agarose, and incubated at 37° C., to monitor β-galactosidase activity. Results were analyzed by scanning and quantification was performed using appropriate software.

e) Results

Co-expression of variants cleaving the SH4.3 target and of variants cleaving the SH4.4 target resulted in cleavage of the SH4 target in 6 cases. Functional combinations are summarized in Table V.

TABLE V

| | | Amino acids positions and residues of the I-CreI variants cleaving the SH4.3 target | | |
|---|---|---|---|---|
| | | 24V 44R 68Y 70S 75Y 77N | 24V 68A 70S 75N 77R | 24V 70D 75N 77R |
| Amino acids positions and resdidues of I-CreI variants cleaving the SH4.4 target | 24V 44Y 70S | + | + | + |
| | 24V 44Y 70S 77V | + | + | + |

Example 2.2

Validation of SH4 Target Cleavage in an Extrachromosomal Model in CHO Cells

In order to identify heterodimers displaying maximal cleavage activity for the SH4 target in CHO cells, the efficiency of several combinations of variants to cut the SH4 target was assessed using an extrachromosomal assay in CHO cells. The screen in CHO cells is a single-strand annealing (SSA) based assay where cleavage of the target by the meganucleases induces homologous recombination and expression of a LagoZ reporter gene (a derivative of the bacterial lacZ gene).

a) Cloning of SH4 Target in a Vector for CHO Screen

The target was cloned as follows. An oligonucleotide of SEQ ID NO: 21, corresponding to the SH4 target sequence flanked by gateway cloning sequence, was ordered from PROLIGO (5'-TGGCATACAAGTTTTTAAAACACTGTA-CACCATTTTGACAATCGTCTGTCA-3'). Double-stranded target DNA, generated by PCR amplification of the single stranded oligonucleotide, was cloned using the Gateway protocol (INVITROGEN) into CHO reporter vector (pCLS1058). The cloned fragment was verified by sequencing (MILLEGEN).

b) Re-cloning of Meganucleases

The ORFs of I-CreI variants cleaving the SH4.5 and SH4.6 targets obtained hereabove were sub-cloned in pCLS2437. ORFs were amplified by PCR on yeast DNA using primers of SEQ ID NO: 22 and 23 (5'-AAAAAGCAGGCTGGCGCGC-CTACACAGCGGCCTTGCCACCATG-3' and 5'-AGAAAGCTGGGTGCTAGCGCTCGAGT-TATCAGTCGG-3') primers. PCR products were cloned in the CHO expression vector pCLS2437 using the AscI and NheI restrictions sites for internal fragment replacement. Selected clones resulting from ligation and *E. coli* transformation steps were verified by sequencing (MILLEGEN).

c) Extrachromosomal Assay in Mammalian Cells

CHO K1 cells were transfected with Polyfect® transfection reagent according to the supplier's protocol (QIAGEN). 72 hours after transfection, culture medium was removed and 150 µl of lysis/revelation buffer for β-galactosidase liquid assay was added (typically 1 liter of buffer contained: 100 ml of lysis buffer (Tris-HCl 10 mM pH7.5, NaCl 150 mM, Triton X100 0.1%, BSA 0.1 mg/ml, protease inhibitors), 10 ml of Mg 100X buffer (MgCl$_2$ 100 mM, β-mercaptoethanol 35%), 110 ml ONPG 8 mg/ml and 780 ml of sodium phosphate 0.1M pH7.5). After incubation at 37° C., OD was measured at 420 nm. The entire process is performed on an automated Velocity11 BioCel platform. Per assay, 150 ng of target vector was cotransfected with 12.5 ng of each one of both variants (12.5 ng of variant cleaving palindromic SH4.3 target and 12.5 ng of variant cleaving palindromic SH4.4 target).

d) Results

The four variants shown in Table VI and described hereabove in Example 2.1, were selected for further analysis.

TABLE VI

| | Amino acids positions and residues of the I-CreI variants |
|---|---|
| SH4.3-MA | 24V 44R 68Y 70S 75Y 77N |
| SH4.3-MC | 24V 68A 70S 75N 77R |
| SH4.4-M1 | 24V 44Y 70S |
| SH4.4-M2 | 24V 44Y 70S 77V |

These variants were cloned in pCLS2437. Then, I-CreI variants cleaving the SH4.3 or SH4.4 targets were assayed together as heterodimers against the SH4 target in the CHO extrachromosomal assay. Analysis of the efficiencies of cleavage and recombination of the SH4 sequence demonstrates that all tested combinations of I-CreI variants were able to transpose their cleavage activity from yeast to CHO cells without additional mutation (Table VII).

TABLE VII

| | | Amino acids positions and residues of the I-CreI variants: variants cleaving SH4.3 | |
|---|---|---|---|
| | | SH4.3-MA: 24V 44R 68Y 70S 75Y 77N | SH4.3-MC: 24V 68A 70S 75N 77R |
| Amino acids positions and residues of the I-CreI variants: variants cleaving SH4.4 | SH4.4-M1: 24V 44Y 70S | + | + |
| | SH4.4-M2: 24V 44Y 70S 77V | + | + |

Example 2.3

Covalent Assembly as Single Chain and Improvement of Meganucleases Cleaving SH4 by Site-directed Mutagenesis Co-expression of the variants described in Example 2.1. leads to a high cleavage activity of the SH4 target in yeast. In addition, some of them have been validated for SH4 cleavage in a mammalian expression system (Example 2.2.).

The MA×M2 SH4 heterodimer gives high cleavage activity in yeast. SH4.3-MA is a SH4.3 cutter that bears the following mutations in comparison with the I-CreI wild type sequence: 24V 44R 68Y 70S 75Y 77N. SH4.4-M2 is a SH4.4 cutter that bears the following mutations in comparison with the I-CreI wild type sequence: 24V 44Y 70S 77V.

As described in example 1.3, single chain constructs were engineered using the linker RM2, thereby resulting in the production of a single chain molecule referred to as MA-LinkerRM2-M2. During this design step, the G19S mutation was introduced in the C-terminal M2 mutant. In addition, K7E and K96E mutations were introduced into the MA mutant, and E8K and E61R mutations into the M2 mutant in order to create a single chain molecule referred to as MA (K7E K96E)-linkerRM2-M2 (E8K E61R G19S) that is called further SCOH-SH4-b1 scaffold.

The Isoleucine 132 to Valine (I132V) mutation was introduced into the coding sequence of either, one, none or both N-terminal and C-terminal protein fragment.

The same strategy was applied to a second scaffold based on the good cutters on SH4.3 (44R 68Y 70S 75Y 77N) and SH4.4 (24V 44Y 70S 77V). This scaffold is further referred to as SCOH-SH4-b56 scaffold.

The design of the derived single chain constructs is shown in Table VIII. The single chain constructs were tested in CHO for their ability to induce cleavage of the SH4 target.

a) Cloning of the Single Chain Molecule

A series of synthetic gene assembly was performed to MWG-EUROFINS. Synthetic genes, coding for the different single chain variants targeting SH4, were cloned in pCLS1853 using AscI and XhoI restriction sites.

b) Extrachromosomal Assay in Mammalian Cells

CHO K1 cells were transfected as described hereabove. 72 hours after transfection, culture medium was removed and 150 µl of lysis/revelation buffer for β-galactosidase liquid assay was added. After incubation at 37° C., OD was measured at 420 nm. The entire process is performed on an automated Velocity11 BioCel platform. Per assay, 150 ng of target vector was cotransfected with an increasing quantity of variant DNA from 3.12 to 25 ng (25 ng of single chain DNA corresponding to 12.5 ng+12.5 ng of heterodimer DNA).

Finally, the transfected DNA variant DNA quantity was 3.12 ng, 6.25 ng, 12.5 ng and 25 ng. The total amount of transfected DNA was completed to 175 ng (target DNA, variant DNA, carrier DNA) using an empty vector (pCLS0002).

c) Results

The single chain molecules described in Table VIII were monitored for their activity against the SH4 target using the previously described CHO assay by comparison to our internal control SCOH-RAG and I-Sce I meganucleases. All activity evaluation was done upon DNA transfected dose of 3.12 ng, 6.25 ng, 12.5 ng, and 25 ng. All single chain molecules were displaying activity on SH4 target as reported in Table VIII.

TABLE VIII

| Name | Mutations on N-terminal monomer | Mutations on C-terminal monomer | SEQ ID No. | Activity on SH4 target in CHO Assay |
|---|---|---|---|---|
| SCOH-SH4-b56-A | 7E 44R 68Y 70S 75Y 77N 96E | 8K 19S 24V 44Y 61R 70S 77V | 33 | + |
| SCOH-SH4-b56-B | 7E 44R 68Y 70S 75Y 77N 96E 132V | 8K 19S 24V 44Y 61R 70S 77V | 34 | + |
| SCOH-SH4-b56-C | 7E 44R 68Y 70S 75Y 77N 96E 132V | 8K 19S 24V 44Y 61R 70S 77V 132V | 35 | + |
| SCOH-SH4-b56-D | 7E 44R 68Y 70S 75Y 77N 96E | 8K 19S 24V 44Y 61R 70S 77V 132V | 36 | + |
| SCOH-SH4-b1-A | 7E 24V 44R 68Y 70S 75Y 77N 96E | 8K 19S 24V 44Y 61R 70S 77V | 37 | + |
| SCOH-SH4-b1-B | 7E 24V 44R 68Y 70S 75Y 77N 96E 132V | 8K 19S 24V 44Y 61R 70S 77V | 38 | + |
| SCOH-SH4-b1-C | 7E 24V 44R 68Y 70S 75Y 77N 96E 132V | 8K 19S 24V 44Y 61R 70S 77V 132V | 39 | + |
| SCOH-SH4-b1-D | 7E 24V 44R 68Y 70S 75Y 77N 96E | 8K 19S 24V 44Y 61R 70S 77V 132V | 40 | + |

Figure 5:
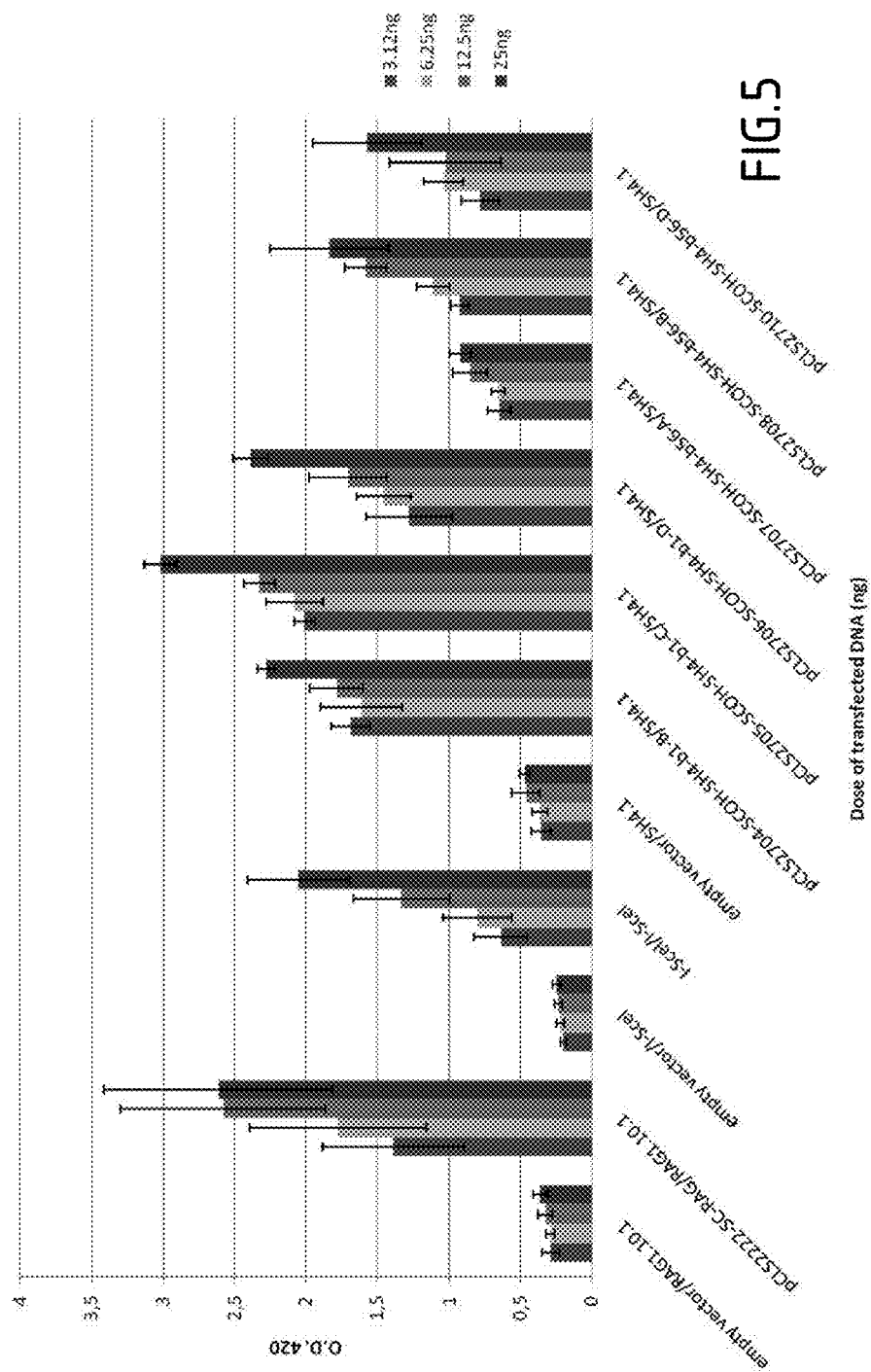
FIGS. 5 and 6 represent SCOH SH4 meganucleases vs. I-SceI and SCOH-RAG DNA dose response in CHO.
Figure 6:
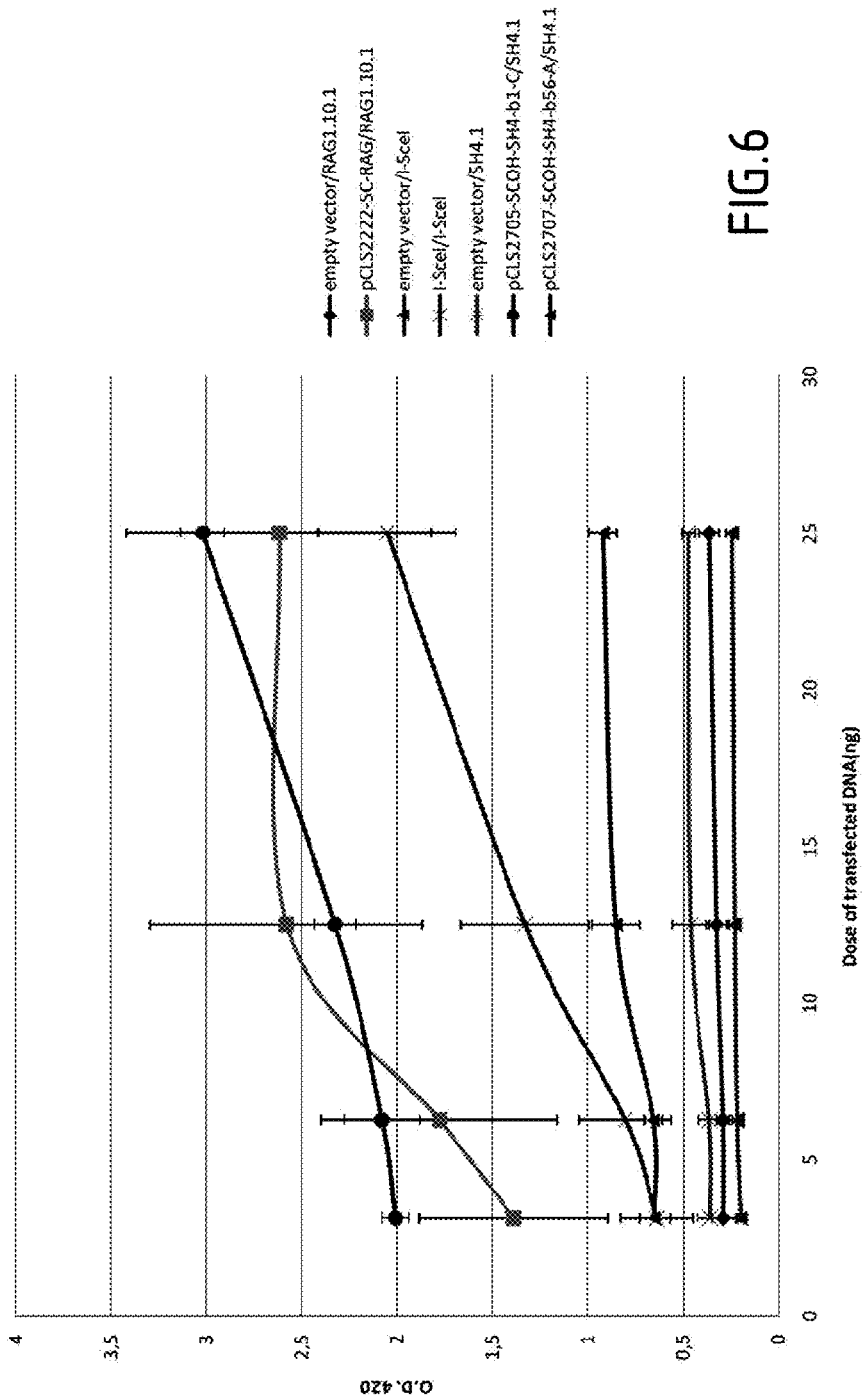

Variants shared specific behaviour upon assayed dose depending on the mutation profile they bear (FIGS. 5 and 6). For example, SCOH-SH4-b1C shows an activity level within the same range as the internal standard SCOH-RAG (: its activity increases from low quantity to high quantity. At the assayed DNA trasfected doses, its activity is superior to that of SCOH-SH4-B56A.

All of these variants are active at different levels of intensity and can thus be used for SH4 genome targeting.

Example 3

Detection of Cleavage Activity at the SH Loci in Human Cell Line

I-CreI variants able to efficiently cleave the SH3 and SH4 targets in yeast and in mammalian cells (CHO K1 cells) have been identified in Examples 1 and 2. The efficiency of the SH3 and SH4 meganucleases to cleave their endogenous DNA target sequences was next tested. This example will demonstrate that meganucleases engineered to cleave the SH3 and SH4 target sequences cleave their cognate endogenous sites in human cells.

Figure 7:
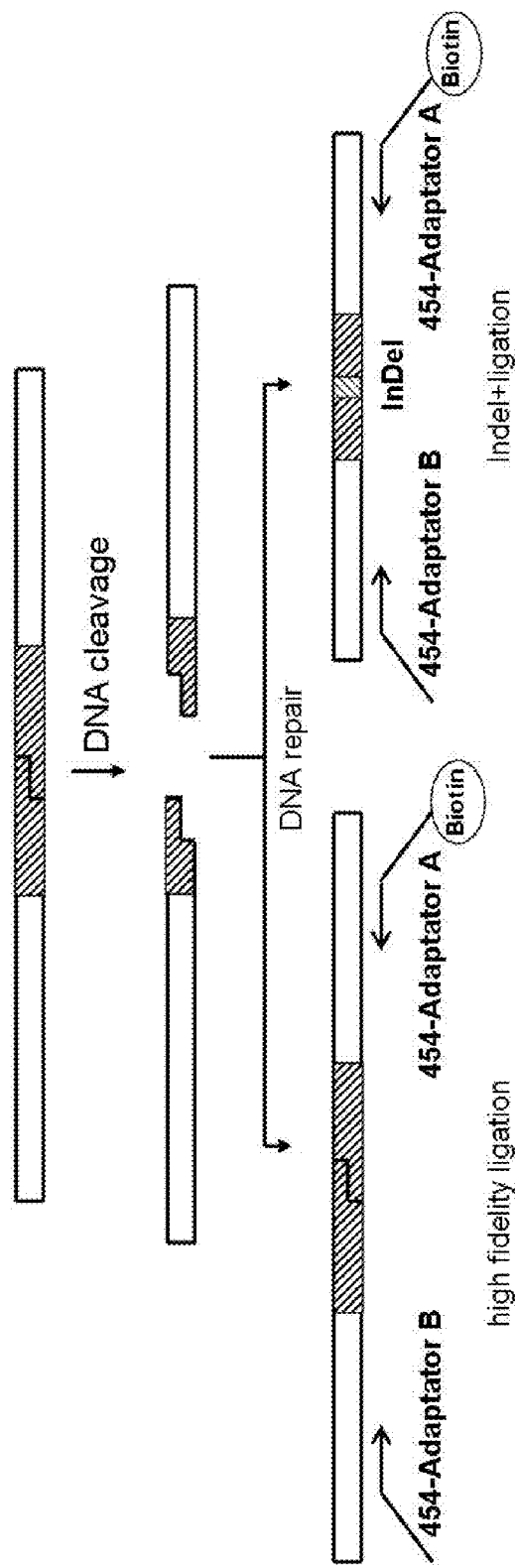
FIG. 7 represents a scheme of the mechanism leading to the generation of small deletions and insertions (InDel) during repair of double-strand break by non homologous end-joining (NHEJ).

Repair of double-strand break by non homologous end-joining (NHEJ) can generate small deletions and insertions (InDel) (FIG. 7). In nature, this error-prone mechanism can be deleterious for the cells survival but provides a rapid indicator of meganucleases activity at endogenous loci.

Example 3.1

Detection of Induced Mutagenesis at the Endogenous Site

The assays based on cleavage-induced recombination in mammal or yeast cells, which are used for screening variants with altered specificity, are described in International PCT Application WO 2004/067736; Epinat et al., Nucleic Acids Res., 2003, 31:2952-2962; Chames et al., Nucleic Acids Res., 2005, 33:e178, and Arnould et al., J. Mol. Biol., 2006, 355: 443-458. These assays result in a functional LacZ reporter gene which can be monitored by standard methods.

Single Chain I-CreI variants for SH3 and SH4 cloned in the pCLS1853 plasmid were used for this experiment. The day previous experiment, cells from the human embryonic kidney cell line, 293-H (Invitrogen) were seeded in a 10 cm dish at density of 1.2 $10^6$ cells/dish. The following day, cells were transfected with 3 µg of an empty plasmid or a meganuclease-expressing plasmid using lipofectamine (Invitrogen). 72 hours after transfection, cells were collected and diluted (dilution 1/20) in fresh culture medium. After 7 days of culture, cells were collected and genomic DNA extracted.

200 ng of genomic DNA were used to amplify the endogenous locus surrounding the meganuclease cleavage site by PCR amplification. A 377 bp fragment corresponding to the SH3 locus was amplified using specific PCR primers A (SEQ ID NO 44; 5'-tggggggtcttactctgtttccc-3') and B (SEQ ID NO 45; 5'-aggagagtccttctttggcc-3'). A 396 bp fragment corresponding to the SH4 locus was amplified using PCR primers C (SEQ ID NO 46; 5'-gagtgatagcataatgaaaacc-3') and D (SEQ ID NO 47; 5'-ctcaccataagtcaactgtctc-3'). PCR amplification was performed to obtain a fragment flanked by specific adaptator sequences (SEQ ID NO 48; 5'-CCATCTCATCCCT-GCGTGTCTCCGACTCAG-3' and SEQ ID NO: 49 5'-CCTATCCCCTGTGTGCCTTGGCAGTCTCAG-3') provided by the company offering sequencing service (GATC Biotech AG, Germany) on the 454 sequencing system (454 Life Sciences). An average of 18,000 sequences was obtained from pools of 2 amplicons (500 ng each). After sequencing, different samples were identified based on barcode sequences introduced in the first of the above adaptators. Sequences were then analyzed for the presence of insertions or deletions in the cleavage site of SH3 or SH4 respectively.

Example 3.2

Results

Table IX summarizes the results that were obtained.

TABLE IX

| | Vector expressing: | Total sequence number | InDel containing sequences | % of InDel events |
|---|---|---|---|---|
| SH 3 | meganuclease | 12841 | 56 | 0.44 |
| | Empty | 2153 | 1 | 0.05 |
| SH 4 | meganuclease | 8259 | 18 | 0.22 |
| | Empty | 12811 | 3 | 0.02 |

The analysis of the genomic DNA extracted from cells transfected with the meganuclease targeting the SH3 locus showed that 56 out of the 12841 analyzed sequences (0.44%) contained InDel events within the recognition site of SH3. Similarly, after transfection with the meganuclease targeting the SH4 locus, 18 out of the 8259 analyzed sequences (0.22%) contained InDel events within the recognition site of SH4.

Since small deletions or insertions could be related to PCR or sequencing artifacts, the same loci were analyzed after transfection with a plasmid that does not express the meganuclease. The analysis of the SH3 and SH4 loci revealed that virtually no InDel events could be detected. Indeed, only 0.05% (1/2153) and 0.02% (3/12811) of the analyzed sequences contained mutations.

Figure 8:
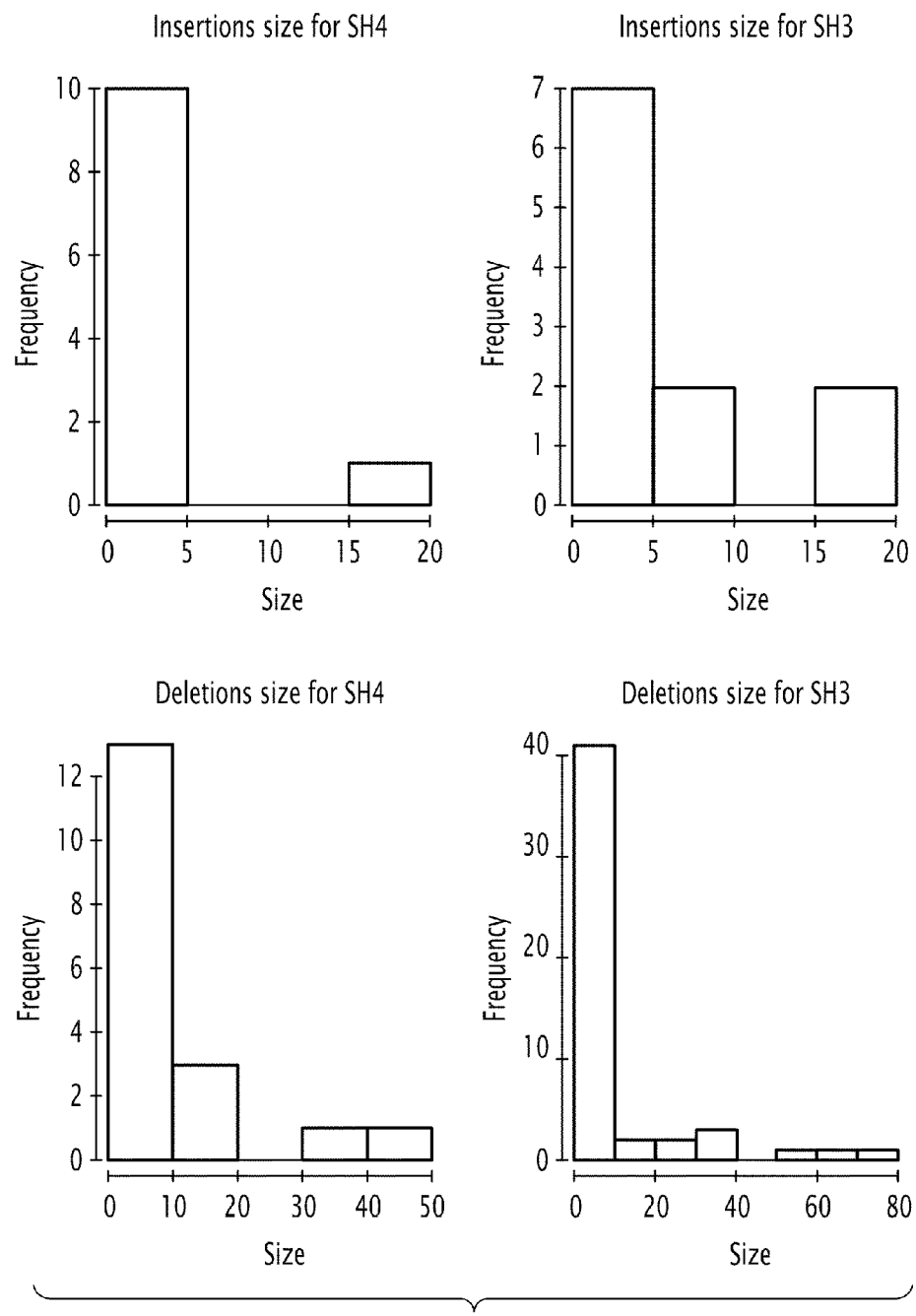
FIG. 8 represents the insertion sites upon cleavage with SH3 or SH4 meganucleases.

Moreover, the analysis of the size of the DNA insertion or deletion sequences (FIG. 8) revealed a similar type of events with a predominance of small insertions (<5 bp) and of small deletions (<10 bp).

These data demonstrate that the meganucleases engineered to target respectively the SH3 or SH4 loci are active in human cells and can cleave their cognate endogenous sequence. Moreover, it shows that meganucleases have the ability to generate small InDel events within a sequence which would disrupt a gene ORF and thus inactivate the corresponding gene expression product.

Example 4

Gene Targeting at the Endogenous SH3 and SH4 Loci in Human Cells

To validate the cleavage activity of engineered single-chain SH3 and SH4 meganucleases, their ability to stimulate homologous recombination at the endogenous human SH3 and SH4 loci was next evaluated. Cells were transfected with mammalian expression plasmids for single chain molecules SCOH-SH3-b1-C or SCOH-SH4-b1-C and a vector comprising a targeting construct. The vector comprising a targeting construct (also referred to as "donor repair plasmid") was the pCLS3777 or pCLS3778 plasmid containing a 2.8 kb sequence consisting of an exogenous DNA sequence, flanked by two sequences homologous to the human SH3 or SH4 loci. The sequences homologous to the human SH3 or SH4 loci had a length of 1.5 kb. Cleavage of the native SH3 or SH4 loci by the meganuclease yields a substrate for homologous recombination, which may use the donor repair plasmid as a repair matrix. Thus, the frequency with which targeted integration occurs at the SH3 or SH4 loci is indicative of the cleavage efficiency of the genomic SH3 or SH4 target site.

Example 4.1

Material and Methods a) Meganuclease Expression Plasmids

The meganucleases used in this example are SCOH-SH3-b1-C and SCOH-SH4-b1-C cloned in a mammalian expression vector, resulting in plasmid pCLS2697 and pCLS2705, respectively.

b) Donor Repair Plasmids

For SH3 gene targeting experiments, the donor plasmid contained:

as the left homology arm: a PCR-generated fragment of the SH3 locus (position 6850510 to 6852051 on chromosome 6, NC_000006.11). This fragment has a length of 1540 bp;

as the right homology arm: a fragment of the SH3 locus (position 6852107 to 6853677 on chromosome 6, NC_000006.11). This fragment has a length of 1571 bp.

For SH4 gene targeting experiments, the donor plasmid contained:

as the left homology arm: a PCR-generated fragment of the SH4 locus (position 114972751 to 114974269 on chromosome 7, NC_000007.13). This fragment has a length of 1519 bp; and as the right homology arm: a fragment of the SH4 locus (position 114974316 to 114976380 on chromosome 7, NC_000007.13). This fragment has a length of 2065 bp.

For both SH3 and SH4, the left and right homology arms were inserted upstream (using an AscI site) and downstream (using a SbfI site), respectively, of an exogenous 2.8 kb DNA fragment containing two CMV promoters and a neomycin resistance gene. The resulting plasmids are referred to as pCLS3777 (for SH3) and pCLS3778 (for SH4).

c) SH3 and SH4 Gene Targeting Experiments

Human embryonic kidney 293H cells (Invitrogen) were plated at a density of $1 \times 10^6$ cells per 10 cm dish in complete medium (DMEM supplemented with 2 mM L-glutamine, penicillin (100 UI/ml), streptomycin (100 µg/ml), amphotericin B (Fongizone) (0.25 µg/ml) (Invitrogen-Life Science) and 10% FBS). The next day, cells were transfected with Lipofectamine 2000 transfection reagent (Invitrogen) according to the supplier's protocol. Briefly, 2 µg of the donor plasmid was co-transfected with 3 µg of single-chain meganuclease expression vectors. After 72 hours of incubation at 37° C., cells were trypsinized and plated in complete medium at 10 or 100 cells per well in 96-well plates. Once cells were 80 to 100% confluent, genomic DNA extraction was performed with the ZR-96 genomic DNA kit (Zymo research) according to the supplier's protocol.

d) PCR Analysis of Gene Targeting Events

The gene targeting frequency was determined by PCR on genomic DNA using the following primers: 5'-CTGTGTGC-TATGATCTTGCC-3' (SH3 GHGF4; SEQ ID NO: 50) and 5'-CCTGTCTCTTGATCAGATCC-3' (NeoR2; SEQ ID NO: 51) for SH3, and 5'-GTGGCCTCTCAGTCTGTTTA-3' (SH4 GHGF2; SEQ ID NO: 52) and 5'-AGTCATAGCCGAAT-AGCCTC-3' (NeoR5; SEQ ID NO: 53) for SH4. The PCRs result in a 2500 bp (SH3) or a 2268 bp (SH4) gene targeting specific PCR product. The SH3 GHGF4 and SH4 GHGF2 primers are forward primers located upstream of the left homology arms of the donor repair plasmids. The NeoR primers are reverse primers located in the exogenous DNA inserted between the two homology arms of the donor repair plasmid.

Example 4.2

Results

Human embryonic kidney 293H cells were co-transfected with a plasmid expressing one of the two single-chain SH3 or SH4 meganucleases and the donor repair plasmid pCLS3777 or pCLS3778. As a control for spontaneous recombination, 293H cells were also transfected with the donor repair plasmid alone. The cells were then plated at 10 or 100 cells per well in 96-well microplates. Genomic DNA derived from these cells was analyzed for gene targeting by PCR as described in Material and Methods.

In the absence of meganuclease (repair plasmid alone), no PCR positive signal was detected among the 22560 and 18800 cells (for SH3 and SH4, respectively) that were analyzed in pools of 10 or 100 cells.

In contrast to this, in the presence of the SH3 meganuclease, 12 positive clones were detected among the 18800 cells analyzed in pools of 100 cells, thereby indicating a frequency of recombination of 0.064%. In the presence of the SH4 meganuclease, 11 positives were detected among the 3760 cells analyzed in pools of 10 cells indicating a frequency of recombination of 0.29%. The results are presented in Table X below. The recombination frequencies indicated here are underestimated because not all plated cells start dividing again. Estimate survival upon plating can thus be estimated to be about 33%. Therefore, frequencies of recombination are probably underestimated by a 3-fold factor.

TABLE X

| Meganuclease | Cells per well | PCR + events | Gene targeting frequency |
|---|---|---|---|
| SH3 | 100 | 12/18800 | 0.064% |
| SH4 | 10 | 11/3760 | 0.29% |
| SH4 | 100 | 15/18800 | 0.08% |
| None (with SH3 repair plasmid) | 100 | 0/18800 | NA |
| None (with SH4 repair plasmid) | 100 | 0/18800 | NA |

NA: not applicable

These results demonstrate that the two single chain molecules SCOH-SH3-b1-C and SCOH-SH4-b1-C are capable of inducing high levels of gene targeting at the endogenous SH3 and SH4 locus, respectively.

Example 5

Engineering Meganucleases Targeting the SH6 Locus

SH6 is a locus comprising a 24 bp non-palindromic target (TTAATACCCCGTACCTAATATTGC, SEQ ID NO: 59) that is present on chromosome 21. SH6 is located in the vicinity of a RIS disclosed in Schwarzwaelder et al. (J Clin Invest 2007:2241-9). The SH6 sequence is not included in any of the CIS described in Deichman et al.

Example 5.1

Identification of Meganucleases Cleaving SH6

I-CreI variants potentially cleaving the SH6 target sequence in heterodimeric form were constructed by genetic engineering. Pairs of such variants were then co-expressed in yeast. Upon co-expression, one obtains three molecular species, namely two homodimers and one heterodimer. It was then determined whether the heterodimers were capable of cutting the SH6 target sequence of SEQ ID NO: 59.

a) Construction of Variants of the I-CreI Meganuclease Cleaving Palindromic Sequences Derived from the SH6 Target Sequence The SH6 sequence is partially a combination of the 10AAT_P (SEQ ID NO: 60), 5CCC_P (SEQ ID NO: 61), 10AAT_P (SEQ ID NO: 60), 5TAG_P (SEQ ID NO: 62) target sequences which are shown on FIG. 9. These sequences are cleaved by meganucleases obtained as described in International PCT applications WO 2006/097784 and WO 2006/097853, Arnould et al. (J. Mol. Biol., 2006, 355, 443-458) and Smith et al. (Nucleic Acids Res., 2006). Thus, SH6 should be cleaved by combinatorial variants resulting from these previously identified meganucleases.

Two palindromic targets, SH6.3 and SH6.4, were derived from SH6 (FIG. 9). Since SH6.3 and SH6.4 are palindromic, they should be cleaved by homodimeric proteins. Therefore, homodimeric I-CreI variants cleaving either the SH6.3 palindromic target sequence of SEQ ID NO: 63 or the SH6.4 palindromic target sequence of SEQ ID NO: 64 were constructed using methods derived from those described in Chames et al. (Nucleic Acids Res., 2005, 33, e178), Arnould et al. (J. Mol. Biol., 2006, 355, 443-458), Smith et al. (Nucleic Acids Res., 2006, 34, e149) and Arnould et al. (Arnould et al. J Mol. Biol. 2007 371:49-65).

b) Construction of Target Vector

The experimental procedure is as described in Example 1.1., with the exception that an oligonucleotide corresponding to the SH6 target sequence (5'-TGGCATACAAGTTTT-TAATACCCCGTACCTAATATTGCCAATCGTCTGTCA-3' (SEQ ID NO: 65) was used.

c) Co-expression of Variants

Yeast DNA was extracted from variants cleaving the SH6.3 and SH6.4 targets in the pCLS542 and pCLS1107 expression vectors using standard protocols and was used to transform E. coli. Transformants were selected on synthetic medium lacking leucine and containing G418.

d) Mating of Meganucleases Coexpressing Clones and Screening in Yeast

Mating was performed using a colony gridder (QpixII, Genetix). Variants were gridded on nylon filters covering YPD plates, using a low gridding density (4-6 spots/cm$^2$). A second gridding process was performed on the same filters to spot a second layer consisting of different reporter-harboring yeast strains for each target. Membranes were placed on solid agar YPD rich medium, and incubated at 30° C. for one night, to allow mating. Next, filters were transferred to synthetic medium, lacking leucine and tryptophan, adding G418, with galactose (2%) as a carbon source, and incubated for five days at 37° C., to select for diploids carrying the expression and target vectors. After 5 days, filters were placed on solid agarose medium with 0.02% X-Gal in 0.5 M sodium phosphate buffer, pH 7.0, 0.1% SDS, 6% dimethyl formamide (DMF), 7 mM β-mercaptoethanol, 1% agarose, and incubated at 37° C., to monitor β-galactosidase activity. Results were analyzed by scanning and quantification was performed using appropriate software.

e) Results

Co-expression of ten variants cleaving the SH6.4 target and of two variants cleaving the SH6.3 target resulted in cleavage of the SH6.1 target in all but two cases. These two cases corresponded in which double transformants were not obtained. Functional combinations are summarized in Table XI.

TABLE XI

|  | | Amino acids positions and residues of the I-CreI variants cleaving the SH6.3 target | |
|---|---|---|---|
|  | | 44K 68T 70G 75N | 44K 70S 75N |
| Amino acids positions and residues of the I-CreI variants cleaving the SH6.4 target | 28Q 40R 44A 70L 75N 96R 111H 144S | + | + |
| | 7R 28Q 40R 44A 70L 75N 85R 103T | + | + |
| | 28Q 40R 44A 70L 75N 103S | + | + |
| | 24F 27V 28Q 40R 44A 70L 75N 99R | + | + |
| | 7R 28Q 40R 44A 70L 75N 81T | + | + |
| | 7R 28Q 40R 44A 70L 75N 77V | Not tested | + |
| | 7R 28Q 40R 44A 70L 75N 103T 121E 132V 160R | + | + |
| | 28Q 40R 44A 70L 75N | Not tested | + |
| | 7R 28Q 40R 44A 70L 75N 103T | + | + |
| | 28Q 34R 40R 44A 70L 75N 81T 103T 108V 160E | + | + |

+ indicates a functional combination

Example 5.2

Validation of SH6 Target Cleavage in an Extrachromosomal Model in CHO Cells

I-CreI variants able to efficiently cleave the SH6 target in yeast when forming heterodimers are described hereabove in example 5.1. In order to identify heterodimers displaying maximal cleavage activity for the SH3 target in CHO cells, the efficiency of some of these variants was compared using an extrachromosomal assay in CHO cells. The screen in CHO cells is a single-strand annealing (SSA) based assay where cleavage of the target by the meganucleases induces homologous recombination and expression of a LagoZ reporter gene (a derivative of the bacterial lacZ gene).

a) Cloning of SH6 Target in a Vector for Cho Screen

The target was cloned as follows: oligonucleotide corresponding to the SH6 target sequence flanked by gateway cloning sequence was ordered from PROLIGO 5'-TG-GCATACAAGTTTTTAATACCCCGTAC-CTAATATTGCCAATCGTCTGTCA-3' (SEQ ID NO: 65). Double-stranded target DNA, generated by PCR amplification of the single stranded oligonucleotide, was cloned using the Gateway protocol (INVITROGEN) into CHO reporter vector (pCLS1058). Cloned target was verified by sequencing (MILLEGEN).

b) Re-cloning of Meganucleases

The ORF of I-CreI variants cleaving the SH6.3 and SH6.4 targets identified in example 5.1 were sub-cloned in pCLS2437. ORFs were amplified by PCR on yeast DNA using the following primers: 5'-AAAAAGCAGGCTG-GCGCGCCTACACAGCGGCCTTGCCACCATG-3' (SEQ ID NO: 66) and 5'-AGAAAGCTGGGTGCTAGCGCTC-GAGTTATCAGTCGG-3' (SEQ ID NO: 67) primers. PCR products were cloned in the CHO expression vector pCLS2437 using the AscI and XhoI for internal fragment replacement. Selected clones resulting from ligation and *E. coli* transformation steps were verified by sequencing (MILLEGEN).

c) Extrachromosomal Assay in Mammalian Cells

CHO K1 cells were transfected with Polyfect® transfection reagent according to the supplier's protocol (QIAGEN). 72 hours after transfection, culture medium was removed and 150 µl of lysis/revelation buffer for β-galactosidase liquid assay was added (typically 1 liter of buffer contained: 100 ml of lysis buffer (Tris-HCl 10 mM pH7.5, NaCl 150 mM, Triton X100 0.1%, BSA 0.1 mg/ml, protease inhibitors), 10 ml of Mg 100X buffer (MgCl$_2$ 100 mM, β-mercaptoethanol 35%), 110 ml ONPG 8 mg/ml and 780 ml of sodium phosphate 0.1M pH7.5). After incubation at 37° C., OD was measured at 420 nm. The entire process is performed on an automated Velocity11 BioCel platform. Per assay, 150 ng of target vector was cotransfected with 12.5 ng of each one of both variants (12.5 ng of variant cleaving palindromic SH6.3 target and 12.5 ng of variant cleaving palindromic SH6.4 target).

d) Results

One couple of variants forming an heterodimeric endonuclease able to cleave SH6 in yeast was chosen for confirmation in CHO using extrachromosomal assay in a transient transfection.

The monomer capable of cleaving SH6.3 comprised the following mutations: 44K 70S 75N (referred to as SH6-3-M1-44K 70S 75N) and the monomer capable of cleaving SH6.4 comprised the following mutations: 28Q 40R 44A 70L 75N 96R 111H 144S (referred to as SH6-4-MB-28Q 40R 44A 70L 75N 96R 111H 144S).

Analysis of the efficiencies of cleavage and recombination of the SH6 sequence demonstrates that the tested combination of I-CreI variants was able to transpose its cleavage activity from yeast to CHO cells without additional mutation.

Example 5.3

Covalent Assembly as Single Chain and Improvement of Meganucleases Cleaving SH6

Co-expression of the cutter described in example 5.1 leads to a high cleavage activity of the SH6 target in yeast. One of them have been validated for SH6 cleavage in a mammalian expression system (example 5.2).

The M1×MA SH6 heterodimer gives high cleavage activity in yeast. M1 is a SH6.3 cutter that bears the following mutations in comparison with the I-CreI wild type sequence: 44K 70S 75N. MA is a SH6.4 cutter that bears the following mutations in comparison with the I-CreI wild type sequence: 7R 28Q 40R 44A 70L 75N 103T 121E 132V 160R.

Single chain constructs were engineered using the linker RM2 (AAGGSDKYNQALSKYNQALSKYN-QALSGGGGS; SEQ ID NO: 15) resulting in the production of the single chain molecule: MA-RM2-M1. During this design step, the G19S mutation was introduced in the C-terminal M1 mutant. In addition, mutations K96E was introduced into the MA mutant and mutations E8K, E61R into the M1 mutant to create the single chain molecule: MA(K96E)-RM2-MA(E8K E61R) that is called further SCOH-SH6 b1 scaffold.

Four additional amino-acid substitutions have been found in previous studies to enhance the activity of I-CreI derivatives: these mutations correspond to the replacement of Phenylalanine 54 with Leucine (F54L), Glutamic acid 80 with Lysine (E80K), Valine 105 with Alanine (V105A) and Isoleucine 132 with Valine (I132V). Some combinations were introduced into the coding sequence of N-terminal and C-terminal protein fragment, and the first batch of resulting proteins were assayed for their ability to induce cleavage of the SH6 target.

a) Introduction of Additional Mutations into the SC-OH Single Chain Construct

Additional mutations were introduced by use of the QuikChange Multi Site-Directed Mutagenesis Kit from Stratagene/Agilent technologies Inc according to the manufacturer's instructions. A first set of oligonucleotides was used to introduce the mutations in the part of the single chain molecule corresponding to the first monomer. A second set of oligonucleotides was designed to introduce the same mutations specifically in the second part of the single chain molecule corresponding to the second monomer as shown in (see Table XII).

Table XII

| SEQ ID NO: | Name | Sequence |
|---|---|---|
| Oligonucleotides used for mutagenesis of the first monomer | | |
| 68 | F54LFor | ACCCAGCGCCGTTGGCTGC TGGACAAACTAGTG |
| 69 | F54LRev | CACTAGTTTGTCCAGCAGC CAACGGCGCTGGGT |
| 70 | 103T_105AFor | AAACAGGCAACCCTGGCTC TGAAAATTATCGAA |
| 71 | 103T_105ARev | TTCGATAATTTTCAGAGCC AGGGTTGCCTGTTT |
| Oligonucleotides used for mutagenesis of the second monomer | | |
| 72 | F54Lmono2_For | CACAAAGAAGGTGGTTGTT GGACAAATTGGTT |
| 73 | F54Lmono2_Rev | AACCAATTTGTCCAACAAC CACCTTCTTTGTG |
| 74 | E80Kmono2_For | TGTCTAAAATTAAGCCTCT TCATAACTTTCTC |

Table XII-continued

| SEQ ID NO: | Name | Sequence |
|---|---|---|
| 75 | E80Kmono2_Rev | GAGAAAGTTATGAAGAGGC TTAATTTTAGACA |

Isolated clones obtained at the term of this process were sequenced to confirm the specific mutation profiles obtained. Profiles of interest were then tested in CHO SSA assay in comparison with the initial construct as described.

b) Extrachromosomal Assay in Mammalian Cells

CHO K1 cells were transfected as described above. 72 hours after transfection, culture medium was removed and 150 μl of lysis/revelation buffer for β-galactosidase liquid assay was added. After incubation at 37° C., OD was measured at 420 nm. The entire process is performed on an automated Velocity11 BioCel platform.

Per assay, 150 ng of target vector was cotransfected with an increasing quantity of variant DNA from 3.12 ng to 25 ng (25 ng of single chain DNA corresponding to 12.5 ng+12.5 ng of heterodimer DNA). Finally, the transfected DNA variant DNA quantity was 3.12 ng, 6.25 ng, 12.5 ng and 25 ng. The total amount of transfected DNA was completed to 175 ng (target DNA, variant DNA, carrier DNA) using empty vector (pCLS0001).

c) Results

Figure 10:
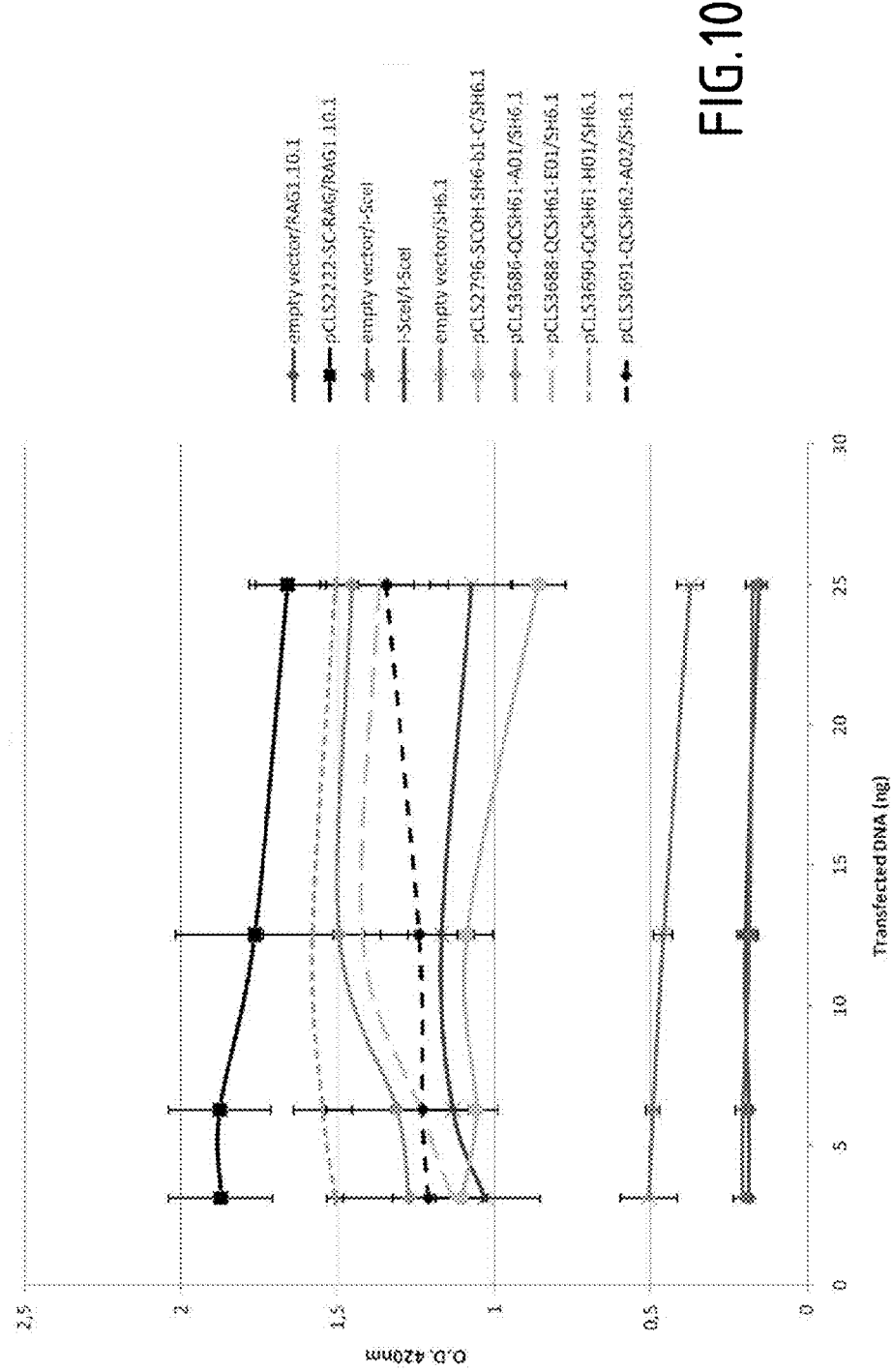
FIG. 10 represents SCOH SH6 meganucleases vs. I-SceI and SCOH-RAG DNA dose response in CHO.

The activity of the SCOH-SH6-b1-C (pCLS2796) and SCOH-SH6-b1-B-(pCLS2928) single chain molecules (see Table XIII) against the SH6 target was monitored using the previously described CHO assay by comparison to the SH6.3-M1×SH6.4-MB forming heterodimer and our internal control SCOH-RAG and I-SceI meganucleases. All comparisons were done at 3.12 ng, 6.25 ng, 12.5 ng, and 25 ng transfected variant DNA (FIG. 10). The two single chain meganucleases were able to cleave more efficiently the SH6 target than the starting heterodimer. The activity of the best molecule, SCOH-SH6-b1-C, was further improved by introduction additional mutations among those described above in a new bath of meganucleases.

TABLE XIII

| Name | Mutations on N-terminal segment | Mutations on C-terminal segment | SEQ ID NO: | SH6 cleavage Activity in CHO |
|---|---|---|---|---|
| SCOH-SH6-b1-B | 7R 28Q 40R 44A 70L 75N 96E 103T 121E 132V 160R | 8K 19S 44K 61R 70S 75N | 76 | + |
| SCOH-SH6-b1-C | 7R 28Q 40R 44A 70L 75N 96E 103T 121E 132V 160R | 8K 19S 44K 61R 70S 75N 132V | 77 | + |

Additional mutations were further introduced into the single chain scaffold according material and method. The molecules obtained and tested are listed in Table XIV.

TABLE XIV

| Name | Mutations on N-terminal segment | Mutations on C-terminal segment | SEQ ID NO: | SH6 cleavage Activity in CHO |
|---|---|---|---|---|
| SCOH-SH6-b1-C | 7R 28Q 40R 44A 70L 75N 96E 103T 121E 132V 160R | 8K 19S 44K 61R 70S 75N 132V | 78 | + |
| QCSH61-A01 | 7R 28Q 40R 44A 70L 75N 96E 103T 105A 121E 132V 160R | 8K 19S 44K 61R 70S 75N 132V | 79 | + |

TABLE XIV-continued

| Name | Mutations on N-terminal segment | Mutations on C-terminal segment | SEQ ID NO: | SH6 cleavage Activity in CHO |
|---|---|---|---|---|
| QCSH61-E01 | 7R 28Q 40R 44A 70L 75N 96E 103T 121E 132V 160R | 8K 19S 44K 54L 61R 70S 75N 132V | 80 | + |
| QCSH61-H01a | 7R 28Q 40R 44A 70L 75N 96E 103T 105A 121E 132V 160R | 8K 19S 44K 54L 61R 70S 75N 80K 132V | 81 | + |
| QCSH61-H01b | 7E 28Q 40R 44A 70L 75N 96E 103T 105A 121E 132 V160R | 8K 19S 44K 54L 61R 70S 75N 80K 132V | 83 | + |
| QCSH61-H01c | 7R 28Q 40R 44A 70L 75N 96E 103T 105A 121E 132V 160R | 8K 19S 44K 54L 61R 80K 132V | 84 | + |
| QCSH61-H01d | 7E 28Q 40R 44A 70L 75N 96E 103T 105A 121E 132V 160R | 8K 19S 44K 54L 61R 80K 132V | 85 | + |
| QCSH62-A02 | 7R 28Q 40R 44A 54L 70L 75N 96E 103T 121E 132V 160R | 8K 19S 44K 61R 70S 75N 132V | 82 | + |

All the variants were active in the described conditions and shared specific behaviour upon assayed dose depending on the mutation profile they bear (FIG. 10). For example, QCSH61-H01a, b, c, d have a similar profile to our internal standard SCOH-RAG. They are very active molecule even at low doses. All of these variants could be used for SH6 genome targeting.

Example 6

Gene Targeting at the Endogenous SH6 Loci in Human Cells

To validate the cleavage activity of engineered single-chain SH6 meganucleases, their ability to stimulate homologous recombination at the endogenous human SH6 loci was evaluated. Cells were transfected with mammalian expression plasmids for single chain molecules SCOH-QCSH6-H01 (SEQ ID NO: 81; pCLS3690) or SCOH-QC-SH6-H01-V2-7E-70R75D (SEQ ID NO: 85; pCLS4373) and the donor repair plasmid pCLS3779 (FIG. 13; SEQ ID NO: 279) containing 2.8 kb of exogenous DNA sequence flanked by two sequences, both 1.5 kb in length, homologous to the human SH6 locus. Cleavage of the native SH6 locus by the meganuclease yields a substrate for homologous recombination, which may use the donor repair plasmid containing 2.8 kb of exogenous DNA flanked by homology arms as a repair matrix. Thus, the frequency with which targeted integration occurs at the SH6 locus is indicative of the cleavage efficiency of the genomic SH6 target site.

Example 6.1

Materials and Methods a) Meganuclease Expression Plasmids

The meganucleases used in this example are SCOH-QCSH6-H01 (SEQ ID NO: 81) or SCOH-QC-SH6-H01-V2-7E-70R75D (SEQ ID NO: 85) cloned in a mammalian expression vector, resulting in plasmid pCLS3690 (FIG. 13) and pCLS4373 respectively.

b) Donor Repair Plasmid

The donor plasmid contains a PCR generated 1517 bp fragment of the SH6 locus (position 18437771 to 18439287 on chromosome 21, NC_000021.8) as the left homology arm and a 1571 bp fragment of the SH6 locus (position 18439343 to 18440846 on chromosome 21, NC_000021.8) as the right homology arm. The left and right homology arms were inserted upstream (using an AscI site) and downstream (using a SbfI site), respectively, of an exogenous 2.8 kb DNA fragment containing two CMV promoters and a neomycin resistance gene. The resulting plasmid is pCLS3779 (FIG. 13; SEQ ID NO: 279).

c) SH6 Gene Targeting Experiments

Human embryonic kidney 293H cells (Invitrogen) were plated at a density of $1 \times 10^6$ cells per 10 cm dish in complete medium (DMEM supplemented with 2 mM L-glutamine, penicillin (100 UI/ml), streptomycin (100 μg/ml), amphotericin B (Fongizone) (0.25 μg/ml) (Invitrogen-Life Science) and 10% FBS). The next day, cells were transfected with Lipofectamine 2000 transfection reagent (Invitrogen) according to the supplier's protocol. Briefly, 2 μg of the donor plasmid was co-transfected with 3 μg of single-chain meganuclease expression vectors. After 72 hours of incubation at 37° C., cells were trypsinized and plated in complete medium at 10 or 100 cells per well in 96-well plates. Alternatively, after 72 hours of incubation at 37° Q cells were trypsinized and plated in complete medium at 300 cells per dish in 10 cm-dishes. After 2 weeks of incubation at 37° C., individual clonal cellular colonies were picked and plated in complete medium in 96-well plates. Once cells were 80 to 100% confluent, genomic DNA extraction was performed with the ZR-96 genomic DNA kit (Zymo research) according to the supplier's protocol.

d) PCR Analysis of Gene Targeting Events

Figure 14:
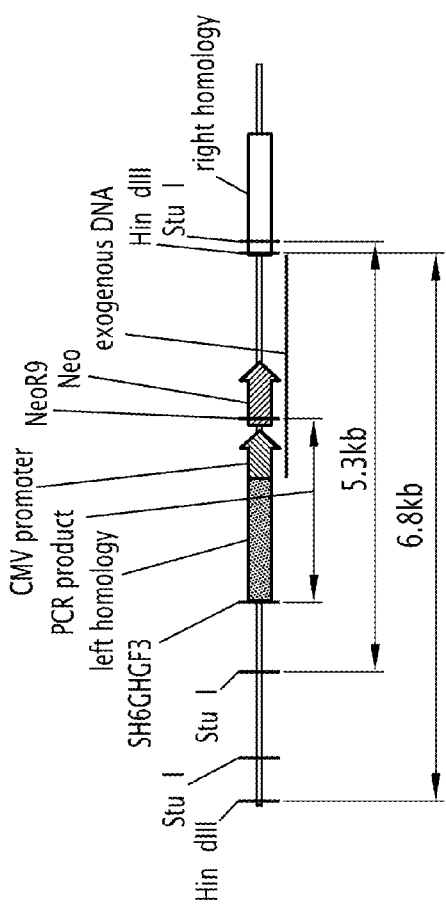

The frequency of gene targeting was determined by PCR on genomic DNA using the primers SH6 GHGF3: 5'-CAATGGAGTTTTGGAGCCAC-3' (SEQ ID NO: 280) and NeoR9: 5'-ATCAGAGCAGCCGATTGTCT-3' (SEQ ID NO: 281). The PCRs result in a 2300 bp gene targeting specific PCR product (FIG. 14). The SH6 GHGF3 primer is a forward primer located upstream of the left homology arms of the donor repair plasmids. The NeoR9 primer is a reverse primer located in the exogenous DNA inserted between the two homology arms of the donor repair plasmid.

Example 6.2

Results

Figure 13:
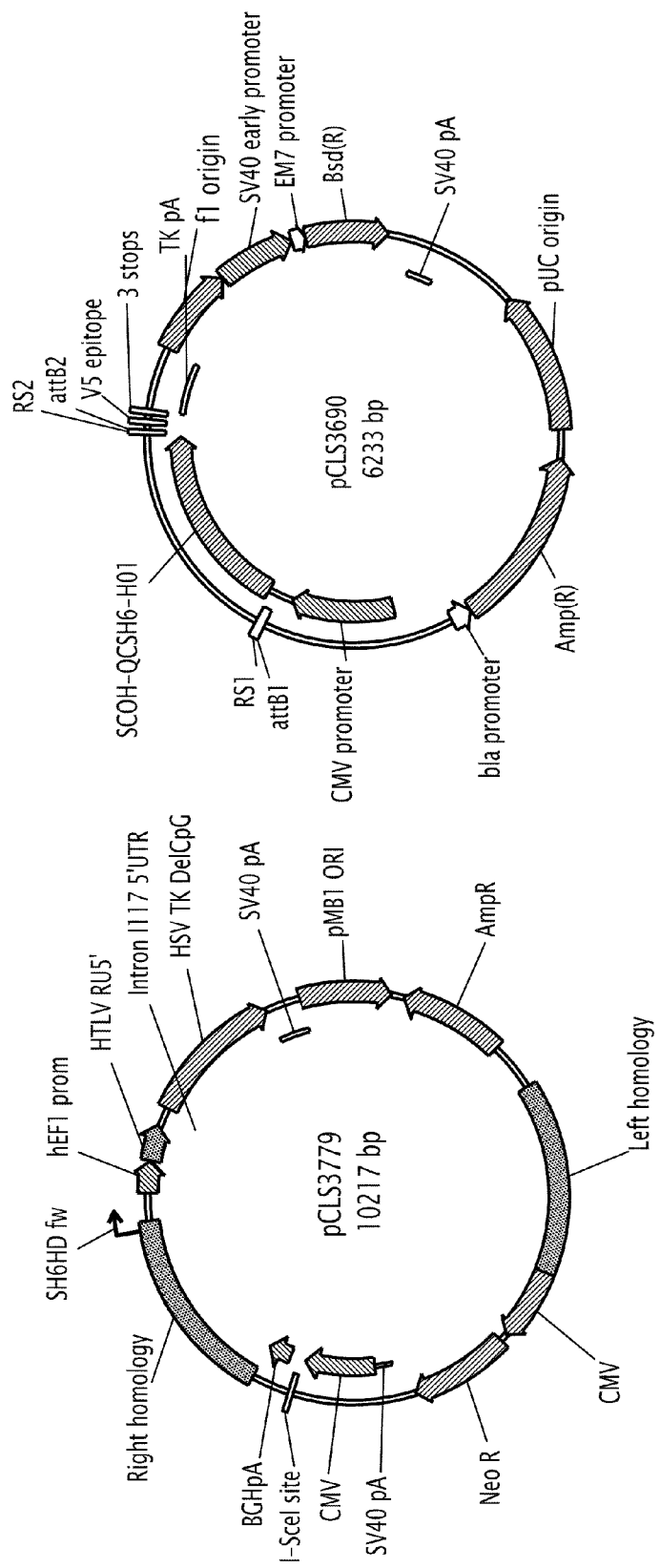
FIGS. 13 to 17 illustrate examples 6 to 9.

Human embryonic kidney 293H cells were co-transfected with 2 vectors: a plasmid expressing one of the two single-chain SH6 meganucleases and the donor repair plasmid pCLS3779 (FIG. 13; SEQ ID NO: 279). As a control for spontaneous recombination, 293H cells were also transfected with the donor repair plasmid alone. The cells were then plated at 10 or 100 cells per well in 96-well microplates or at 300 cells per 10 cm-dishes and 2 weeks later clonal colonies were isolated and plated in 96-well microplates. Genomic DNA derived from these cells was analyzed for gene targeting by PCR as described in Material and Methods. In the absence of meganuclease (repair plasmid alone), 5 PCR positive signals were detected among the 67680 cells analyzed in pools of 10 or 100 cells indicating a frequency of spontaneous of recombination of 0.007%. In contrast, in the presence of the SCOH-QCSH6-H01 (SEQ ID NO: 81; pCLS3690) or SCOH-QC-SH6-H01-V2-7E-70R75D meganucleases (SEQ ID NO: 85; pCLS4773), 177 and 35 positives were detected among the 73320 and 18800 cells analyzed in pools of 10 or 100 cells indicating a frequency of recombination of 0.24% and 0.19% respectively. Results are presented in Table XV. These results demonstrate that the two single chain molecules SCOH-QCSH6-H01 (SEQ ID NO: 81; pCLS3690) and SCOH-QC-SH6-H01-V2-7E-70R75D (SEQ ID NO: 85; pCLS4773) are capable of inducing high levels of gene targeting at the endogenous sh6 locus.

TABLE XV

Frequency of gene targeting events at the sh6 locus in human 293H cells

| Meganuclease | Cells per well | PCR + events | Gene targeting frequency |
|---|---|---|---|
| SCOH-QCSH6-H01 (SEQ ID NO: 81) | 100 | 151/65800 | 0.23% |
| SCOH-QC-SH6-H01-V2-7E-70R75D (SEQ ID NO: 85) | 100 | 35/18800 | 0.19% |
| None (with SH6 repair plasmid) | 100 | 5/56400 | 0.009% |
| SCOH-QCSH6-H01 (SEQ ID NO: 81) | 10 | 26/7520 | 0.35% |
| None (with SH6 repair plasmid) | 10 | 0/11280 | NA |
| SCOH-QCSH6-H01 (SEQ ID NO: 81) | monoclonal | 9/650 | 1.38% |
| SCOH-QC-SH6-H01-V2-7E-70R75D (SEQ ID NO: 85) | monoclonal | 2/116 | 1.72% |
| None (with SH6 repair plasmid) | monoclonal | 0/752 | NA |

NA: not applicable

Example 7

Transgene Expression After Gene Targeting at the Endogenous sh6 Loci in Human Cells To validate the capacity of sh6 locus to support transgene expression at sh6 locus cleavage activity of engineered single-chain SH6 meganucleases, gene targeting experiments were conducted with a repair plasmid containing a neomycin-resistance gene expression cassette and the ability of modified cells to grow in Neomycin-containing media was measured. The survival and growth of cells in the presence of Neomycin is dependent on the expression of the neomycin-resistance gene and is therefore indicative of transgene expression at the SH6 locus following targeted integration.

Example 7.1

Materials and Methods a) Meganuclease Expression Plasmids

The meganuclease used in this example is SCOH-QCSH6-H01 (SEQ ID NO: 81) cloned in a mammalian expression vector, resulting in plasmid pCLS3690.

b) Donor Repair Plasmid

The donor plasmid contains a PCR generated 1517 bp fragment of the SH6 locus (position 18437771 to 18439287 on chromosome 21, NC_000021.8) as the left homology arm and a 1571 bp fragment of the SH6 locus (position 18439343 to 18440846 on chromosome 21, NC_000021.8) as the right homology arm. The left and right homology arms were inserted upstream (using an AscI site) and downstream (using a SbfI site), respectively, of an exogenous 2.8 kb DNA fragment containing two CMV promoters and a neomycin resistance gene. The resulting plasmid is pCLS3779 (FIG. 13; SEQ ID NO: 279).

c) SH6 Gene Targeting Experiments

Human embryonic kidney 293H cells (Invitrogen) were plated at a density of $1\times10^6$ cells per 10 cm dish in complete medium (DMEM supplemented with 2 mM L-glutamine, penicillin (100 UI/ml), streptomycin (100 µg/ml), amphotericin B (Fongizone) (0.25 µg/ml) (Invitrogen-Life Science) and 10% FBS). The next day, cells were transfected with Lipofectamine 2000 transfection reagent (Invitrogen) according to the supplier's protocol. Briefly, 2 µg of the donor plasmid was co-transfected with 3 µg of single-chain meganuclease expression vectors. After 72 hours of incubation at 37° C., cells were trypsinized and plated in complete medium at 300 cells per dish in 10 cm-dishes. After 2 weeks of incubation at 37° C., individual clonal cellular colonies were picked and plated in complete medium in 96-well plates. After one week of incubation at 37° C., cells were trypsined, plated into 2 replicate 96-well plates and incubated at 37° C. Once cells were 80 to 100% confluent, genomic DNA extraction was performed on one of the replicate plate with the ZR-96 genomic DNA kit (Zymo research) according to the supplier's protocol. The other replicate was used to isolate gene-targeted clone and expand them.

d) PCR Identification of Gene Targeted Clones

Figure 15:
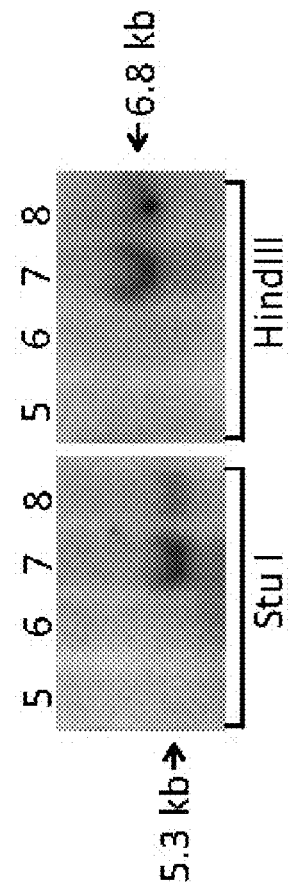

Gene targeting was determined by PCR on genomic DNA using the primers SH6 GHGF3: 5'-CAATGGAGTTTTG-GAGCCAC-3' (SEQ ID NO: 280) and NeoR9: 5'-ATCA-GAGCAGCCGATTGTCT-3' (SEQ ID NO: 281). The PCRs result in a 2300 bp gene targeting specific PCR product (FIG. 14). The SH6 GHGF3 primer is a forward primer located upstream of the left homology arms of the donor repair plasmids. The NeoR9 primer is a reverse primer located in the exogenous DNA inserted between the two homology arms of the donor repair plasmid.

e) Validation of Targeted Integration by Southern Blot:

Genomic DNA from cellular clones was digested with StuI or HindIII restriction enzymes (New England Biolabs), separated by electrophoresis on a 0.8% agarose gela and transferred onto a nitrocellulose membrane. A DNA probe was prepared from 25 ng of a DNA fragment homologous to the Neomycin resistance gene with $^{32}$P-radiolabeled dCTP and Rediprime II random prime labelling system (GE Healthcare) according to supplier's protocol and added to the nitrocellulose membrane that had preincubated in hybridization buffer (NaPi 20 mM, 7% SDS, 1 mM EDTA). After overnight incubation at 65° C., the membrane was washed and exposed to a radiography film. The size of expected bands on the radiograph are 5.3 kb for StuI digestion and 6.8 kb for HindIII digestion (FIG. 15).

f) Neomycin-resistance Test:

Cellular clones identified by PCR as targeted at SH6 locus were plated at 300 cells per well in 96-well microplates in the presence of G418 antibiotics (PAA laboratories). After 10 days of incubation at 37° C., viability was measured using Vialight bioassay kit (Lonza) and a Victor luminescence reader (Perkin Elmer) according to supplier's protocol.

Example 7.2

Results

Figure 16:
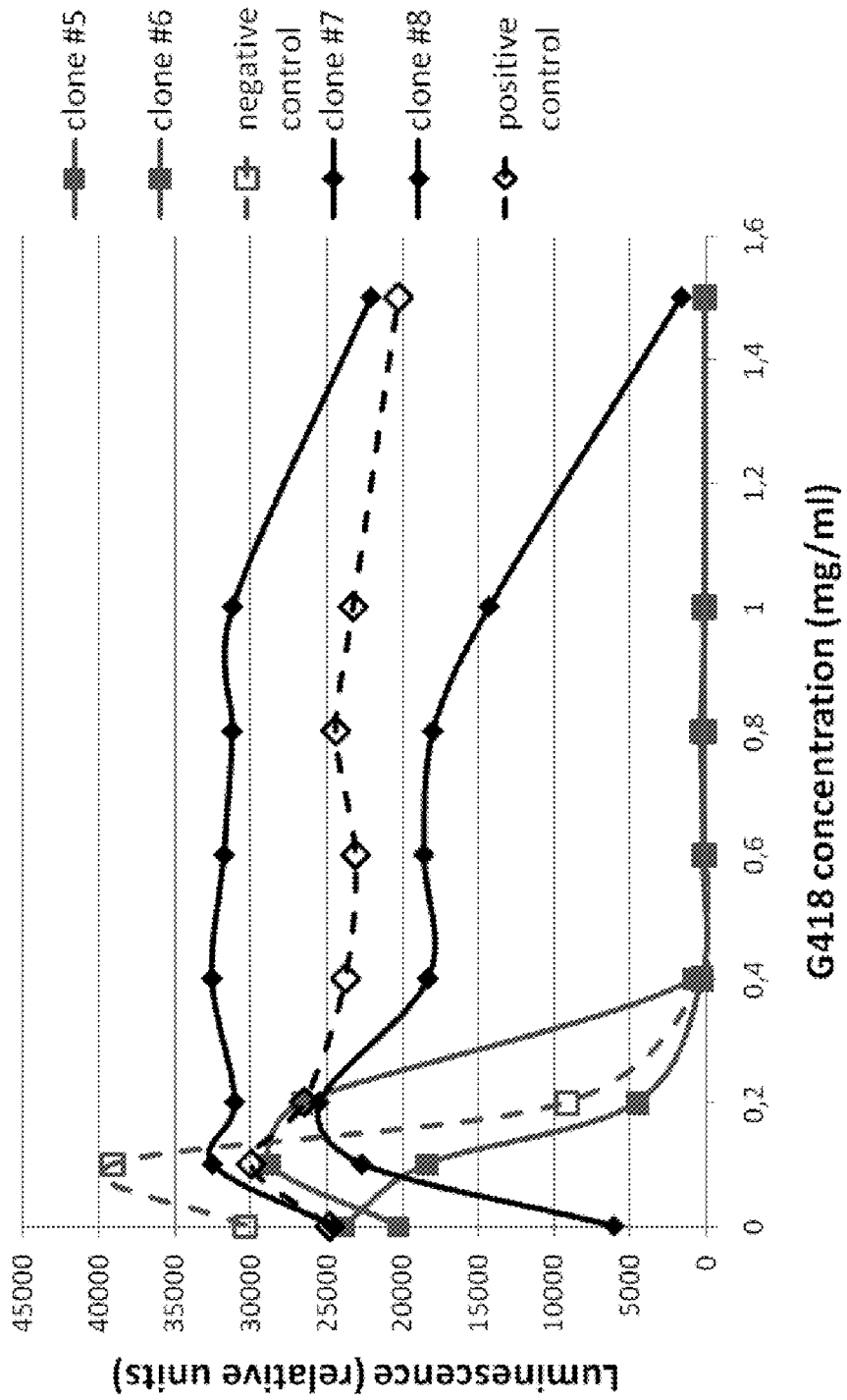

Human embryonic kidney 293H cells were co-transfected with 2 vectors: a plasmid expressing one of the two single-chain SH6 meganucleases and the donor repair plasmid pCLS3779. The cells were then plated at 300 cells per 10-cm dish and 2 weeks later clonal colonies were isolated and plated in 96-well microplates. Genomic DNA derived from these cells was analyzed for gene targeting by PCR as described in Material and Methods. Genomic DNA was then used to validate targeted integration by southern blot analysis. The clones number 7 and 8 showed bands of the expected size whereas negative control clones number 5 and 6 did not (FIG. 16). Those cellular clones were tested for their ability to survive in the presence of G418 (PAA laboratories). Only clones with targeted integration (number 7 and 8) showed resistance to G418 at concentrations superior to 0.4 mg/ml (FIG. 16). This indicates that targeted integration at sh6 locus can support functional transgene expression.

Example 8

Neighboring Gene Expression after Gene Targeting at the Endogenous sh6 Loci in Human Cells To validate the capacity of sh6 locus to support transgene integration without disturbing the expression of neighboring genes, gene targeting experiments were conducted with a repair plasmid containing a 2.8 kb exogenous DNA fragment and cellular clones were identified that contained the targeted integration. The expression of genes upstream and downstream of the sh6 integration site was measured and compared to that of cellular clones that had not undergone targeted integration.

Example 8.1

Materials and Methods a) Meganuclease Expression Plasmids

The meganucleases used in this example is SCOH-QCSH6-H01 (SEQ ID NO:81) cloned in a mammalian expression vector, resulting in plasmid pCLS3690.

b) Donor Repair Plasmid

The donor plasmid contains a PCR generated 1517 bp fragment of the SH6 locus (position 18437771 to 18439287 on chromosome 21, NC_000021.8) as the left homology arm and a 1571 bp fragment of the SH6 locus (position 18439343 to 18440846 on chromosome 21, NC_000021.8) as the right homology arm. The left and right homology arms were inserted upstream (using an AscI site) and downstream (using a SbfI site), respectively, of an exogenous 2.8 kb DNA fragment containing two CMV promoters and a neomycin resistance gene. The resulting plasmid is pCLS3779 (FIG. 13; SEQ ID NO: 279).

c) Sh6 Gene Targeting Experiments

Human embryonic kidney 293H cells (Invitrogen) were plated at a density of 1×10$^6$ cells per 10 cm dish in complete medium (DMEM supplemented with 2 mM L-glutamine, penicillin (100 UI/ml), streptomycin (100 µg/ml), amphotericin B (Fongizone) (0.25 µg/ml) (Invitrogen-Life Science) and 10% FBS). The next day, cells were transfected with Lipofectamine 2000 transfection reagent (Invitrogen) according to the supplier's protocol. Briefly, 2 µg of the donor plasmid was co-transfected with 3 µg of single-chain meganuclease expression vectors. After 72 hours of incubation at 37° C., cells were trypsinized and plated in complete medium at 300 cells per dish in 10 cm-dishes. After 2 weeks of incubation at 37° C., individual clonal cellular colonies were picked and plated in complete medium in 96-well plates. After one week of incubation at 37° C., cells were trypsined, plated into 2 replicate 96-well plates and incubated at 37° C. Once cells were 80 to 100% confluent, genomic DNA extraction was performed on one of the replicate plate with the ZR-96 genomic DNA kit (Zymo research) according to the supplier's protocol. The other replicate was used to isolate gene-targeted clone and expand them.

d) PCR Identification of Gene Targeted Clones

Gene targeting was determined by PCR on genomic DNA using the primers

SH6 GHGF3: 5'-CAATGGAGTTTTGGAGCCAC-3' (SEQ ID NO: 280) and NeoR9: 5'-ATCAGAGCAGCCGAT-TGTCT-3' (SEQ ID NO: 281). The PCRs result in a 2300 bp gene targeting specific PCR product (Figure XX). The SH6 GHGF3 primer (SEQ ID NO: 280) is a forward primer located upstream of the left homology arms of the donor repair plasmids. The NeoR9 primer (SEQ ID NO: 281) is a reverse primer located in the exogenous DNA inserted between the two homology arms of the donor repair plasmid.

e) Expression of Genes Upstream and Downstream from Sh6 Locus:

Gene expression was measured by quantitative RT-PCR. RNA was isolated from subconfluent cellular clones using RNeasy RNA isolation kit (Qiagen) according to manufacturer's protocol. 3 µg of RNA was used to generate cDNA using Superscript III First-strand kit (Invitrogen). Quantitative PCR was performed on 10 ng of cDNA per 12 µl-reaction, in duplicate samples, using SYBR® Premix Ex TaqTm DNA Polymerase (Lonza) on Stratagene MPX3000 instrument. For each gene, the primers used are listed in the following table:

| Gene | Forward primer | SEQ ID NO: | Reverse primer | SEQ ID NO: |
|---|---|---|---|---|
| HPRT | 5'-GCCAGACTTTGTTGGATTTG-3' | 282 | 5'-CTCTCATCTTAGGCTTTGTATTTTG-3' | 283 |
| USP25 | 5'-CAGAGGACATGATGAAGAATTGA-3' | 284 | 5'-CTCGATCCTCTCCAGATTCG-3' | 285 |
| NRIP1 | 5'-GCACTGTGGTCAGACTGCAT-3' | 286 | 5'-TTCCATCGCAATCAGAGAGA-3' | 287 |
| CXADR | 5'-CTTATCATCTTTTGCTGTCG-3' | 288 | 5'-TACTGCCGATGTAGCTTCTG-3' | 289 |
| BTG3 | 5'-CCAGAAAAACCATCGAAAGG-3' | 290 | 5'-GGTCACTATACAAGATGCAGC-3' | 291 |
| C21orf91 | 5'-AAACACTCTCCTTCTGCCACA-3' | 292 | 5'-ATGGCCCCTTAATGATTTGG-3' | 293 |

The threshold cycles (Ct) were determined with Stratagene software on fluorescence (dRn) after normalization by the ROX reference dye. The intensity of gene expression was calculated using the formula $2^{Ct(HPRT)-Ct(Gene)}$, the expression of the housekeeping gene HPRT being used as an internal normalizing factor.

Example 8.2

Results

Figure 17:
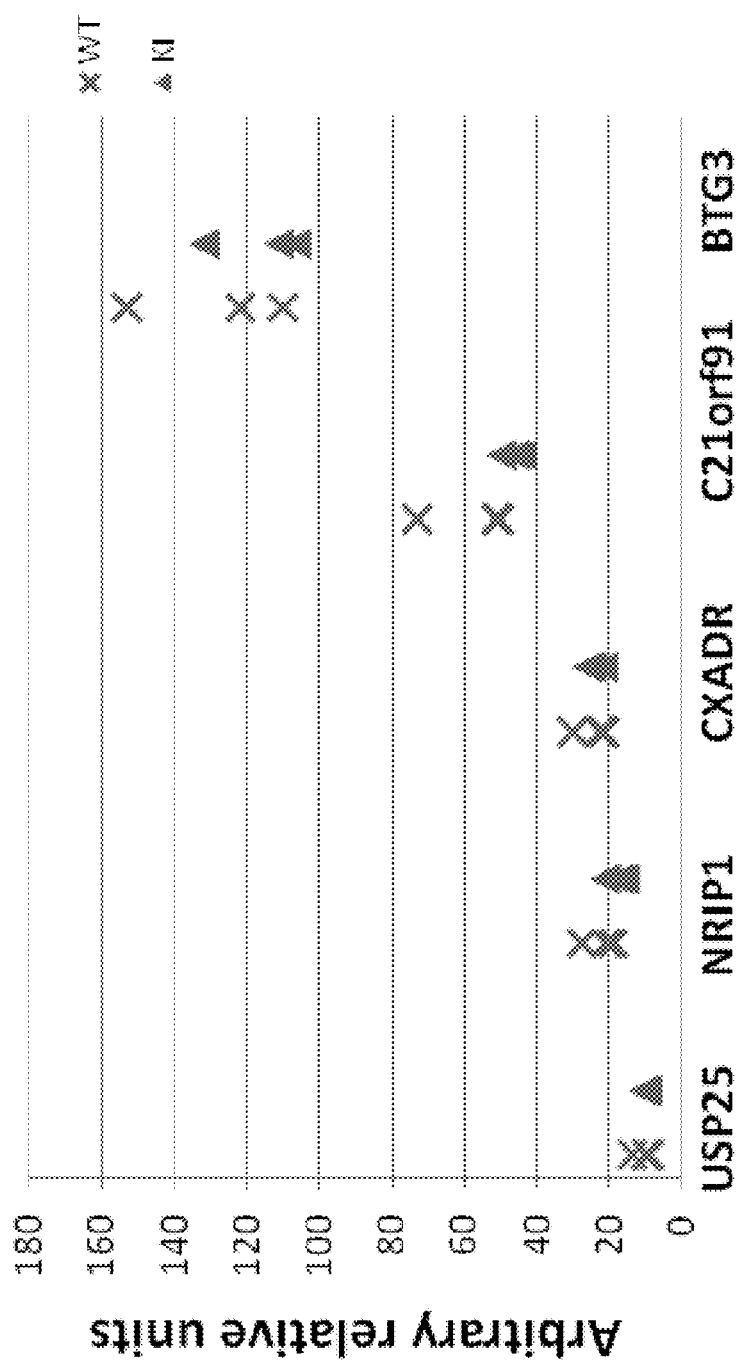

Human embryonic kidney 293H cells were co-transfected with 2 vectors: a plasmid expressing one of the three single-chain SH6 meganucleases and the donor repair plasmid pCLS3779. The cells were then plated at 300 cells per 10-cm dish and 2 weeks later clonal colonies were isolated and plated in 96-well microplates. Genomic DNA derived from these cells was analyzed for gene targeting by PCR as described in Material and Methods. RNA was isolated from clones showing targeted integration and negative controls. Quantitative RT-PCR was performed to measure expression of genes surrounding the locus of targeted integration. The data are presented in FIG. 17 where the average intensity of duplicate samples is shown for 3 individual targeted clones (KI) and 3 individual non-targeted clones (WT) after normalization with the housekeeping gene HPRT. No significant difference is observed for each of the 5 genes measured, indicating that targeted integration at the sh6 locus has no consequence on the expression of neighboring genes.

Example 9

Mutagenesis at Endogenous Safe Harbor Loci in Human Cells

To validate the cleavage activity of engineered single-chain Safe Harbor meganucleases, their ability to stimulate mutagenesis at endogenous human safe harbor loci was evaluated. Cells were transfected with mammalian expression plasmids for single chain molecules. Cleavage of a native safe harbor locus by the meganuclease yields a substrate for non-homologous end joining, which is an error-prone process and can result in small insertion or deletions at the meganuclease target site. Thus, the frequency at which mutations occur at an endogenous safe harbor locus is indicative of the cleavage efficiency of the genomic target site by the meganuclease.

Example 9.1

Materials and Methods a) Meganuclease Expression Plasmids

The coding sequences for the meganucleases used in this example were cloned in a mammalian expression vector, resulting in the plasmids listed in table XVI.

TABLE XVI

| Meganucleases targeting safe harbour sequences | | | |
|---|---|---|---|
| locus targeted | meganuclease | plasmid | SEQ ID NO |
| sh3 | SCOH-SH3-b1-C | pCLS2697 | 31 |
| sh4 | SCOH-SH4-b1-C | pCLS2705 | 39 |
| sh6 | QCSH61-H01 | pCLS3690 | 81 |
| sh6 | QC-SH6-H01_V2_7E_70R75D | pCLS4373 | 85 |
| sh6 | QC-SH6-H01_7E | pCLS4377 | 83 |
| sh6 | SCOH-SH6-b12-G2_BQY | pCLS6567 | 294 |
| sh6 | SCOH-SH6-b11-G2.2_BQY | PCLS6570 | 295 |
| sh8 | SCOH-SH8 | pCLS3894 | 88 |
| sh13 | SCOH-SH13 | pCLS3897 | 90 |
| sh18 | SCOH-SH18-b11-C.2 | pCLS5519 | 128 |
| sh19 | SCOH-SH19 | pCLS3899 | 91 |
| sh31 | SCOH-SH31.2 | pCLS4076 | 132 |
| sh39 | SCOH-SH39-b11-C | pCLS6038 | 133 |
| sh41 | SCOH-SH41-b11-C | pCLS5187 | 135 |
| sh42 | SCOH-SH42-b11-C | pCLS5549 | 137 |
| sh43 | SCOH-SH43-b12-C | pCLS5595 | 140 |
| sh44 | SCOH-SH44-b11-C | pCLS5868 | 141 |
| sh52 | SCOH-SH52-b12-C | pCLS5871 | 144 | b) Safe Harbor Locus Mutagenesis Experiments

Human embryonic kidney 293H cells (Invitrogen) were plated at a density of $1\times10^6$ cells per 10 cm dish in complete medium (DMEM supplemented with 2 mM L-glutamine, penicillin (100 UI/ml), streptomycin (100 µg/ml), amphotericin B (Fongizone) (0.25 µg/ml) (Invitrogen-Life Science) and 10% FBS). The next day, cells were transfected with 3 µg of single-chain meganuclease expression vector using Lipofectamine 2000 transfection reagent (Invitrogen) according to the supplier's protocol. After 2 to 6 days of incubation at 37° C., cells were trypsinized and genomic DNA extraction was performed with the DNeasy blood and tissue kit (Qiagen) according to the supplier's protocol.

c) Deep Sequencing Analysis of Mutagenesis Events

The frequency of mutagenesis was determined by deep sequencing analysis. Oligonucleotides were designed for PCR amplification of a DNA fragment surrounding each safe harbour target and are listed in table XVII.

Table XVII

PCR primers for mutagenesis analysis of safe harbour targets

| locus targeted | forward primer | SEQ ID NO | reverse primer | SEQ ID NO |
|---|---|---|---|---|
| sh3 | 5'-TGGGGGTCTTACTCTGTTTCCCAG-3' | 296 | 5'-AGGAGAGTCCTTCTTTGGCCAAT-3' | 297 |
| sh4 | 5'-GAGTGATAGCATAATGAAAACCCA-3' | 298 | 5'-CTCACCATAAGTCAACTGTCTCAG-3' | 299 |
| sh6 | 5'-TCTTTGTGTTTCCAAAGAGTTCCTTTGGCTTTCAC-3' | 300 | 5'-GAATGGTCTGAAAATGGAGAGGTTAAATGAGATTT-3' | 301 |
| sh8 | 5'-ACTAAATATGTTAATTGTGTGTATACAGTTTTTGT-3' | 302 | 5'-ATTGCTACTTCATTTGTTATGTTAACTATGACATG-3' | 303 |
| sh13 | 5'-TTTTTGTGGGTCCACAGTAGGTGTATATATTTATGG-3' | 304 | 5'-CAGTTGAACTCATGGATGTAGAGAGTAGAAGAATG-3' | 305 |
| sh18 | 5'-GACCTGAAGCTCAGGTACTT-3' | 306 | 5'-AGTGGTGGTAGGCAGGACAT-3' | 307 |
| sh19 | 5'-CTTAGGTAAACCTCAAAACAACAAGAGAGGAGCAA-3' | 308 | 5'-CTGCTAGAGCCCGTAATGTTTCAATCATAGTTATT-3' | 309 |
| sh31 | 5'-TTCAGGTTAGGTGACCTTCAAACT-3' | 310 | 5'-AAGACCAGGCTGGGCAACCATAGC-3' | 311 |
| sh39 | 5'-GAATAATGGAATAAACCCAGAGAAAACAGAG-3' | 312 | 5'-GTGTTCAAGGAAAATGGAGTGATATTAGGAAT-3' | 313 |
| sh41 | 5'-GGAGATATCATTAAAAGAGGCATT-3' | 314 | 5'-ATTACAATAGCCTTAGGAAACTAG-3' | 315 |
| sh42 | 5'-GAGTCACAGCCACCTTACATTTTACTTTTC-3' | 316 | 5'-AAGTAGAACACATTCCTATTTCCATTAAGT-3' | 317 |
| sh43 | 5'-ATTAAGTACAAAATTTGGTCCAAT-3' | 318 | 5'-AAAGTTGATTCATCTGAAACATG-3' | 319 |
| sh44 | 5'-GCAGCGATCCATGGTGGAGA-3' | 320 | 5'-TAACACAGGCTCATGTAGGT-3' | 321 |
| sh52 | 5'-ATGTTATTCGAGGACCCACT-3' | 322 | 5'-GTGACAACTCTGCTAGAAGA-3' | 323 |

Nucleotides were added to obtain a fragment flanked by specific adaptator sequences (5'-CCATCTCATCCCTGCGTGTCTCCGACTCAG-3'; SEQ ID NO 324) and (5'-CCTATCCCTGTGTGCCTTGGCAGTCTCAG-3'; SEQ ID NO 325) provided by the company offering sequencing service (GATC Biotech AG, Germany) on the 454 sequencing system (454 Life Sciences). An average of 18,000 sequences was obtained from pools of 2 to 3 amplicons (500 ng each). After sequencing, different samples were identified based on barcode sequences introduced in the first of the above adaptators.

Example 9.2

Results

Human embryonic kidney 293H cells were transfected with a plasmid expressing a single-chain safe harbor meganuclease. After 2 to 6 days of incubation at 37° C., genomic DNA was isolated and PCR was used to amplify the genomic sequence surrounding the meganuclease target site. Sequences were then analyzed for the presence of insertions or deletions events (InDel) in the cleavage site of each safe harbor target. Results are summarized in table XVIII.

TABLE XVIII

Mutagenesis by meganucleases targeting safe harbor loci:

| locus targeted | Cleaved by meganucleases of SEQ ID NO: | Plasmids | % InDels |
|---|---|---|---|
| sh3 | 31 | 2697 | 0.8 |
| sh4 | 39 | 2705 | 0.2 |
| sh6 | 81 | 3690 | 0.6 |
|  | 85 | 4373 | 3.5 |
|  | 83 | 4377 | 1.5 |
|  | 294 | 6567 | 1 |
|  | 295 | 6570 | 3 |
| sh8 | 88 | 3894 | 0.5 |
| sh13 | 90 | 3897 | 1.5 |
| sh18 | 128 | 5519 | 1.2 |
| sh19 | 91 | 3899 | 0.9 |
| sh31 | 132 | 4076 | 5 |
| sh39 | 133 | 6038 | 1.5 |
| sh41 | 135 | 5187 | 0.4 |
| sh42 | 137 | 5549 | 0.7 |
| sh43 | 140 | 5595 | 0.4 |
| sh44 | 141 | 5868 | 3.6 |
| sh52 | 144 | 5871 | 3.2 |

Example 10

Conclusion

In conclusion, Examples 1, 2, 3 and 5 demonstrate that both I-CreI heterodimeric proteins and single-chain meganucleases capable of cleaving the SH3, the SH4 and the SH6 loci can be obtained. Moreover, these endonucleases are capable of cleaving these loci with a strong cleavage activity.

Example 4 demonstrates that single-chain meganucleases capable of cleaving the SH3 and the SH4 loci allow efficiently inserting a transgene into a target site of a human cell.

These endonucleases can thus advantageously be used to insert a transgene into the SH3, the SH4 loci or the SH6 loci of an individual.

Example 6 demonstrates that at least two single chain molecules according to the invention are capable of inducing high levels of gene targeting at an endogenous sh6 locus.

Example 7 demonstrates that targeted integration a locus can support functional transgene expression.

Example 8 demonstrates that a targeted integration at a locus does not substantially modify expression of five genes located in the vicinity of the target sequence.

Example 9 demonstrates mutagenesis frequencies for different meganucleases targeting safe harbor sequences, which are indicative of the cleavage efficiency of the genomic target site by said meganucleases.

The invention claimed is:

1. A method for inserting a transgene into the genome of a human cell comprising:
   a) selecting, within the genome of said human cell, a retroviral insertion site (RIS) that is neither associated with cancer nor with abnormal cell proliferation;
   b) bringing said human cell in contact with an endonuclease capable of cleaving a target sequence of 12-45 base pairs that is located at a distance of at most 200 kb from the RIS,
   wherein the endonuclease comprises a sequence selected from the group consisting of SEQ ID Nos. 81, 82-85, 294, 295, 76, 77, 79-80, 25-40, 86-96, 127-150, 182-213, 235, 236, 238, 239, 241, 242, 244, 245, 250-252, 254-270, and 275-278;
   c) bringing said human cell contacted according to step b) in contact with a targeting construct comprising a transgene and two sequences homologous to the genomic sequence flanking the target sequence, thereby inserting said transgene into said genome,
   wherein said target sequence is located within a locus selected from the group consisting of the SH6 locus on human chromosome 21 at 21q21.1, the SH3 locus on human chromosome 6 at 6p25.1, the SH4 locus on human chromosome 7 at 7q31.2, the SH12 locus on human chromosome 13 at 13q34, the SH13 locus on human chromosome 3 at 3p12.2, the SH19 locus on human chromosome 22, the SH20 locus on human chromosome 12 at 12q21.2, the SH21 locus on human chromosome 3 at 3p24.1, the SH33 locus on human chromosome 6 at 6p12.2, the SH7 locus on human chromosome 2 at 2p16.1, the SH8 locus on human chromosome 5, the SH18 locus, the SH31 locus, the SH38 locus, the SH39 locus, the SH41 locus, the SH42 locus, the SH43 locus, the SH44 locus, the SH45 locus, the SH46 locus, the SH47 locus, the SH48 locus, the SH49 locus, the SH50 locus, the SH51 locus, the SH52 locus, the SH70 locus, the SH71 locus, the SH72 locus, the SH73 locus, the SH74 locus, the SH75 locus, the SH101 locus, the SH106 locus, the SH107 locus, the SH102 locus, the SH105 locus, the SH103 locus, the SH104 locus, the SH113 locus, the SH109 locus, the SH112 locus, the SH108 locus, the SH110 locus, the SH114 locus, the SH116 locus, the SH111 locus, the SH115 locus, the SH121 locus, the SH120 locus, the SH122 locus, the SH117 locus, the SH118 locus, the SH119 locus, the SH123 locus, the SH126 locus, the SH128 locus, the SH129 locus, the SH124 locus, the SH131 locus, the SH125 locus, the SH127 locus, the SH130 locus , the SH11 locus, the SH17 locus, the SH23 locus, the SH34 locus, the SH40 locus, the SH53 locus, the SH54 locus, the SH55 locus, the SH56 locus, the SH57 locus, the SH58 locus, the SH59 locus, the SH60 locus, the SH61 locus, the SH62 locus, the SH65 locus, the SH67 locus, the SH68 locus and the SH69 locus.

2. The method of claim 1, wherein said inserted transgene produces a recombinant protein.

3. The method of claim 1, wherein said target sequence is located within the SH3 locus.

4. The method of claim 1, wherein said target sequence is located within the SH4 locus.

5. The method of claim 1, wherein said target sequence is located within the SH6 locus.

6. The method of claim 1, wherein said target sequence is located within the SH6 locus on human chromosome 21 at 21q21.1, the SH3 locus on human chromosome 6 at 6p25.1, the SH4 locus on human chromosome 7 at 7q31.2, the SH12 locus on human chromosome 13 at 13q34, the SH13 locus on human chromosome 3 at 3p12.2, the SH19 locus on human chromosome 22, the SH20 locus on human chromosome 12 at 12q21.2, the SH21 locus on human chromosome 3 at 3p24.1, the SH33 locus on human chromosome 6 at 6p12.2, the SH7 locus on human chromosome 2 at 2p16.1, the SH8 locus on human chromosome 5, the SH18 locus, the SH31 locus, the SH38 locus, the SH39 locus, the SH41 locus, the SH42 locus, the SH43 locus, the SH44 locus, the SH45 locus, the SH46 locus, the SH47 locus, the SH48 locus, the SH49 locus, the SH50 locus, the SH51 locus, the SH52 locus, the SH70 locus, the SH71 locus, the SH72 locus, the SH73 locus, the SH74 locus, or the SH75 locus.

7. The method of claim 1, wherein said target sequence is located within the SH101 locus, the SH106 locus, the SH107 locus, the SH102 locus, the SH105 locus, the SH103 locus, the SH104 locus, the SH113 locus, the SH109 locus, the SH112 locus, the SH108 locus, the SH110 locus, the SH114 locus, the SH116 locus, the SH111 locus, the SH115 locus, the SH121 locus, the SH120 locus, the SH122 locus, the SH117 locus, the SH118 locus, the SH119 locus, the SH123 locus, the SH126 locus, the SH128 locus, the SH129 locus, the SH124 locus, the SH131 locus, the SH125 locus, the SH127 locus, or the SH130 locus.

8. The method of claim 1, wherein said target sequence is located within the SH11 locus, the SH17 locus, the SH23 locus, the SH34 locus, the SH40 locus, the SH53 locus, the SH54 locus, the SH55 locus, the SH56 locus, the SH57 locus, the SH58 locus, the SH59 locus, the SH60 locus, the SH61 locus, the SH62 locus, the SH65 locus, the SH67 locus, the SH68 locus, or the SH69 locus.

* * * * *